US012534704B2

(12) United States Patent
Cho et al.

(10) Patent No.: US 12,534,704 B2
(45) Date of Patent: Jan. 27, 2026

(54) ORGAN EXTRACELLULAR MATRIX-DERIVED SCAFFOLD FOR CULTURE AND TRANSPLANTATION OF ORGANOID AND METHOD OF PREPARING THE SAME

(71) Applicant: CELLARTGEN INC., Seoul (KR)

(72) Inventors: Seung Woo Cho, Seodaemun-gu Seoul (KR); Su Kyeom Kim, Seodaemun-gu Seoul (KR); Yi Sun Choi, Seoul (KR); Soo Han Bae, Seodaemun-gu Seoul (KR); Dai Hoon Han, Seodaemun-gu Seoul (KR); Su Ran Kim, Seodaemun-gu Seoul (KR); Sung Jin Min, Seodaemun-gu Seoul (KR); Yu Heun Kim, Seodaemun-gu Seoul (KR); Jin Gu Lee, Seongdong-gu Seoul (KR)

(73) Assignee: CELLARTGEN INC., Seoul (KR)

( * ) Notice: Subject to any disclaimer, the term of this patent is extended or adjusted under 35 U.S.C. 154(b) by 660 days.

(21) Appl. No.: 17/904,082

(22) PCT Filed: Feb. 15, 2021

(86) PCT No.: PCT/KR2021/001929

§ 371 (c)(1),
(2) Date: Aug. 11, 2022

(87) PCT Pub. No.: WO2021/162533

PCT Pub. Date: Aug. 19, 2021

(65) Prior Publication Data

US 2023/0067199 A1 Mar. 2, 2023

(30) Foreign Application Priority Data

Feb. 14, 2020 (KR) ........................ 10-2020-0018361
Feb. 14, 2020 (KR) ........................ 10-2020-0018362
Feb. 14, 2020 (KR) ........................ 10-2020-0018363
Feb. 14, 2020 (KR) ........................ 10-2020-0018364

(51) Int. Cl.
*C12N 5/07* (2010.01)

(52) U.S. Cl.
CPC ............ *C12N 5/06* (2013.01); *C12N 2500/05* (2013.01); *C12N 2500/30* (2013.01); *C12N 2513/00* (2013.01)

(58) Field of Classification Search
CPC .. C12N 5/06; C12N 2500/30; C12N 2513/00; C12N 5/0068; C12N 2533/90; C12M 23/20; C12M 25/14
See application file for complete search history.

(56) References Cited

U.S. PATENT DOCUMENTS

| | | | |
|---|---|---|---|
| 2009/0202977 A1 | 8/2009 | Ott et al. | |
| 2013/0288375 A1 | 10/2013 | Zhang et al. | |
| 2015/0202348 A1 | 7/2015 | Dvir et al. | |
| 2015/0238656 A1* | 8/2015 | Orlando | A61L 27/3808 435/402 |
| 2016/0002602 A1 | 1/2016 | Almeida-Porada et al. | |
| 2018/0256642 A1 | 9/2018 | Freytes et al. | |

FOREIGN PATENT DOCUMENTS

| | | | | |
|---|---|---|---|---|
| EP | 3587564 A1 | 1/2020 | | |
| JP | 2019017393 A | 2/2019 | | |
| KR | 10-2015-0074672 A | 7/2015 | | |
| KR | 10-2018-0025817 A | 3/2018 | | |
| WO | WO-2015168254 A1 * | 11/2015 | | A61L 27/34 |
| WO | 2017136786 A1 | 8/2017 | | |

OTHER PUBLICATIONS

Jenna L. Balestrini et al., "Production of decellularized porcine lung scaffolds for use in tissue engineering", Integrative Biology, vol. 7, Dec. 12, 2015, pp. 1598-1610.
Jung Seung Lee et al., "Liver Extracellular Matrix Providing Dual Functions of Two-Dimensional Substrate Coating and Three-Dimensional Injectable Hydrogel Platform for Liver Tissue Engineering", Biomacromolecules, 2014, 15, pp. 206-218.
European Search Report for EP application No. 21 753 518.6, mailed Feb. 21, 2024.
International Search Report of PCT/KR2021/001929 dated Jun. 14, 2021, with English translation.
Giobbe et al., "Extracellular matrix hydrogel derived from decellularized tissues enables endodermal organoid culture", Nature Communications, Article No. 5658, 2019.
Mazza et al., "Decellularized human liver as a natural 3D-scaffold for liver bioengineering and transplantation", Scientific Reports, 2015, Article No. 13079.

* cited by examiner

*Primary Examiner* — Fereydoun G Sajjadi
*Assistant Examiner* — Masudur Rahman
(74) *Attorney, Agent, or Firm* — HSML P.C.

(57) ABSTRACT

A scaffold composition that includes an organ extracellular matrix, wherein the organ is selected from the group consisting of intestine, stomach, liver, and lung. Preparing a scaffold composition may include decellularizing an isolated organ tissue to prepare a decellularized organ tissue; drying the decellularized organ tissue to prepare an organ extracellular matrix; and gelating the dried organ extracellular matrix. Culturing an organoid includes culturing an organoid in the scaffold composition.

1 Claim, 128 Drawing Sheets

*FIG. 3D*

| | Intestine 1 | Intestine 2 | Intestine 3 |
|---|---|---|---|
| Collagens | Collagen type I, alpha 1 | Collagen type I, alpha 1, 2 | Collagen type I, alpha 1, 2 |
| | Collagen type V, alpha 1 | Collagen type IV, alpha 1, 2 | Collagen type IV, alpha 1, 2 |
| | Collagen type VI, alpha 1, 2, 3, 4, 5, 6 | Collagen type V, alpha 1 | Collagen type VI, alpha 1, 2, 3, 4, 5, 6 |
| | Collagen type VII, alpha 1 | Collagen type VI, alpha 1, 2, 3, 4, 5, 6 | Collagen type VII, alpha 1 |
| | Collagen type XII, alpha 1 | Collagen type VII, alpha 1 | Collagen type XII, alpha 1 |
| | Collagen type XIV, alpha 1 | Collagen type XIV, alpha 1 | Collagen type XV, alpha 1 |
| | Collagen type XV, alpha 1 | Collagen type XV, alpha 1 | Collagen type XIV, alpha 1 |
| | Collagen type XVIII, alpha 1 | Collagen type XVIII, alpha 1 | Collagen type XVIII, alpha 1 |
| Proteoglycans | Heparan sulfate | Heparan sulfate | Heparan sulfate |
| | Asporin | Biglycan | Asporin |
| | Fibromodulin | Decorin | Biglycan |
| | Versican | Lumican | Decorin |
| | Lumican | | Lumican |
| Glycoproteins | Laminin, alpha 4, 5 chain | Fibronectin | Fibronectin |
| | Laminin, beta 1, 2 chain | Laminin, alpha 4, 5 chain | Laminin, alpha 3, 4, 5 chain |
| | Laminin, gamma 1 chain | Laminin, beta 1, 2 chain | Laminin, beta 1, 2, 3 chain |
| | Nidogen 1, 2 | Laminin, gamma 1 chain | Laminin, gamma 1, 2 chain |
| | Vitronectin | Nidogen 1, 2 | Nidogen 1, 2 |
| | Tenascin | Vitronectin | Vitronectin |
| | Tenascin X | Tenascin | Tenascin |
| | Fibulin | Tenascin X | Tenascin X |
| | Fibrinogen, alpha chain | Emilin 1 | Emilin 1 |
| | Fibrinogen, beta chain | Fibulin | Fibulin |
| | Fibrinogen, gamma chain | Fibrinogen, alpha chain | Fibrinogen, alpha chain |
| | Elastin | Fibrinogen, beta chain | Fibrinogen, beta chain |
| | | Fibrinogen, gamma chain | Fibrinogen, gamma chain |
| | | Elastin | Elastin |
| | | Dermatopontin | Dermatopontin |
| | | | Hemicentin |
| Others | Prolargin | Prolargin | Prolargin |
| | Mimecan | Mimecan | Mimecan |

*FIG. 8A*
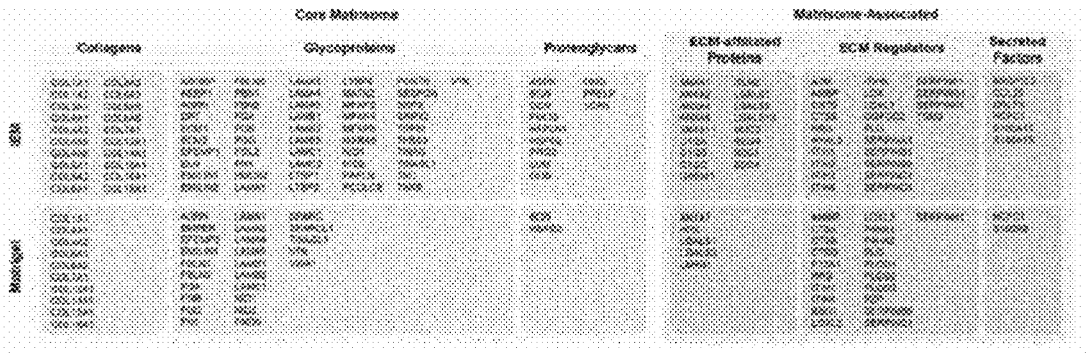
*FIG. 8B*
| iBAQ (value) | | Matrigel | | IEM | |
|---|---|---|---|---|---|
| Matrisome proteins | Collagens | 987970950 | 0.389 % | 46563122800 | 45.293 % |
| | Glycoproteins | 244869052260 | 96.338 % | 17099795040 | 16.634 % |
| | Proteoglycans | 2793769900 | 1.099 % | 36724758511 | 35.723 % |
| | ECM-affiliated proteins | 1844389800 | 0.726 % | 1321758300 | 1.286 % |
| | ECM regulators | 3675133300 | 1.446 % | 933408560 | 0.908 % |
| | Secreted factors | 5338800 | 0.002 % | 160476470 | 0.156 % |
*FIG. 9A*
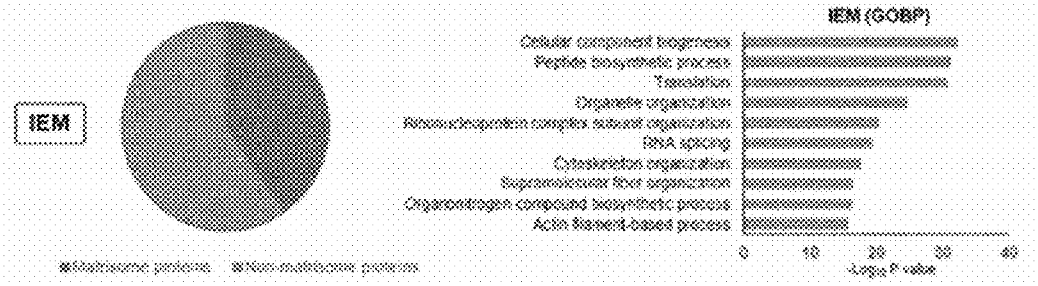

FIG. 37

| | Stomach 1 | Stomach 2 | Stomach 3 | Stomach 4 |
|---|---|---|---|---|
| Collagens | Collagen type IV, alpha 2 | Collagen type IV, alpha 2 | Collagen type I, alpha 1 | Collagen type I, alpha 1 |
| | Collagen type VI, alpha 1, 2, 3, 5 | Collagen type V, alpha 1 | Collagen type III, alpha 1 | Collagen type III, alpha 1 |
| | Collagen type XII, alpha 1 | Collagen type VI, alpha 1, 2, 3, 5, 6 | Collagen type IV, alpha 1, 2 | Collagen type IV, alpha 1, 2 |
| | Collagen type XIV, alpha 1 | Collagen type XII, alpha 1 | Collagen type VI, alpha 1, 2, 3, 5, 6 | Collagen type VI, alpha 1, 2, 3, 5, 6 |
| | Collagen type XV, alpha 1 | Collagen type XIV, alpha 1 | Collagen type XII, alpha 1 | Collagen type XII, alpha 1 |
| | Collagen type XVIII, alpha 1 | Collagen type XV, alpha 1 | Collagen type XIV, alpha 1 | Collagen type XIV, alpha 1 |
| | | Collagen type XVIII, alpha 1 | Collagen type XV, alpha 1 | Collagen type XV, alpha 1 |
| | | | Collagen type XVIII, alpha 1 | Collagen type XVIII, alpha 1 |
| | | | | Collagen type XXI, alpha 1 |
| Proteoglycans | Heparan sulfate | Heparan sulfate | Heparan sulfate | Heparan sulfate |
| | Asporin | Asporin | Asporin | Asporin |
| | Decorin | Biglycan | Biglycan | Biglycan |
| | Fibromodulin | Decorin | Decorin | Decorin |
| | Lumican | Fibromodulin | Fibromodulin | Fibromodulin |
| | | Versican | Versican | Versican |
| | | Lumican | Lumican | Lumican |
| Glycoproteins | Fibronectin | Fibronectin | Fibronectin | Fibronectin |
| | Laminin, alpha 4, 5 | Laminin, alpha 4, 5 | Laminin, alpha 3, 4, 5 | Laminin, alpha 2, 4, 5 |
| | Laminin, beta 2 | Laminin, beta 1, 2 | Laminin, beta 1, 2 | Laminin, beta 1, 2 |
| | Laminin, gamma 1 | Laminin, gamma 1 | Laminin, gamma 1 | Laminin, gamma 1 |
| | Nidogen 1, 2 | Nidogen 1, 2 | Nidogen 1, 2 | Nidogen 1, 2 |
| | Thrombospondin 3 | Thrombospondin 3 | Thrombospondin 4 | Thrombospondin 4 |
| | Emilin 1 | Tenascin | Vitronectin | Vitronectin |
| | Fibulin 1, 5 | Emilin 1 | Tenascin X | Tenascin X |
| | Fibrinogen, alpha chain | Fibrinogen, alpha chain | Emilin 1 | Emilin 1 |
| | Fibrinogen, beta chain | Fibrinogen, beta chain | Fibulin 1, 3 | Fibulin 1, 2, 5 |
| | Fibrinogen, gamma chain | Fibrinogen, gamma chain | Fibrillin 1 | Fibrinogen, alpha chain |
| | Elastin | Elastin | Fibrinogen, alpha chain | Fibrinogen, beta chain |
| | | Hemicentin 2 | Fibrinogen, beta chain | Fibrinogen, gamma chain |
| | | | Fibrinogen, gamma chain | Elastin |
| | | | Elastin | Dermatopontin |
| | | | Dermatopontin | |
| | | | Hemicentin 2 | |
| Others | Prolargin | Prolargin | Prolargin | Prolargin |
| | Mimecan | Mimecan | Mimecan | Mimecan |

FIG. 38A

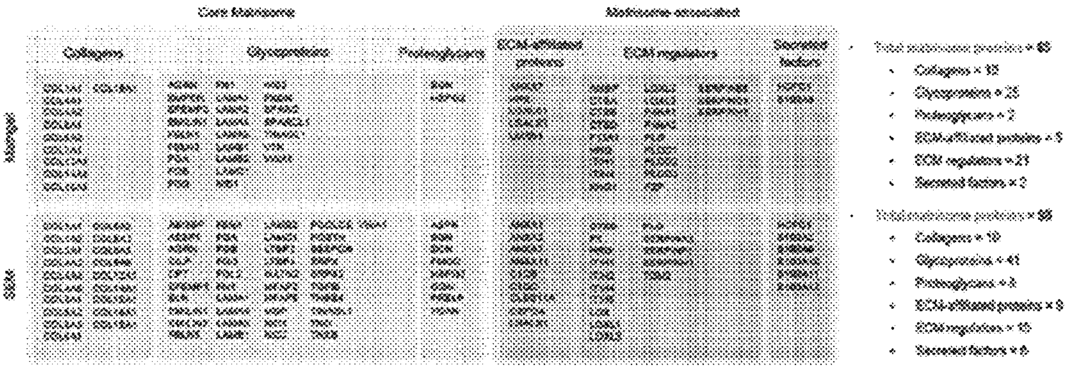

| iBAQ (value) | | Matrigel | | SEM | |
|---|---|---|---|---|---|
| Matrisome proteins | Collagens | 937970950 | 0.369 % | 16713937990 | 39.759 % |
| | Glycoproteins | 244869052250 | 96.338 % | 6510452250 | 15.487 % |
| | Proteoglycans | 2793765900 | 1.099 % | 14758444370 | 35.107 % |
| | ECM-affiliated proteins | 1844389920 | 0.726 % | 2080906350 | 4.950 % |
| | ECM regulators | 3675193300 | 1.446 % | 1030128490 | 2.450 % |
| | Secreted factors | 5338500 | 0.002 % | 944051500 | 2.246 % |

FIG. 64A

Proteins enriched in native liver (MAT)

| |
|---|
| COL18A1 |
| FGG |
| FGB |
| FGA |
| ALB |
| CFH |
| CLU |
| P4HB |
| AHSG |
| APOA1 |
| VTN |
| C3 |
| HSP90B1 |
| ACAA2 |
| KNG1 |
| PLOD2 |
| PZP |
| GC |
| HRG |
| PRDX4 |
| PLG |
| TF |
| APOE |
| ITIH4 |
| APCS |
| CP |
| SERPINC1 |
| SERPINC1 |
| ITIH1 |
| LDHA |
| HPX |
| HYOU1 |

Proteins enriched in native liver (LEM)

| | | | |
|---|---|---|---|
| BHMT | SLC25A10 | CTH | A1CF |
| EHHADH | SULT2A1 | APOA5 | UGDH |
| ADH4 | SLC25A20 | GC | RPRD1B |
| DECR1 | SLC27A5 | HSDL2 | HSD17B7 |
| ALDOB | MPC1 | MMAA | FMO3 |
| CPS1 | QPRT | C8G | SLC27A4 |
| DPYS | ECHDC2 | ALDH1L1 | APOB |
| VKORC1 | ISOC2 | SNTB1 | GNPNAT1 |
| MAT1A | ALDH1A1 | PC | TTC36 |
| MGST1 | AOX1 | DHCR7 | PEMT |
| CLU | BDH1 | COMT | GCKR |
| HMGCL | MAOB | RARRES2 | HMGCS2 |
| SFXN1 | DHODH | ASS1 | HSP90B1 |
| CYP27A1 | ACOT13 | CES1 | TTR |
| GLYAT | CAT | UROC1 | SARDH |
| UGP2 | FH | DECR2 | ACAT1 |
| SDSL | CBS | LECT2 | GGCX |
| ECHS1 | ARG1 | SLC27A2 | KLKB1 |
| DCXR | IQGAP2 | NADK2 | MOCOS |
| ACAA2 | APCS | SORD | ECI2 |
| ALDH9A1 | FBP1 | ACSMSGA22 | ACADM |
| SLC25A13 | GSTZ1 | CYP2E1 | PNPO |
| APOE | ALAD | C4BPA | PKLR |
| GLUD1 | HOGA1 | UGT1A6 | OTC |
| ACSL1 | HPD | GLYCTK | ARMC8 |
| ACAA1 | PRDX4 | DDT | FTCD |
| PECR | FMO5 | PROC | ASPDH |
| AGXT | SFXN5 | GCDH | MYO1B |
| C3 | AKR1C1 | ALDH6A1 | C1S |
| AHSG | P4HB | MTCH2 | SLC22A18 |
| CP | ALB | APOC2 | ALDH2 |
| CPT2 | AKR1D1 | TF | AFM |
| NIT2 | PCK2 | METTL7B | TDO2 |
| MTHFD1 | PAH | ETFB | THNSL1 |
| GYS2 | SCP2 | ACADSB | HAL |
| HSD17B2 | UGT1A1 | RGN | KMO |
| GSTA2 | SEPSECS | ACY1 | CFB |
| SHMT1 | GSTO1 | ACSM2B | SUCLG2 |
| SULT1A1 | SLC25A15 | PBLD | GPAM |
| NIPSNAP1 | CYP1A2 | MTTP | PDIA4 |
| ACOX1 | APOH | C4A | CYP3A4 |
| CRP | GNE | G6PC | |

Lung extracellular matrix

FIG. 91

| Lung |
| --- |
| Collagen type I, alpha 1 |
| Collagen type IV, alpha 1, 2, 4, 6 |
| Collagen type VI, alpha 1, 2, 3, 5, 6 |
| Collagen type VII, alpha 1 |
| Collagen type XII, alpha 1 |
| Collagen type XV, alpha 1 |
| Collagen type XIV, alpha 1 |
| Collagen type XVI, alpha 1 |
| Collagen type XVIII, alpha 1 |
| Collagen type XXI, alpha 1 |
| Heparan sulfate |
| Asporin |
| Biglycan |
| Decorin |
| Fibromodulin |
| Versican |
| Lumican |
| Agrin |
| Dermatopontin |
| Elastin 13, 15, 24 |
| Emilin 1 |
| Fibronectin |
| Fibrillin 1 |
| Laminin, alpha 3, 4, 5 |
| Laminin, beta 1, 2, 3 |
| Laminin, gamma 1, 2 |
| Nidogen 1, 2 |
| Thrombospondin |
| Vitronectin |
| Tenascin X |
| Fibulin 1, 2, 5 |
| Fibrinogen, alpha chain |
| Fibrinogen, beta chain |
| Fibrinogen, gamma chain |
| Hemicentin 1 |
| Mimecan |
| Prolargin |

FIG. 92A
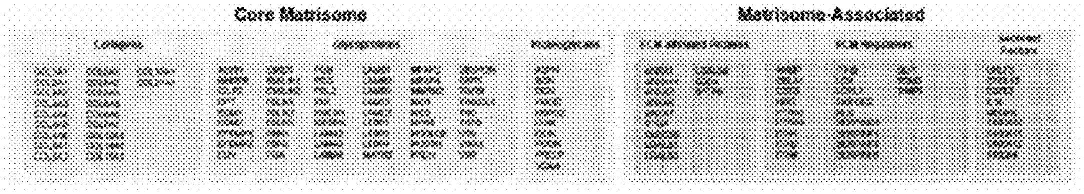
FIG. 92B
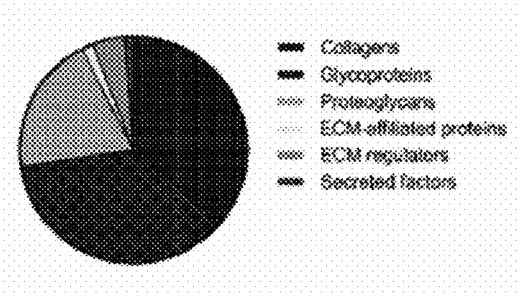
| Matrisome proteins | Collagens | 36.0 ~ 40.4 % |
|---|---|---|
| | Glycoproteins | 34.1 ~ 39.3 % |
| | Proteoglycans | 16.6 ~ 18.3 % |
| | ECM-affiliated proteins | 1.2 ~ 2.2 % |
| | ECM regulators | 3.9 ~ 5.2 % |
| | Secreted factors | 1.1 ~ 1.4 % |
FIG. 92C
Top 10 matrisome proteins
COL6A1 FGA
COL6A2 BGN
COL6A3 TGM2
DCN LUM
ELN FBN1
Matrisome proteins enriched in native lung
COL6A6
COL6A5
CLEC3B
SFTPB

ORGAN EXTRACELLULAR MATRIX-DERIVED SCAFFOLD FOR CULTURE AND TRANSPLANTATION OF ORGANOID AND METHOD OF PREPARING THE SAME

TECHNICAL FIELD

The present disclosure relates to an organ extracellular matrix-derived scaffold for culture and transplantation of an organoid and a method of preparing the same.

BACKGROUND

With respect to an intestinal extracellular matrix-derived scaffold for culture and transplantation of an intestinal organoid and a method of preparing the same, a stem cell-based intestinal organoid is the most effective in vitro model in implementing the composition and function of the human intestinal tissue among models constructed so far, and has infinite potential to be used in disease models, new drug development and transplantation therapy. Accordingly, there has been a lot of interest in efficient 3D organoid production, culture and transplantation technology.

Most intestinal organoid studies use MATRIGEL®, a cell culture scaffold based on a natural polymer extracted from mouse sarcoma. Since MATRIGEL® contains abundant extracellular matrix components, various types of tissue organoids can be cultured, but there is a limitation in that it cannot properly provide a tissue-specific microenvironment.

In fact, intestinal stem cells grow and change while constantly interacting with a tissue-specific extracellular fluid and a tissue-specific extracellular matrix in the body. A culture protocol that mimics a tissue-specific extracellular fluid environment through an intestinal tissue culture medium when producing an intestinal organoid using such stem cells has been relatively established. However, there have been few studies on methods of providing a tissue-specific extracellular matrix environment, and only MATRIGEL® has been used for culturing intestinal organoids. Therefore, due to the absence of an intestinal tissue-specific extracellular matrix environment, there is a need to further promote the development and maturation of the structure and function of intestinal organoids cultured in MATRIGEL®.

Also, since MATRIGEL® is a material extracted from mouse sarcoma, there is a possibility of infection and transmission of animal pathogens and viruses during transplantation of an organoid cultured in MATRIGEL® and there is a risk of inducing a serious immune response. Therefore, it is difficult to apply MATRIGEL® to clinical research for cell treatment and tissue regeneration such as organoid transplantation. Further, since MATRIGEL® is an expensive product and has a high unit price, It is difficult to use when a large amount of culture scaffold is needed, such as organoid-based drug screening for new drug development. Therefore, due to the current MATRIGEL®-dependent intestinal organoid culture method, basic research and applied research on intestinal organoids are greatly limited.

To solve this problem, in the present disclosure, an intestinal tissue mimicking scaffold having unique components and characteristics of an intestinal tissue-specific extracellular matrix was developed by decellularizing porcine small intestine. Through three-dimensional intestinal organoid culture using the decellularized intestinal tissue-derived hydrogel scaffold, proliferation and stable maintenance of intestinal organoids were possible, and it was confirmed that differentiation, development and function of an organoid were improved.

Since the scaffold developed in the present disclosure uses only an intestinal tissue-specific extracellular matrix obtained by removing all cellular components from the porcine small intestine, it is possible to overcome lack of tissue specificity and risk of inducing infection and immune response of MATRIGEL®, which is an existing organoid culture scaffold. Also, porcine small intestinal tissue is more advantageous in terms of economic efficiency than expensive MATRIGEL®.

With respect to a stomach extracellular matrix-derived scaffold for culture and transplantation of a gastric organoid and a method of preparing the same, an organoid, which has recently attracted a lot of interest, is the technology that has been rapidly growing worldwide and can be applied as a tissue analogue to various application fields, such as drug screening, drug toxicity evaluation, disease modeling and cell therapeutic agent.

Various types of organoids exist for each organ such as the brain, intestine, liver and stomach. Numerous research teams around the world researching these types of organoids are using MATRIGEL® as culture scaffolds to culture organoids. However, since MATRIGEL® is an extracellular matrix component extracted from mouse sarcoma tissue, it is difficult to maintain the uniform quality of products and it is expensive and has a safety problem such as metastasis of animal pathogens and viruses. Therefore, MATRIGEL®, as an organoid culture system, has a lot of problems to be solved. In particular, as a material derived from cancer tissue, it cannot provide an optimal tissue-specific microenvironment necessary for culturing a specific tissue-derived organoid. There have been some studies on the development of polymer-based hydrogels to replace MATRIGEL®, but no material has been reported that can replace MATRIGEL®.

A gastric organoid can be produced by extracting stem cells from stomach tissue and culturing them in a three-dimensional manner. Although a gastric organoid cultured by the existing protocol using MATRIGEL® can be cultured for a long time while maintaining its proliferation ability, it cannot be differentiated into functional cells, such as parietal cells and chief cells. Accordingly, there is a demand for the development of a new culture material that can produce more structurally and functionally matured gastric organoids than MATRIGEL®-based culture system.

Also, there are limits to only drug treatment for diseases resulting in a large amount of tissue damage such as gastric ulcer and gastric cancer resection. Accordingly, there is a need to develop cell therapy and tissue engineering technology capable of essentially regenerating tissue. Since the gastric organoid contains various cells, including stem cells, actually present in the stomach tissue, organoid-based transplantation and treatment are favored. However, it is also essential to develop a material for transplantation that can promote efficient transplantation and engraftment of an organoid into a living body.

The present disclosure proposes a novel culture platform that produces a hydrogel scaffold based on a stomach extracellular matrix component from porcine stomach tissue through decellularization and applies the hydrogel scaffold to gastric organoid culture. The developed decellularized tissue-derived scaffold can be easily mass-produced at low cost and contains various stomach tissue-specific extracellular matrix components and growth factors and thus provides a gastric organoid-specific three-dimensional microenvironment. The developed scaffold enabled the formation and proliferation of a gastric organoid at a level similar to that of the conventional MATRIGEL®, and it was verified that differentiation into stomach tissue-specific cells and function can be further improved. Furthermore, the decellularized scaffold improves gastric organoid transplantation efficiency and engraftment in damaged stomach tissue and thus has a high potential for use as a material for organoid transplantation.

With respect to a liver extracellular matrix-derived scaffold for culture and transplantation of liver organoids and a method of preparing the same, an organoid, which has recently attracted a lot of interest, is the technology that has been rapidly growing worldwide and can be applied as a tissue analogue to various clinical applications, such as drug screening, drug toxicity evaluation, disease modeling, cell therapeutic agent and tissue engineering. Organoids are three-dimensional structure composed of various cells of a specific human organ and tissue and can recapitulate interactions between them. Therefore, it can be applied as a more accurate in vitro model platform than conventionally used drug evaluation models such as cell line or animal models.

Various types of organoids exist for each organ. Numerous research teams around the world researching these types of organoids are using MATRIGEL® as culture scaffolds to culture organoids. However, since MATRIGEL® is extracted from mouse sarcoma tissue, it is difficult to maintain the uniform quality of products and it is expensive and has a safety problem such as metastasis of animal pathogens and viruses. Therefore, MATRIGEL®, as an organoid culture system, has a lot of problems to be solved. In particular, as a material derived from cancer tissue, it cannot provide an optimal tissue-specific microenvironment necessary for culturing a specific tissue organoid. There have been some studies on the development of polymer-based hydrogels to replace MATRIGEL®, but no material has been reported that can replace MATRIGEL®.

Liver organoids are produced by extracting adult stem cells from liver tissue and culturing them or by differentiating pluripotent stem cells, such as human induced pluripotent stem cells or embryonic stem cells, into hepatocytes and culturing them. Since MATRIGEL® cannot recapitulate a complex liver tissue-specific microenvironment, liver organoid differentiation efficiency and function need to be improved. Accordingly, the development of culture systems to produce more mature and functional liver organoids is urgently required.

Also, intractable liver diseases resulting in a large amount of tissue loss and liver failure, such as liver fibrosis, hepatitis, hepatocirrhosis and liver cancer, are difficult to treat with drugs. Accordingly, there is a need for therapeutic techniques that can essentially regenerate liver tissue. Since the liver organoid contains various liver tissue cells, including stem cells, actually present in the liver tissue, organoid-based liver tissue engineering and cell therapy are highly favored. However, there is also a need to develop a scaffold that can help efficient transplantation and engraftment of Organoids within the diseased site when a large-tissue analogue like an organoid is transplanted.

To solve the present technical problems in liver organoid culture and transplantation, in the present disclosure, a decellularized scaffold derived from liver tissue was prepared from liver tissue through decellularization, and a new platform used for liver organoid culture is proposed. The developed decellularized liver tissue-derived hydrogel scaffold abundantly contains various liver tissue-specific extracellular matrices and growth factors and thus improves differentiation, maturity, and functionality of a liver organoid compared to MATRIGEL®. Further, the decellularized liver tissue-derived hydrogel shows potential as a transplantation scaffold that enables efficient transplantation of liver organoids into a body.

With respect to a lung extracellular matrix-derived scaffold for culture and transplantation of a lung organoid and a method of preparing the same, an organoid is a three-dimensional structure composed of various cells constituting the tissue and thus can mimic the in vivo environment. Therefore, the organoid has recently attracted a lot of interest. For this reason, it is widely studied and used in various application fields, such as new drug development, disease modeling and regenerative therapy, as well as basic biology field.

Currently, most disease models are animal models. Since animals are different from humans in terms of physiology, there are limits to mimicking human diseases in animals. Also, ethical issues with animal testing constantly emerge. When an organoid model made from patient-derived cells is used, it is possible to study the mechanism of disease as well as to provide customized diagnosis to patients. Therefore, the organoid model is favored.

Currently, various types of organoid models derived from stem cells of different organs in vivo have been constructed. To culture these various types of organoids, most researchers around the world use MATRIGEL® as a culture scaffold. However, since MATRIGEL® is derived from mouse sarcoma, concerns are raised about attempts to transplant organoids cultured in MATRIGEL® into humans due to the risk of infection and immune rejection. Also, since MATRIGEL® is not a tissue-specific extracellular matrix component, it cannot provide a microenvironment optimized for organoid differentiation. Accordingly, there is an urgent need for development of a biocompatible and tissue-specific organoid culture scaffold that can replace MATRIGEL®.

Lung diseases caused by genetic factors, excessive smoking, particulate matter from air pollution, viruses, bacteria and the like are one of the leading causes of death worldwide. However, due to the absence of a disease model, it is not easy to study the mechanisms of lung diseases, and it is very difficult to develop medical treatment. Accordingly, there is a desperate need for the development of an in vitro lung disease model that can precisely mimic human lung diseases.

The present disclosure proposes a novel platform that uses a lung tissue-specific extracellular component obtained from lung tissue by decellularization as a hydrogel scaffold for lung organoid culture. Since the scaffold obtained by decellularization of lung tissue contains various extracellular matrix components and growth factors present in the lung tissue and thus, it is expected to promote development, growth and differentiation of a lung organoid. Lung organoids prepared using the decellularized scaffold are highly likely to be applied as various lung disease models.

DISCLOSURE OF THE INVENTION

Problems to be Solved by the Invention

With respect to an intestinal extracellular matrix-derived scaffold for culture and transplantation of an intestinal organoid and a method of preparing the same, the present disclosure is conceived to use only an intestinal tissue-specific extracellular matrix, which is obtained by removing cells from intestinal tissue by decellularization, as an artificial scaffold for effective three-dimensional culture of an intestinal organoid.

With respect to a stomach extracellular matrix-derived scaffold for culture and transplantation of a gastric organoid and a method of preparing the same, the present disclosure establishes a method for mass-producing decellularized scaffolds through a simple chemical treatment on stomach tissue and uses the prepared decellularized stomach tissue matrix for gastric organoid culture.

With respect to a liver extracellular matrix-derived scaffold for culture and transplantation of liver organoids and a method of preparing the same, the present disclosure is conceived to prepare a decellularized liver tissue in which all cell components are removed and liver-specific extracellular matrix components are preserved through decellularization of liver tissue and apply a three-dimensional hydrogel based on the decellularized liver tissue to liver organoid culture.

With respect to a lung extracellular matrix-derived scaffold for culture and transplantation of a lung organoid and a method of preparing the same, the present disclosure is conceived to obtain a large amount of decellularized tissue through a simple chemical treatment on porcine lung tissue, prepare a hydrogel scaffold based on the decellularized tissue and apply it to lung organoid culture.

However, the problems to be solved by the present disclosure are not limited to the above-described problems. Although not described herein, other problems to be solved by the present disclosure can be clearly understood by a person with ordinary skill in the art from the following descriptions.

Means for Solving the Problems

Hereafter, the present disclosure will be described in detail with reference to the accompanying drawings. However, it is to be noted that the present disclosure is not limited to examples described herein but can be embodied in various other ways. It is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Unless otherwise indicated, the practice of the disclosure involves conventional techniques commonly used in molecular biology, microbiology, protein purification, protein engineering, protein and DNA sequencing, and recombinant DNA fields, which are within the skill of the art. Such techniques are known to a person with ordinary skill in the art and are described in numerous standard texts and reference works.

Unless otherwise defined herein, all technical and scientific terms used herein have the same meaning as commonly understood by a person with ordinary skill in the art to which this disclosure belongs.

Various scientific dictionaries that include the terms included herein are well known and available to those in the art. Although any methods and materials similar or equivalent to those described herein find use in the practice or testing of the disclosure, some preferred methods and materials are described. It is to be understood that this disclosure is not limited to the particular methodology, protocols, and reagents described, as these may vary depending upon the context in which they are used by a person with ordinary skill in the art. Hereinafter, the present disclosure will be described in more detail.

The present disclosure provides a scaffold composition containing an organ extracellular matrix.

In an embodiment of the present disclosure, the organ may be any one of intestine, stomach, liver and lung.

Further, in an embodiment of the present disclosure, the organ extracellular matrix may be contained at a concentration of 0.01 mg/ml to 10 mg/mL.

The present disclosure also provides a method of preparing a scaffold composition, including: a process (a) of decellularizing an isolated organ tissue to prepare a decellularized organ tissue; a process (b) of drying the decellularized organ tissue to prepare an organ extracellular matrix; and a process (c) of gelating the dried organ extracellular matrix.

In an embodiment of the present disclosure, the organ may be any one of intestine, stomach, liver and lung.

In an embodiment of the present disclosure, in the process (a), the organ tissue may be stirred in a decellularization solution.

In an embodiment of the present disclosure, the decellularization solution may include 0.1% to 5% TRITON X-100™ (t-Octylphenoxypolyethoxyethanol) and 0.01% to 0.5% ammonium hydroxide.

In an embodiment of the present disclosure, in the decellularization of the process (a), 95% to 99.9% of organic tissue cells may be removed.

In an embodiment of the present disclosure, the method may further include a process of adjusting the organ extracellular matrix to be contained at a concentration of 0.01 mg/ml to 10 mg/ml after the process (b).

The present disclosure provides a method of culturing an organoid in the scaffold composition or a scaffold composition prepared by the preparation method.

In an embodiment of the present disclosure, the organ may be any one of intestine, stomach, liver and lung.

Hereinafter, a more detailed description of each organ will be made.

With respect to an intestinal extracellular matrix-derived scaffold for culture and transplantation of an intestinal organoid and a method of preparing the same, one aspect of the present disclosure provides a scaffold composition containing an intestinal extracellular matrix (IEM).

The term "extracellular matrix" refers to a natural scaffold for cell growth that is prepared by decellularization of tissue found in mammals and multicellular organisms. The extracellular matrix can be further processed through dialysis or crosslinking.

The extracellular matrix may be a mixture of structural or non-structural biomolecules including, but not limited to, collagens, elastins, laminins, glycosaminoglycans, proteoglycans, antimicrobials, chemoattractants, cytokines and growth factors.

In mammals, the extracellular matrix may contain about 90% collagen in various forms. The extracellular matrices derived from various living tissues may differ in their overall structure and composition due to the unique role needed for each tissue. In an embodiment of the present disclosure, the intestinal tissue may be any mucosal layer of porcine intestine, more specifically, any mucosal layer of porcine small intestine and/or large intestine, which is improved compared to the prior art techniques in which only the submucosal layer of porcine small intestine is used. Since raw materials are used in a non-limiting manner, the ease of production can be increased and the prepared scaffold composition contains more abundant extracellular matrix proteins than that of a conventional process.

The term "derive" or "derived" refers to a component obtained from any stated source by any useful method.

Further, in an embodiment of the present disclosure, the IEM may be contained at a concentration of 0.01 mg/ml to 10 mg/mL, specifically from 0.5 mg/ml to 8 mg/mL, more specifically, from 1 mg/ml to 5 mg/mL, and most specifically, 1 mg/mL, 2 mg/ml, 3 mg/mL, 4 mg/ml or 5 mg/mL. In an optimized embodiment, the IEM may be contained at a concentration of 2 mg/ml. The IEM contained with a concentration out of the above-described range may make it impossible to achieve the intended effect of the present disclosure, or may be unsuitable for preparation or application.

In an embodiment of the present disclosure, the composition may have an elastic modulus of 1 Pa to 80 Pa at 0.1 Hz to 1 Hz. When the composition has an elastic modulus in the above-described range, a stable polymer network can be formed.

The scaffold composition includes a three-dimensional hydrogel prepared based on an intestinal tissue matrix composition obtained by decellularization, and can be effectively used for intestinal organoid culture.

The decellularized intestinal tissue contains native tissue-specific extracellular matrix components and thus can provide the physical, mechanical and biochemical environment of the tissue, and is highly efficient in enhancing differentiation into intestinal tissue cells and tissue-specific functionality.

The term "organoid" refers to an ultraminiature body organ prepared in the form of an artificial organ by culturing cells derived from adult stem cells or pluripotent stem cells from tissues in a 3D form.

The organoid is a three-dimensional tissue analogue that contains organ-specific cells which originate from stem cells and self-organize (or self-pattern) in a similar manner to the in vivo condition. The organoid can be developed into a specific tissue by patterning a restricted element (for example, a growth factor).

The organoid can have the intrinsic physiological properties of the cells and can have an anatomical structure that mimics the original state of a cell mixture (including all remaining stem cells and the neighboring physiological niche as well as limited cell types). A three-dimensional culture method allows the organoid to be better arranged in terms of cell-to-cell functions and to have an organ-like form with functionality and a tissue-specific function.

Another aspect of the present disclosure provides a method of preparing a scaffold composition, including: a process (a) of decellularizing an isolated intestinal tissue to prepare a decellularized intestinal tissue; a process (b) of drying the decellularized intestinal tissue to prepare an intestinal extracellular matrix (IEM); and a process (c) of gelating the dried IEM.

The process (a) is a process of preparing a decellularized intestinal tissue by decellularizing an isolated intestinal tissue.

In an embodiment of the present disclosure, in the process (a), the intestinal tissue may be any mucosal layer of porcine intestine, more specifically, any mucosal layer of porcine small intestine and/or large intestine, which is improved compared to the prior art techniques in which only the submucosal layer of porcine small intestine is used. Since raw materials are used in a non-limiting manner, the ease of production can be increased and the prepared scaffold composition contains more abundant extracellular matrix proteins than that of a conventional process.

In an embodiment of the present disclosure, the intestinal tissue may be stirred in a decellularization solution in the process (a).

The decellularization solution may include various components for removing cells from the intestinal tissue, and may include, for example, hypertonic saline, peracetic acid, TRITON X-100™, SDS or other detergent components. In an embodiment of the present disclosure, the decellularization solution may include 0.1% to 5% TRITON X-100™ and 0.01% to 0.5% ammonium hydroxide and more specifically 1% TRITON X-100™ and 0.1% ammonium hydroxide. By using the decellularization solution as described above, it is possible to perform decellularization under more mild conditions than conventional processes. Thus, it is possible to effectively remove DNA in the prepared scaffold and preserve various proteins in the intestinal tissue.

The stirring may be performed for 24 hours to 72 hours, more specifically 36 hours to 60 hours and most specifically 44 hours to 52 hours. The stirring may be performed for, for example, 48 hours. Through this stirring process (decellularization), 95% to 99.9%, more specifically 96% to 98% and most specifically 97.68% of intestinal tissue cells may be removed. When decellularization is performed for a period of time out of the above-described range, the quality of the prepared scaffold composition may be degraded or the economic efficiency of the process may be decreased.

The process (b) is a process of preparing an IEM by drying the decellularized intestinal tissue.

The decellularized intestinal tissue may be dried by a known method. The decellularized intestinal tissue may be naturally dried or lyophilized. After drying, the decellularized intestinal tissue may be exposed to ethylene oxide gas or supercritical carbon dioxide by electron beam or gamma radiation for sterilization.

In an embodiment of the present disclosure, the method may further include a process of adjusting the IEM to be contained at a concentration of 0.01 mg/ml to 10 mg/ml, specifically from 0.5 mg/ml to 8 mg/ml, more specifically, from 1 mg/ml to 5 mg/ml, and most specifically, 1 mg/mL, 2 mg/mL, 3 mg/mL, 4 mg/ml or 5 mg/ml after the process (b). In an optimized embodiment, the IEM may be adjusted to be contained at a concentration of 2 mg/ml. The IEM contained with a concentration out of the above-described range may make it impossible to achieve the intended effect of the present disclosure, or may be unsuitable for preparation or application.

The dried extracellular matrix may be comminuted by methods including tearing, milling, cutting, grinding and shearing. The comminuted extracellular matrix may be processed into a powder form by a method such as grinding or milling in a frozen or lyophilized state.

The process (c) is a process of gelating the dried IEM.

Through the gelation, the IEM may be crosslinked to prepare a three-dimensional hydrogel-type scaffold, and the gelated scaffold can be used in various ways in the fields related to tests, screening and organoid culture.

The term "hydrogel" is a material in which a liquid that contains water as a dispersion medium is hardened through a sol-gel phase transition to lose fluidity and form a porous structure. The hydrogel can be formed by causing a hydrophilic polymer that has a three-dimensional network structure and a microcrystalline structure to contain water and to be expanded.

The gelation may be performed at a temperature of 37° C. for 30 minutes after dissolving the IEM in an acidic solution with a protease such as pepsin or trypsin and mixing and uniformly blending water, an IEM solution, a PBS buffer and NaOH at a ratio of 69:20:10:1.

Yet another aspect of the present disclosure provides a method of culturing an intestinal organoid in the scaffold composition or in a scaffold composition prepared by the preparation method.

The conventional MATRIGEL®-based culture system is an extract derived from animal cancer tissue, has a large difference between the batches, cannot mimic the native intestinal environment, and exhibits insufficient efficiency in differentiation or development into an intestinal organoid. The scaffold composition can create an intestinal tissue-like environment and thus is suitable for intestinal organoid culture.

The culture refers to a process of maintaining and growing cells under suitable conditions, and the suitable conditions may refer to, for example, the temperature, nutrient availability, atmospheric $CO_2$ level and cell density at which the cells are maintained.

Appropriate culture conditions for maintaining, proliferating, expanding and differentiating different types of cells are known in the art and are documented. Suitable conditions for formation of the organoid may facilitate or allow cell differentiation and formation of a multicellular structure.

Also, with respect to a stomach extracellular matrix-derived scaffold for culture and transplantation of a gastric organoid and a method of preparing the same, one aspect of the present disclosure provides a scaffold composition containing a stomach extracellular matrix (SEM).

The term "extracellular matrix" refers to a natural scaffold for cell growth that is prepared by decellularization of tissue found in mammals and multicellular organisms. The extracellular matrix can be further processed through dialysis or crosslinking.

The extracellular matrix may be a mixture of structural or non-structural biomolecules including, but not limited to, collagens, elastins, laminins, glycosaminoglycans, proteoglycans, antimicrobials, chemoattractants, cytokines and growth factors.

In mammals, the extracellular matrix may contain about 90% collagen in various forms. The extracellular matrices derived from various living tissues may differ in their overall structure and composition due to the unique role needed for each tissue.

The term "derive" or "derived" refers to a component obtained from any stated source by any useful method.

Further, in an embodiment of the present disclosure, the SEM may be contained at a concentration of 0.01 mg/ml to 10 mg/mL, specifically from 0.5 mg/mL to 8 mg/mL, more specifically, from 1 mg/ml to 5 mg/mL, and most specifically, 1 mg/ml, 3 mg/ml, 5 mg/mL or 7 mg/ml. In an optimized embodiment, the SEM may be contained at a concentration of 5 mg/mL. The SEM contained with a concentration out of the above-described range may make it impossible to achieve the intended effect of the present disclosure, or may be unsuitable for preparation or application.

In an embodiment of the present disclosure, the composition may have an elastic modulus of 1 Pa to 100 Pa at 0.1 Hz to 10 Hz. When the composition has an elastic modulus in the above-described range, a stable polymer network can be formed.

The scaffold composition includes a three-dimensional hydrogel prepared based on an stomach tissue matrix composition obtained by decellularization, and can be effectively used for stomach organoid culture.

The decellularized stomach tissue contains actual tissue-specific extracellular matrix components and thus can provide the physical, mechanical and biochemical environment of the tissue, and is highly efficient in enhancing differentiation into gastric epithelial cells and tissue-specific functionality.

The term "organoid" refers to an ultraminiature body organ prepared in the form of an artificial organ by culturing cells derived from adult stem cells or pluripotent stem cells from tissues in a 3D form.

The organoid is a three-dimensional tissue analogue that contains organ-specific cells which originate from stem cells and self-organize (or self-pattern) in a similar manner to the in vivo condition. The organoid can be developed into a specific tissue by patterning a restricted element (for example, a growth factor).

The organoid can have the intrinsic physiological properties of the cells and can have an anatomical structure that mimics the original state of a cell mixture (including all remaining stem cells and the neighboring physiological niche as well as limited cell types). A three-dimensional culture method allows the organoid to be better arranged in terms of cell-to-cell functions, and to have an organ-like form with functionality and a tissue-specific function.

Another aspect of the present disclosure provides a method of preparing a scaffold composition, including: a process (a) of decellularizing an isolated stomach tissue to prepare a decellularized stomach tissue; a process (b) of drying the decellularized stomach tissue to prepare a stomach extracellular matrix (SEM); and a process (c) of gelating the dried SEM.

The process (a) is a process of preparing a decellularized stomach tissue by decellularizing an isolated stomach tissue.

In an embodiment of the present disclosure, the process (a) may further include a process of slicing the isolated stomach tissue before decellularization. According to the present disclosure, the process of slicing the stomach tissue before decellularization makes it possible to remove cells more efficiently and completely. The isolated stomach tissue may be sliced by a known method.

In an embodiment of the present disclosure, the stomach tissue may be stirred in a decellularization solution in the process (a).

The decellularization solution may include various components for removing cells from the stomach tissue, and may include, for example, hypertonic saline, peracetic acid, TRITON X-100™, SDS or other detergent components. In an embodiment of the present disclosure, the decellularization solution may include 0.1% to 5% TRITON X-100™ and 0.01% to 0.5% ammonium hydroxide and more specifically 1% TRITON X-100™ and 0.1% ammonium hydroxide. By using the decellularization solution as described above, it is possible to perform decellularization under more mild conditions than conventional processes. Thus, it is possible to effectively remove DNA in the prepared scaffold and preserve various proteins in the stomach tissue.

The stirring may be performed for 24 hours to 72 hours, more specifically 36 hours to 60 hours and most specifically 40 hours to 56 hours. The stirring may be performed for, for example, 48 hours. Through this stirring process (decellularization), 95% to 99.9% and more specifically 96% to 98% of cells may be removed. When decellularization is performed for a period of time out of the above-described range, the quality of the prepared scaffold composition may be declined or the economic efficiency of the process may be decreased.

The process (b) is a process of preparing an SEM by drying the decellularized stomach tissue.

The decellularized stomach tissue may be dried by a known method. The decellularized stomach tissue may be naturally dried or lyophilized. After drying, the decellularized stomach tissue may be exposed to ethylene oxide gas or supercritical carbon dioxide by electron beam or gamma radiation for sterilization.

In an embodiment of the present disclosure, the method may further include a process of adjusting the SEM to be contained at a concentration of 0.01 mg/ml to 10 mg/ml, specifically from 0.5 mg/mL to 8 mg/ml, more specifically, from 1 mg/ml to 5 mg/mL, and most specifically, 1 mg/ml, 3 mg/ml, 5 mg/ml or 7 mg/ml after the process (b). In an optimized embodiment, the SEM may be adjusted to be contained at a concentration of 5 mg/ml. The SEM contained with a concentration out of the above-described range may make it impossible to achieve the intended effect of the present disclosure, or may be unsuitable for preparation or application.

The dried extracellular matrix may be comminuted by methods including tearing, milling, cutting, grinding and shearing. The comminuted extracellular matrix may be processed into a powder form by a method such as grinding or milling in a frozen or lyophilized state.

The process (c) is a process of gelating the dried SEM.

Through the gelation, the SEM may be crosslinked to prepare a three-dimensional hydrogel-type scaffold, and the gelated scaffold can be used in various ways in the fields related to tests, screening and organoid culture.

The term "hydrogel" is a material in which a liquid that contains water as a dispersion medium is hardened through a sol-gel phase transition to lose fluidity and form a porous structure. The hydrogel can be formed by causing a hydrophilic polymer that has a three-dimensional network structure and a microcrystalline structure to contain water and to be expanded.

The gelation may be performed at a temperature of 37° C. for 30 minutes after dissolving the SEM in an acidic solution with a protease such as pepsin or trypsin and setting a neutral pH in an electrolyte state of 1×PBS buffer by using 10×PBS and 1 M NaOH.

In an embodiment of the present disclosure, the method of preparing the scaffold composition may not include a perfusion method. It is possible to reduce wastage of the decellularization solution by not applying a perfusion method.

Yet another aspect of the present disclosure provides a method of culturing a gastric organoid in the scaffold composition or in a scaffold composition prepared by the preparation method.

The conventional MATRIGEL®-based culture system is an extract derived from animal cancer tissue, has a large difference between the batches, cannot mimic the actual gastric environment, and exhibits insufficient efficiency in differentiation or development into a gastric organoid. The scaffold composition can create a stomach tissue-like environment and thus is suitable for gastric organoid culture.

The culture refers to a process of maintaining and growing cells under suitable conditions, and the suitable conditions may refer to, for example, the temperature, nutrient availability, atmospheric $CO_2$ level and cell density at which the cells are maintained.

Appropriate culture conditions for maintaining, proliferating, expanding and differentiating different types of cells are known in the art and are documented. Suitable conditions for formation of the organoid may facilitate or allow cell differentiation and formation of a multicellular structure.

With respect to a liver extracellular matrix-derived scaffold for culture and transplantation of liver organoids and a method of preparing the same, one aspect of the present disclosure provides a scaffold composition containing a liver extracellular matrix (LEM).

The term "extracellular matrix" refers to a natural scaffold for cell growth that is prepared by decellularization of tissue found in mammals and multicellular organisms. The extracellular matrix can be further processed through dialysis or crosslinking.

The extracellular matrix may be a mixture of structural or non-structural biomolecules including, but not limited to, collagens, elastins, laminins, glycosaminoglycans, proteoglycans, antimicrobials, chemoattractants, cytokines and growth factors.

In mammals, the extracellular matrix may contain about 90% collagen in various forms. The extracellular matrices derived from various living tissues may differ in their overall structure and composition due to the unique role needed for each tissue.

The term "derive" or "derived" refers to a component obtained from any stated source by any useful method.

Further, in an embodiment of the present disclosure, the LEM may be contained at a concentration of 0.01 mg/mL to 10 mg/mL, specifically from 0.5 mg/ml to 9 mg/mL, more specifically, from 1 mg/ml to 8 mg/mL, and most specifically, 2 mg/mL, 4 mg/ml, 6 mg/ml or 8 mg/ml. In an optimized embodiment, the LEM may be contained at a concentration of 4 mg/ml or 6 mg/ml. The LEM contained with a concentration out of the above-described range may make it impossible to achieve the intended effect of the present disclosure, or may be unsuitable for preparation or application.

In an embodiment of the present disclosure, the composition may have an elastic modulus of 20 Pa to 100 Pa at 0.1 Hz to 10 Hz. When the composition has an elastic modulus in the above-described range, a stable polymer network can be formed.

The scaffold composition includes a three-dimensional hydrogel prepared based on a liver tissue matrix composition obtained by decellularization, and can be effectively used for liver organoid culture.

The decellularized liver tissue contains actual tissue-specific extracellular matrix components and thus can provide the physical, mechanical and biochemical environment of the tissue, and is highly efficient in enhancing differentiation into liver tissue cells and tissue-specific functionality.

The term "organoid" refers to an ultraminiature body organ prepared in the form of an artificial organ by culturing cells derived from adult tissues or pluripotent stem cells in a 3D form.

The organoid is a three-dimensional tissue analogue that contains organ-specific cells which originate from stem cells and self-organize (or self-pattern) in a similar manner to the in vivo condition. The organoid can be developed into a specific tissue by patterning a restricted element (for example, a growth factor).

The organoid can have the intrinsic physiological properties of the cells and can have an anatomical structure that mimics the original state of a cell mixture (including all remaining stem cells and the neighboring physiological niche as well as limited cell types). A three-dimensional culture method allows the organoid to be better arranged in terms of cell-to-cell functions, and to have an organ-like form with functionality and a tissue-specific function.

Another aspect of the present disclosure provides a method of preparing a scaffold composition, including: a process (a) of decellularizing an isolated liver tissue to prepare a decellularized liver tissue; a process (b) of drying the decellularized liver tissue to prepare a liver extracellular matrix (LEM); and a process (c) of gelating the dried LEM.

The process (a) is a process of preparing a decellularized liver tissue by decellularizing an isolated liver tissue.

In an embodiment of the present disclosure, the process (a) may further include a process of slicing the isolated liver tissue before decellularization. According to the present disclosure, the process of slicing the liver tissue before decellularization makes it possible to remove cells more efficiently and completely. The isolated liver tissue may be sliced into a known size by a known method (device).

In an embodiment of the present disclosure, the liver tissue may be stirred in a decellularization solution in the process (a).

The decellularization solution may include various components for removing cells from the liver tissue, and may include, for example, hypertonic saline, peracetic acid, TRITON X-100™, SDS or other detergent components. In an embodiment of the present disclosure, the decellularization solution may include 0.1% to 5% TRITON X-100™ and 0.01% to 0.5% ammonium hydroxide and more specifically 1% TRITON X-100™ and 0.1% ammonium hydroxide. By using the decellularization solution as described above, it is possible to perform decellularization under more mild conditions than conventional processes. Thus, it is possible to effectively remove DNA in the prepared scaffold and preserve various proteins in the liver tissue.

The stirring may be performed for 24 hours to 72 hours, more specifically 36 hours to 60 hours and most specifically 40 hours to 56 hours. The stirring may be performed for, for example, 48 hours. Through this stirring process (decellularization), 95% to 99.9%, more specifically 96% to 98% and most specifically 97.18% of liver tissue cells may be removed. When decellularization is performed for a period of time out of the above-described range or at a level of removal of liver tissue cells, the quality of the prepared scaffold composition may be degraded or the economic efficiency of the process may be decreased The process (b) is a process of preparing an LEM by drying the decellularized liver tissue.

The decellularized liver tissue may be dried by a known method. The decellularized liver tissue may be naturally dried or lyophilized. After drying, the decellularized liver tissue may be exposed to ethylene oxide gas or supercritical carbon dioxide by electron beam or gamma radiation for sterilization.

In an embodiment of the present disclosure, the LEM may be contained at a concentration of 0.01 mg/ml to 10 mg/mL, specifically from 0.5 mg/ml to 9 mg/mL, more specifically, from 1 mg/ml to 8 mg/mL, and most specifically, 2 mg/ml, 4 mg/ml, 6 mg/ml or 8 mg/ml after the process (b). In an optimized embodiment, the LEM may be adjusted to be contained at a concentration of 4 mg/ml or 6 mg/mL. The LEM contained with a concentration out of the above-described range may make it impossible to achieve the intended effect of the present disclosure, or may be unsuitable for preparation or application.

The dried extracellular matrix may be comminuted by methods including tearing, milling, cutting, grinding and shearing. The comminuted extracellular matrix may be processed into a powder form by a method such as grinding or milling in a frozen or lyophilized state.

The process (c) is a process of gelating the dried LEM. Through the gelation, the LEM may be crosslinked to prepare a three-dimensional hydrogel-type scaffold, and the gelated scaffold can be used in various ways in the fields related to tests, screening and organoid culture.

The term "hydrogel" is a material in which a liquid that contains water as a dispersion medium is hardened through a sol-gel phase transition to lose fluidity and to form a porous structure. The hydrogel can be formed by causing a hydrophilic polymer that has a three-dimensional network structure and a microcrystalline structure to contain water and to be expanded.

The gelation may be performed at a temperature of 37° C. for 30 minutes after dissolving the LEM in an acidic solution with a protease such as pepsin or trypsin and setting a neutral pH in an electrolyte state of 1×PBS buffer by using 10×PBS and 1 M NaOH.

Yet another aspect of the present disclosure provides a method of culturing a liver organoid in the scaffold composition or in a scaffold composition prepared by the preparation method.

The conventional MATRIGEL®-based culture system is an extract derived from animal cancer tissue, has a large difference between the batches, cannot mimic the actual liver environment, and exhibits insufficient efficiency in differentiation or development into a liver organoid. The scaffold composition can create a liver tissue-like environment and thus is suitable for liver organoid culture.

The culture refers to a process of maintaining and growing cells under suitable conditions, and the suitable conditions may refer to, for example, the temperature, nutrient availability, atmospheric $CO_2$ level and cell density at which the cells are maintained.

Appropriate culture conditions for maintaining, proliferating, expanding and differentiating different types of cells are known in the art and are documented. Suitable conditions for formation of the organoid may facilitate or allow cell differentiation and formation of a multicellular structure.

With respect to a lung extracellular matrix-derived scaffold for culture and transplantation of a lung organoid and a method of preparing the same, one aspect of the present disclosure provides a scaffold composition containing a lung extracellular matrix (LuEM).

The term "extracellular matrix" refers to a natural scaffold for cell growth that is prepared by decellularization of tissue found in mammals and multicellular organisms. The extracellular matrix can be further processed through dialysis or crosslinking.

The extracellular matrix may be a mixture of structural or non-structural biomolecules including, but not limited to, collagens, elastins, laminins, glycosaminoglycans, proteoglycans, antimicrobials, chemoattractants, cytokines and growth factors.

In mammals, the extracellular matrix may contain about 90% collagen in various forms. The extracellular matrices derived from various living tissues may differ in their overall structure and composition due to the unique role needed for each tissue.

The term "derive" or "derived" refers to a component obtained from any stated source by any useful method.

Further, in an embodiment of the present disclosure, the LuEM may be contained at a concentration of 0.01 mg/ml to 10 mg/mL, specifically from 0.5 mg/ml to 9 mg/mL, more specifically, from 1 mg/ml to 8 mg/ml, and most specifically, 1 mg/ml, 3 mg/ml, 5 mg/ml or 7 mg/ml. In an optimized embodiment, the LuEM may be contained at a concentration of 7 mg/ml. The LuEM contained with a concentration out of the above-described range may make it impossible to achieve the intended effect of the present disclosure, or may be unsuitable for preparation or application.

In an embodiment of the present disclosure, the composition may have an elastic modulus of 1 Pa to 100 Pa at 0.1 Hz to 10 Hz. When the composition has an elastic modulus in the above-described range, a stable polymer network can be formed.

The scaffold composition includes a three-dimensional hydrogel prepared based on a lung tissue matrix composition obtained by decellularization, and can be effectively used for lung organoid culture.

The decellularized lung tissue contains actual tissue-specific extracellular matrix components and thus can provide the physical, mechanical and biochemical environment of the tissue, and is highly efficient in enhancing differentiation into lung tissue cells and tissue-specific functionality.

The term “organoid” refers to an ultraminiature body organ prepared in the form of an artificial organ by culturing cells derived from adult stem cells or pluripotent stem cells from tissues in a 3D form.

The organoid is a three-dimensional tissue analogue that contains organ-specific cells which originate from stem cells and self-organize (or self-pattern) in a similar manner to the in vivo condition. The organoid can be developed into a specific tissue by patterning a restricted element (for example, a growth factor).

The organoid can have the intrinsic physiological properties of the cells and can have an anatomical structure that mimics the original state of a cell mixture (including all remaining stem cells and the neighboring physiological niche as well as limited cell types). A three-dimensional culture method allows the organoid to be better arranged in terms of cell-to-cell functions, and to have an organ-like form with functionality and a tissue-specific function.

Another aspect of the present disclosure provides a method of preparing a scaffold composition, including: a process (a) of decellularizing an isolated lung tissue to prepare a decellularized lung tissue; a process (b) of drying the decellularized lung tissue to prepare a lung extracellular matrix (LuEM); and a process (c) of gelating the dried LuEM.

The process (a) is a process of preparing a decellularized lung tissue by decellularizing an isolated lung tissue.

In an embodiment of the present disclosure, the process (a) may further include a process of slicing the isolated lung tissue before decellularization. According to the present disclosure, the process of slicing the lung tissue before decellularization makes it possible to remove cells more efficiently and completely. The isolated lung tissue may be sliced into a known size by a known method (device).

In an embodiment of the present disclosure, the lung tissue may be stirred in a decellularization solution in the process (a).

The decellularization solution may include various components for removing cells from the lung tissue, and may include, for example, hypertonic saline, peracetic acid, TRITON X-100™, SDS or other detergent components. In an embodiment of the present disclosure, the decellularization solution may include 0.1% to 5% TRITON X-100™ and 0.01% to 0.5% ammonium hydroxide and more specifically 1% TRITON X-100™ and 0.1% ammonium hydroxide. By using the decellularization solution as described above, it is possible to perform decellularization under more mild conditions than conventional processes. Thus, it is possible to effectively remove DNA in the prepared scaffold and preserve various proteins in the lung tissue.

The stirring may be performed for 24 hours to 72 hours, more specifically 36 hours to 60 hours and most specifically 40 hours to 56 hours. The stirring may be performed for, for example, 48 hours. Through this stirring process (decellularization), 95% to 99.9%, more specifically 96% to 98% and most specifically 96.75% of lung tissue cells may be removed. When decellularization is performed for a period of time out of the above-described range, the quality of the prepared scaffold composition may be declined or the economic efficiency of the process may be decreased.

The process (b) is a process of preparing an LuEM by drying the decellularized lung tissue.

The decellularized lung tissue may be dried by a known method. The decellularized lung tissue may be naturally dried or lyophilized. After drying, the decellularized lung tissue may be exposed to ethylene oxide gas or supercritical carbon dioxide by electron beam or gamma radiation for sterilization.

In an embodiment of the present disclosure, the LuEM may be contained at a concentration of 0.01 mg/ml to 10 mg/mL, specifically from 0.5 mg/mL to 9 mg/mL, more specifically, from 1 mg/ml to 8 mg/mL, and most specifically, 1 mg/ml, 3 mg/mL, 5 mg/ml or 7 mg/ml after the process (b). In an optimized embodiment, the LuEM may be adjusted to be contained at a concentration of 7 mg/mL. The LuEM contained with a concentration out of the above-described range may make it impossible to achieve the intended effect of the present disclosure, or may be unsuitable for preparation or application.

The dried extracellular matrix may be comminuted by methods including tearing, milling, cutting, grinding and shearing. The comminuted extracellular matrix may be processed into a powder form by a method such as grinding or milling in a frozen or lyophilized state.

The process (c) is a process of gelating the dried LuEM.

Through the gelation, the LuEM may be crosslinked to prepare a three-dimensional hydrogel-type scaffold, and the gelated scaffold can be used in various ways in the fields related to tests, screening and organoid culture.

The term “hydrogel” is a material in which a liquid that contains water as a dispersion medium is hardened through a sol-gel phase transition to lose fluidity and to form a porous structure. The hydrogel can be formed by causing a hydrophilic polymer that has a three-dimensional network structure and a microcrystalline structure to contain water and to be expanded.

The gelation may be performed at a temperature of 37° C. for 30 minutes after dissolving the LuEM in an acidic solution with a protease such as pepsin or trypsin and setting a neutral pH in an electrolyte state of 1×PBS buffer by using 10×PBS and 1 M NaOH.

Yet another aspect of the present disclosure provides a method of culturing a lung organoid in the scaffold composition or in a scaffold composition prepared by the preparation method.

The conventional MATRIGEL®-based culture system is an extract derived from animal cancer tissue, has a large difference between the batches, cannot mimic the actual lung environment, and exhibits insufficient efficiency in differentiation or development into a lung organoid. The scaffold composition can create a lung tissue-like environment and thus is suitable for lung organoid culture.

The culture refers to a process of maintaining and growing cells under suitable conditions, and the suitable conditions may refer to, for example, the temperature, nutrient availability, atmospheric $CO_2$ level and cell density at which the cells are maintained.

Appropriate culture conditions for maintaining, proliferating, expanding and differentiating different types of cells are known in the art and are documented. Suitable conditions for formation of the organoid may facilitate or allow cell differentiation and formation of a multicellular structure.

Effects of the Invention

With respect to an intestinal extracellular matrix-derived scaffold for culture and transplantation of an intestinal organoid and a method of preparing the same, a decellularized intestinal tissue-derived artificial scaffold developed in the present disclosure was developed as a new intestinal organoid culture scaffold that overcomes the limitations of MATRIGEL®, which is a representative conventional organoid culture scaffold, and is expected to be used as an elemental technology for various preclinical and clinical studies such as a large-scale drug screening platform based on intestinal organoids or cell therapeutic agent for tissue regeneration and to create high added value in industrial and economic terms and to promote the development of new medical industries.

The decellularized intestinal tissue-derived artificial matrix scaffold is expected to be widely used in various fields, such as disease modeling research that implements various intractable bowel diseases (inflammatory bowel disease, Crohn's disease, colorectal cancer, etc.) in vitro and reveals the mechanisms thereof, and establishment of a transplantation treatment platform. Since the prevalence of such intractable bowel diseases has increased significantly in recent years, a lot of research is needed. Therefore, the decellularized intestinal tissue-derived artificial matrix scaffold can create profits as a research reagent. Also, it is expected to have infinite applicability as it can be used for microbiome research, which has recently attracted a lot of interest in association with co-culture of an intestinal organoid and intestinal microorganisms in an intestinal tissue-specific extracellular matrix microenvironment but has been difficult to be practically researched.

The artificial scaffold developed in the present disclosure can be applied to the culture of human induced pluripotent stem cell- and embryonic stem cell-derived intestinal organoids and colorectal cancer-derived three-dimensional spheroids and thus can contribute to the construction of a disease model customized for intractable disease and cancer patient and can also be used as a precision medicine platform technology. Further, it is expected to create enormous added value in consideration of the size of the precision medicine market that has been rapidly increasing in recent years.

Overall, as described above, for the application of an intestinal organoid, a culture scaffold called MATRIGEL® is essentially required. Compared to MATRIGEL®, the artificial scaffold developed in the present disclosure is verified to have advantages in terms of safety and cost, showing better functionality as a culture system than MATRIGEL®. Unlike the conventional commercialized MATRIGEL® culture scaffold, it is possible to commercialize the artificial scaffold developed in the present disclosure at a GMP level at which transplantation into humans is possible. Therefore, it is expected to replace MATRIGEL® and create huge economic profits.

Also, with respect to a stomach extracellular matrix-derived scaffold for culture and transplantation of a gastric organoid and a method of preparing the same, a decellularized stomach tissue-derived artificial scaffold developed in the present disclosure was developed as a new gastric organoid culture scaffold that overcomes the limitations of MATRIGEL®, which is a representative conventional organoid culture scaffold, and is expected to be used as an elemental technology for various preclinical and clinical studies such as a large-scale drug screening platform based on gastric organoids or cell therapeutic agent for tissue regeneration and to create high added value in industrial and economic terms and to promote the development of new medical industries.

The decellularized stomach tissue-derived artificial matrix scaffold is expected to be widely used in various fields, such as disease modeling research that implements various intractable stomach diseases (gastric ulcer, gastric cancer, etc.) in vitro and reveals the mechanisms thereof, and establishment of a treatment platform for transplantation. Since the prevalence of such intractable stomach diseases has increased significantly in recent years, a lot of research is needed. Therefore, the decellularized stomach tissue-derived artificial matrix scaffold can create profits as a research reagent. Also, it is expected to have infinite applicability as it can be used for basic research, which has recently attracted a lot of interest in association with co-culture of a gastric organoid and *bacillus* (e.g., *Helicobacter pylori*) in a stomach tissue-specific extracellular matrix microenvironment but has been difficult to be practically researched.

The artificial scaffold developed in the present disclosure can be applied to the culture of tissue stem cell-derived gastric organoids and gastric cancer-derived organoids and thus can contribute to the construction of a disease model customized for intractable disease and cancer patient and can also be used as a precision medicine platform technology. Further, it is expected to create enormous added value in consideration of the size of the precision medicine market that has been rapidly increasing in recent years.

Overall, as described above, for the application of a gastric organoid, a culture scaffold called MATRIGEL® is essentially required. Compared to MATRIGEL®, the artificial scaffold developed in the present disclosure is verified to have advantages in terms of safety and cost, showing better functionality as a culture system than MATRIGEL®. Therefore, it is expected to replace MATRIGEL® and create huge economic profits.

With respect to a liver extracellular matrix-derived scaffold for culture and transplantation of liver organoids and a method of preparing the same, a decellularized liver tissue-derived artificial scaffold developed in the present disclosure was developed as a new liver organoid culture scaffold that overcomes the limitations of MATRIGEL®, which is a representative conventional organoid culture scaffold, and is expected to be used as an elemental technology for various preclinical and clinical studies such as a large-scale drug screening platform based on liver organoids or cell therapeutic agent for tissue regeneration and to create high added value in industrial and economic terms and to promote the development of new medical industries.

By using the decellularized liver tissue-derived scaffold developed in the present disclosure, it is possible to produce an advanced liver organoid compared to that of conventional culture methods. Therefore, it can be used as a more economical and more accurate platform than conventional in vitro models for drug testing. Liver toxicity is an important indicator that must be analyzed for new drug development and drug evaluation. Thus, an advanced liver organoid-based in vitro model platform can greatly increase the success rate of new drug development and significantly reduce costs and time. Therefore, it is expected to greatly contribute to the advancement of the medical industry.

The decellularized liver tissue-derived artificial matrix scaffold is expected to be widely used in various fields, such as disease modeling research that implements various intractable liver diseases (hepatocirrhosis, liver fibrosis, non-alcoholic hepatitis, etc.) in vitro and reveals the mechanisms thereof, and establishment of a transplantation treatment platform. Since the prevalence of such intractable liver diseases has increased significantly in recent years, a lot of research is needed. Therefore, the decellularized liver tissue-derived artificial matrix scaffold can create profits as a research reagent.

The artificial scaffold developed in the present disclosure can be applied to evaluation. Thus, of tissue stem cell-derived liver organoids and liver cancer organoids and thus can contribute to the construction of a disease model customized for intractable disease and cancer patient and can also be used as a precision medicine platform technology. Further, it is expected to create enormous added value in consideration of the size of the precision medicine market that has been rapidly increasing in recent years.

Overall, as described above, for the application of a liver organoid, a culture scaffold called MATRIGEL® is essentially required. Compared to MATRIGEL®, the artificial scaffold developed in the present disclosure is verified to have advantages in terms of safety and cost, showing better functionality as a culture system than MATRIGEL®. Therefore, it is expected to replace MATRIGEL® and create huge economic profits.

With respect to a lung extracellular matrix-derived scaffold for culture and transplantation of a lung organoid and a method of preparing the same, a decellularized lung tissue-derived artificial scaffold developed in the present disclosure was developed as a new lung organoid culture scaffold that overcomes the limitations of MATRIGEL®, which is a representative conventional organoid culture scaffold, and is expected to be used as an elemental technology for various preclinical and clinical studies such as a large-scale drug screening platform based on lung organoids or cell therapeutic agent for tissue regeneration and to create high added value in industrial and economic terms and to promote the development of new medical industries.

Since the lung organoid constructed in the present disclosure can structurally and functionally mimic the lung tissue with high precision, it can be used for production of various lung disease models that are currently difficult to implement. Currently, particulate matter from air pollution caused by industrialization and urbanization is emerging as a serious social problem, but its harmful effects on the human body have not yet been clearly identified and there is no proper model to study them. Also, there is a need to produce models for various intractable lung diseases such as cystic fibrosis, idiopathic pulmonary fibrosis, chronic obstructive pulmonary disease, etc. The mature lung organoid culture technology established through the present disclosure is expected to further facilitate the production of such lung disease models and to be used to study the mechanisms of lung diseases, which greatly contributes to medical research.

The decellularized scaffold developed in the present disclosure can be applied to culture of tissue stem cell-derived lung organoids and lung cancer-derived organoids and thus can contribute to the construction of a disease model customized for intractable disease and cancer patient and can also be used as a precision medicine platform technology. Further, it is expected to create enormous added value in consideration of the size of the precision medicine market that has been rapidly increasing in recent years.

For the application of a lung organoid, MATRIGEL® as a culture scaffold is essentially required. Compared to MATRIGEL® having various problems, the decellularized scaffold developed in the present disclosure is verified to have advantages in terms of safety and cost, showing better functionality as a culture system than MATRIGEL®. Therefore, it is expected to replace MATRIGEL® and create huge economic profits.

BRIEF DESCRIPTION OF THE DRAWINGS

FIG. 3D shows the analysis of the components of the decellularized intestinal tissue-derived artificial scaffold.

FIG. 8A shows the comparative analysis of the proteome of the scaffold composition of the present disclosure and the conventional culture scaffold (MATRIGEL®).

FIG. 8B shows the comparative analysis of the proteome of the scaffold composition of the present disclosure and the conventional culture scaffold (MATRIGEL®).

FIG. 9A shows the comparative analysis of the proteome of the scaffold composition of the present disclosure and the conventional culture scaffold (MATRIGEL®).

FIG. 37 shows the proteomic analysis of the SEM.

FIG. 38A shows the types of matrisome proteins in the SEM and the result of quantitative analysis.

FIG. 52A shows the long-term culture of a gastric organoid using the decellularized stomach tissue-derived hydrogel scaffold.

FIG. 52B shows the long-term culture of a gastric organoid using the decellularized stomach tissue-derived hydrogel scaffold.

FIG. 52C shows the long-term culture of a gastric organoid using the decellularized stomach tissue-derived hydrogel scaffold.

FIG. 53A shows the analysis of the transcriptome expression of a gastric organoid cultured using the decellularized stomach tissue-derived hydrogel scaffold.

FIG. 53B shows the analysis of the transcriptome expression of a gastric organoid cultured using the decellularized stomach tissue-derived hydrogel scaffold.

FIG. 53C shows the analysis of the transcriptome expression of a gastric organoid cultured using the decellularized stomach tissue-derived hydrogel scaffold.

FIG. 54A shows the analysis of the transcriptome expression of a gastric organoid cultured using the decellularized stomach tissue-derived hydrogel scaffold.

FIG. 54B shows the analysis of the transcriptome expression of a gastric organoid cultured using the decellularized stomach tissue-derived hydrogel scaffold.

FIG. 55A shows the in vivo transplantation of a gastric organoid using the decellularized stomach tissue-derived hydrogel scaffold.

FIG. 55B shows the in vivo transplantation of a gastric organoid using the decellularized stomach tissue-derived hydrogel scaffold.

FIG. 55C shows the in vivo transplantation of a gastric organoid using the decellularized stomach tissue-derived hydrogel scaffold.

Figure 56A:
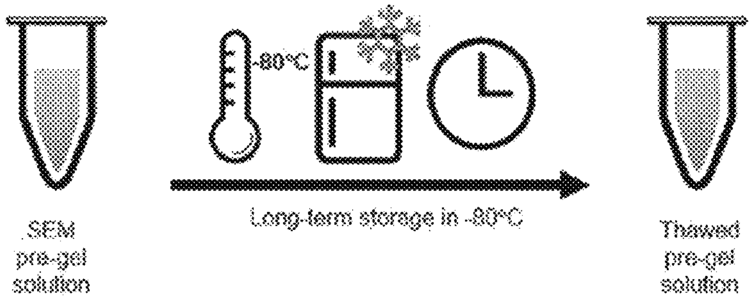

FIG. 56A verifies the possibility of long-term storage of a decellularized stomach tissue-derived hydrogel.

Figure 56B:
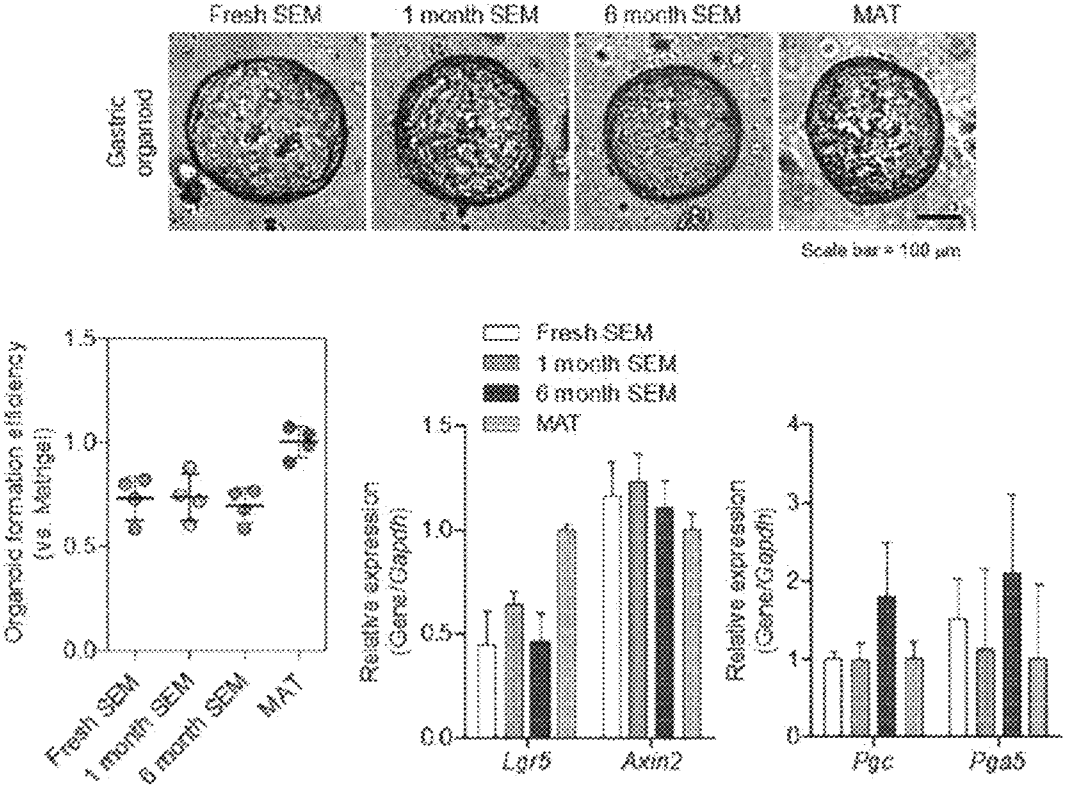

FIG. 56B verifies the possibility of long-term storage of a decellularized stomach tissue-derived hydrogel.

Figure 57A:
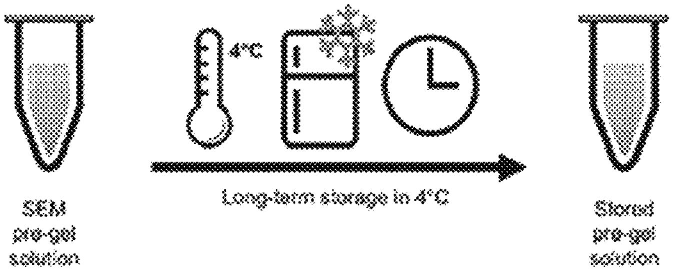

FIG. 57A verifies the possibility of long-term storage of a decellularized stomach tissue-derived hydrogel.

Figure 57B:
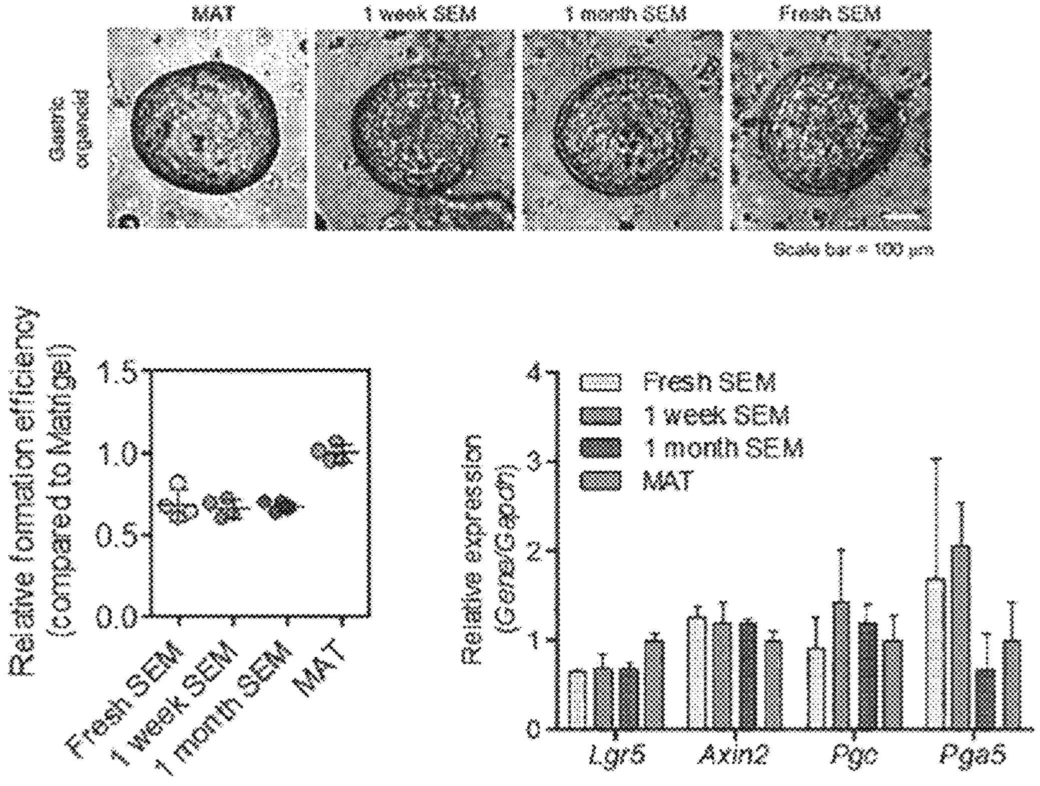

FIG. 57B verifies the possibility of long-term storage of a decellularized stomach tissue-derived hydrogel.

Figure 58:
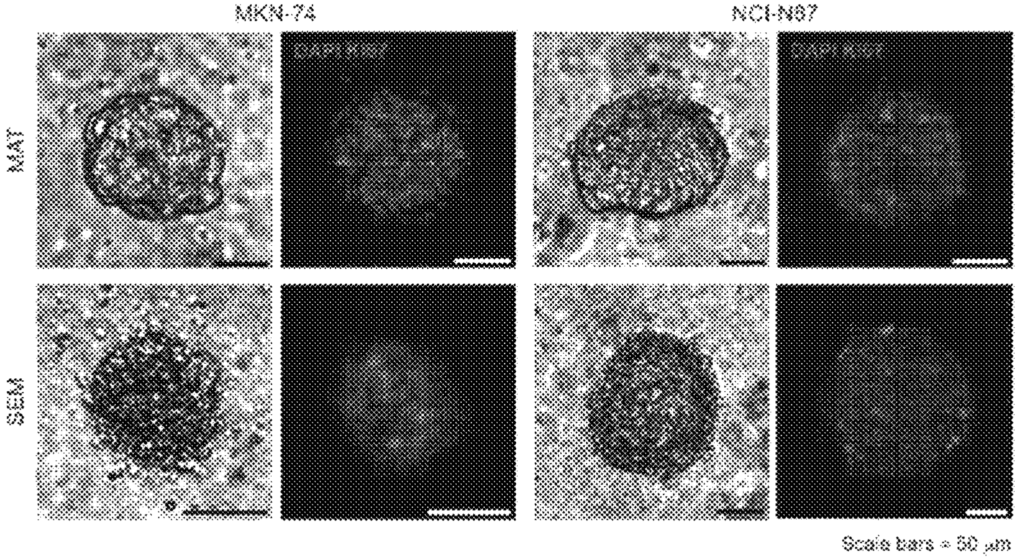

FIG. 58 shows the culture of a gastric cancer organoid using the decellularized stomach tissue-derived hydrogel scaffold.

Figure 59A:
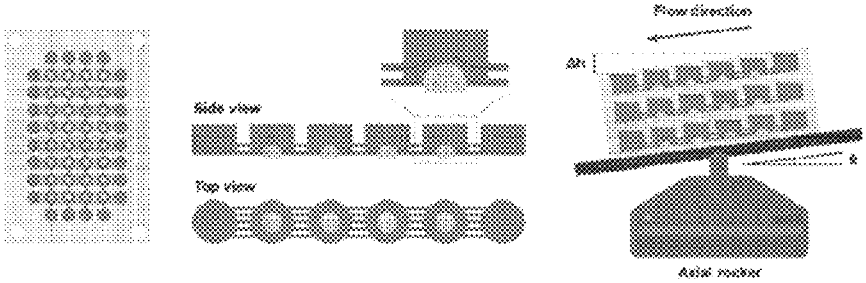

FIG. 59A shows the result confirming the possibility of mass culture of gastric organoids using a microfluidic device and the decellularized stomach tissue-derived hydrogel.

Figure 59B:
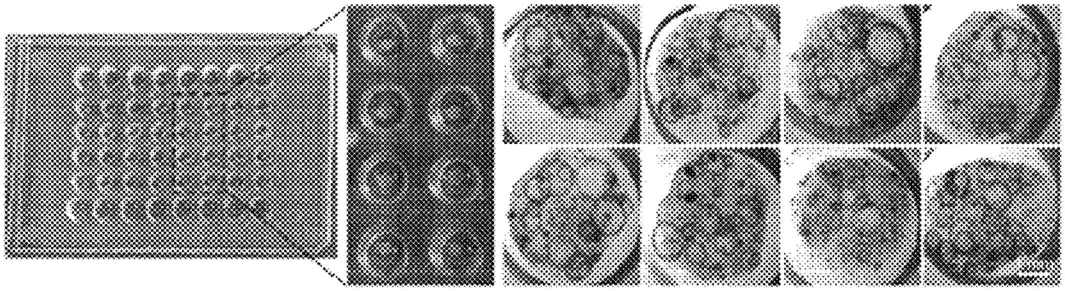

FIG. 59B shows the result confirming the possibility of mass culture of gastric organoids using a microfluidic device and the decellularized stomach tissue-derived hydrogel.

Figure 60A:
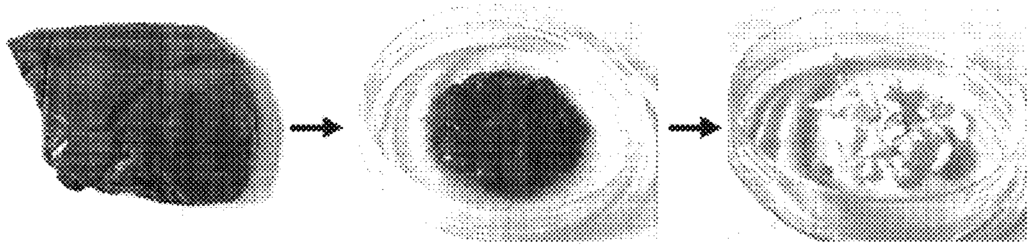

FIG. 60A shows the fabrication of a liver extracellular matrix (LEM) for liver organoid culture.

Figure 60B:
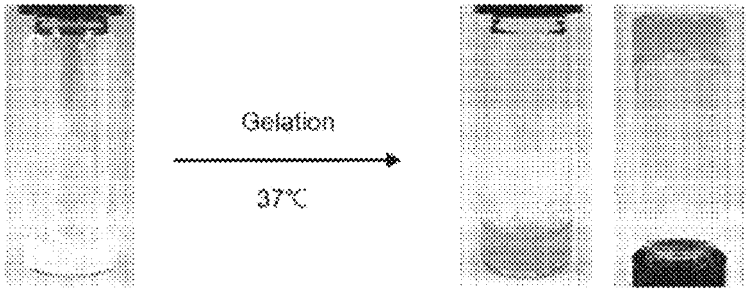

FIG. 60B shows the fabrication of a liver extracellular matrix (LEM) for liver organoid culture.

Figure 61A:
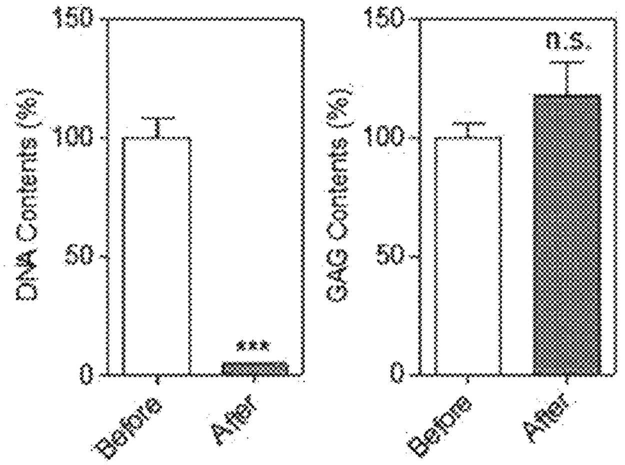

FIG. 61A shows the analysis of the LEM for liver organoid culture.

Figure 61B:
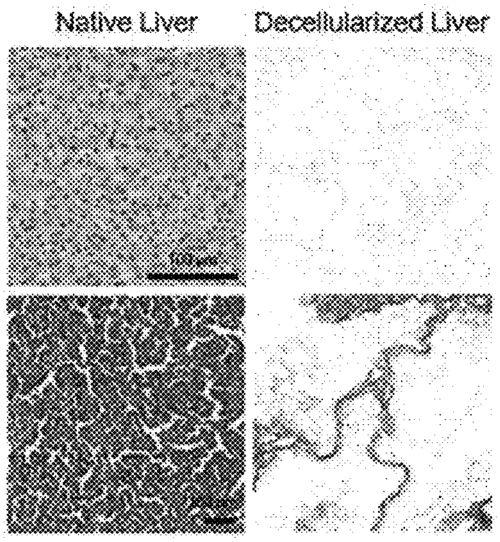

FIG. 61B shows the analysis of the LEM for liver organoid culture.

Figure 61C:
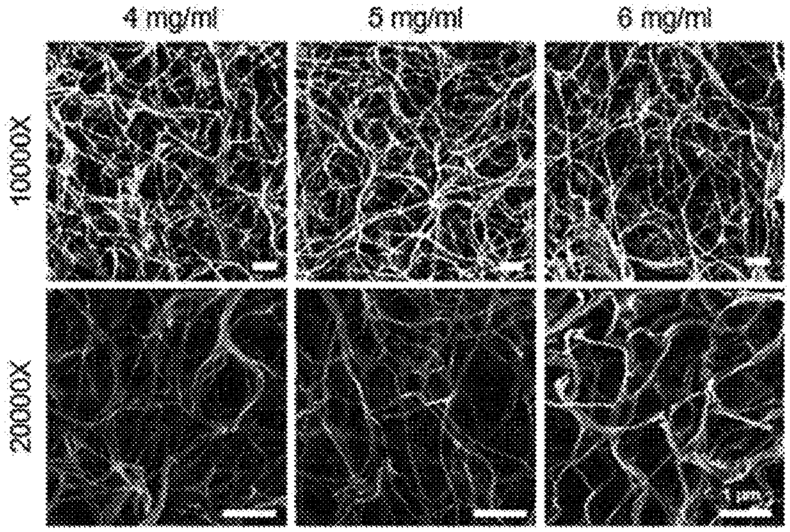

FIG. 61C shows the analysis of the LEM for liver organoid culture.

Figure 62:
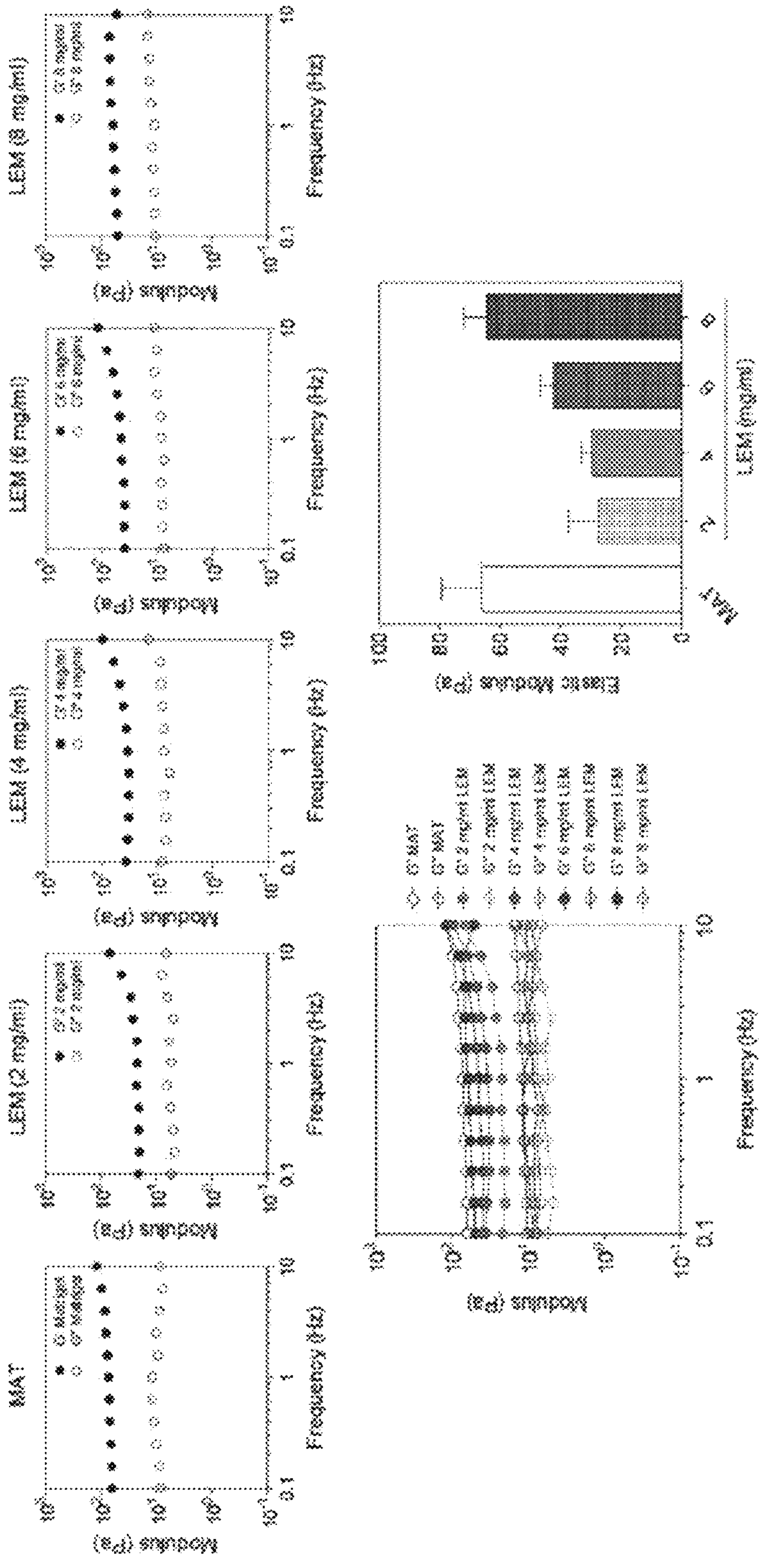

FIG. 62 shows the analysis of mechanical properties of the LEM depending on concentration.

Figure 63:
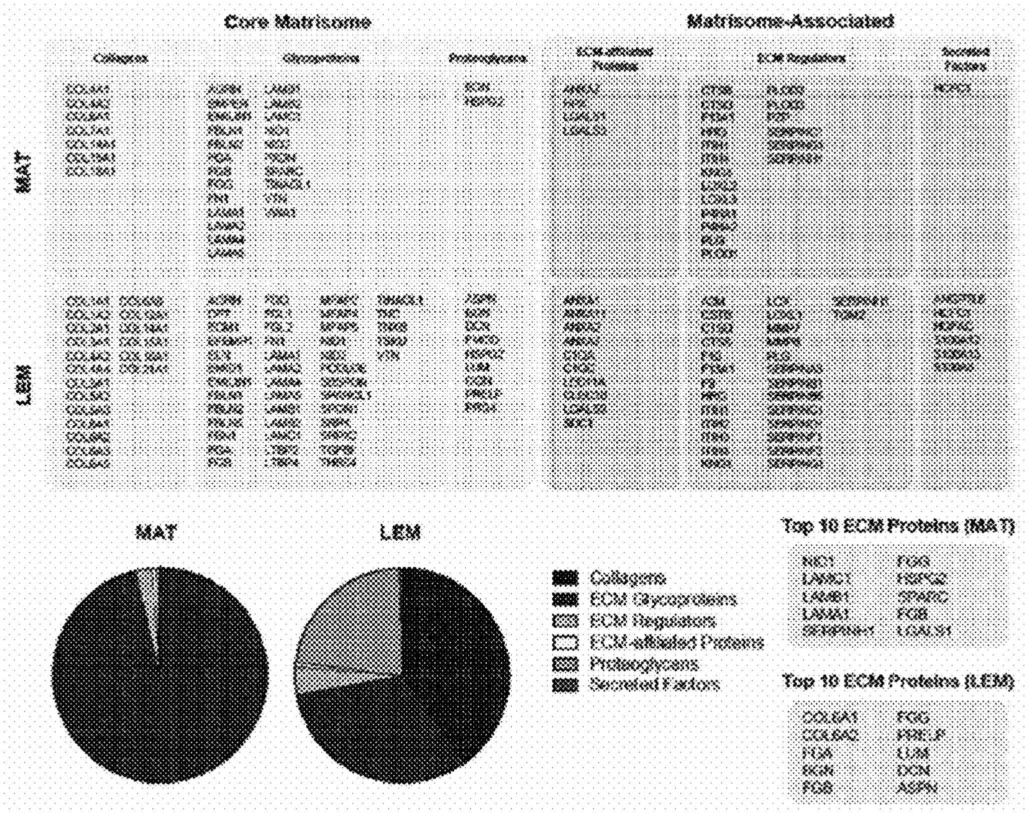

FIG. 63 shows the proteomic analysis of the LEM.

FIG. 64A shows the analysis of proteome from the LEM.

Figure 64B:
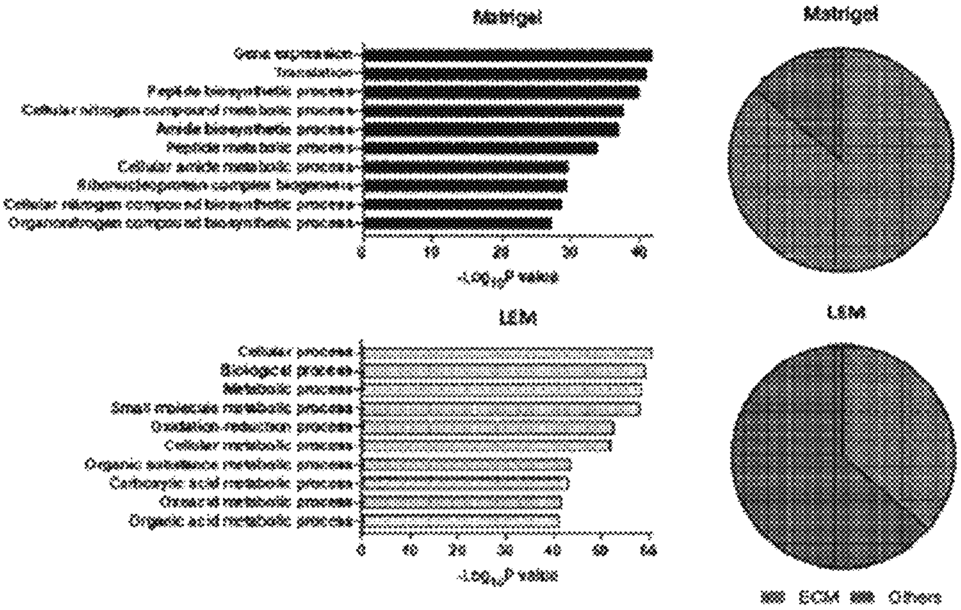

FIG. 64B shows the analysis of proteome from the LEM.

Figure 65A:
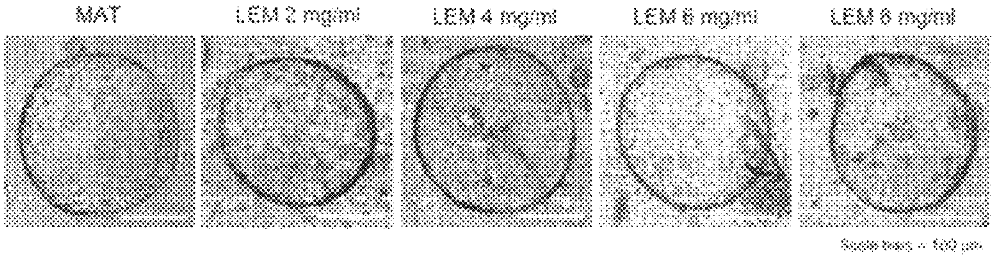

FIG. 65A shows the optimization of liver organoid (cholangiocyte-derived liver organoid (CLO)) culture depending on the concentration of a decellularized liver tissue-derived hydrogel scaffold.

Figure 65B:
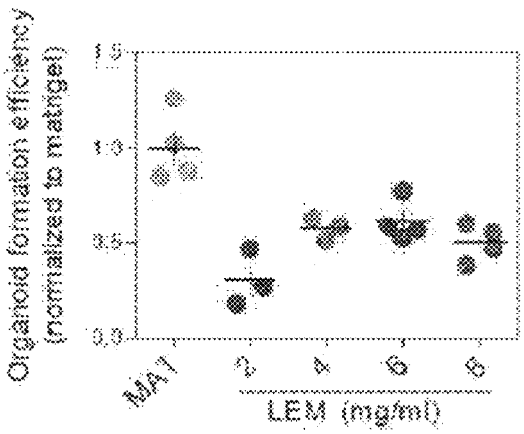

FIG. 65B shows the culture and concentration selection of a liver organoid (cholangiocyte-derived liver organoid (CLO)) depending on the concentration of a decellularized liver tissue-derived hydrogel scaffold.

Figure 66:
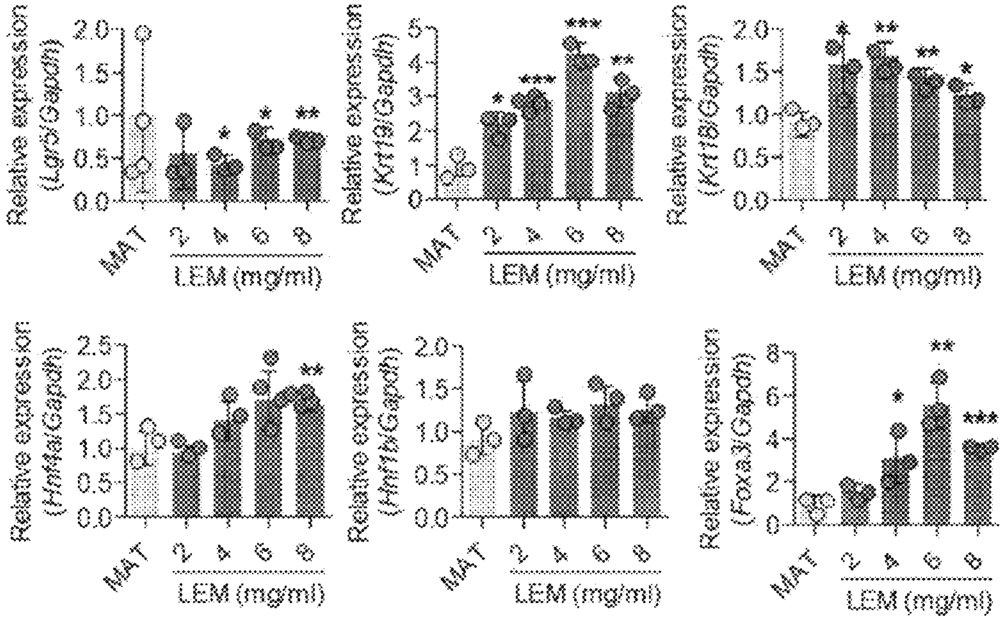

FIG. 66 shows the analysis of the difference in differentiation ability of the liver organoid (cholangiocyte-derived liver organoid (CLO)) depending on the LEM concentration of a decellularized liver tissue-derived hydrogel scaffold.

Figure 67:
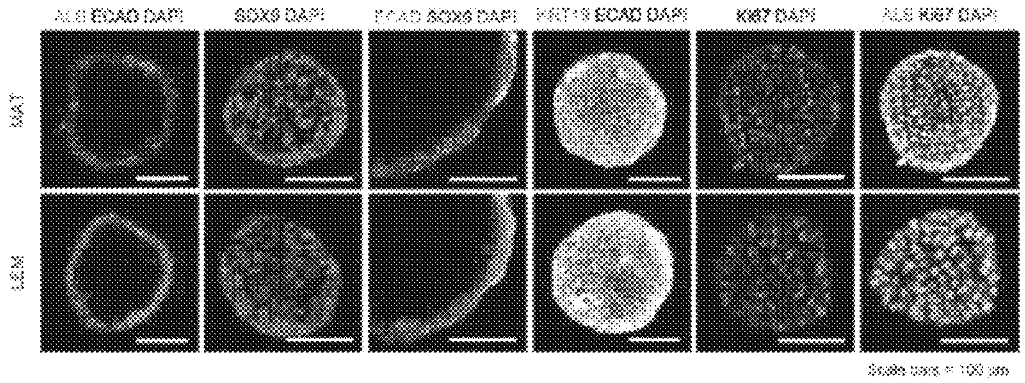

FIG. 67 shows the analysis of the liver organoid (cholangiocyte-derived liver organoid (CLO)) cultured in the decellularized liver tissue-derived hydrogel scaffold.

Figure 68A:
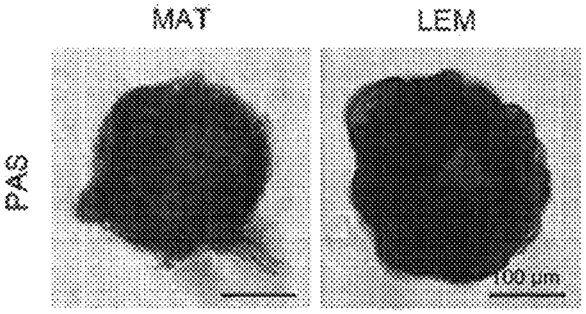

FIG. 68A shows the analysis of the functionality of the liver organoid (cholangiocyte-derived liver organoid (CLO)) cultured in the decellularized liver tissue-derived hydrogel scaffold.

Figure 68B:
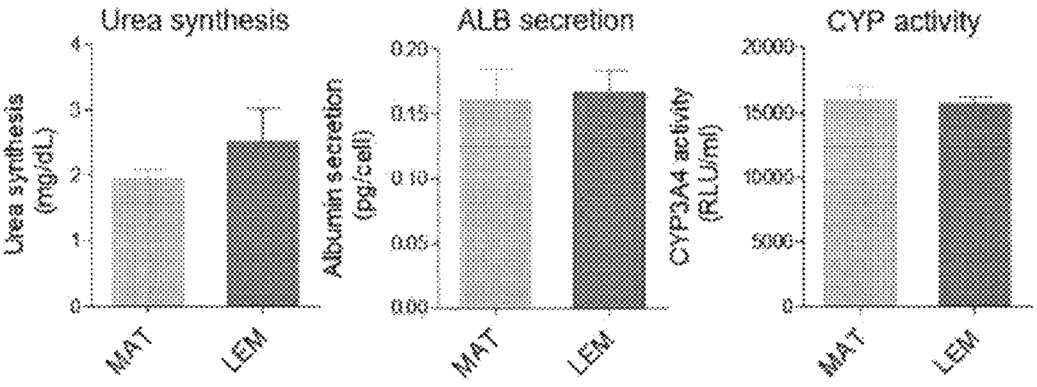

FIG. 68B shows the analysis of the functionality of the liver organoid (cholangiocyte-derived liver organoid (CLO)) cultured in the decellularized liver tissue-derived hydrogel scaffold.

Figure 69A:
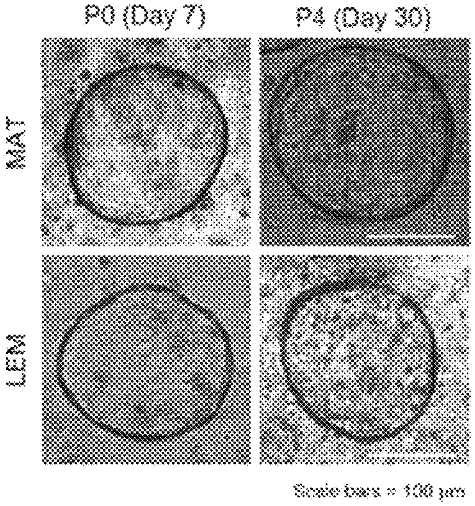

FIG. 69A shows the long-term culture of the liver organoid (cholangiocyte-derived liver organoid (CLO)) using the decellularized liver tissue-derived hydrogel scaffold.

Figure 69B:
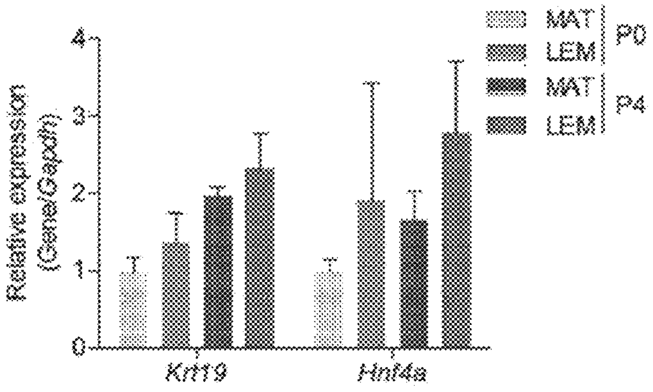

FIG. 69B shows the long-term culture of the liver organoid (cholangiocyte-derived liver organoid (CLO)) using the decellularized liver tissue-derived hydrogel scaffold.

Figure 70A:
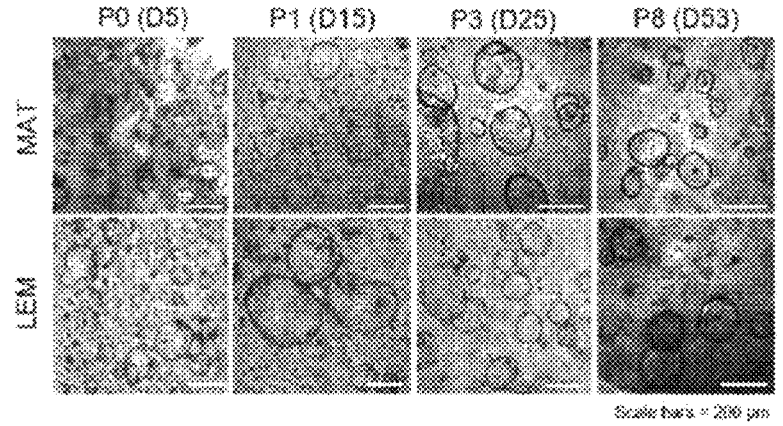

FIG. 70A shows the culture of a human liver organoid (human cholangiocyte-derived liver organoid (hCLO))

using the decellularized liver tissue-derived hydrogel scaffold and the analysis thereon.

Figure 70B:
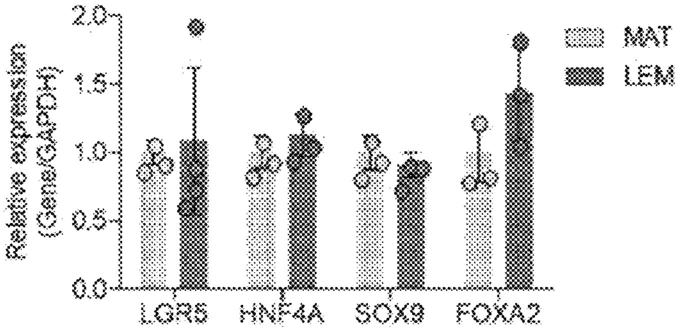

FIG. 70B shows the culture of a human liver organoid (human cholangiocyte-derived liver organoid (hCLO)) using the decellularized liver tissue-derived hydrogel scaffold and the analysis thereon.

Figure 71:
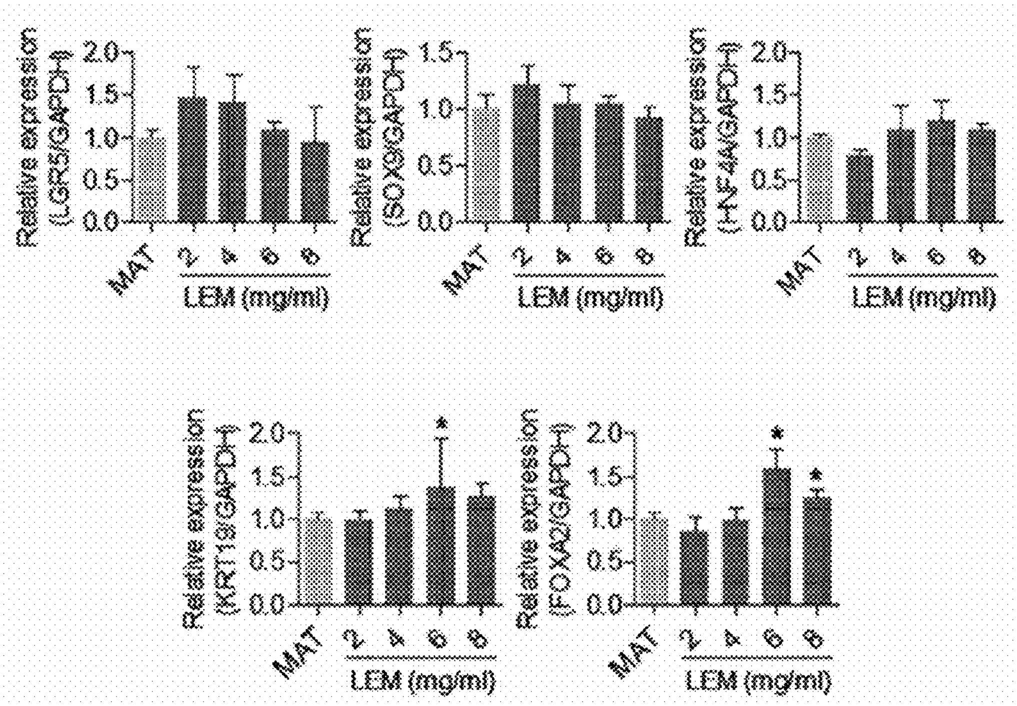

FIG. 71 shows the culture of a human liver organoid (human cholangiocyte-derived liver organoid (hCLO)) using the decellularized liver tissue-derived hydrogel scaffold and the analysis thereon.

Figure 72A:
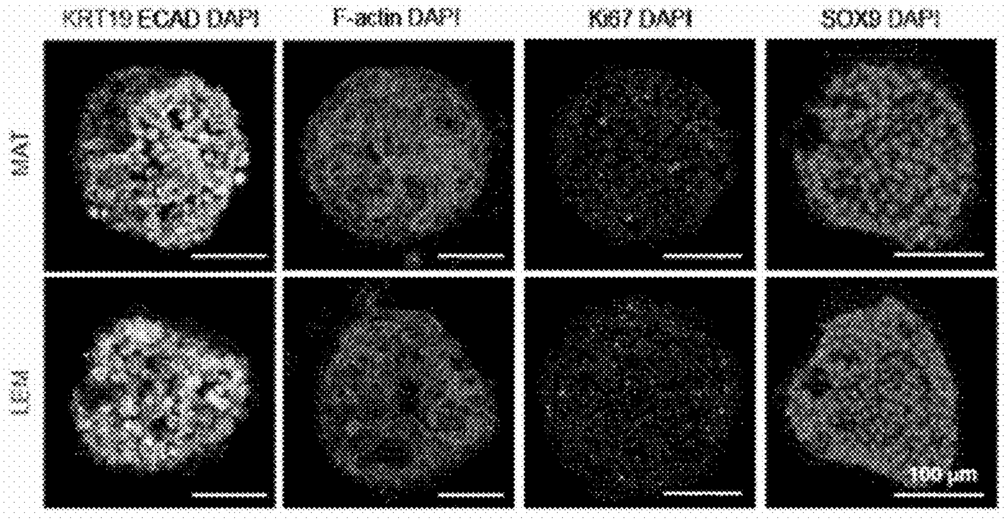

FIG. 72A shows the culture of a human liver organoid (human cholangiocyte-derived liver organoid (hCLO)) using the decellularized liver tissue-derived hydrogel scaffold and the analysis thereon.

Figure 72B:
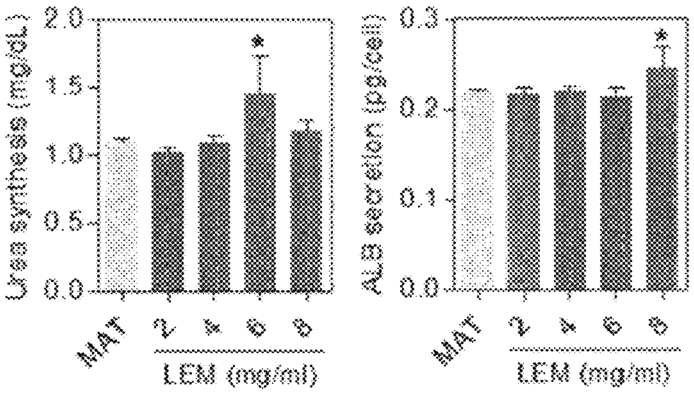

FIG. 72B shows the culture of a human liver organoid (human cholangiocyte-derived liver organoid (hCLO)) using the decellularized liver tissue-derived hydrogel scaffold and the analysis thereon.

Figure 73A:
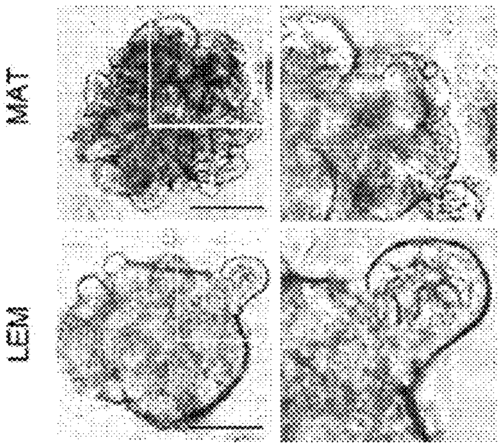

FIG. 73A shows the culture of a liver organoid (hepatocyte-derived liver organoid (HLO)) in different concentrations of the decellularized liver tissue-derived hydrogel scaffold and the determination of optimal concentration.

Figure 73B:
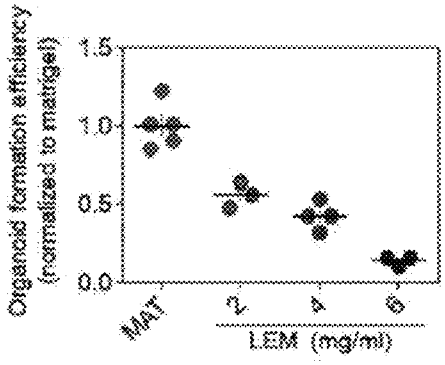

FIG. 73B shows the culture of a liver organoid (hepatocyte-derived liver organoid (HLO)) in different concentrations of the decellularized liver tissue-derived hydrogel scaffold and the selection of optimal concentration.

Figure 73C:
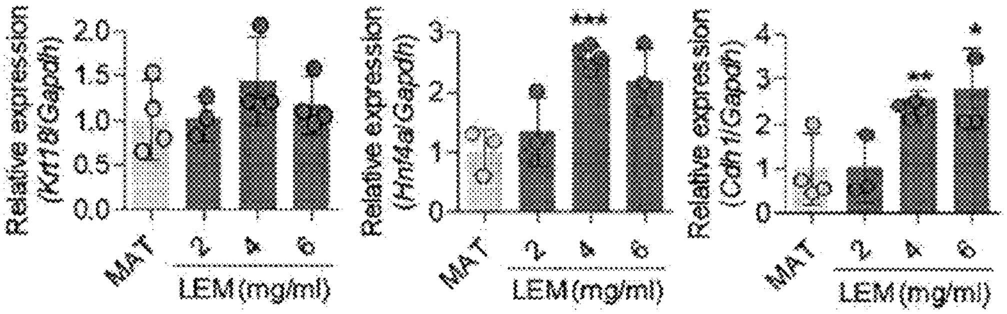

FIG. 73C shows the culture of a liver organoid (hepatocyte-derived liver organoid (HLO)) in different concentrations of the decellularized liver tissue-derived hydrogel scaffold and the selection of optimal concentration.

Figure 74:
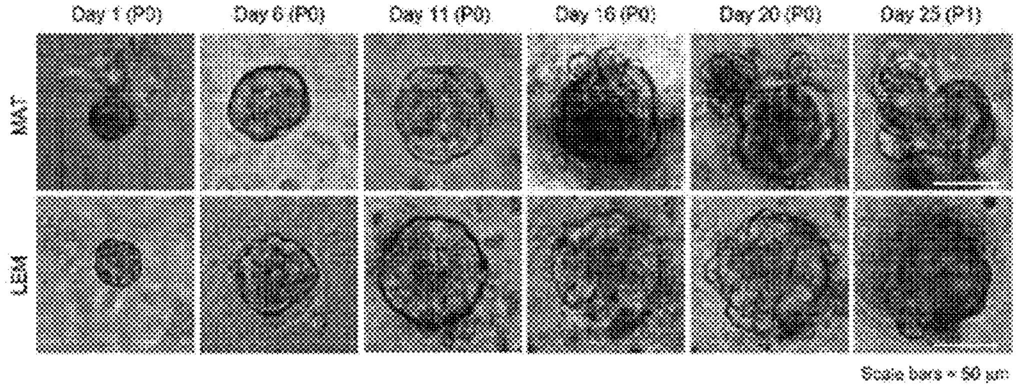

FIG. 74 compares the growth of liver organoids (HLO) formed in the decellularized liver tissue-derived hydrogel scaffold (LEM) and a conventional culture scaffold (MAT).

Figure 75A:
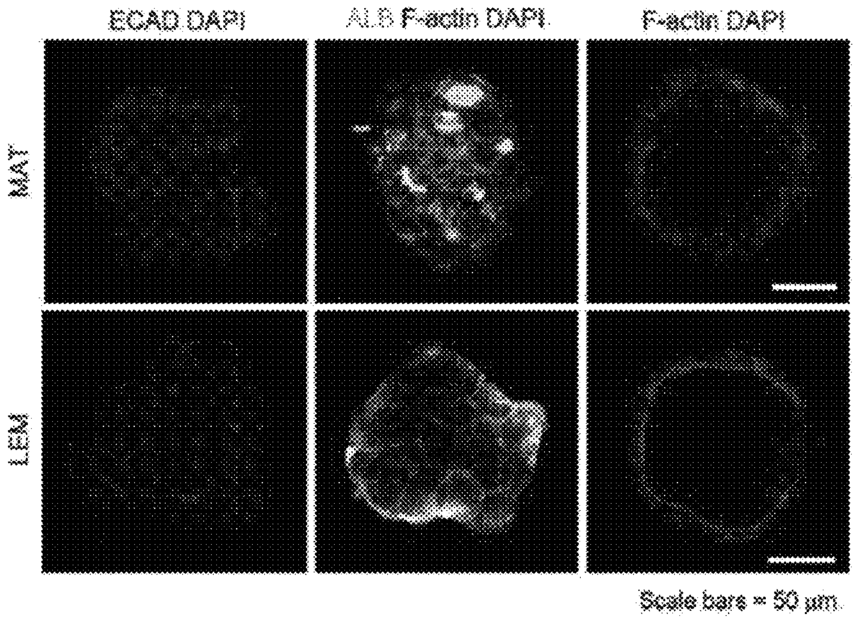

FIG. 75A shows the analysis of the hepatocyte-derived liver organoid (HLO) cultured in the decellularized liver tissue-derived hydrogel scaffold (LEM).

Figure 75B:
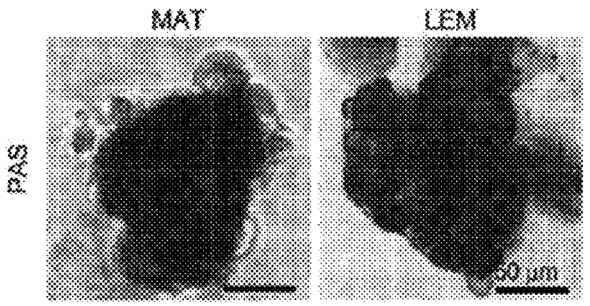

FIG. 75B shows the analysis of the hepatocyte-derived liver organoid (HLO) cultured in the decellularized liver tissue-derived hydrogel scaffold (LEM).

Figure 75C:
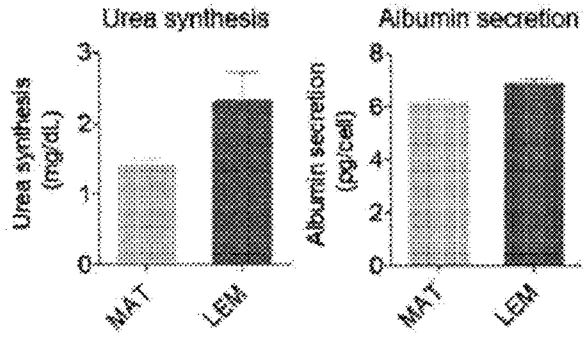

FIG. 75C shows the analysis of the hepatocyte-derived liver organoid (HLO) cultured in the decellularized liver tissue-derived hydrogel scaffold (LEM).

Figure 76A:
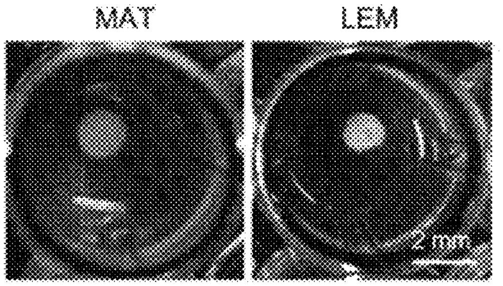

FIG. 76A shows the culture of a human induced pluripotent stem cell (hiPSC)-derived liver organoid using the decellularized liver tissue-derived hydrogel scaffold.

Figure 76B:
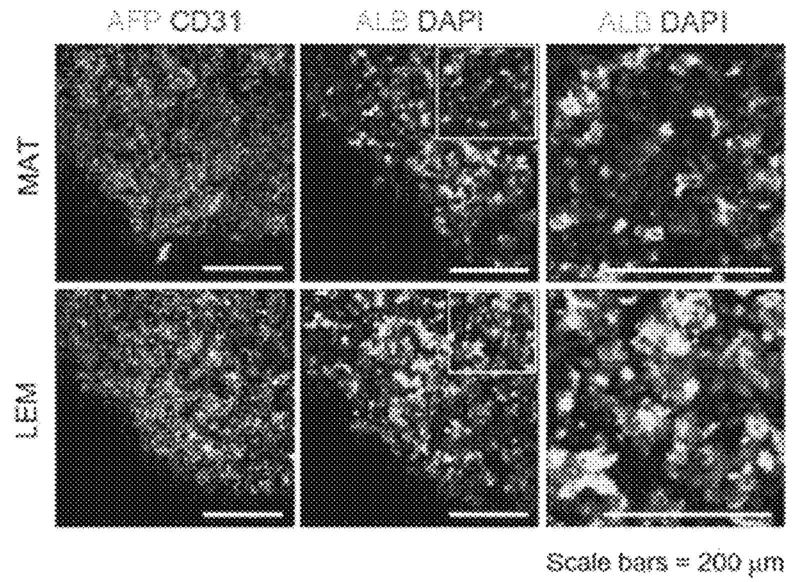

FIG. 76B shows the culture of a human induced pluripotent stem cell (hiPSC)-derived liver organoid using the decellularized liver tissue-derived hydrogel scaffold.

Figure 77A:
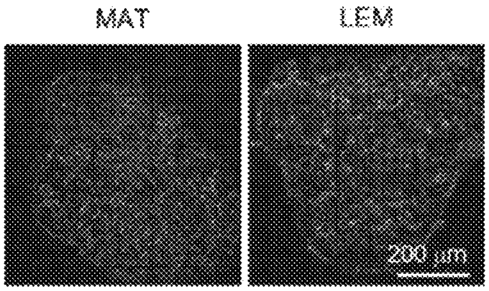

FIG. 77A shows the analysis of a human induced pluripotent stem cell-derived liver organoid (hiPSC-LO) cultured in the decellularized liver tissue-derived hydrogel scaffold.

Figure 77B:
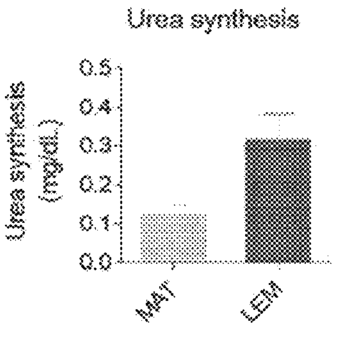

FIG. 77B shows the analysis of a human induced pluripotent stem cell-derived liver organoid (hiPSC-LO) cultured in the decellularized liver tissue-derived hydrogel scaffold.

Figure 77C:
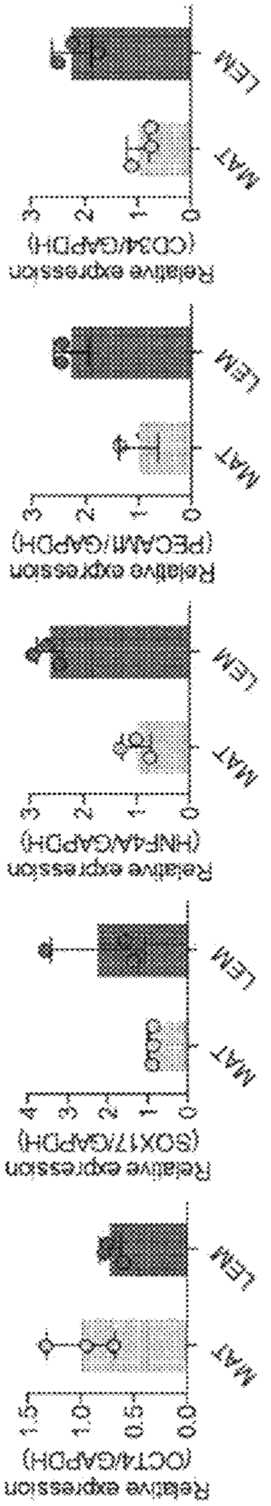

FIG. 77C shows the analysis of a human induced pluripotent stem cell-derived liver organoid (hiPSC-LO) cultured in the decellularized liver tissue-derived hydrogel scaffold.

Figure 78A:
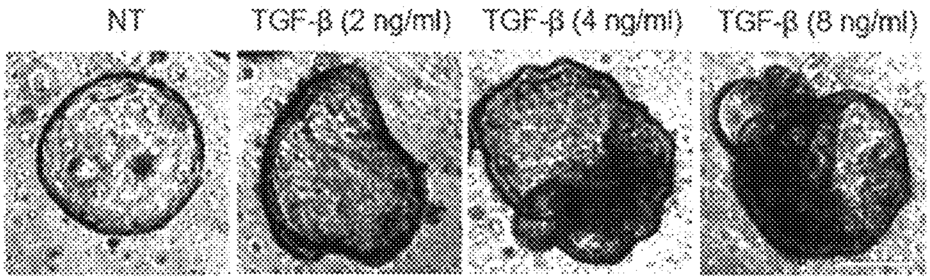

FIG. 78A shows the fabrication of a liver fibrosis model using a liver organoid (CLO) cultured in the decellularized liver tissue-derived hydrogel scaffold (LEM).

Figure 78B:
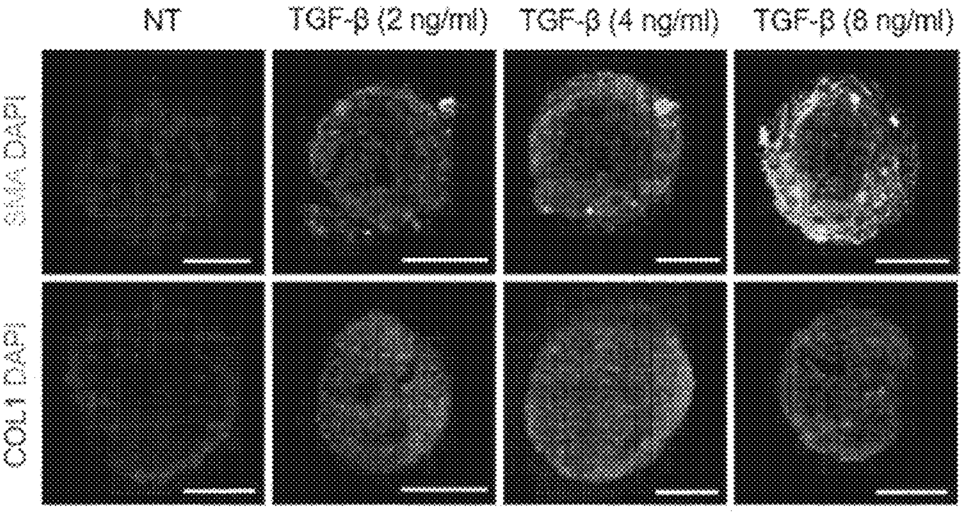

FIG. 78B shows the fabrication of a liver fibrosis model using a liver organoid (CLO) cultured in the decellularized liver tissue-derived hydrogel scaffold (LEM).

Figure 78C:
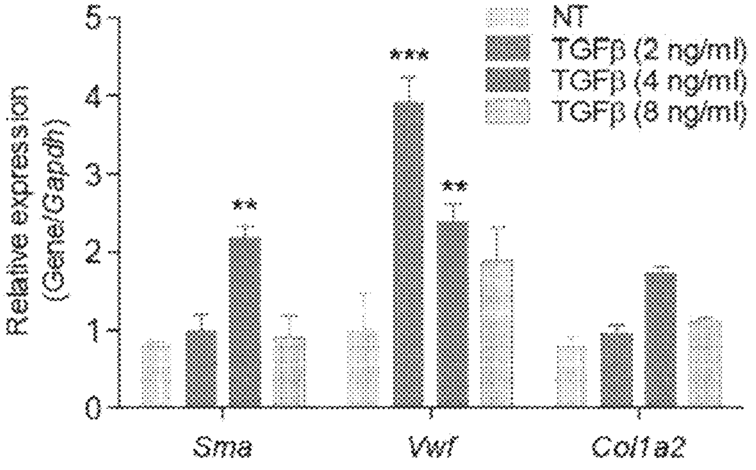

FIG. 78C shows the fabrication of a liver fibrosis model using a liver organoid (CLO) cultured in the decellularized liver tissue-derived hydrogel scaffold (LEM).

Figure 78D:
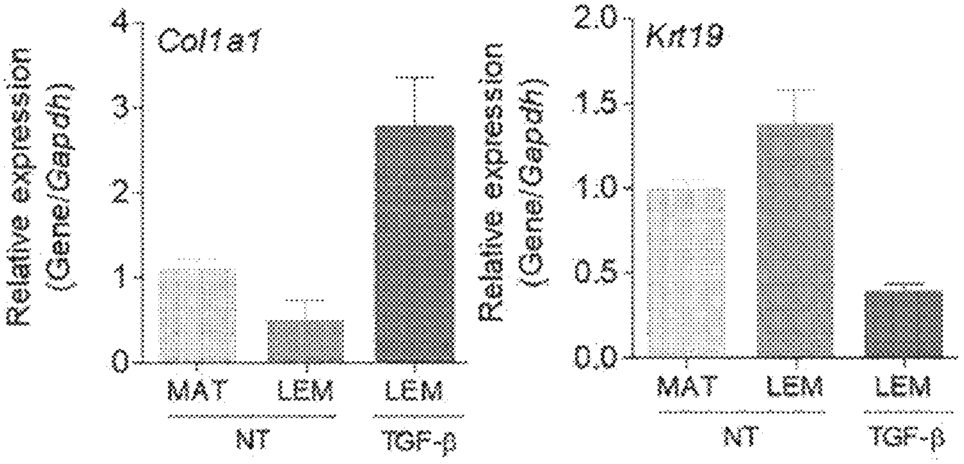

FIG. 78D shows the fabrication of a liver fibrosis model using a liver organoid (CLO) cultured in the decellularized liver tissue-derived hydrogel scaffold (LEM).

Figure 79A:
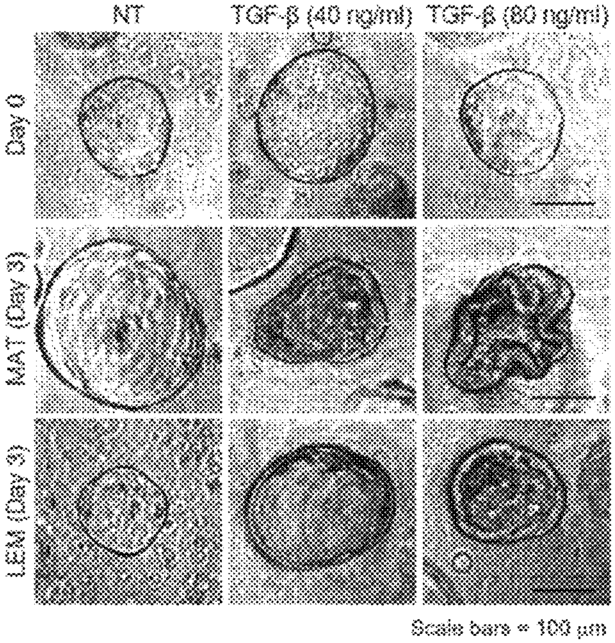

FIG. 79A shows the fabrication of a liver fibrosis model using a liver organoid (hCLO) cultured in the decellularized liver tissue-derived hydrogel scaffold.

Figure 79B:
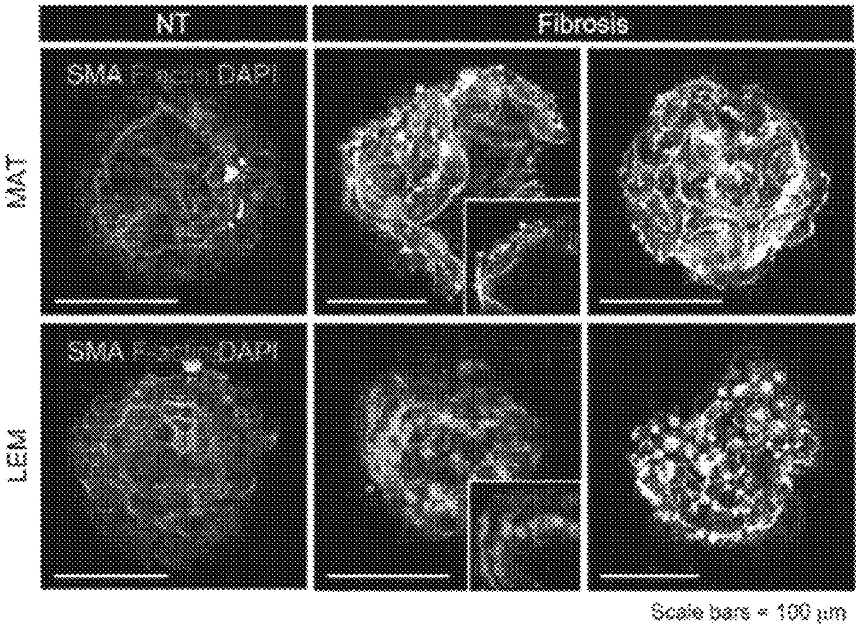

FIG. 79B shows the fabrication of a liver fibrosis model using a liver organoid (hCLO) cultured in the decellularized liver tissue-derived hydrogel scaffold.

Figure 80A:
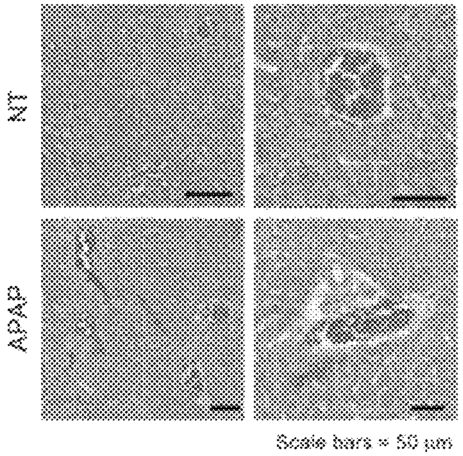

FIG. 80A shows the in vivo transplantation of the liver organoid using the decellularized liver tissue-derived hydrogel scaffold.

Figure 80B:
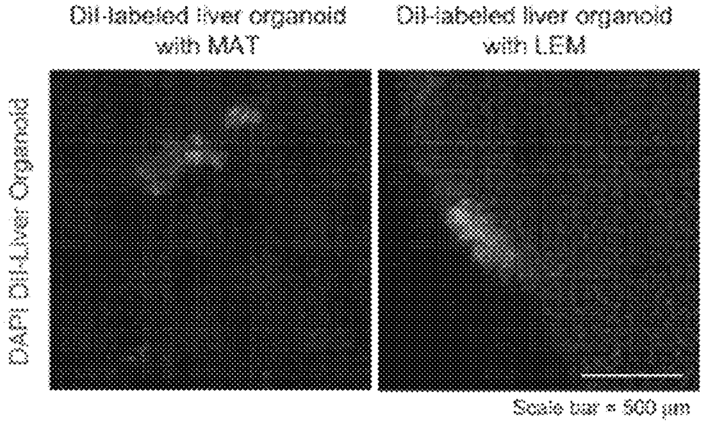

FIG. 80B shows the in vivo transplantation of the liver organoid using the decellularized liver tissue-derived hydrogel scaffold.

Figure 81A:
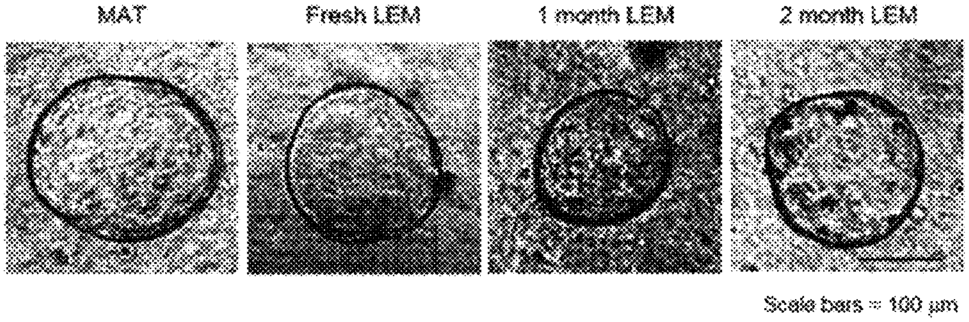

FIG. 81A verifies the possibility of long-term storage of a decellularized liver tissue-derived hydrogel.

Figure 81B:
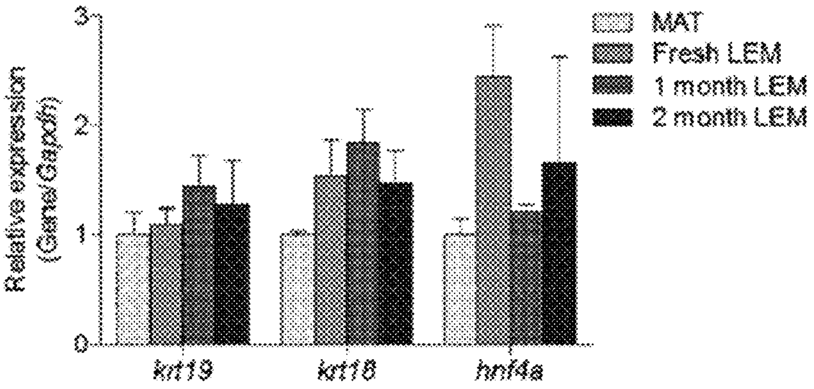

FIG. 81B verifies the possibility of long-term storage of a decellularized liver tissue-derived hydrogel.

Figure 82A:
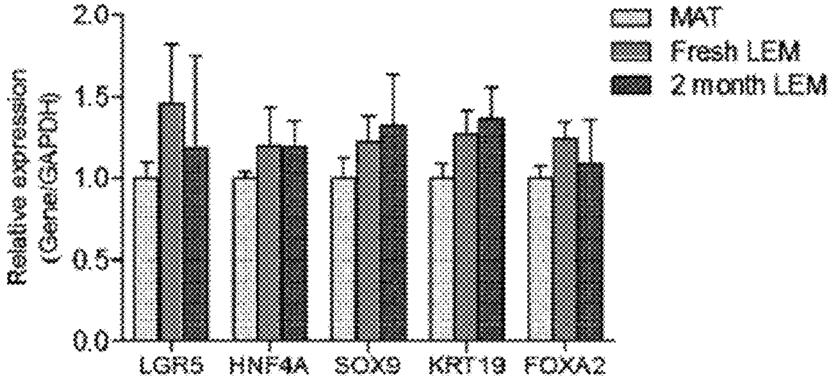

FIG. 82A verifies the possibility of long-term storage of a decellularized liver tissue-derived hydrogel.

Figure 82B:
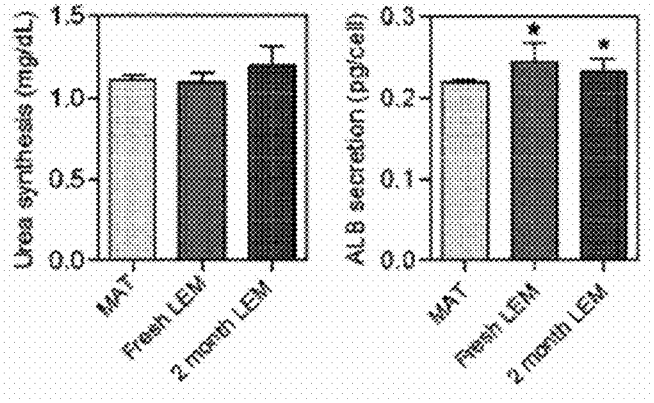

FIG. 82B verifies the possibility of long-term storage of a decellularized liver tissue-derived hydrogel.

Figure 83A:
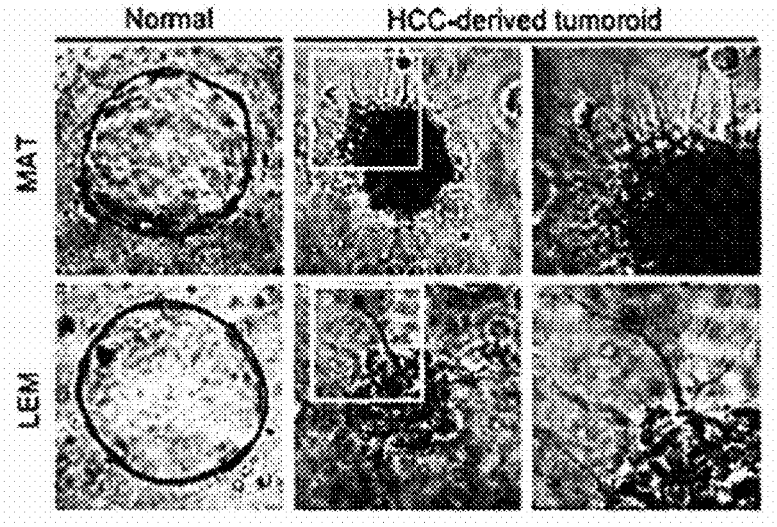

FIG. 83A shows the result of liver cancer organoid culture using the decellularized liver tissue-derived hydrogel scaffold.

Figure 83B:
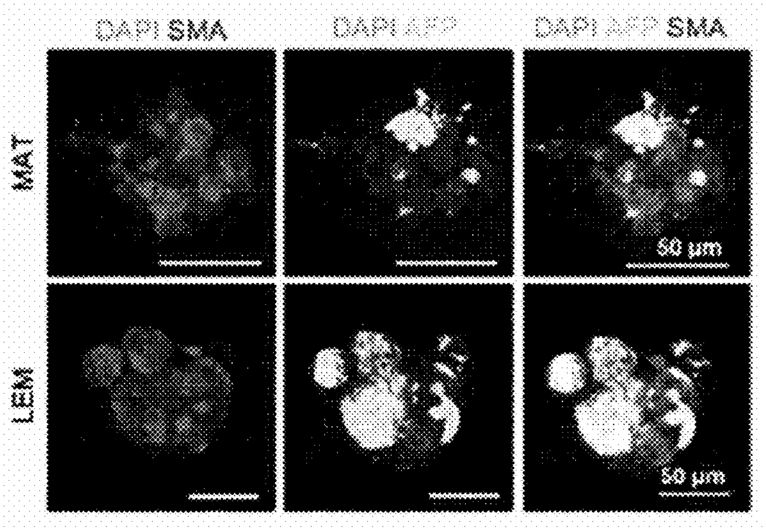

FIG. 83B shows the result of liver cancer organoid culture using the decellularized liver tissue-derived hydrogel scaffold.

Figure 83C:
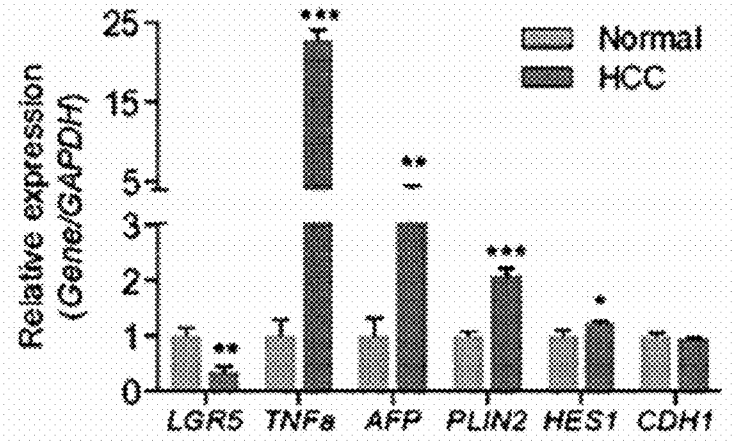

FIG. 83C shows the result of liver cancer organoid culture using the decellularized liver tissue-derived hydrogel scaffold.

Figure 84A:
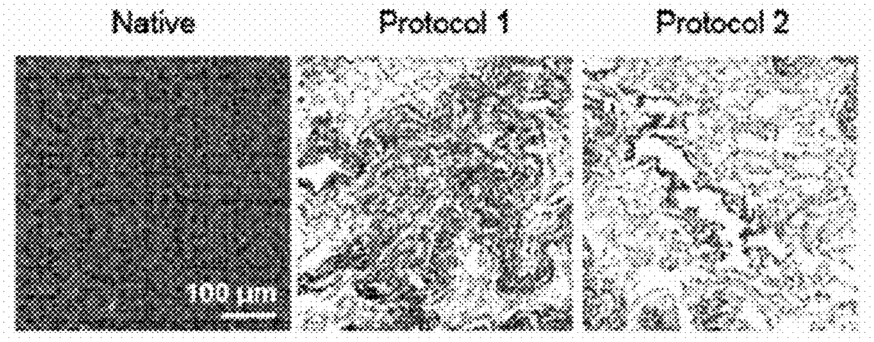

FIG. 84A shows the result of verification of the superiority of the LEM of the present disclosure through comparison of liver tissue decellularization protocol.

Figure 84B:
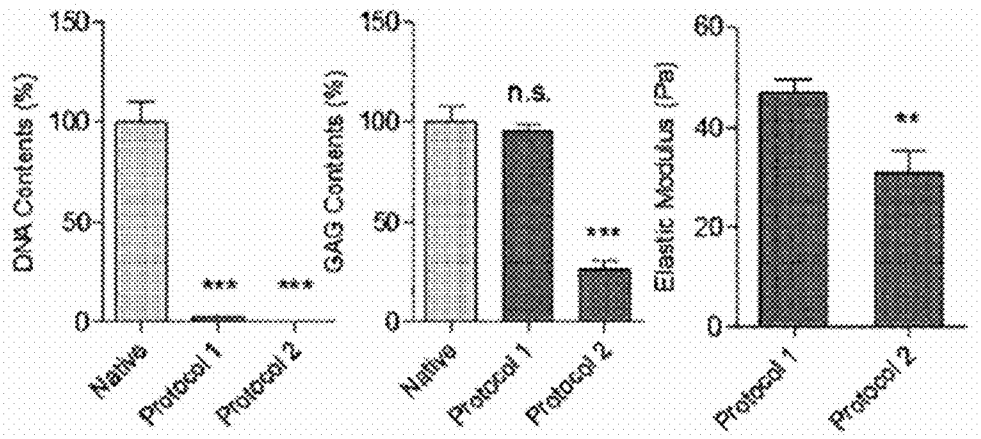

FIG. 84B shows the result of verification of the superiority of the LEM of the present disclosure through comparison of liver tissue decellularization protocol.

Figure 85A:
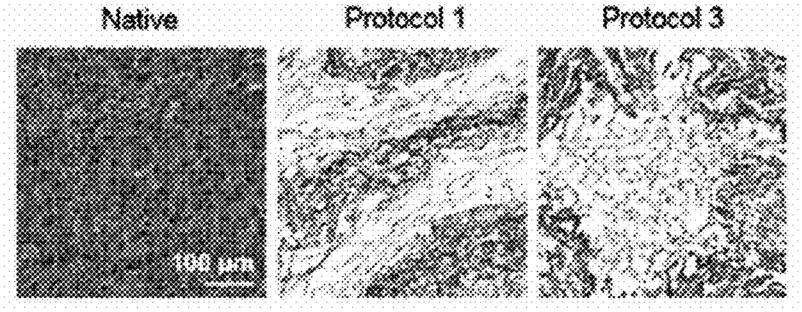

FIG. 85A shows the result of verification of the superiority of the LEM of the present disclosure through comparison of liver tissue decellularization protocol.

Figure 85B:
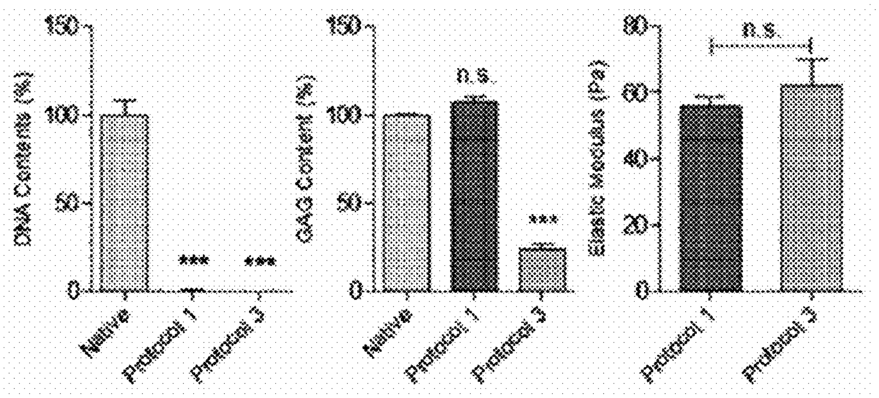

FIG. 85B shows the result of verification of the superiority of the LEM of the present disclosure through comparison of liver tissue decellularization protocol.

Figure 85C:
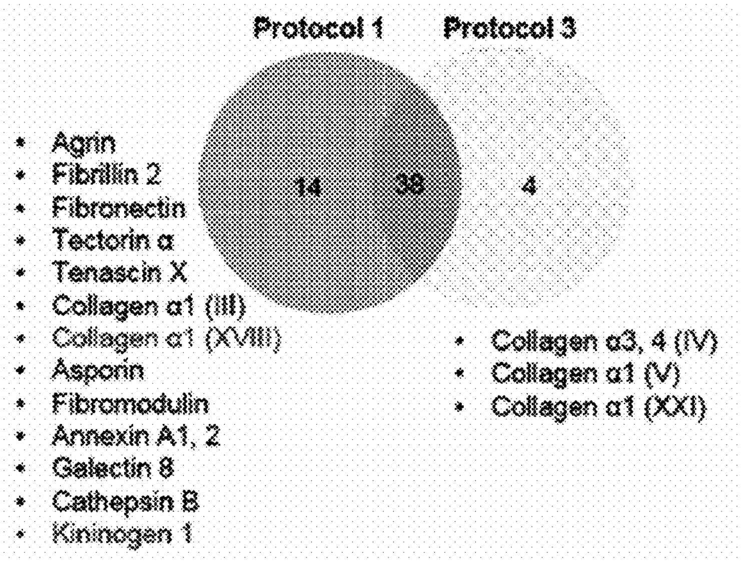

FIG. 85C shows the result of verification of the superiority of the LEM of the present disclosure through comparison of liver tissue decellularization protocol.

Figure 86A:
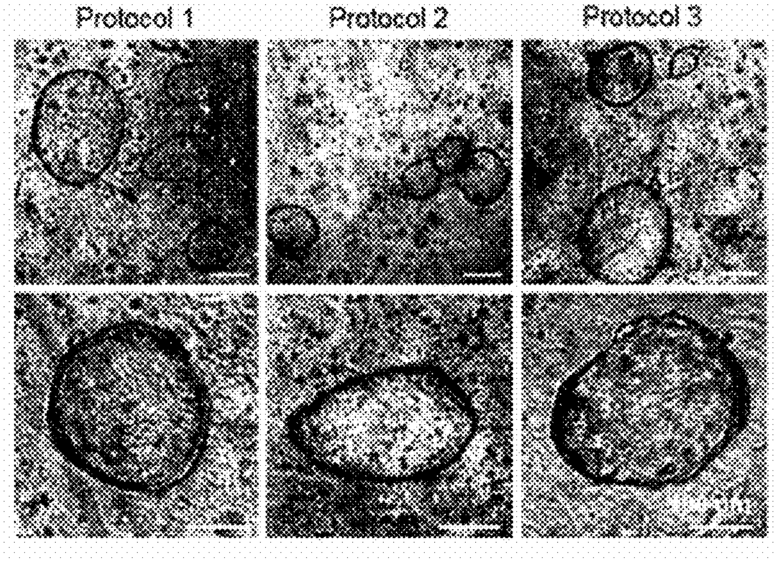

FIG. 86A shows the result of verification of the superiority (organoid culture test) of the LEM of the present disclosure through comparison of liver tissue decellularization protocol.

Figure 86B:
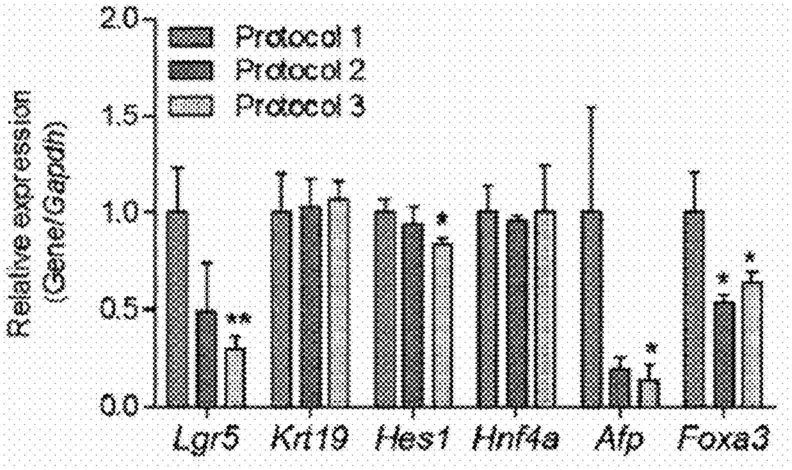

FIG. 86B shows the result of verification of the superiority (organoid culture test) of the LEM of the present disclosure through comparison of liver tissue decellularization protocol.

Figure 86C:
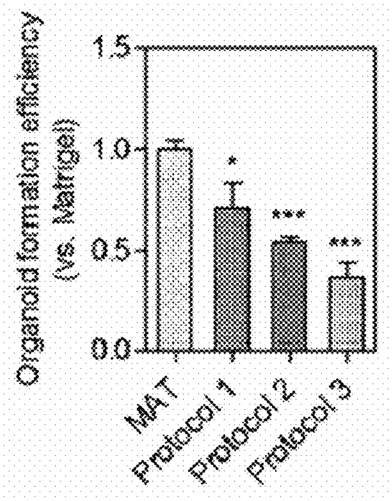

FIG. 86C shows the result of verification of the superiority (organoid culture test) of the LEM of the present disclosure through comparison of liver tissue decellularization protocol.

Figure 87A:
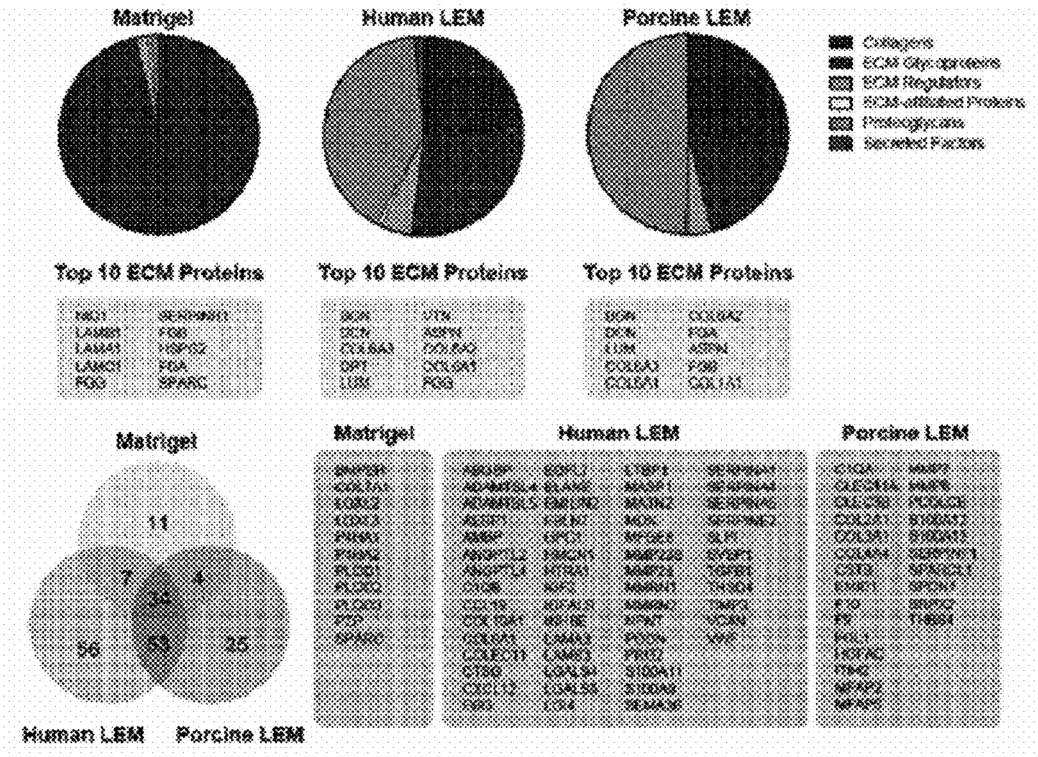

FIG. 87A shows the result of cross-species comparative analysis of decellularized liver tissue-derived hydrogel scaffolds (pig vs. human).

Figure 87B:
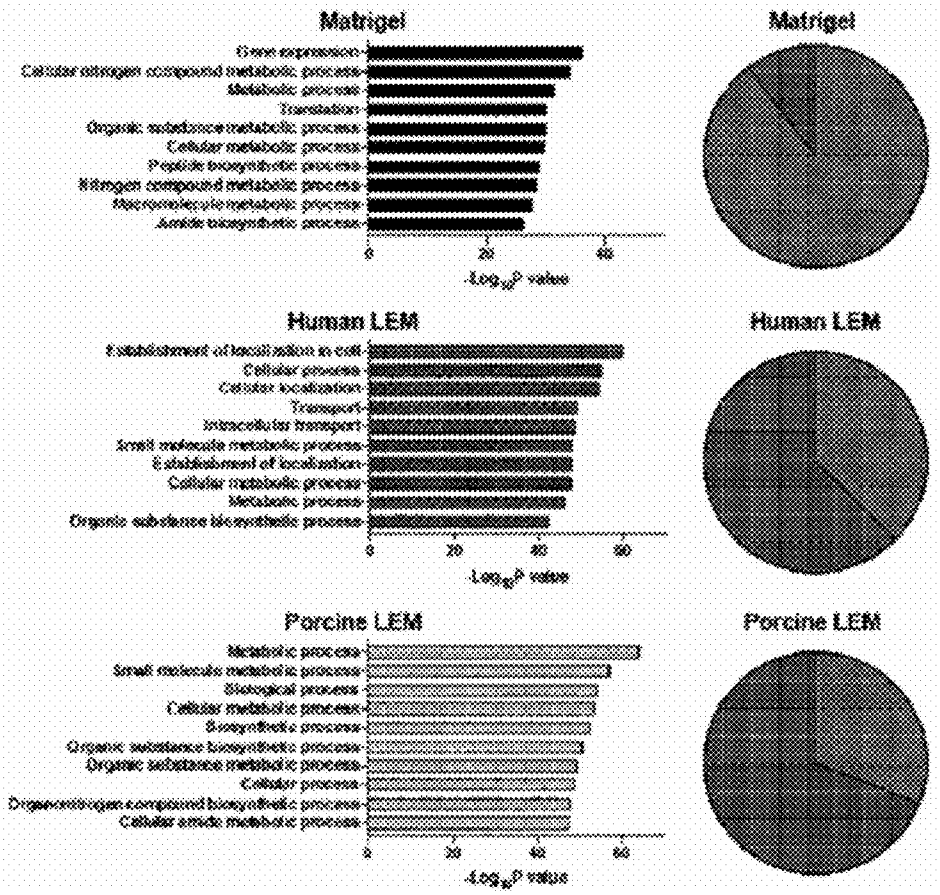

FIG. 87B shows the result of cross-species comparative analysis of decellularized liver tissue-derived hydrogel scaffolds (pig vs. human).

Figure 88A:
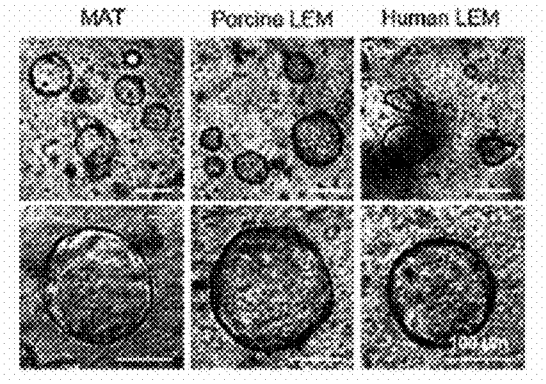

FIG. 88A shows the result of comparison of human cholangiocyte-derived liver organoids (hCLO) cultured in decellularized human and porcine liver tissue-derived hydrogel scaffolds.

Figure 88B:
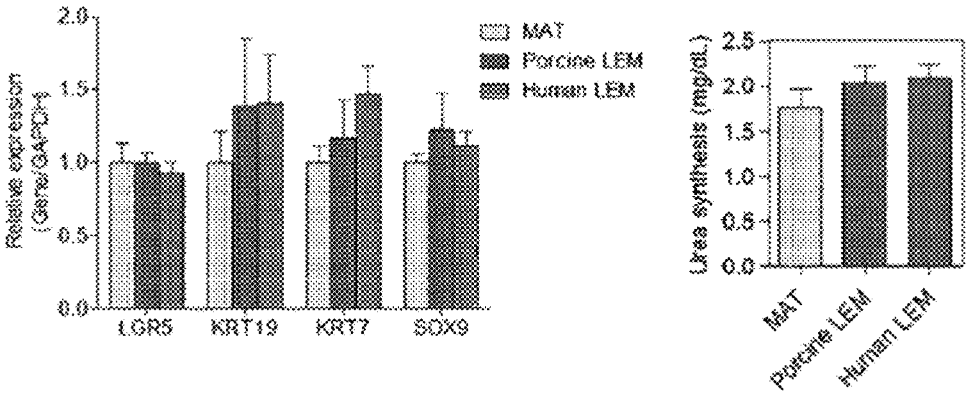

FIG. 88B shows the result of comparison of human cholangiocyte-derived liver organoids (hCLO) cultured in decellularized human and porcine liver tissue-derived hydrogel scaffolds.

Figure 89A:
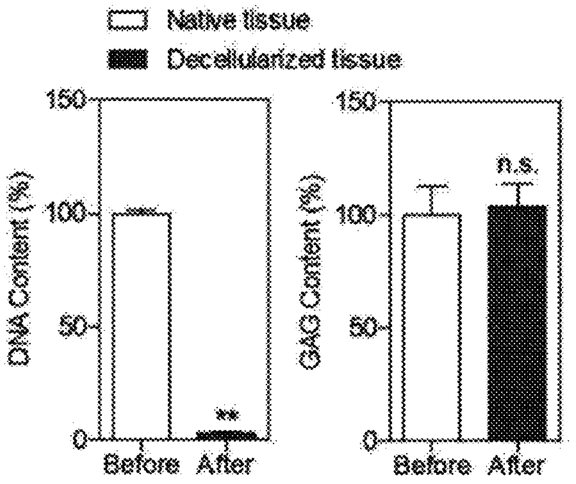

FIG. 89A shows the fabrication of a lung extracellular matrix (LuEM) for lung organoid culture and the analysis thereon.

Figure 89B:
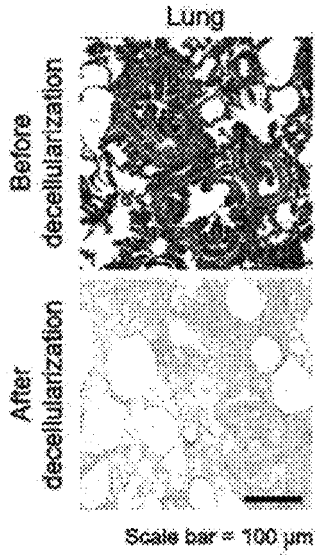

FIG. 89B shows the fabrication of a lung extracellular matrix (LuEM) for lung organoid culture and the analysis thereon.

Figure 89C:
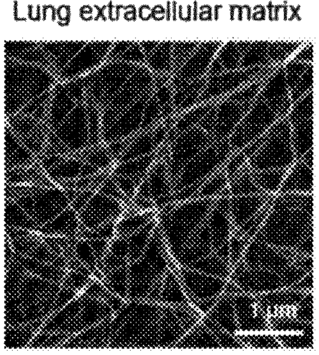

FIG. 89C shows the fabrication of a lung extracellular matrix (LuEM) for lung organoid culture and the analysis thereon.

Figure 90:
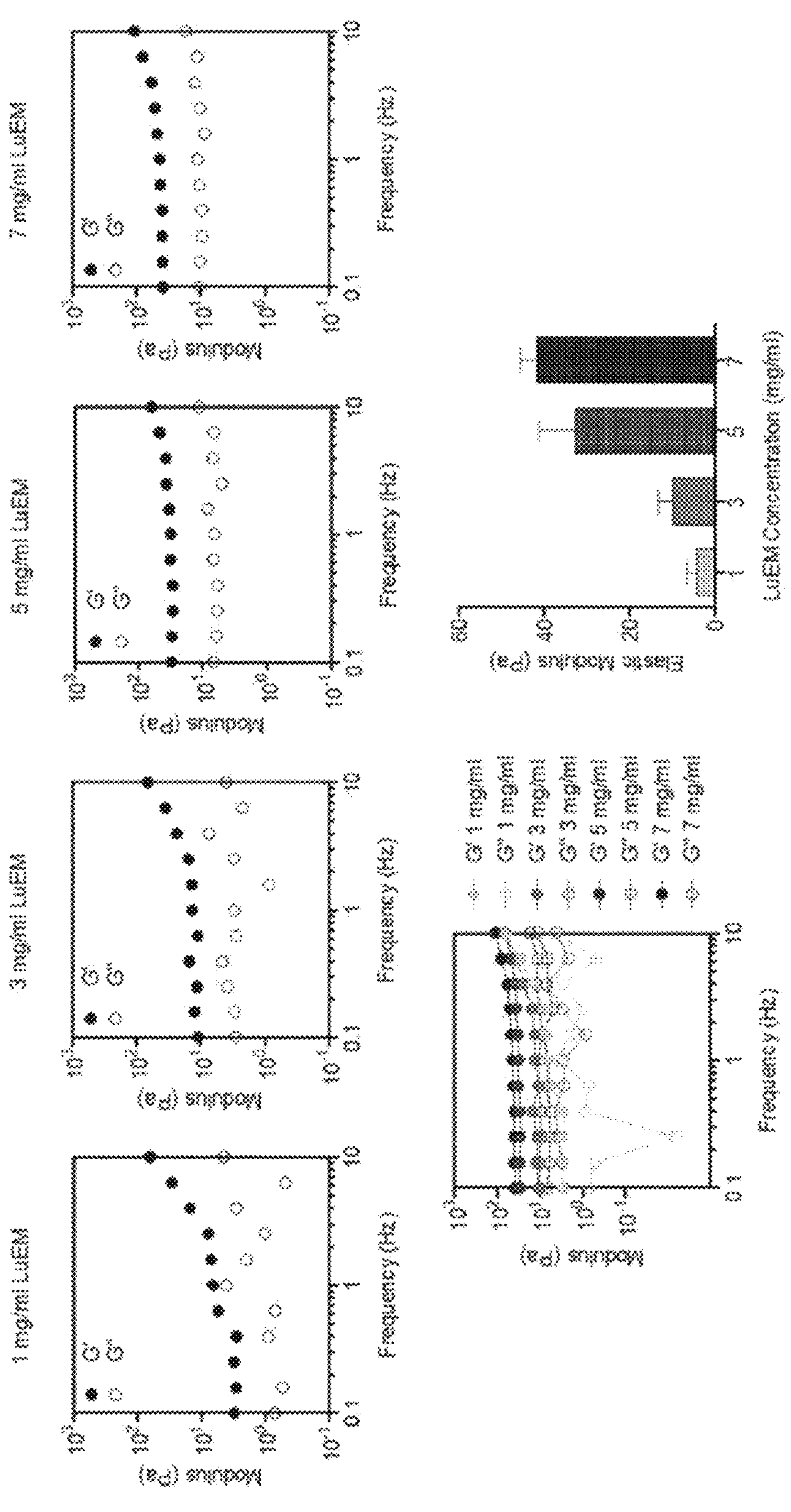

FIG. 90 shows the analysis of mechanical properties of the LuEM for lung organoid culture.

FIG. 91 shows the proteomic analysis of the LuEM for lung organoid culture.

FIG. 92A shows the types of matrisome proteins contained in the LuEM and the result of quantitative analysis.

FIG. 92B shows the types of matrisome proteins contained in the LuEM and the result of quantitative analysis.

FIG. 92C shows the types of matrisome proteins contained in the LuEM and the result of quantitative analysis.

Figure 93A:
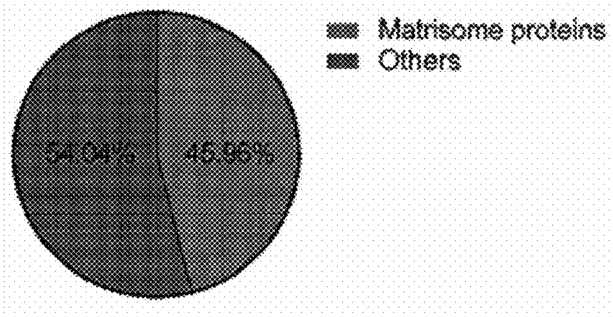

FIG. 93A shows the result of analysis of non-matrisome proteins contained in the LuEM.

Figure 93B:
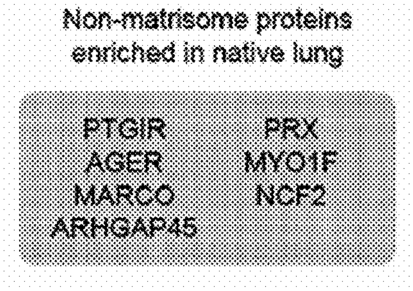

FIG. 93B shows the result of analysis of non-matrisome proteins contained in the LuEM.

Figure 93C:
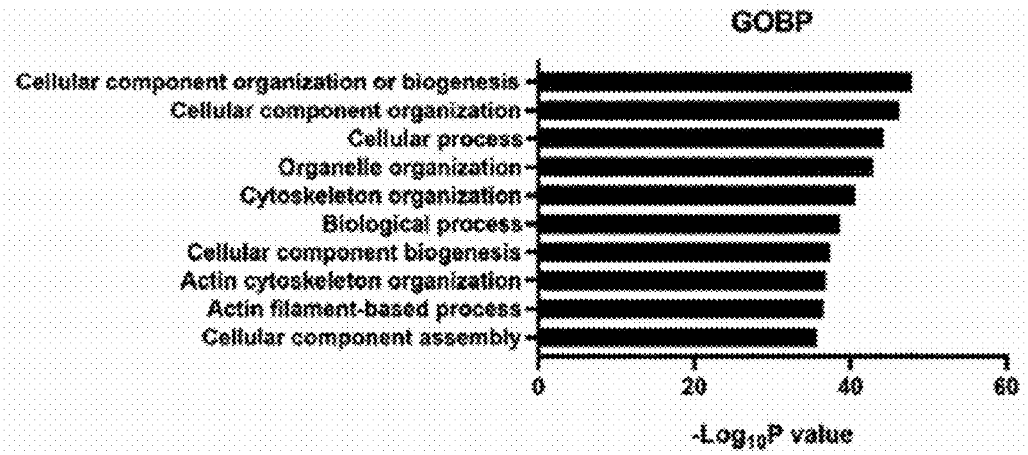

FIG. 93C shows the result of analysis of non-matrisome proteins contained in the LuEM.

Figure 94A:
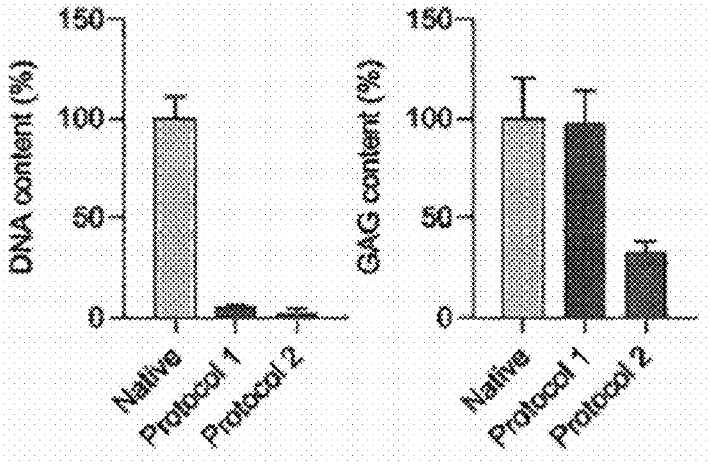

FIG. 94A shows the result of comparative analysis of decellularized lung tissues depending on the decellularization method.

Figure 94B:
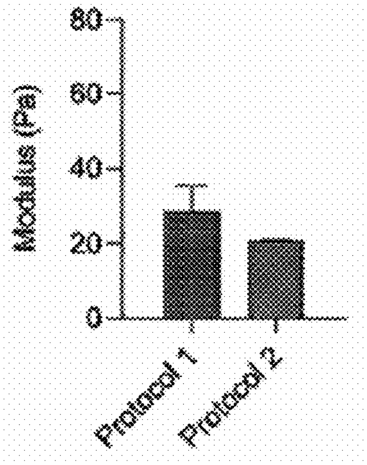

FIG. 94B shows the result of comparative analysis of decellularized lung tissues depending on the decellularization method.

Figure 94C:
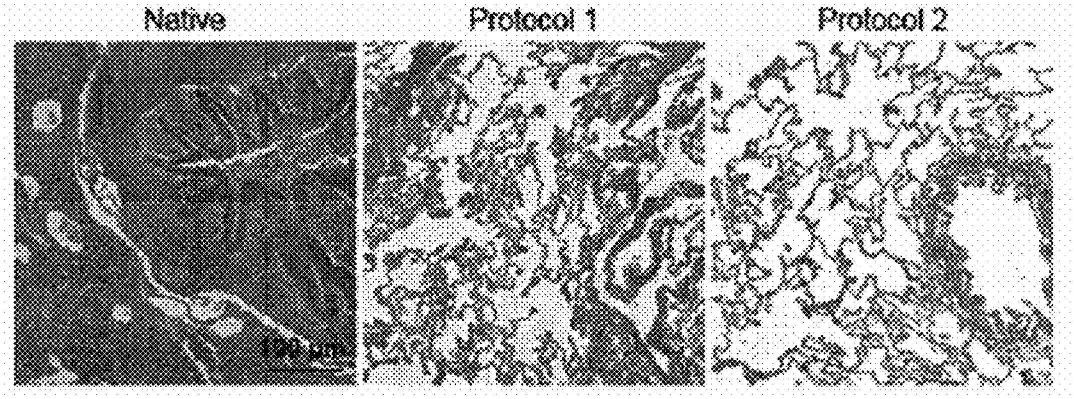

FIG. 94C shows the result of comparative analysis of decellularized lung tissues depending on the decellularization method.

Figure 94D:
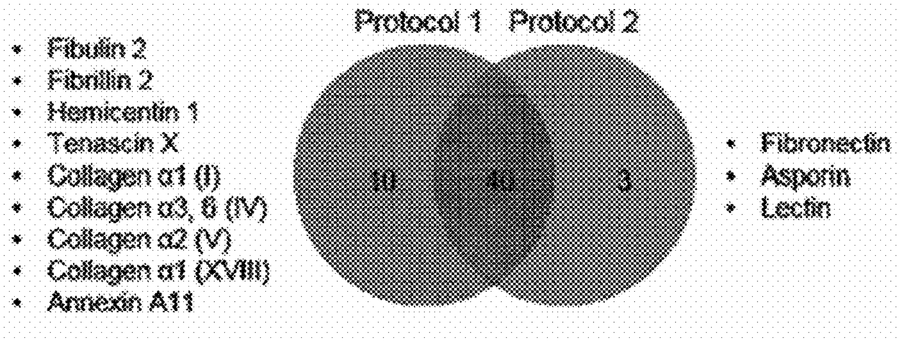

FIG. 94D shows the result of comparative analysis of decellularized lung tissues depending on the decellularization method.

Figure 95A:
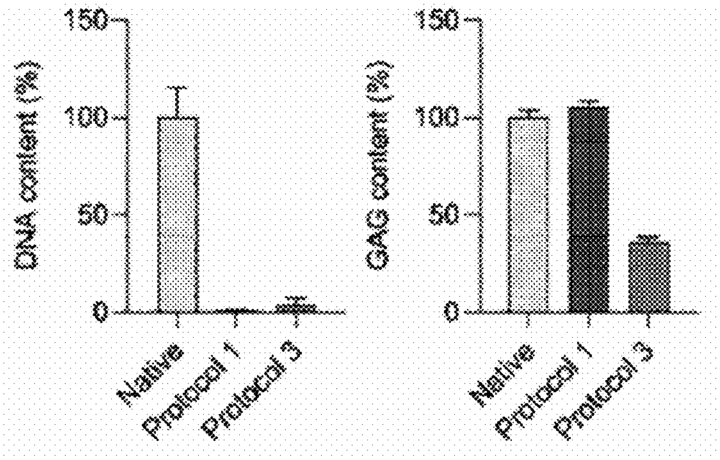

FIG. 95A shows the result of comparative analysis of decellularized lung tissues depending on the decellularization method.

Figure 95B:
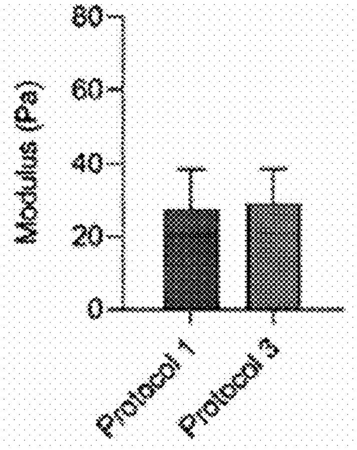

FIG. 95B shows the result of comparative analysis of decellularized lung tissues depending on the decellularization method.

Figure 95C:
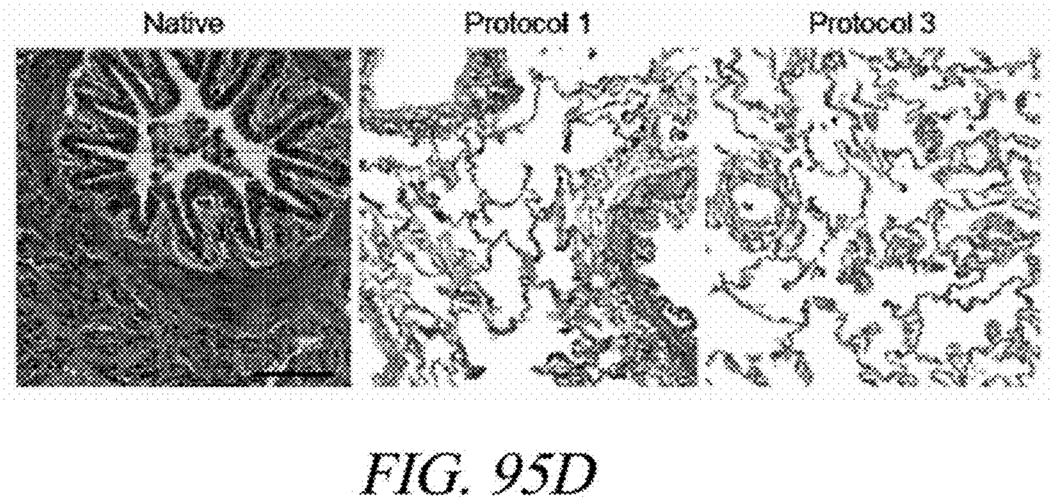

FIG. 95C shows the result of comparative analysis of decellularized lung tissues depending on the decellularization method.

Figure 95D:
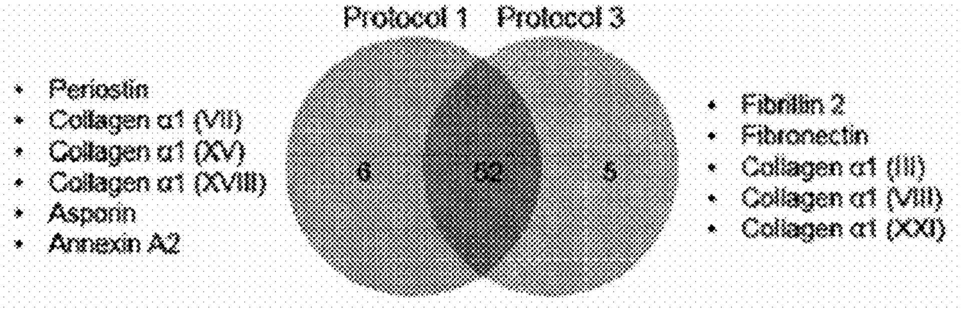

FIG. 95D shows the result of comparative analysis of decellularized lung tissues depending on the decellularization method.

Figure 96A:
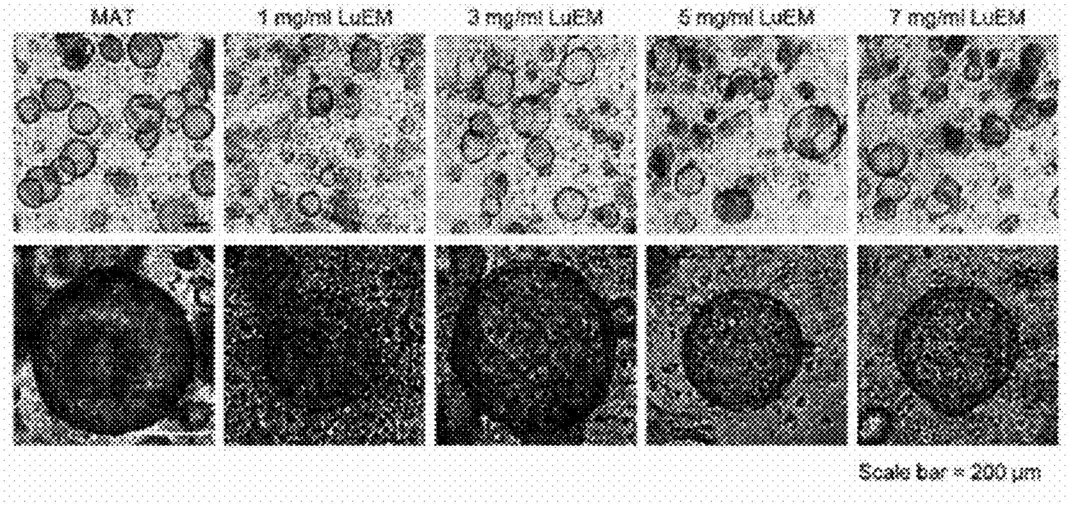

FIG. 96A shows the analysis of the formation of a mouse lung organoid depending on the concentration of the LuEM.

Figure 96B:
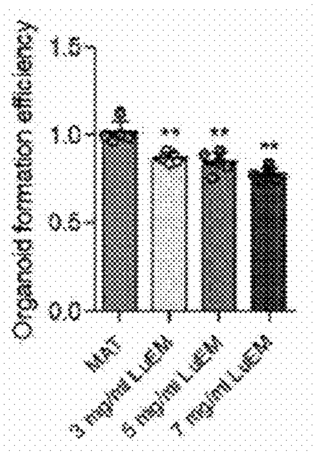

FIG. 96B shows the analysis of the formation of a mouse lung organoid depending on the concentration of the LuEM.

Figure 97:
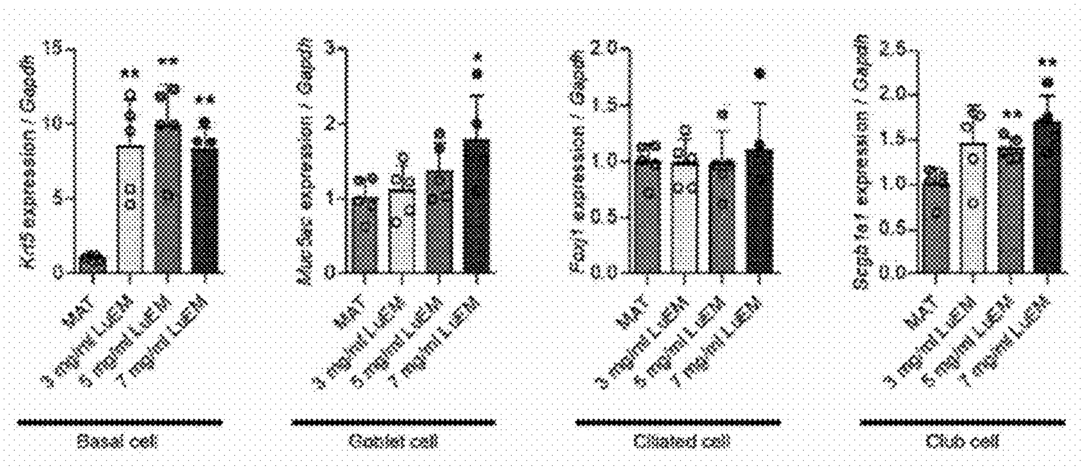

FIG. 97 shows the analysis of the degree of differentiation of the mouse lung organoid depending on the concentration of the LuEM.

Figure 98:
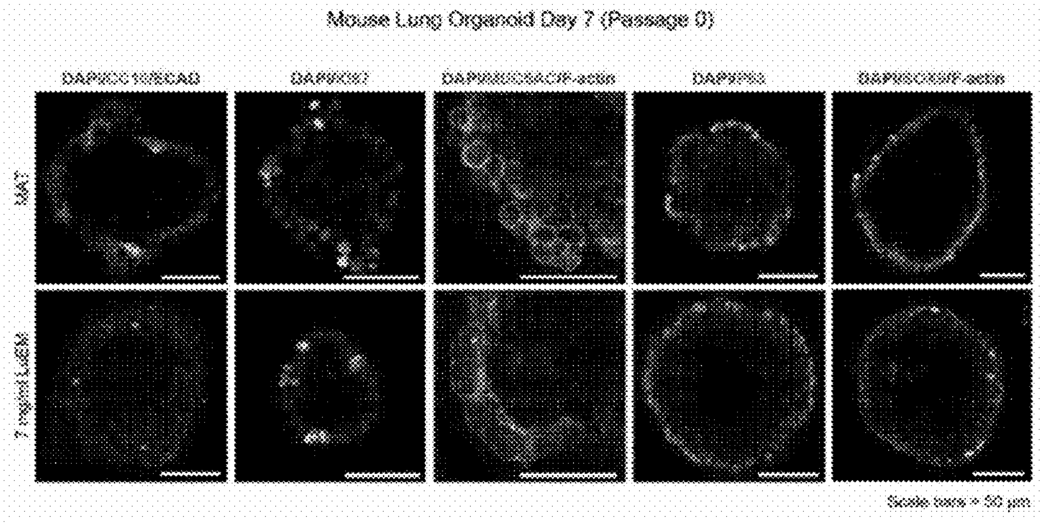

FIG. 98 shows the comparative analysis of the specific marker protein expression of mouse lung organoids cultured in the LuEM and MATRIGEL®.

Figure 99:
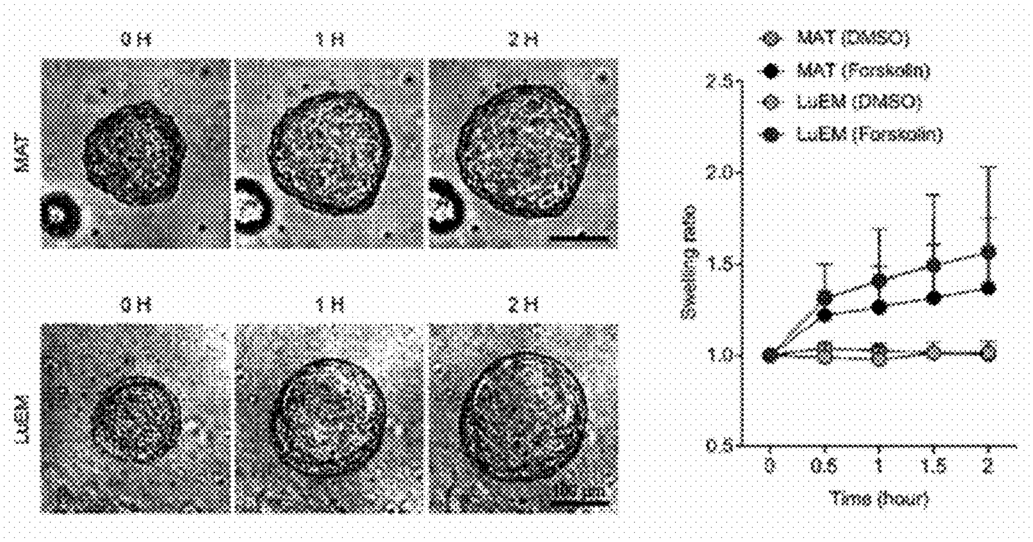

FIG. 99 shows the result of analysis of the functionality of the mouse lung organoids cultured in the LuEM and MATRIGEL®.

Figure 100A:
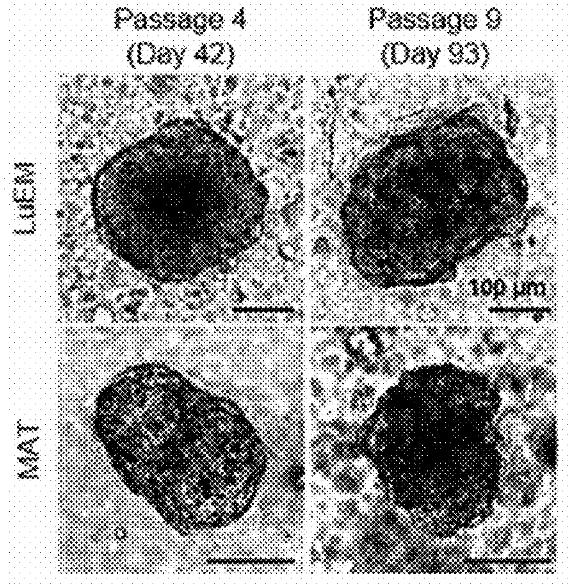

FIG. 100A shows the analysis of mouse lung organoids which are long-term cultured in the LuEM and MATRIGEL®.

Figure 100B:
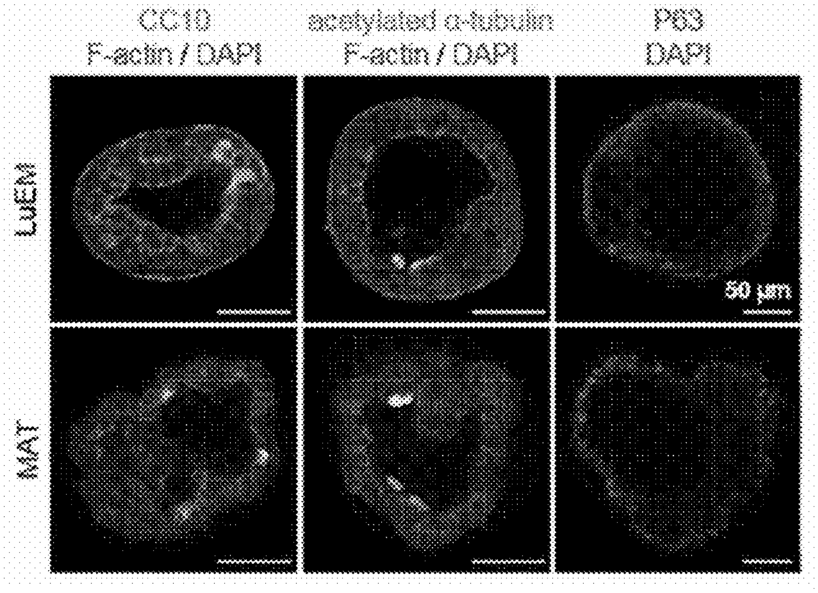

FIG. 100B shows the analysis of mouse lung organoids which are long-term cultured in the LuEM and MATRIGEL®.

Figure 100C:
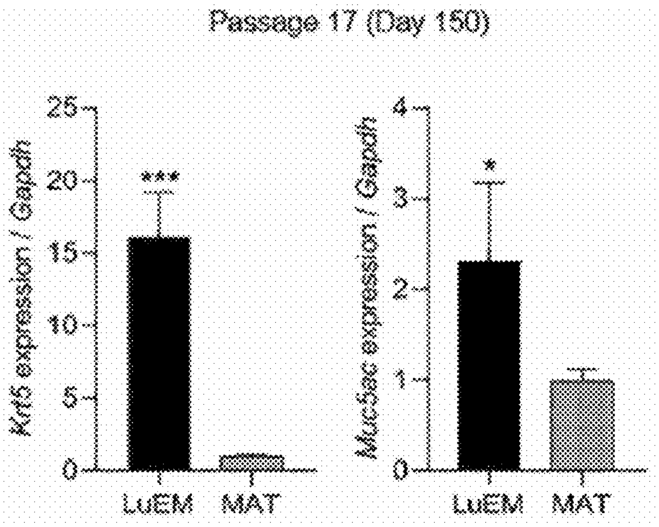

FIG. 100C shows the analysis of mouse lung organoids which are long-term cultured in the LuEM and MATRIGEL®.

Figure 101:
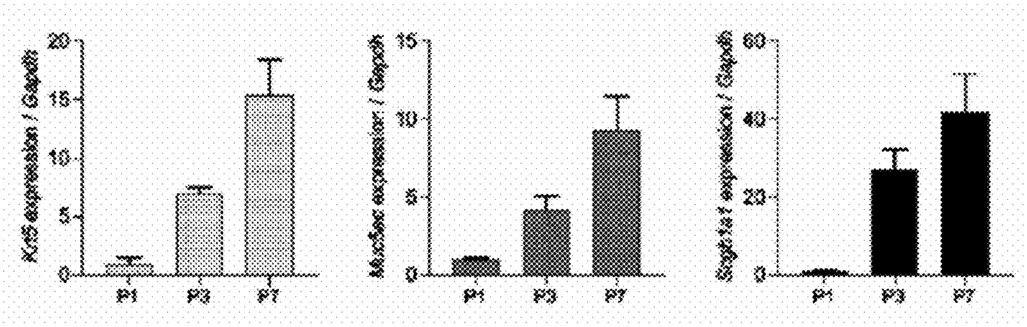

FIG. 101 shows the analysis of mouse lung organoids which are long-term cultured in the LuEM and MATRIGEL®.

Figure 102A:
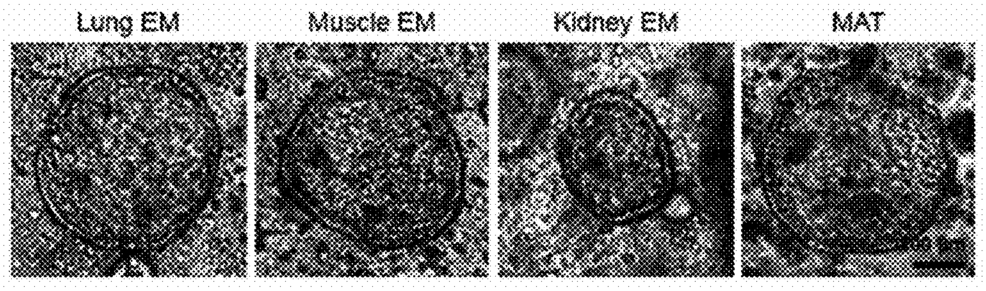

FIG. 102A shows the result confirming the tissue-specific effect of the LuEM.

Figure 102B:
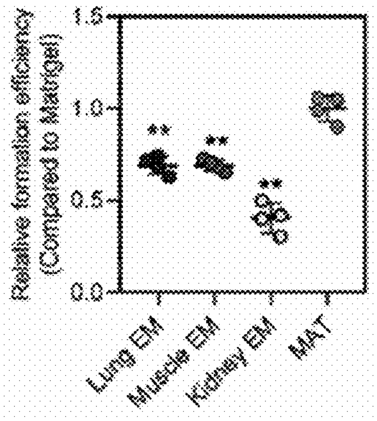

FIG. 102B shows the result confirming the tissue-specific effect of the LuEM.

Figure 102C:
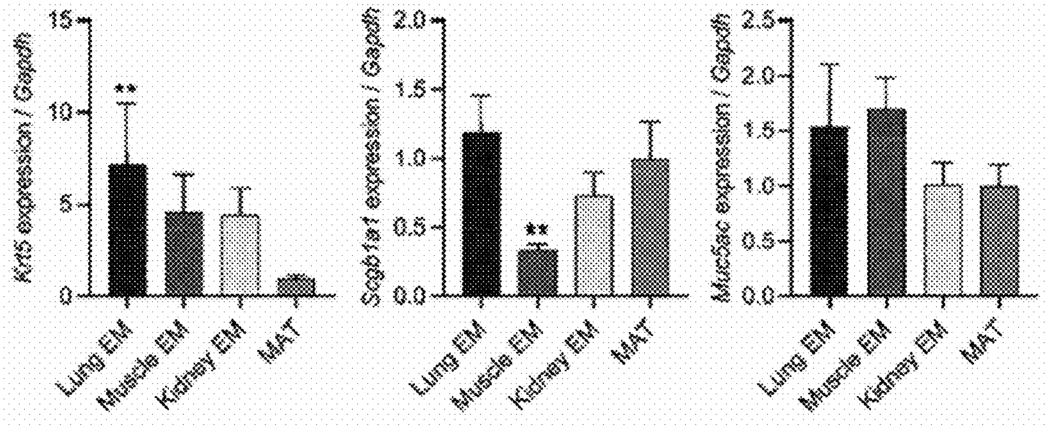

FIG. 102C shows the result confirming the tissue-specific effect of the LuEM.

Figure 103A:
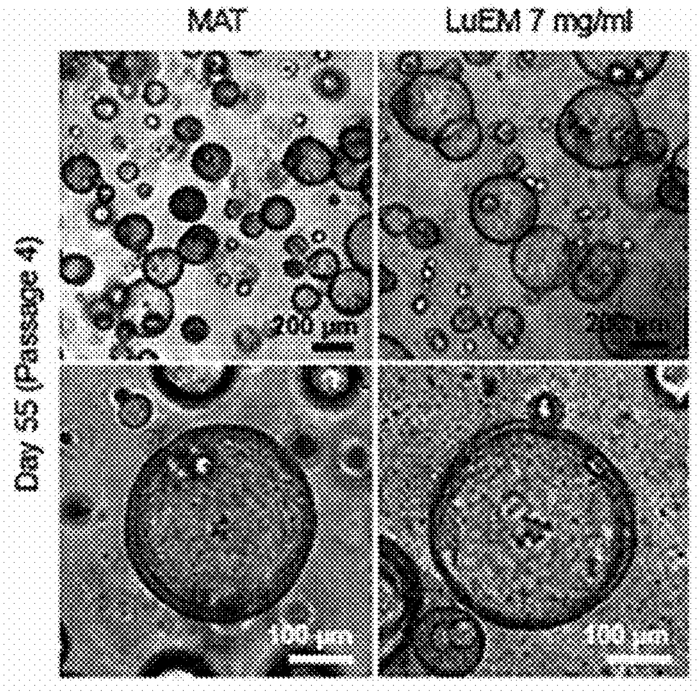

FIG. 103A shows the result of human lung organoid culture using the LuEM.

Figure 103B:
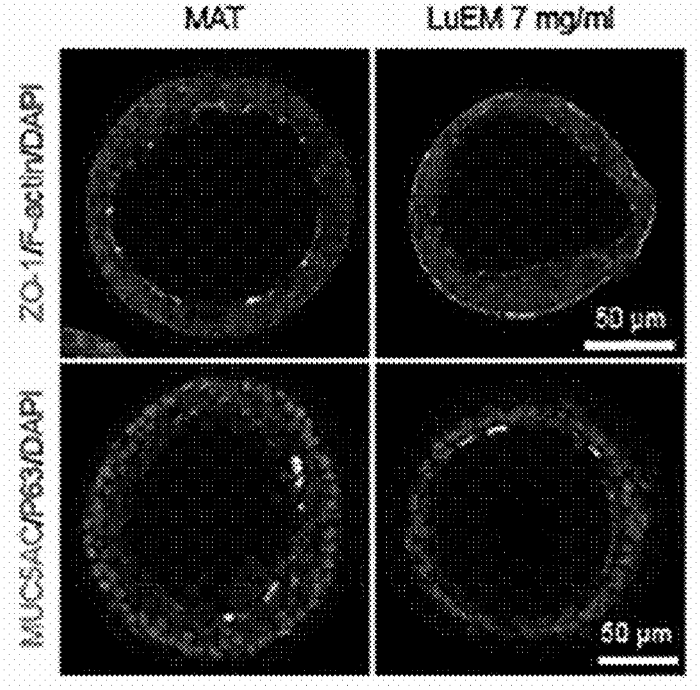

FIG. 103B shows the result of human lung organoid culture using the LuEM.

Figure 103C:
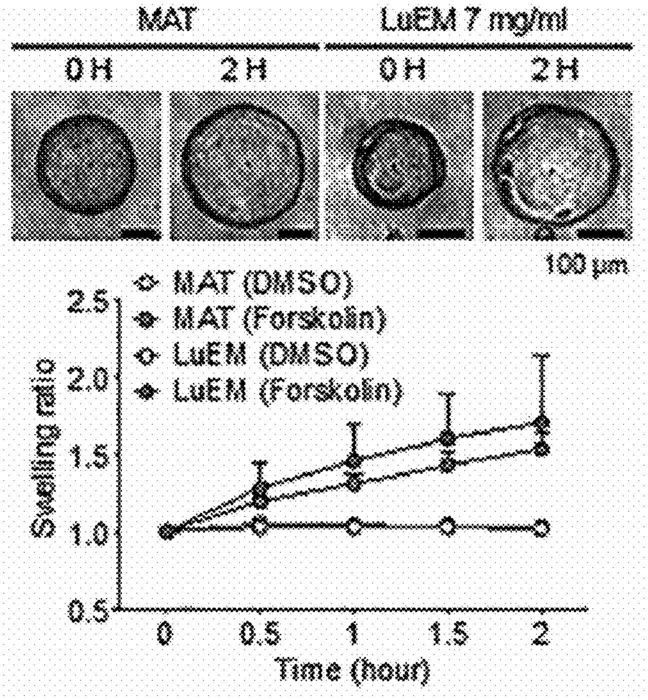

FIG. 103C shows the result of human lung organoid culture using the LuEM.

Figure 104A:
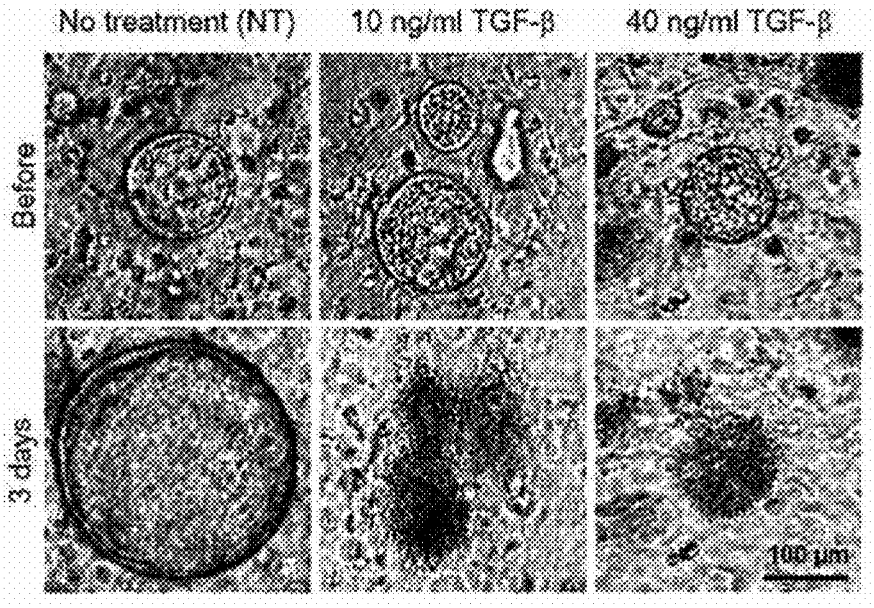

FIG. 104A shows the possibility of fabricating a lung fibrosis model using a mouse lung organoid cultured in the LuEM.

Figure 104B:
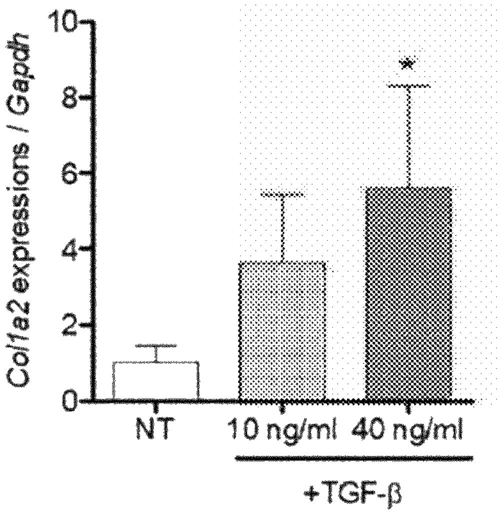

FIG. 104B shows the possibility of fabricating a lung fibrosis model using a mouse lung organoid cultured in the LuEM.

Figure 104C:
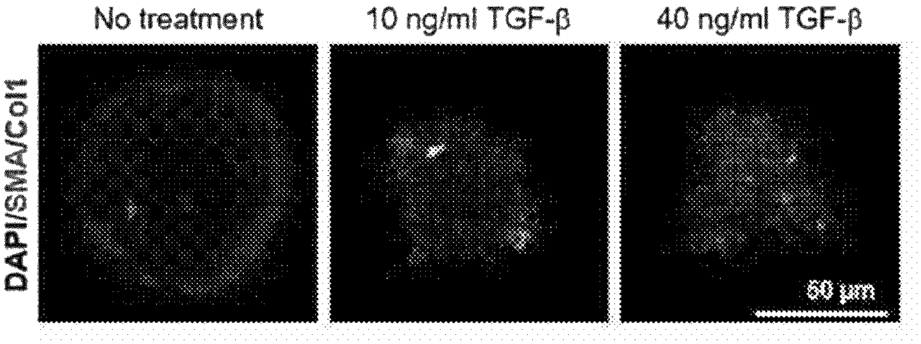

FIG. 104C shows the possibility of fabricating a lung fibrosis model using a mouse lung organoid cultured in the LuEM.

Figure 105A:
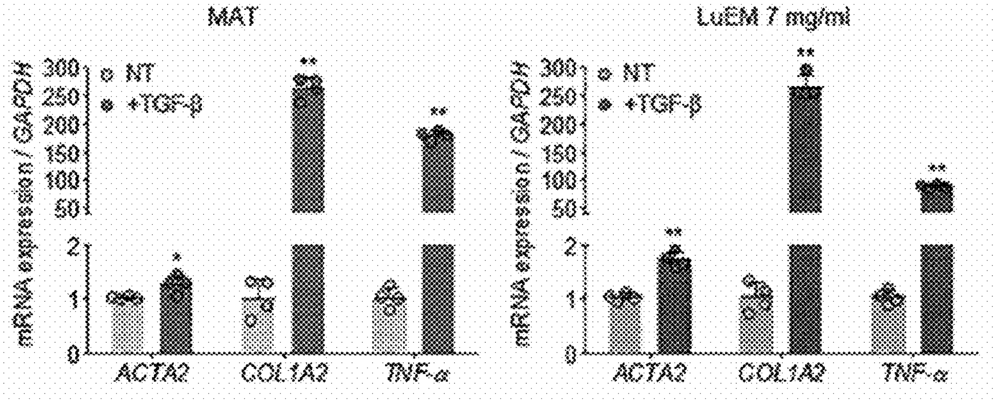

FIG. 105A shows the fabrication of a human lung fibrosis model using a human lung organoid cultured in the LuEM.

Figure 105B:
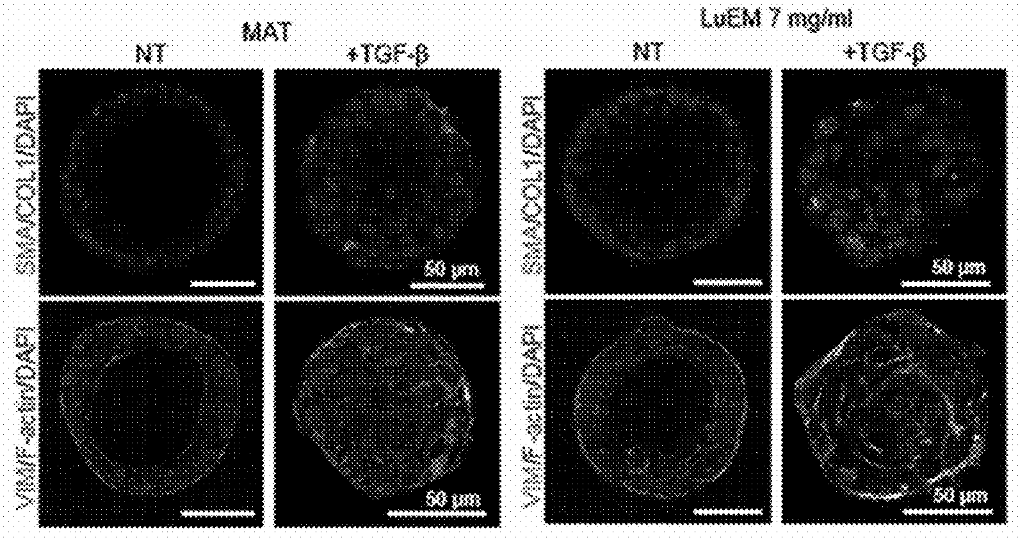

FIG. 105B shows the fabrication of a human lung fibrosis model using a human lung organoid cultured in the LuEM.

Figure 106:
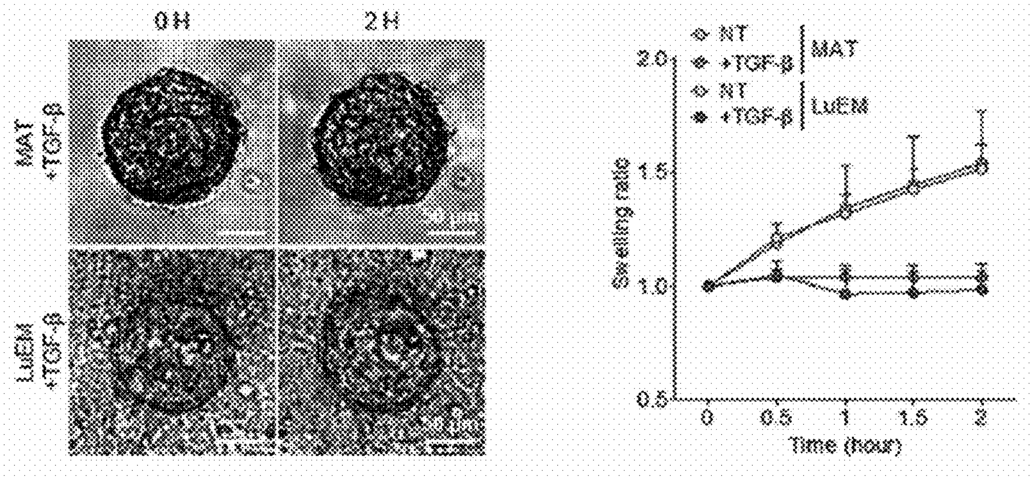

FIG. 106 shows the result of analysis of the functionality of the human lung fibrosis model fabricated in the LuEM.

Figure 107A:
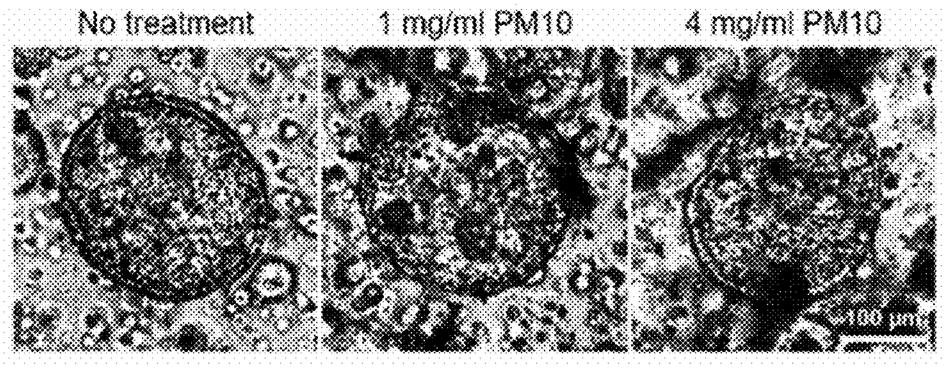

FIG. 107A shows the fabrication of a particulate matter disease model using a mouse lung organoid cultured in the LuEM.

Figure 107B:
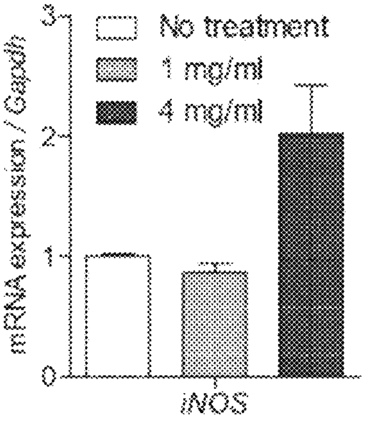

FIG. 107B shows the fabrication of a particulate matter disease model using a mouse lung organoid cultured in the LuEM.

Figure 108A:
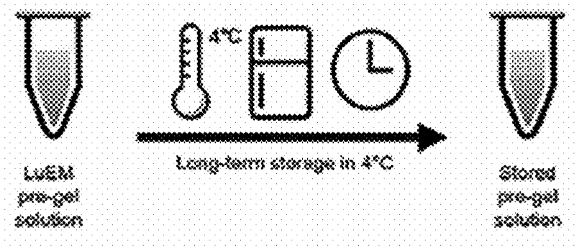

FIG. 108A shows the result verifying the possibility of long-term storage of the LuEM.

Figure 108B:
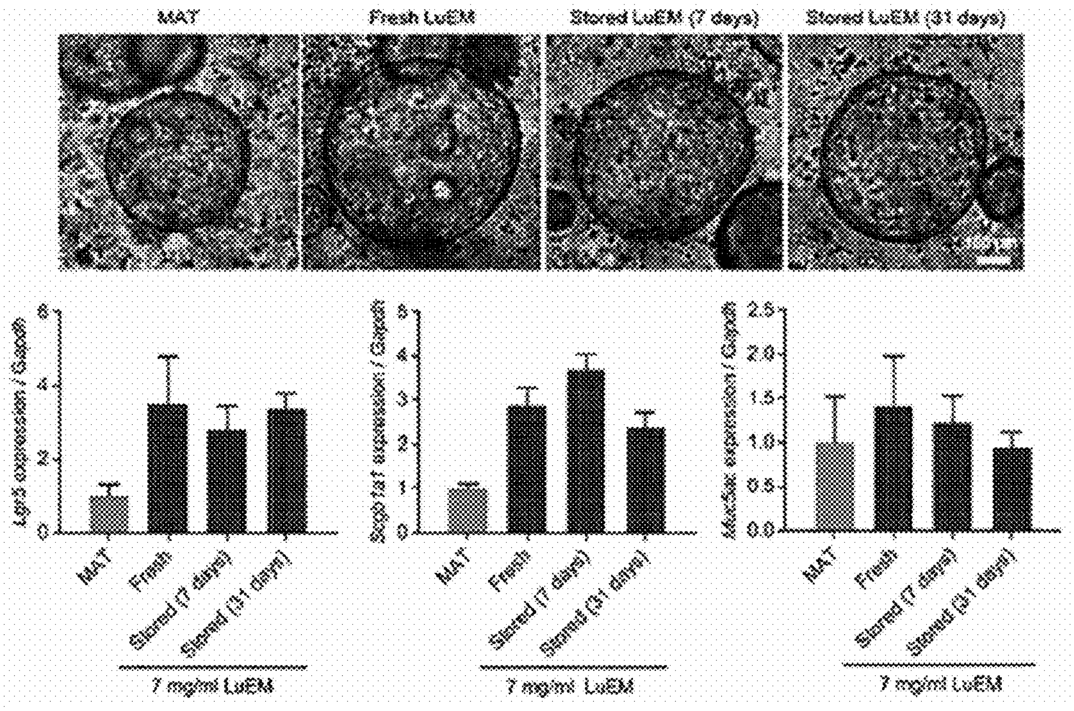

FIG. 108B shows the result verifying the possibility of long-term storage of the LuEM.

Figure 109A:
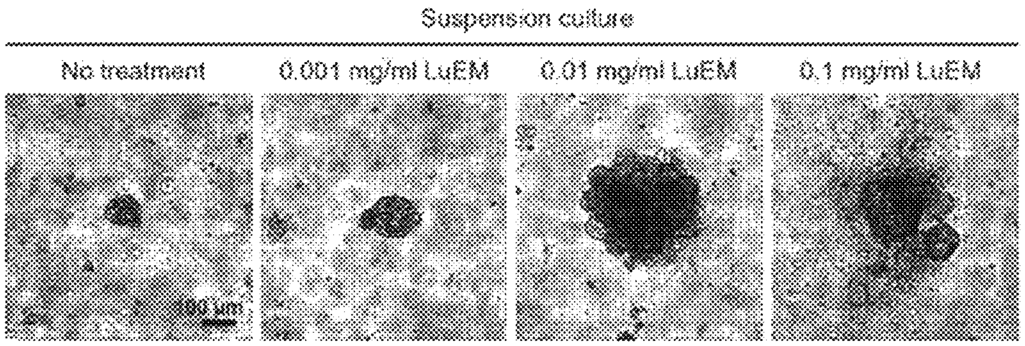

FIG. 109A confirms the possibility of forming a lung organoid under scaffold-free culture conditions by using LuEM components.

Figure 109B:
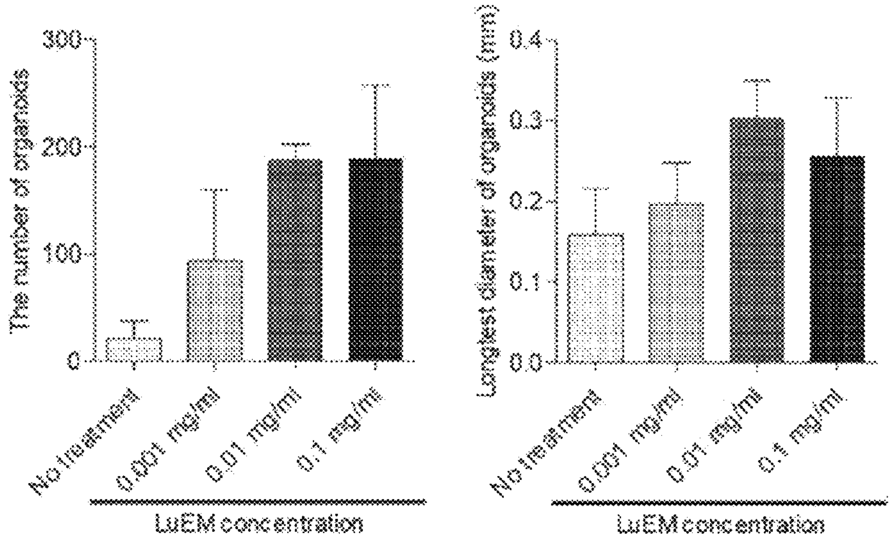

FIG. 109B confirms the possibility of forming a lung organoid under scaffold-free culture conditions by using LuEM components.

Figure 110A:
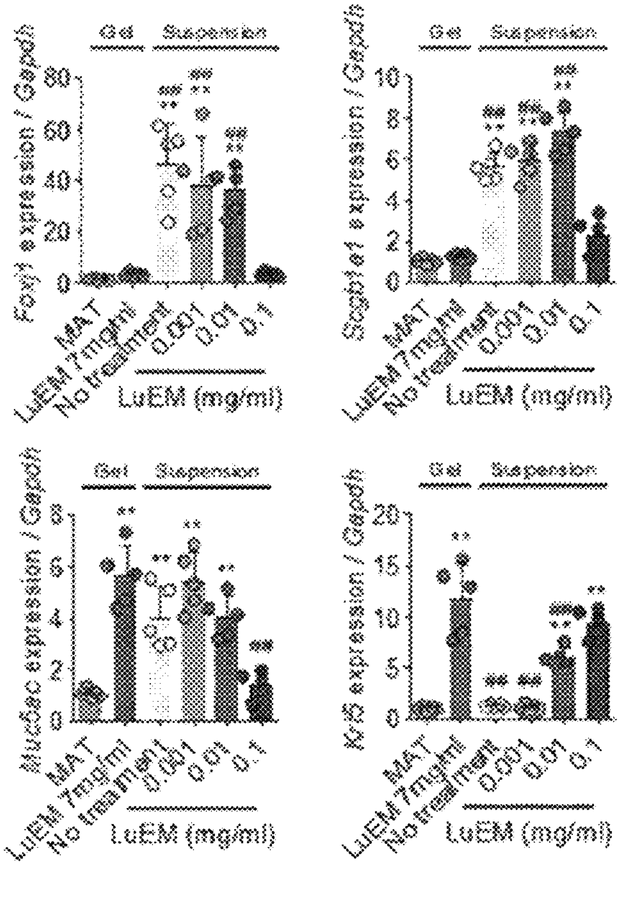

FIG. 110A shows the result of analysis of the gene and protein expression of a mouse lung organoid formed without a culture scaffold.

Figure 110B:
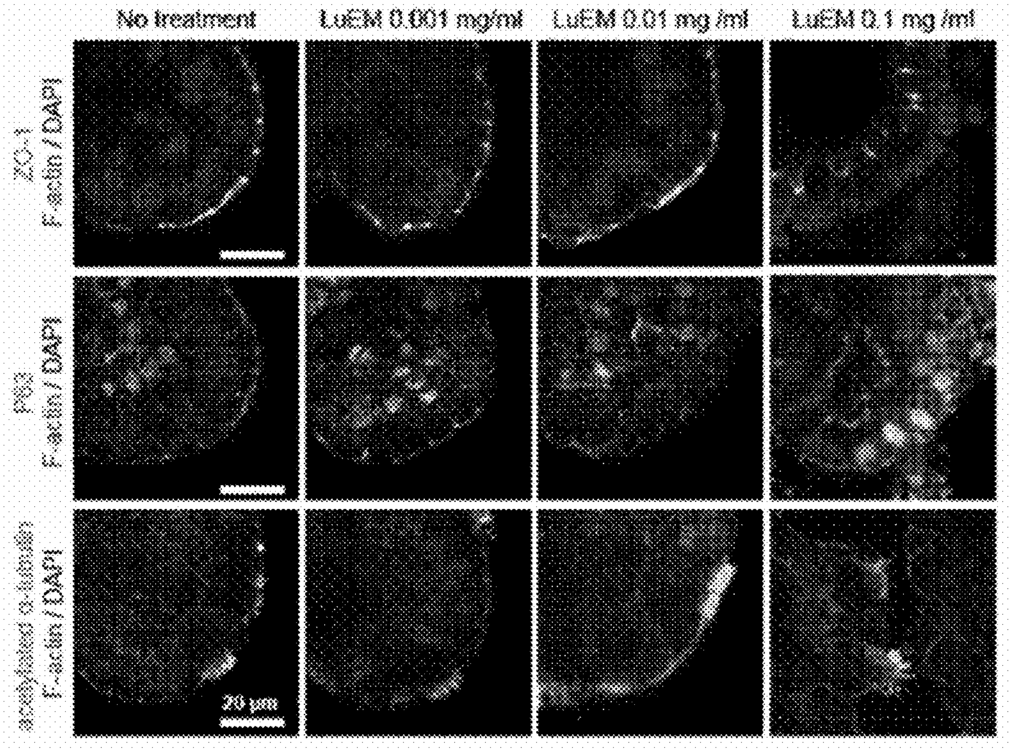

FIG. 110B shows the result of analysis of the gene and protein expression of a mouse lung organoid formed without a culture scaffold.

Figure 111:
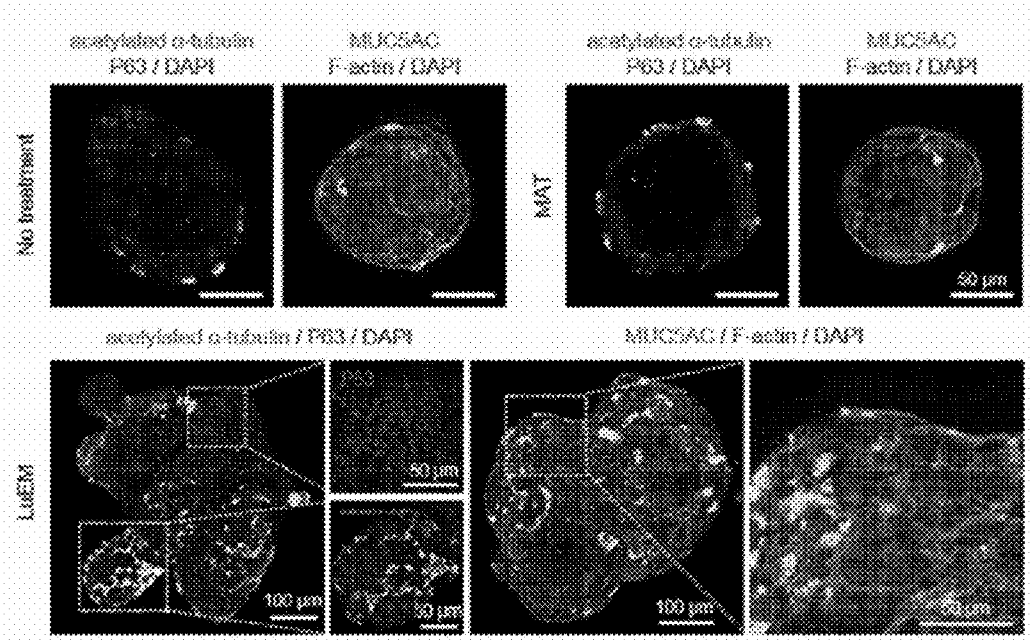

FIG. 111 shows the result of analysis of the protein expression of a human lung organoid formed without a culture scaffold.

Figure 112:
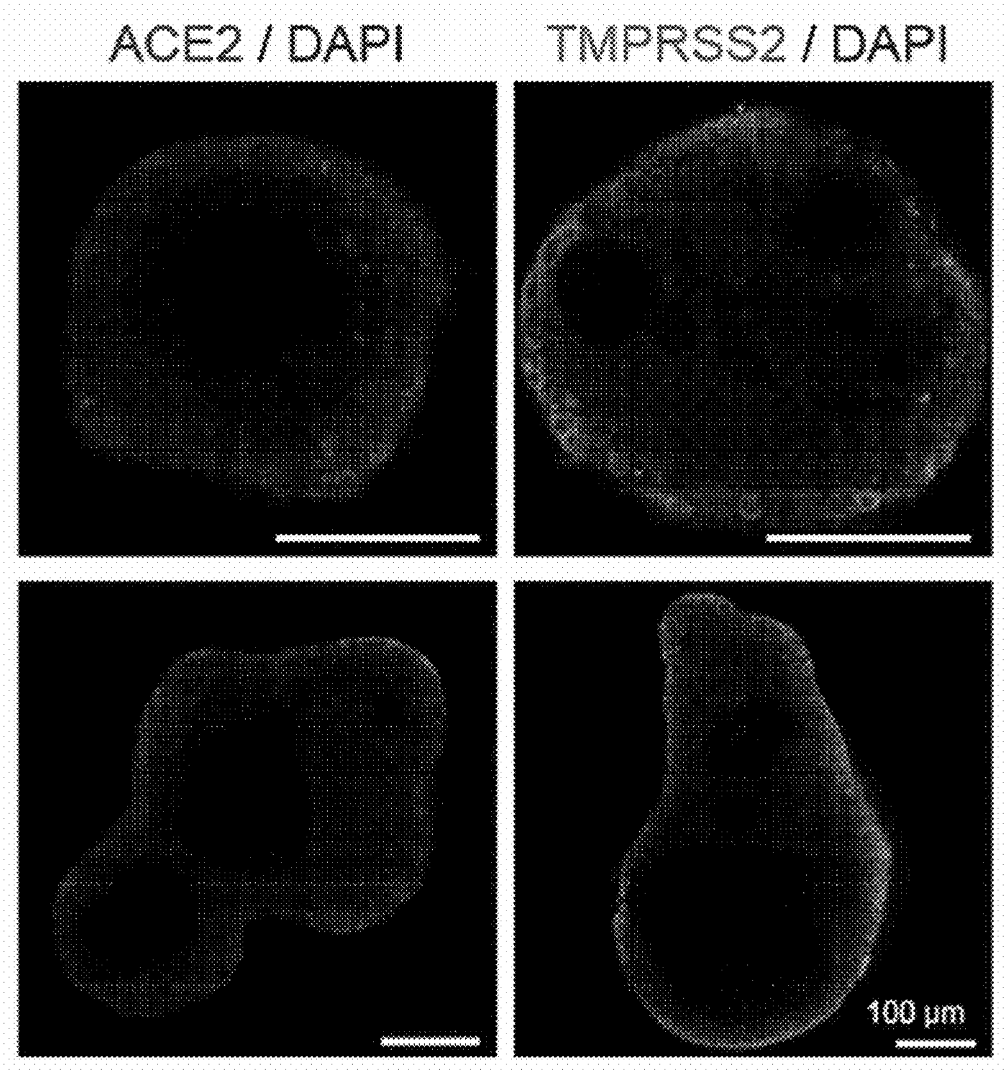

FIG. 112 shows the result of analysis of the protein expression of a human lung organoid formed without a culture scaffold.

Figure 113A:
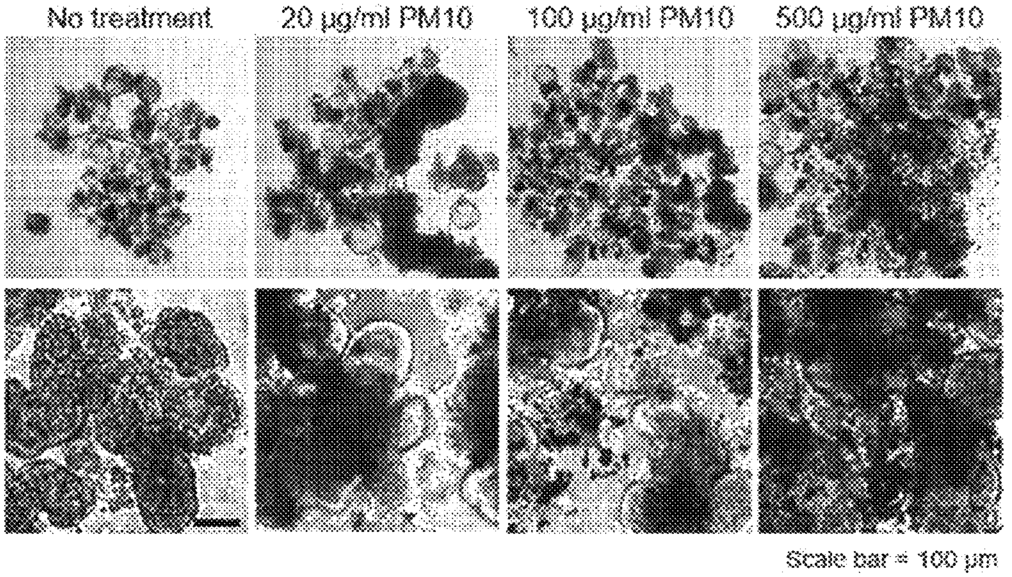

FIG. 113A shows a particulate matter test with a mouse lung organoid formed without a culture scaffold.

Figure 113B:
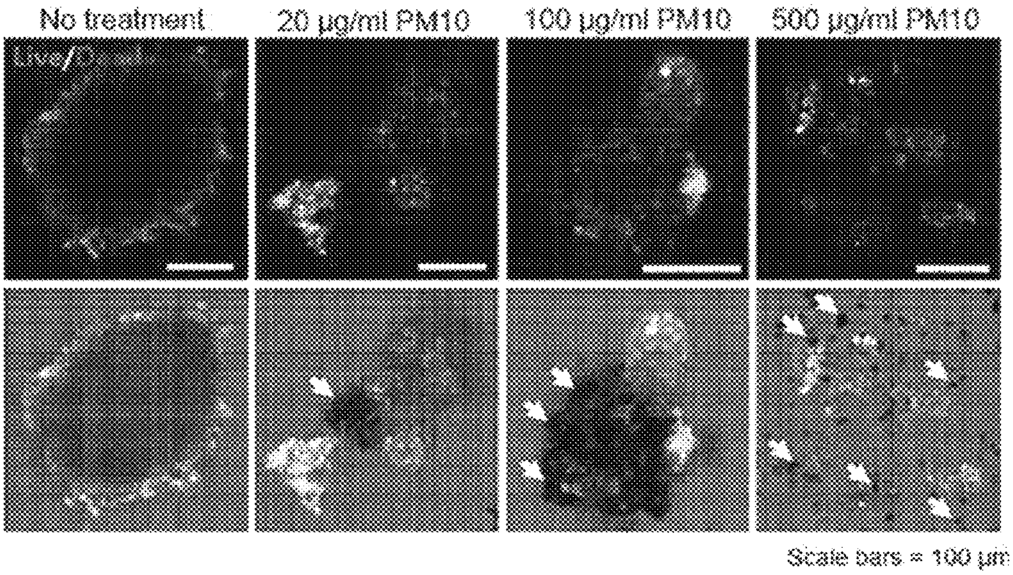

FIG. 113B shows a particulate matter test with a mouse lung organoid formed without a culture scaffold.

Figure 114A:
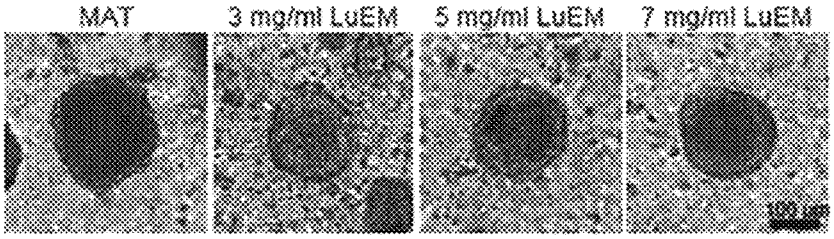

FIG. 114A shows the result of promoting differentiation of a mouse lung organoid into alveoli by the LuEM.

Figure 114B:
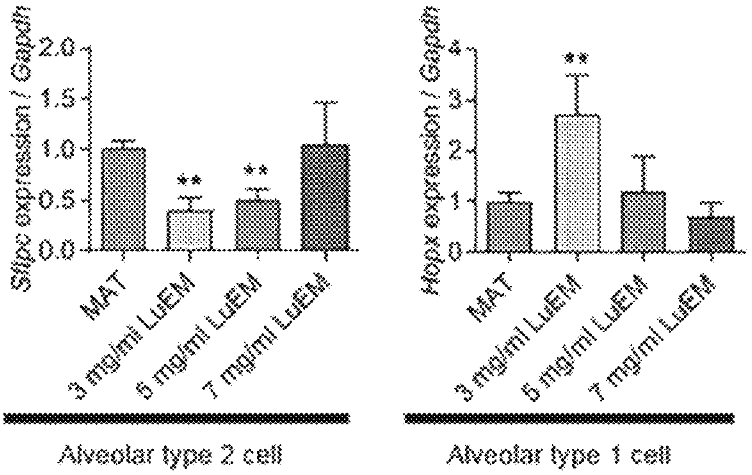

FIG. 114B shows the result of promoting differentiation of a mouse lung organoid into alveoli by the LuEM.

Figure 114C:
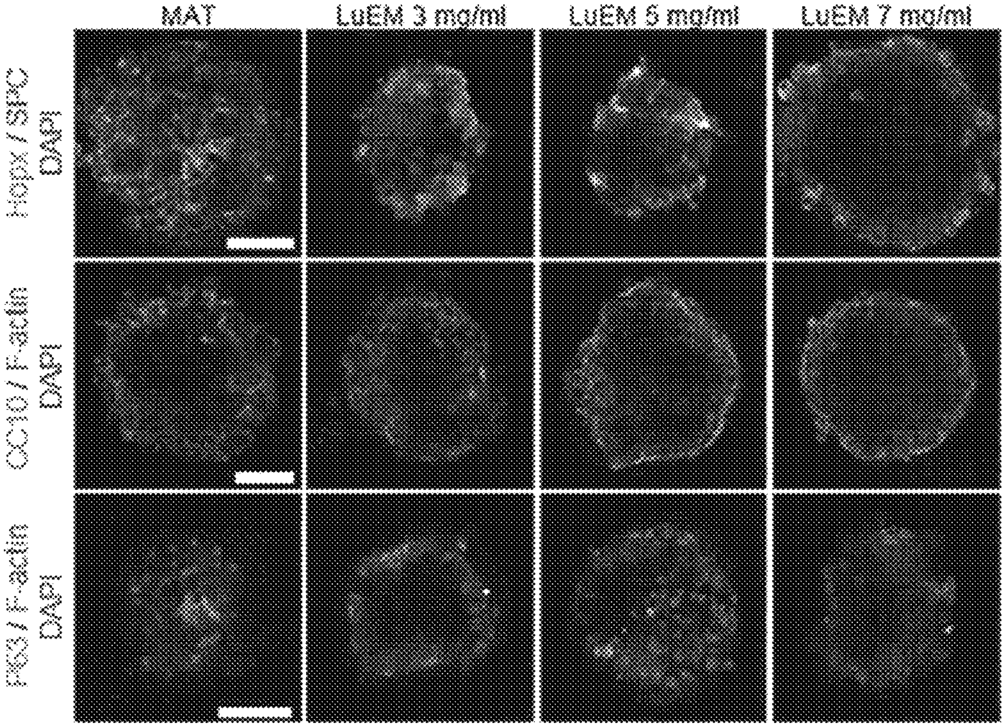

FIG. 114C shows the result of promoting differentiation of a mouse lung organoid into alveoli by the LuEM.

Figure 115A:
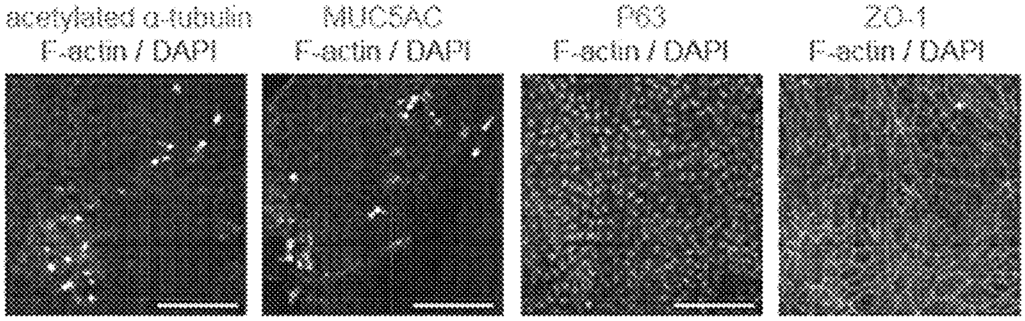

FIG. 115A shows the formation of a monolayer of a human lung organoid cultured in the LuEM and the result of analysis thereon.

Figure 115B:
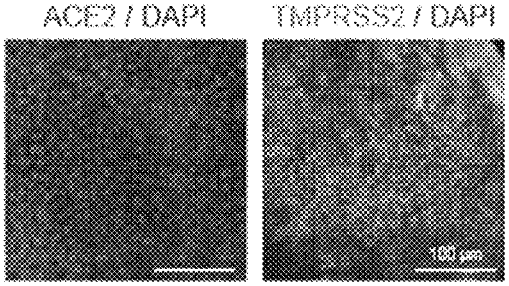

FIG. 115B shows the formation of a monolayer of a human lung organoid cultured in the LuEM and the result of analysis thereon.

BEST MODE FOR CARRYING OUT THE INVENTION

The present disclosure provides a scaffold composition containing an organ extracellular matrix.

In an embodiment of the present disclosure, the organ may be any one of intestine, stomach, liver and lung.

Further, in an embodiment of the present disclosure, the organ extracellular matrix may be contained at a concentration of 0.01 mg/ml to 10 mg/mL.

The present disclosure also provides a method of preparing a scaffold composition, including: a process (a) of decellularizing an isolated organ tissue to prepare a decellularized organ tissue; a process (b) of drying the decellularized organ tissue to prepare an organ extracellular matrix; and a process (c) of gelating the dried organ extracellular matrix.

In an embodiment of the present disclosure, the organ may be any one of intestine, stomach, liver and lung.

In an embodiment of the present disclosure, in the process (a), the organ tissue may be stirred in a decellularization solution.

In an embodiment of the present disclosure, the decellularization solution may include 0.1% to 5% TRITON X-100™ and 0.01% to 0.5% ammonium hydroxide.

In an embodiment of the present disclosure, in the decellularization of the process (a), 95% to 99.9% of cells may be removed.

In an embodiment of the present disclosure, the method may further include a process of adjusting the organ extracellular matrix to be contained at a concentration of 0.01 mg/ml to 10 mg/ml after the process (b).

The present disclosure provides a method of culturing an organoid in the scaffold composition or a scaffold composition prepared by the preparation method.

In an embodiment of the present disclosure, the organ may be any one of intestine, stomach, liver and lung.

MODE FOR CARRYING OUT THE INVENTION

With respect to an intestinal extracellular matrix-derived scaffold for culture and transplantation of an intestinal organoid and a method of preparing the same, the present disclosure relates to a technique of using only an intestinal tissue-specific extracellular matrix, which is obtained by removing cells from intestinal tissue by decellularization, as an artificial scaffold for effective three-dimensional culture of an intestinal organoid. A hydrogel developed based on the decellularized intestinal tissue matrix shows promise as a substitute for MATRIGEL®.

An artificial scaffold of the present disclosure is composed of pure extracellular matrix components from which cellular antigens have been removed. Thus, it does not cause inflammatory reaction and immune rejection of tissue during transplantation and is cheap with excellent biocompatibility. Therefore, it can greatly improve the safety and economics of organoid culture and transplantation treatment. Further, compared to MATRIGEL®, which is a conventional commercialized organoid culture scaffold, it provides a tissue-specific microenvironment for organoid growth. Therefore, it can greatly improve differentiation, development and function of an organoid. That is, it is possible to provide a culture system suitable for the advancement of an organoid.

It was confirmed that the decellularized intestinal tissue-derived artificial scaffold can be fabricated and applied at various concentrations. It was also verified that an intestinal organoid could be formed at each concentration and various cell types of intestinal tissue could be developed.

Also, an intestinal organoid cultured in the decellularized intestinal tissue-derived hydrogel scaffold was similar to an organoid cultured in MATRIGEL® in terms of formation efficiency, growth rate, size, cell development and functionality. Accordingly, it was confirmed that the scaffold developed in the present disclosure can replace MATRIGEL®.

It was confirmed that an intestinal tissue-derived scaffold had the best efficacy in culturing an intestinal organoid compared to artificial matrix scaffolds prepared by decellularizing other types of tissues (heart, skin, lymph, stomach and muscle). This result implies that development of a tissue-specific matrix for organoid culture by decellularization is important. It was found that the scaffold containing an intestinal tissue-specific extracellular matrix component provides an optimized microenvironment for intestinal organoid culture.

By using the decellularized intestinal tissue scaffold of the present disclosure, it is possible to perform long-term subculture of an intestinal organoid. The developed scaffold maintained the characteristics and differentiation degree of intestinal stem cells at a level similar to that of MATRIGEL® even during the long-term culture period. Therefore, it was confirmed that the developed scaffold is an effective culture system that can maintain stable long-term culture of the intestinal organoid. Also, it was confirmed that even when a decellularized intestinal tissue-derived hydrogel solution is used after long-term freezing (more than 3 months) and long-term refrigeration (more than 1 month), it can be used for intestinal organoid culture without any problems. Therefore, it can be developed as a highly convenient product that can be stored over a long-term period while being used.

The decellularized intestinal tissue-derived hydrogel scaffold of the present disclosure can be applied as a transplantation material for in vivo delivery of an organoid as well as a culture system. Actually, it was confirmed through animal tests that it is effective in transplanting an organoid into an intestinal injury site and inducing engraftment thereof. It was also confirmed that the decellularized intestinal tissue-derived hydrogel scaffold can be successfully applied to culture of intestinal organoids derived from various stem cells (e.g., human induced pluripotent stem cells, embryonic stem cells) in addition to intestinal tissue-derived adult stem cells and three-dimensional culture of spheroids derived from colorectal cancer. Therefore, it is possible to provide an in vitro model system that can implement various disease models.

Hereinafter, Examples will be presented for understanding of the present disclosure. However, the following Examples are illustrative only for better understanding of the present disclosure but do not limit the present disclosure.

Figure 1:
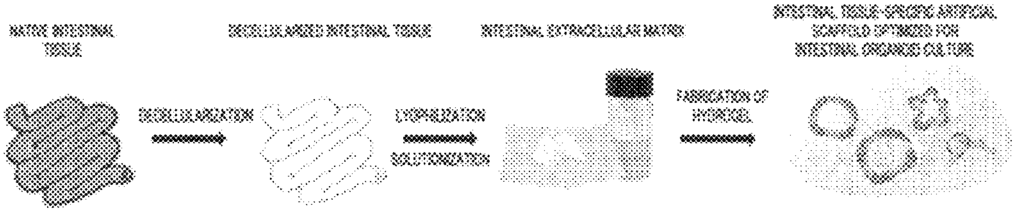
FIG. 1 is a schematic diagram showing the fabrication of a decellularized intestinal tissue-derived artificial scaffold.

Example 1: Preparation of Scaffold Composition Containing Intestinal Extracellular Matrix A scaffold composition containing an intestinal extracellular matrix was prepared as described below (see FIG. 1).

Example 1-1. Preparation of Intestinal Extracellular Matrix (IEM)

All mucosal layers of the porcine small intestine were prepared, and the intestinal tissue was stirred with 1% TRITON X-100™ and 0.1% ammonium hydroxide for 48 hours to remove only the cells of the intestinal tissue and prepare a decellularized intestinal tissue.

Thereafter, the decellularized intestinal tissue was lyophilized and ground to prepare an intestinal extracellular matrix (IEM).

Example 1-2. Preparation of Scaffold Composition 10 mg of the IEM was dissolved in a 4 mg/ml pepsin solution (a solution of 4 mg of pepsin powder derived from porcine intestinal mucosa in 1 ml of 0.02 M HCl) for 48 hours. Water:IEM solution:PBS buffer:NaOH was mixed at a ratio of 69:20:10:1, blended uniformly, and gelated at a temperature of 37° C. for 30 minutes to prepare a scaffold composition in the form of a hydrogel.

Test Example 1: Analysis of IEM

The IEM of Example 1-1 was analyzed as follows.

Test Example 1-1. Examination of Degree of Decellularization of IEM, Etc

The degree of decellularization of the IEM prepared in Example 1-1 and the formation of a hydrogel was examined.

Figure 2A:
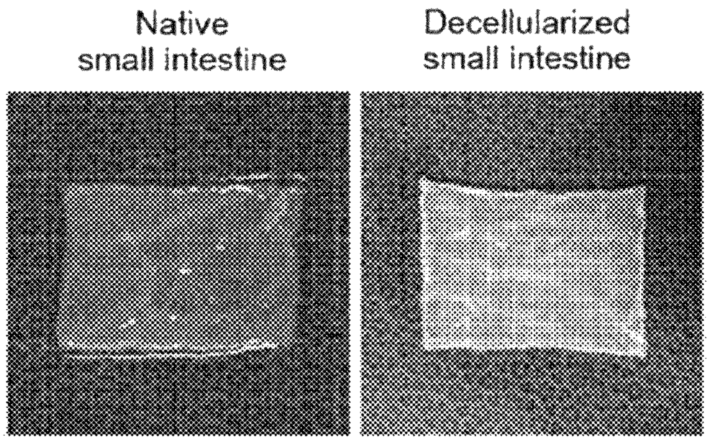
FIG. 2A shows the fabrication of a decellularized intestinal tissue-derived hydrogel scaffold and the analysis of its microstructure.
Figure 2B:
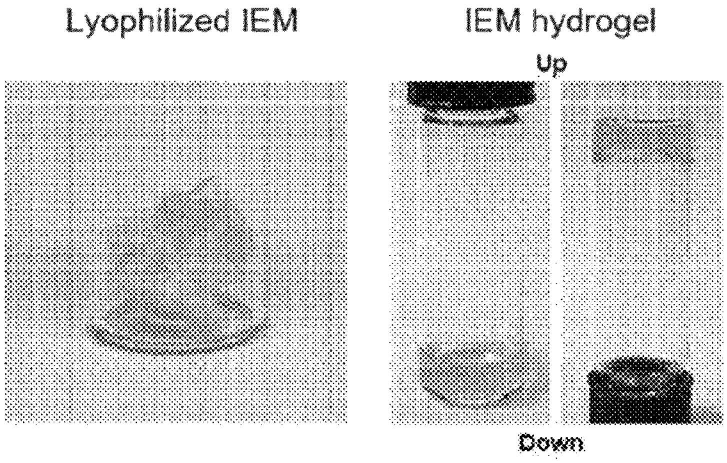
FIG. 2B shows the fabrication of a decellularized intestinal tissue-derived hydrogel scaffold and the analysis of its microstructure.
Figure 2C:
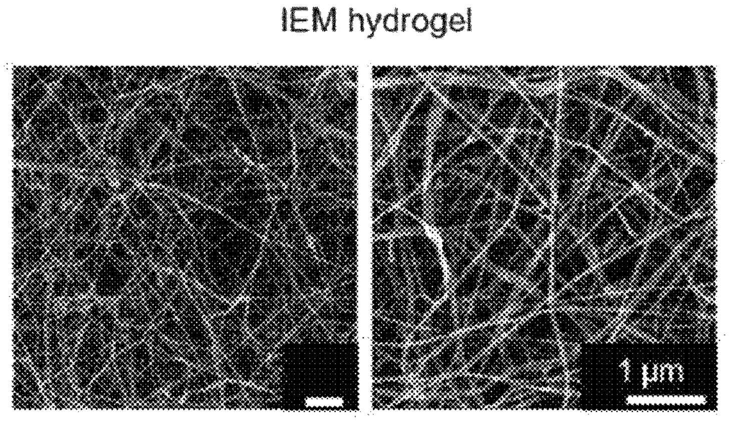
FIG. 2C shows the fabrication of a decellularized intestinal tissue-derived hydrogel scaffold and the analysis of its microstructure.

As a result, as shown in FIG. 2, it was visually observed that the decellularized intestinal tissue of Example 1-1 turned white because the cells were removed by decellularization, but the overall intestinal tissue structure remained intact. (FIG. 2A). As for a hydrogel prepared using the decellularized intestinal tissue, a solution was put in a glass vial and subjected to gelation. Then, it was observed that the solution did not flow down when turned over after gelation. Thus, it was confirmed that the hydrogel was solidified by crosslinking by temperature (FIG. 2B). Thereafter, when a microstructure inside the three-dimensional IEM hydrogel was analyzed using a scanning electron microscope (SEM), it was observed to have a nanofibrous structure similar to collagen (FIG. 2C).

Test Example 1-2. Analysis of Components of IEM

Components of the IEM prepared in Example 1-1 were analyzed and a level of preservation of the IEM was examined.

Specifically, DNAs extracted from the intestinal tissue before and after decellularization were compared, and the glycosaminoglycan (GAG) content was compared by 1,9-dimethylmethylene blue staining.

For histological analysis, the tissue before and after decellularization was fixed for 1 day using a 4% paraformaldehyde solution, embedded in paraffin and sliced, followed by hematoxylin and eosin (H&E) staining.

To analyze proteome of the decellularized intestinal tissue-derived scaffold, the prepared scaffold was solubilized using a lysis buffer [4% sodium dodecyl sulfate (SDS), 0.1 M Tris-HCl (pH 7.6) and 1× protease inhibitor] and protein components were extracted and degraded to the peptide level. Then, the types and relative values of the peptides were detected using a mass spectrometer and MaxQuant software. Thereafter, a detailed classification, such as into matrisome, was performed using the existing library.

Figure 3A:
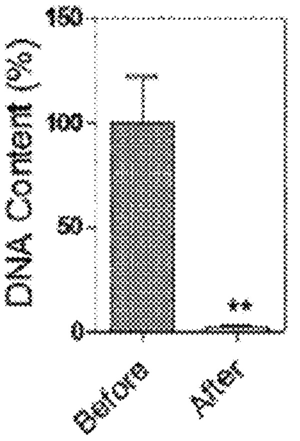
FIG. 3A shows the analysis of the components of the decellularized intestinal tissue-derived artificial scaffold.
Figure 3B:
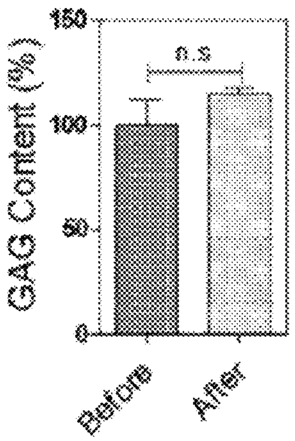
FIG. 3B shows the analysis of the components of the decellularized intestinal tissue-derived artificial scaffold.
Figure 3C:
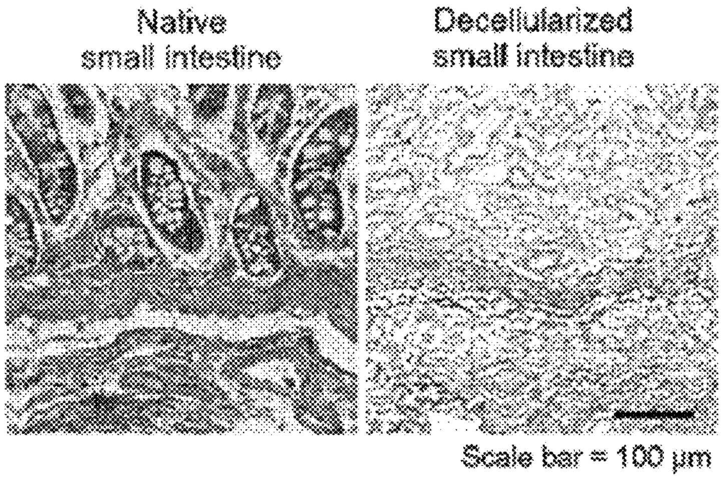
FIG. 3C shows the analysis of the components of the decellularized intestinal tissue-derived artificial scaffold.

As shown in FIG. 3, as a result of comparing the amount of DNA in the intestinal tissue before decellularization (Before) and after decellularization (After), it was confirmed that 97.68% of the cells were efficiently removed by decellularization (FIG. 3A). As a result of comparing the amount of GAG in the intestinal tissue before decellularization (Before) and after decellularization (After), it was confirmed that the extracellular matrix components remained even after decellularization (FIG. 3B). As a result of comparing H&E staining of the intestinal tissue before and after decellularization, it was confirmed that most of the cell nuclei were removed from the tissue after decellularization and the extracellular matrix components were preserved (FIG. 3C). As a result of proteomics for each batch of the decellularized intestinal tissue using mass spectrometry, it was confirmed that various types of intestinal tissue-specific extracellular matrix components remained in common (FIG. 3D).

Test Example 1-3. Comparison Between IEM of Present Disclosure and Prior Art (1)

The IEM of the present disclosure was compared with the prior art. Specifically, decellularization was performed using the same porcine small intestine according to Protocol 1 for a decellularization process developed in the present disclosure and Protocol 2 for a decellularization process of the prior art.

Specifically, DNAs extracted from the intestinal tissue before and after decellularization were compared, and the GAG content was compared by 1,9-dimethylmethylene blue staining.

For histological analysis, the tissue before and after decellularization was each fixed for 1 day using a 4% paraformaldehyde solution, embedded in paraffin and sliced, followed by H&E staining.

To analyze proteome of the decellularized intestinal tissue-derived scaffold, the prepared scaffold was solubilized using a lysis buffer [4% sodium dodecyl sulfate (SDS), 0.1 M Tris-HCl (pH 7.6) and 1× protease inhibitor] and protein components were extracted and degraded to the peptide level. Then, the types and relative values of the peptides were detected using a mass spectrometer and MaxQuant software. Thereafter, a detailed classification, such as into matrisome, was performed using the existing library.

Figure 4A:
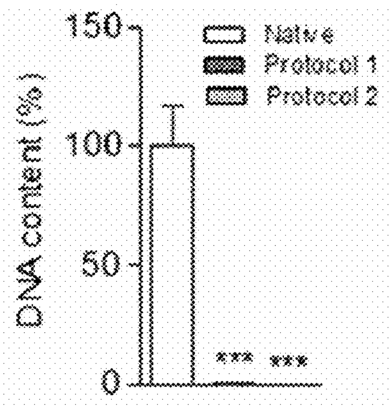
FIG. 4A shows the comparison between a decellularization protocol of the present disclosure and a conventional protocol in terms of matrix components and properties.

As a result of comparing the amount of DNA in the native intestinal tissue (Native), the intestinal tissue decellularized according to the protocol of the present disclosure (Protocol 1), and the intestinal tissue decellularized according to the previously reported protocol (Protocol 2), it was confirmed that the cells can be efficiently removed from in the tissue according to both protocols (FIG. 4A).

Figure 4B:
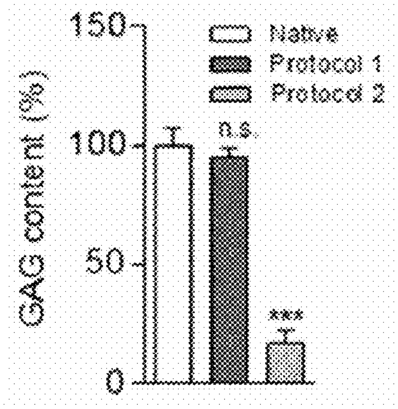
FIG. 4B shows the comparison between a decellularization protocol of the present disclosure and a conventional protocol in terms of matrix components and properties.

As a result of comparing the amount of GAG, it was confirmed that the GAG content according to Protocol 1 was preserved at the native tissue level, but the GAG content according to Protocol 2 was only preserved to about 16% of the GAG content in the native tissue (FIG. 4B).

Figure 4C:
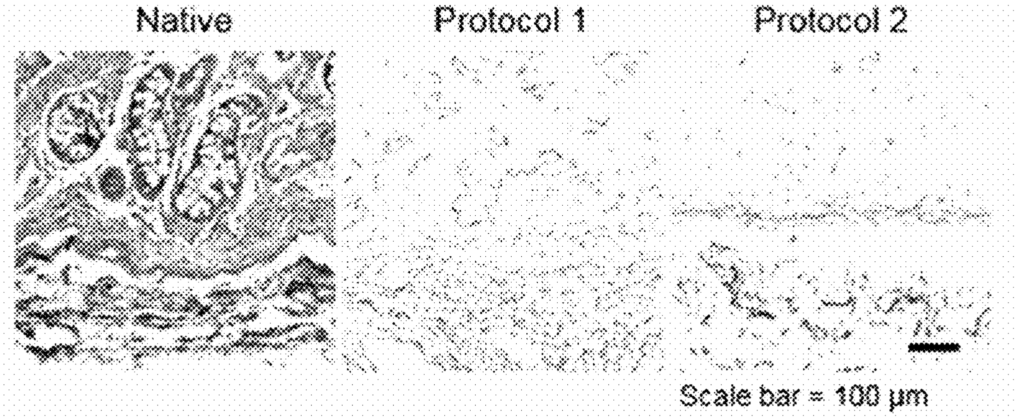
FIG. 4C shows the comparison between a decellularization protocol of the present disclosure and a conventional protocol in terms of matrix components and properties.

As a result of comparing H&E staining, it was confirmed that most of the cell nuclei were removed from the tissue after decellularization and the extracellular matrix components were preserved (FIG. 4C).

Figure 4D:
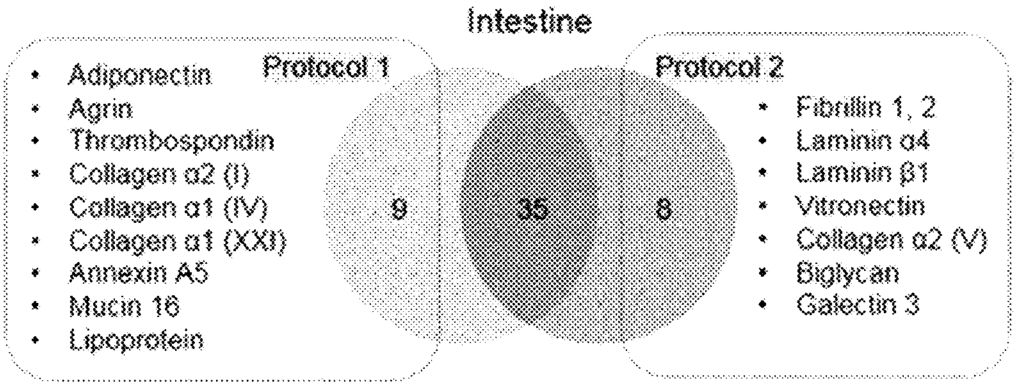
FIG. 4D shows the comparison between a decellularization protocol of the present disclosure and a conventional protocol in terms of matrix components and properties.

Also, as a result of comparing the types of proteins detected from each extracellular matrix, it was confirmed that various types of proteins remained in the intestinal tissue processed according to the protocol of the present disclosure (FIG. 4D).

Figure 4E:
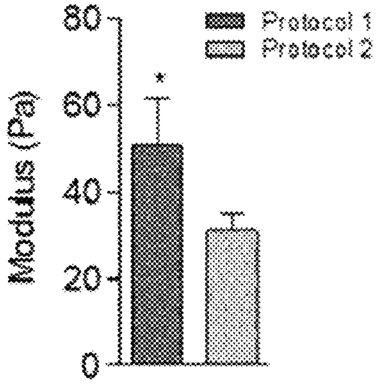
FIG. 4E shows the comparison between a decellularization protocol of the present disclosure and a conventional protocol in terms of matrix components and properties.

Meanwhile, when 5 mg/ml hydrogel scaffolds were fabricated using the decellularized intestinal tissues prepared according to the respective protocols and the mechanical properties (modulus) thereof were compared, it was confirmed that the decellularized intestinal tissue-derived hydrogel scaffold fabricated according to the protocol of the present disclosure has better mechanical properties even at the same concentration (FIG. 4E).

The previously reported protocol (Protocol 2) uses an ionic sodium deoxycholate-based decellularization solution, whereas the protocol of the present disclosure uses more mild conditions based on a mixed solution of non-ionic 1% TRITON X-100™ and 0.1% ammonium hydroxide. Therefore, it was confirmed that according to the protocol of the present disclosure, more proteins can be preserved in the intestinal tissue and the hydrogel scaffold prepared accordingly has better mechanical properties.

Test Example 1-4. Comparison Between IEM of Present Disclosure and Prior Art (2)

The IEM of the present disclosure was compared with the prior art. Specifically, decellularization was performed using the same porcine small intestine according to Protocol 1 for the decellularization process developed in the present disclosure and Protocol 3 for a typical decellularization process which is not optimized for intestinal tissue.

Specifically, DNAs extracted from the intestinal tissue before and after decellularization were compared, and the GAG content was compared by 1,9-dimethylmethylene blue staining.

For histological analysis, the tissue before and after decellularization was each fixed for 1 day using a 4% paraformaldehyde solution, embedded in paraffin and sliced, followed by H&E staining.

To analyze proteome of the decellularized intestinal tissue-derived scaffold, the prepared scaffold was solubilized using a lysis buffer [4% sodium dodecyl sulfate (SDS), 0.1 M Tris-HCl (pH 7.6) and 1× protease inhibitor] and protein components were extracted and degraded to the peptide level. Then, the types and relative values of the peptides were detected using a mass spectrometer and MaxQuant software. Thereafter, a detailed classification, such as into matrisome, was performed using the existing library.

Figure 5A:
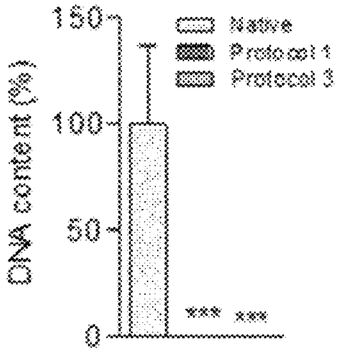
FIG. 5A shows the comparison between the decellularization protocol of the present disclosure and the conventional protocol in terms of matrix components and properties.

As a result of comparing the amount of DNA in the native intestinal tissue (Native), the intestinal tissue decellularized according to the protocol of the present disclosure (Protocol 1), and the intestinal tissue decellularized according to the typical protocol (Protocol 3), it was confirmed that the cells can be efficiently removed from in the tissue according to both protocols (FIG. 5A).

Figure 5B:
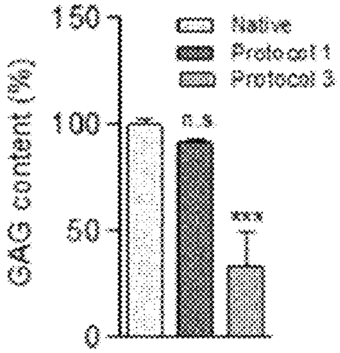
FIG. 5B shows the comparison between the decellularization protocol of the present disclosure and the conventional protocol in terms of matrix components and properties.

As a result of comparing the amount of GAG, it was confirmed that the GAG content according to Protocol 1 was preserved at the native tissue level, but the GAG content according to Protocol 3 was only preserved to about 33% of the GAG content in the native tissue (FIG. 5B).

Figure 5C:
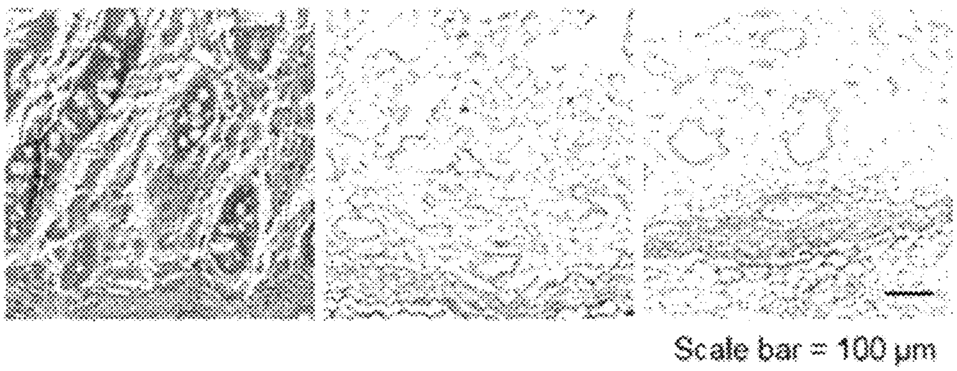
FIG. 5C shows the comparison between the decellularization protocol of the present disclosure and the conventional protocol in terms of matrix components and properties.

As a result of comparing H&E staining, it was confirmed that most of the cell nuclei were removed from the tissue after decellularization and the extracellular matrix components were preserved (FIG. 5C).

Figure 5D:
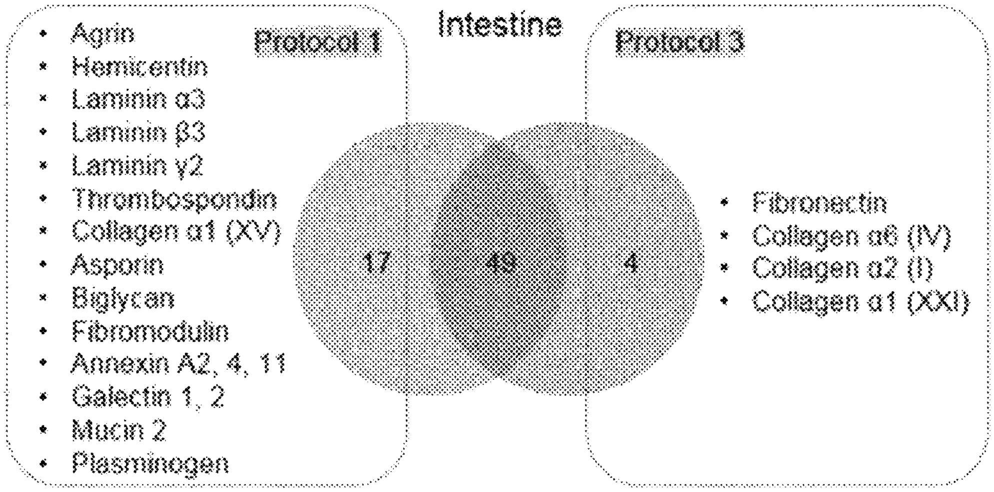
FIG. 5D shows the comparison between the decellularization protocol of the present disclosure and the conventional protocol in terms of matrix components and properties.

Also, as a result of comparing the types of detected proteins, it was confirmed that various types of proteins remained in the intestinal tissue processed according to the protocol of the present disclosure (FIG. 5D).

Figure 5E:
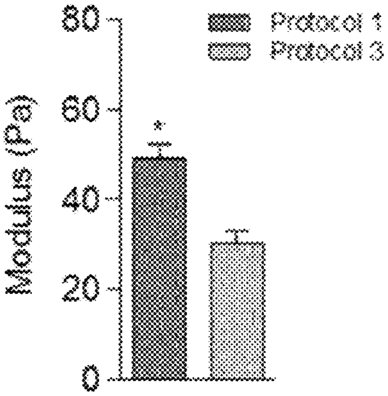
FIG. 5E shows the comparison between the decellularization protocol of the present disclosure and the conventional protocol in terms of matrix components and properties.

When 5 mg/ml hydrogel scaffolds were fabricated using the decellularized intestinal tissues prepared according to the respective protocols and the mechanical properties (modulus) thereof were compared, it was confirmed that the decellularized intestinal tissue-derived hydrogel scaffold fabricated according to the protocol of the present disclosure has better mechanical properties even at the same concentration (FIG. 5E).

The typical protocol (Protocol 3) as a comparative protocol uses TRITON X-100™ and ionic sodium deoxycholate, whereas the protocol of the present disclosure (Protocol 1) uses only a mixed solution of 1% TRITON X-100™ and 0.1% ammonium hydroxide. Therefore, it was confirmed that according to Protocol 1, more proteins can be preserved in the intestinal tissue and the hydrogel scaffold fabricated accordingly has better mechanical properties.

Test Example 1-5. Comparison Between IEM of Present Disclosure and Prior Art (3)

The IEM of the present disclosure was compared with the prior art in terms of intestinal organoid growth pattern. Specifically, decellularization was performed using the same porcine small intestine according to Protocol 1 for the decellularization process developed in the present disclosure and Protocol 3 for the typical decellularization process which is not optimized for intestinal tissue. The hydrogels were fabricated with decellularized tissues and tests using the hydrogels as intestinal organoid culture scaffolds were conducted.

Specifically, intestinal crypts containing intestinal stem cells were extracted and three-dimensionally cultured for 6 days in the decellularized intestinal tissue-derived hydrogels fabricated according to Protocol 1 and Protocol 3, respectively. The growth pattern of organoids formed on the $6^{th}$ day was examined, and the formation efficiency was quantified.

Figure 6A:
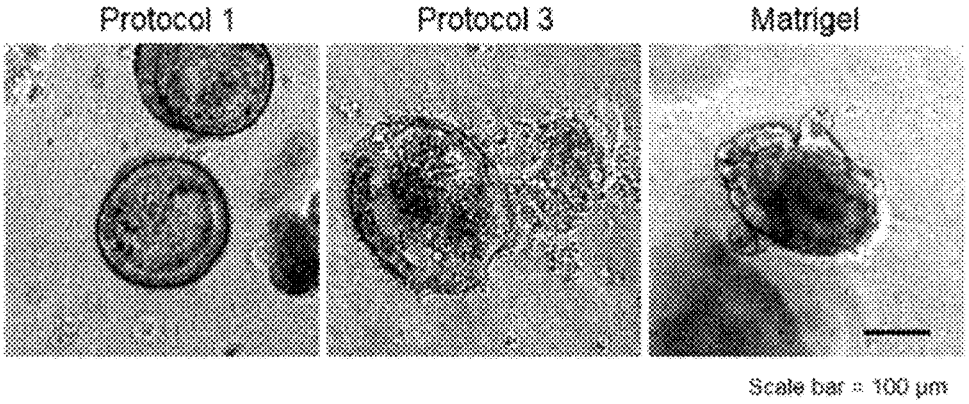
FIG. 6A shows the comparison between the decellularization protocol of the present disclosure and the conventional protocol in terms of organoid growth pattern.
Figure 6B:
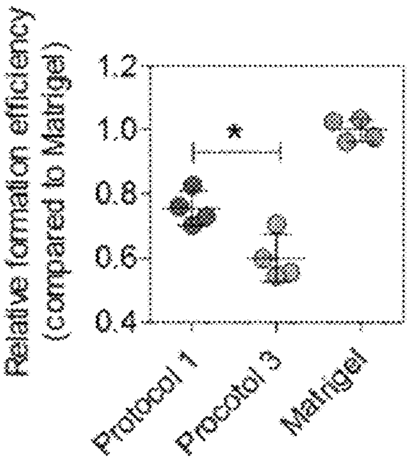
FIG. 6B shows the comparison between the decellularization protocol of the present disclosure and the conventional protocol in terms of organoid culture pattern.

As a result of comparing the formation pattern and formation efficiency of the intestinal organoids cultured in the decellularized intestinal tissue-derived hydrogel (Protocol 1) prepared according to the protocol of the present disclosure and the intestinal tissue-derived hydrogel (Protocol 3) prepared by decellularization according to the typical protocol as can be seen from FIG. 6A and FIG. 6B, it was confirmed that the intestinal organoids formed irregularly in the decellularized intestinal tissue-derived scaffold fabricated by the typical protocol (Protocol 3) with a low formation efficiency, whereas the intestinal organoids were formed in a normal pattern in the decellularized intestinal tissue-derived scaffold fabricated by the protocol of the present disclosure (Protocol 1) with a high formation efficiency.

According to these results, the extracellular matrix hydrogel fabricated by the typical decellularization process has weak mechanical properties and a lot of extracellular matrix proteins unique to the intestinal tissue are lost, whereas the extracellular matrix hydrogel fabricated according to the protocol of the present disclosure has better mechanical properties and is rich in extracellular matrix proteins unique to the intestinal tissue. Therefore, it can be seen that the decellularization process of the present disclosure is more suitable for preparing an intestinal organoid culture scaffold.

Test Example 1-6. Comparative Analysis of Proteome of IEM of Present Disclosure and Prior Art The IEM of the present disclosure and the prior art (MATRIGEL®) were compared and analyzed in terms of proteome.

Specifically, to analyze proteome of the decellularized intestinal tissue-derived scaffold, the prepared scaffold was solubilized using a lysis buffer [4% sodium dodecyl sulfate (SDS), 0.1 M Tris-HCl (pH 7.6) and 1× protease inhibitor] and protein components were extracted and degraded to the peptide level. Then, the types and relative values of the peptides were detected using a mass spectrometer and MaxQuant software. Thereafter, a detailed classification, such as into matrisome, was performed using the existing library.

Figure 7A:
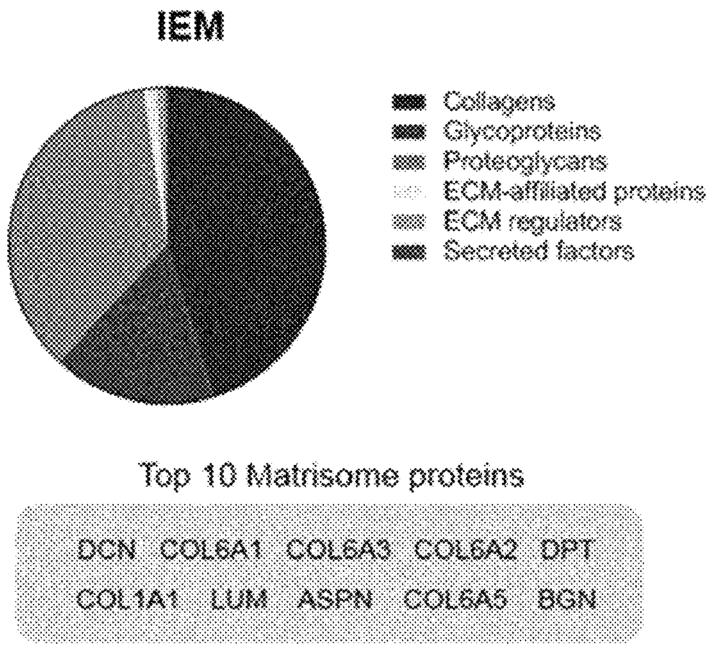
FIG. 7A shows the comparative analysis of proteome of a scaffold composition of the present disclosure and a conventional culture scaffold (MATRIGEL®).
Figure 7B:
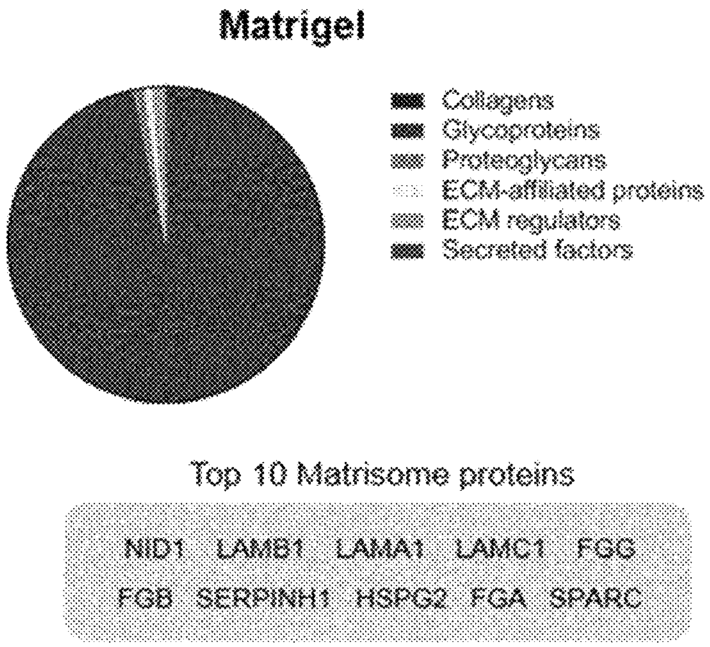
FIG. 7B shows the comparative analysis of proteome of a scaffold composition of the present disclosure and a conventional culture scaffold (MATRIGEL®).

As a result, as can be seen from FIG. 7, the content ratio of matrisome proteins [extracellular matrix proteins (ECM proteins)+extracellular matrix component-associated proteins (ECM-associated proteins)] in the IEM scaffold (IEM) (pie chart) and the top 10 most abundant matrisome proteins, and the content ratio of matrisome proteins in MATRIGEL®, which is a conventional organoid culture scaffold (pie chart) and top 10 most abundant matrisome proteins were checked (FIG. 7A and FIG. 7B).

Figure 7C:
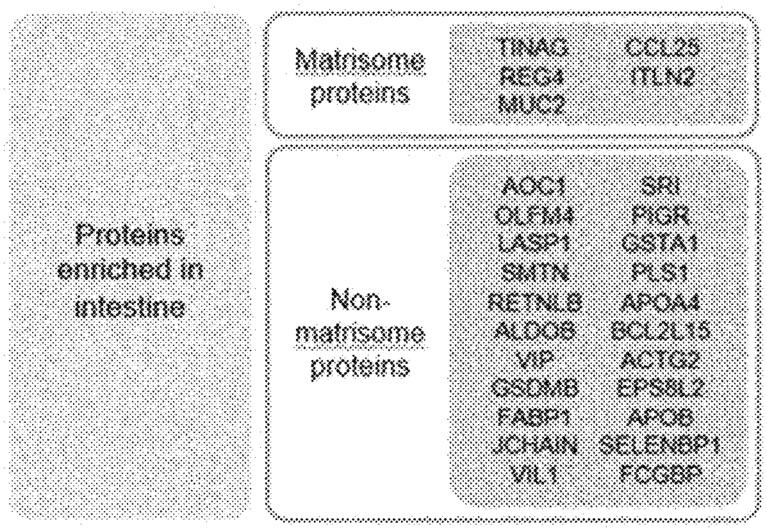
FIG. 7C shows the comparative analysis of proteome of a scaffold composition of the present disclosure and a conventional culture scaffold (MATRIGEL®).
Figure 7D:
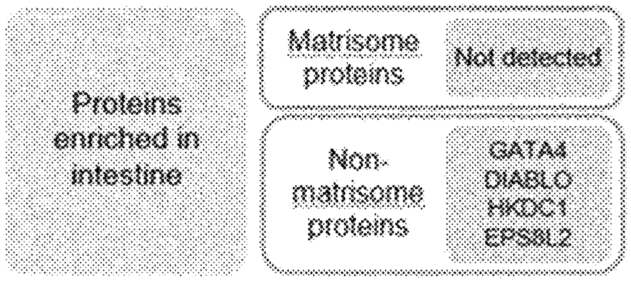
FIG. 7D shows the comparative analysis of proteome of a scaffold composition of the present disclosure and a conventional culture scaffold (MATRIGEL®).

The types of proteins that are highly expressed specifically in the intestinal tissue and present in the IEM scaffold (IEM) and the types of proteins that are highly expressed specifically in the intestinal tissue and present in MATRIGEL® were identified (FIG. 7C and FIG. 7D).

Accordingly, it was confirmed that the decellularized intestinal tissue-derived IEM scaffold has a high content of matrisome proteins present in the intestinal tissue such as collagen type 6, decorin (DCN), dermatopontin (DPT), and biglycan (BGN). Also, it was confirmed that the decellularized intestinal tissue-derived IEM scaffold contains 5 types of matrisome proteins and 22 types of non-matrisome proteins enriched in the intestinal tissue, whereas MATRIGEL® is mainly composed of glycoprotein unlike the intestinal tissue and contains only 4 types of non-matrisome proteins as intestinal tissue-specific proteins.

According to these results, it can be predicted that the decellularized intestinal tissue-derived IEM scaffold can provide an extracellular matrix microenvironment more suitable for the formation and differentiation of an intestinal organoid than the conventional MATRIGEL®.

Also, as can be seen from FIG. 8, as a result of comparing the types of matrisome proteins contained in the decellularized intestinal tissue-derived IEM scaffold and MATRIGEL®, much more diverse types of matrisome proteins and matrisome-associated proteins are present in the IEM scaffold than in MATRIGEL® (FIG. 8A).

Further, it was confirmed that in the decellularized intestinal tissue-derived IEM scaffold, collagen is present with the highest content of about 45%, proteoglycan accounts for 35% and glycoprotein accounts for about 16%. Also, it was confirmed that in MATRIGEL®, which is a conventional culture scaffold, glycoprotein accounts for about 96% and the amount of the remaining proteins is very small around 1% (FIG. 8B). That is, it can be seen that the IEM scaffold has a composition ratio of matrisome proteins more similar to that of the intestinal tissue compared to MATRIGEL®.

Meanwhile, as can be seen from FIG. 9, not matrisome proteins but non-matrisome proteins account for about 59% of the prepared decellularized intestinal tissue-derived IEM scaffold. The genomic functions of the non-matrisome proteins were analyzed by gene ontology of biological process, and it was confirmed that the non-matrisome proteins contained in the IEM scaffold are mainly responsible for the functions related to cellular component biogenesis, cytoskeleton organization, and structural development (FIG. 9A).

Figure 9B:
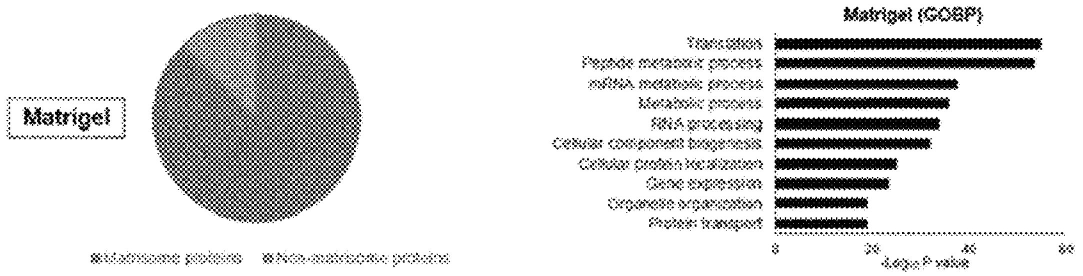
FIG. 9B shows the comparative analysis of the proteome of the scaffold composition of the present disclosure and the conventional culture scaffold (MATRIGEL®).

However, matrisome proteins account for about 12% of MATRIGEL® and most of the rest are non-matrisome proteins, and it can be seen that the proteins are responsible for the functions involved in translation and RNA and peptide metabolism (FIG. 9B).

According to these results, the decellularized intestinal tissue-derived IEM scaffold prepared in the present disclosure contains matrisome proteins similar to those of the intestinal tissue and also contains non-matrisome proteins mainly responsible for cell composition formation and structure formation. Thus, it can be predicted that the decellularized intestinal tissue-derived IEM scaffold can be more effective in the formation and development of an intestinal organoid than MATRIGEL®.

Test Example 2: Analysis of Scaffold Composition Containing IEM

The scaffold composition prepared in Example 1-2 was analyzed as described below.

Test Example 2-1. Examination of Mechanical Properties of Scaffold Composition

The mechanical properties of the scaffold composition (hydrogel) prepared in Example 1-2 were compared and checked.

Specifically, an elastic modulus G' and a viscous modulus G" at a frequency in the range of 0.1 Hz to 1 Hz were measured with a rotary rheometer to analyze the mechanical properties of the hydrogel scaffold based on decellularized intestinal tissue-derived extracellular matrix components of 1 mg/ml to 5 mg/ml (IEM $1^{-5}$ mg/ml).

Figure 10A:
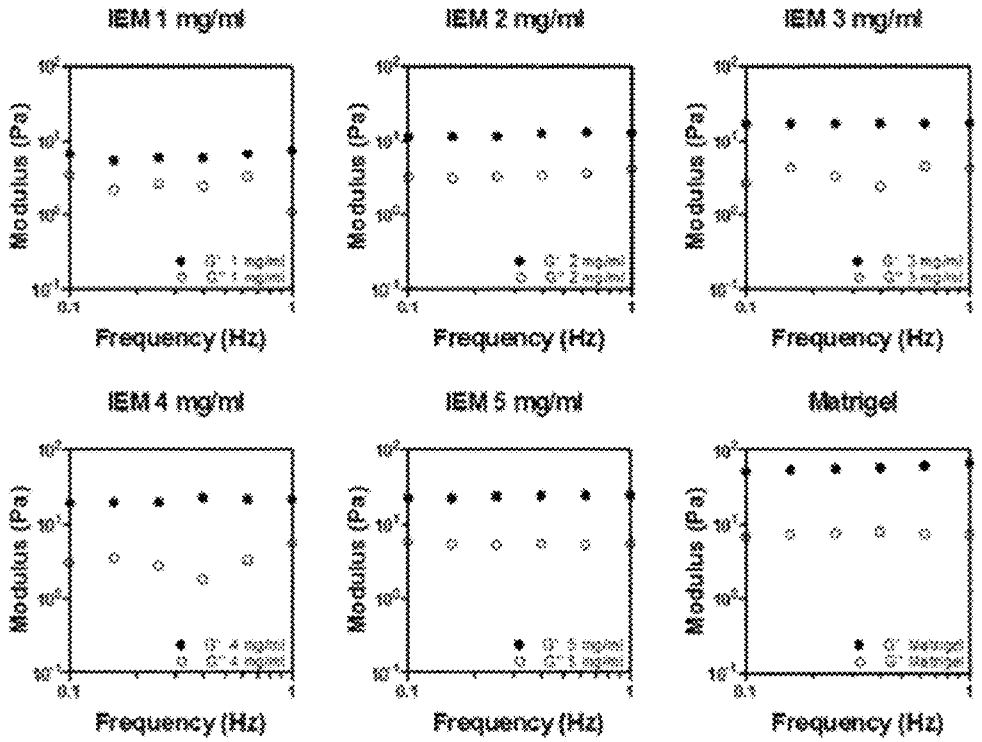
FIG. 10A shows the analysis of elastic modulus of the decellularized intestinal tissue-derived hydrogel scaffold.
Figure 10B:
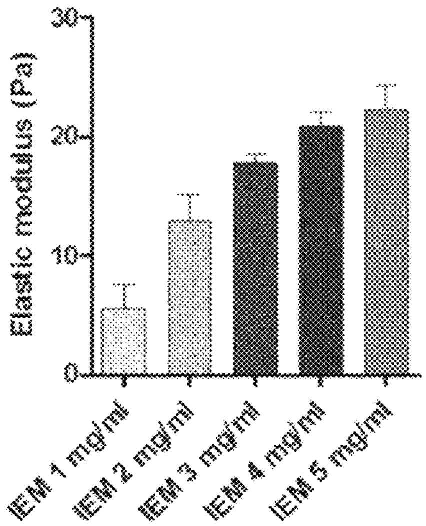
FIG. 10B shows the analysis of properties of the decellularized intestinal tissue-derived hydrogel scaffold.
Figure 11A:
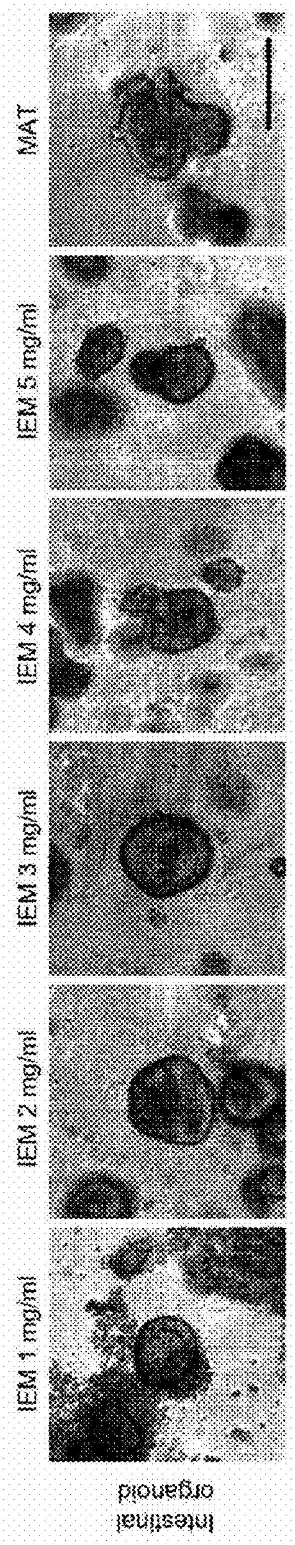
FIG. 11A shows the determination of optimal concentration of the decellularized intestinal tissue-derived hydrogel scaffold for intestinal organoid culture.
Figure 11B:
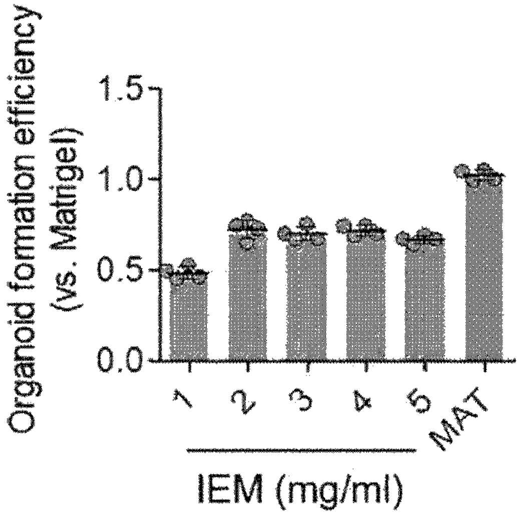
FIG. 11B shows the determination of optimal concentration of the decellularized intestinal tissue-derived hydrogel scaffold for intestinal organoid culture.
Figure 11C:
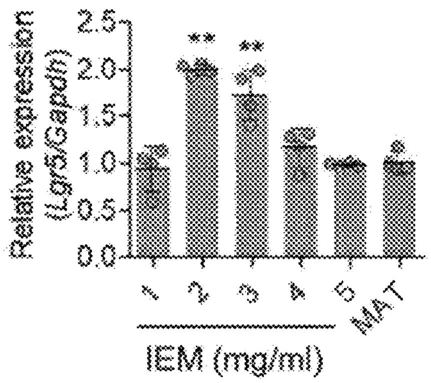
FIG. 11C shows the determination of optimal concentration of the decellularized intestinal tissue-derived hydrogel scaffold for intestinal organoid culture.
Figure 11D:
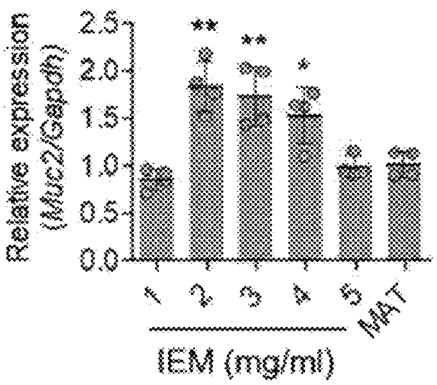
FIG. 11D shows the determination of optimal concentration of the decellularized intestinal tissue-derived hydrogel scaffold for intestinal organoid culture.

As a result, it was confirmed that in the IEM hydrogels of all concentrations including an IEM hydrogel of the lowest concentration of 1 mg/ml, a stable polymer network was formed therein after crosslinking for 30 minutes (G'>G''') (FIG. 10A). It was found that as the IEM concentration increased, the mechanical properties (modulus) of the IEM hydrogel also increased (FIG. 10B).

Test Example 2-2. Examination of Optimal Condition for Scaffold Composition

The optimal conditions for the scaffold composition (hydrogel) prepared in Example 1-2 were examined.

Specifically, the jejunum of a mouse was collected and the food and villi were removed, followed by washing several times. Then, the crypt where intestinal stem cells are present was isolated with high efficiency through ethylenediaminetetraacetic acid (EDTA) treatment and washing several times. The crypt tissue was cultured in the hydrogel scaffold of each concentration according to the present disclosure and MATRIGEL®, and a three-dimensional intestinal organoid development pattern was compared and examined.

As a result, as shown in FIG. 11, it was confirmed from the analyses described above that an intestinal organoid can be cultured in the decellularized intestinal tissue-derived IEM hydrogel scaffolds of all concentrations and the intestinal organoid cultured in the IEM hydrogel of a concentration of 2 mg/ml exhibits the most excellent stemness and ability to differentiate into intestine-specific cells.

Test Example 2-3. Examination of Growth Pattern of Intestinal Organoid Cultured in Scaffold Composition A growth pattern of the intestinal organoid cultured in the scaffold composition (hydrogel) prepared in Example 1-2 was examined.

Specifically, growth patterns of intestinal organoids developed from the intestinal crypts three-dimensionally cultured in the scaffold composition (hydrogel) of the present disclosure and MATRIGEL® were traced and checked according to the date (from day 1 to day 6 of culture).

Figure 12:
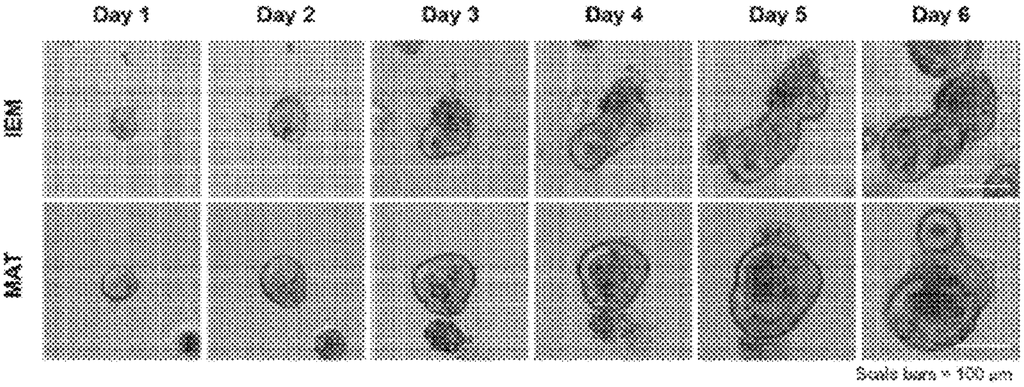
FIG. 12 shows the growth pattern of an intestinal organoid cultured in the decellularized intestinal tissue-derived hydrogel scaffold.

As a result, as shown in FIG. 12, it was confirmed that the intestinal organoid in the decellularized intestinal tissue-derived IEM hydrogel scaffold grew at a similar growth rate to a similar size to the intestinal organoid in MATRIGEL®. It was found that the developed IEM hydrogel scaffold has the ability to culture an intestinal organoid, similarly to the commercially available MATRIGEL® scaffold.

Test Example 2-4. Analysis of Expression of Stem Cells and Differentiation Markers of Intestinal Organoid Cultured in Scaffold Composition (Cell Immunostaining Analysis)

The expression of stem cells and differentiation markers of the intestinal organoid cultured in the scaffold composition (hydrogel) prepared in Example 1-2 was analyzed by cell immunostaining analysis.

Specifically, the cultured organoid was fixed in 4% paraformaldehyde for 1 hour and treated with 0.5% TRITON X-100™ for 1 hour, followed by blocking (suppression of non-specific protein reaction) with a 5% BSA solution. Thereafter, the organoid was treated with tissue-specific antibodies for cell immunostaining.

Figure 13A:
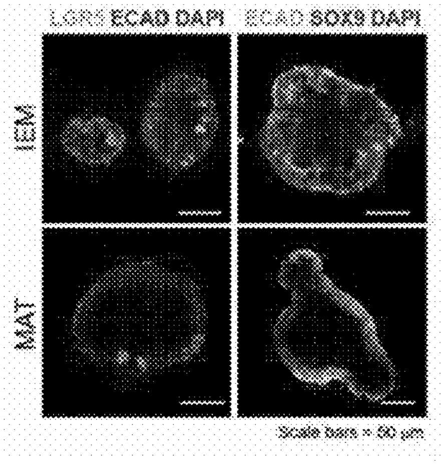
FIG. 13A shows the analysis of the expression of stem cells and differentiation markers of the intestinal organoid cultured in the decellularized intestinal tissue-derived hydrogel scaffold (cell immunostaining analysis).
Figure 13B:
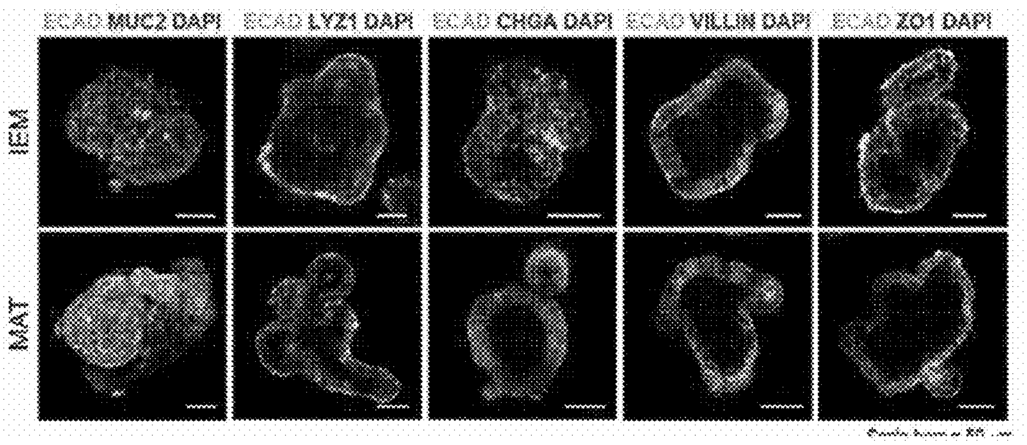
FIG. 13B shows the analysis of the expression of stem cells and differentiation markers of the intestinal organoid cultured in the decellularized intestinal tissue-derived hydrogel scaffold (cell immunostaining analysis).

As a result, as can be seen from FIG. 13, the result of cell immunostaining for analysis of the expression of stemness markers (LGR5 and SOX9) of the intestinal organoids cultured in the decellularized intestinal tissue-derived IEM hydrogel and MATRIGEL® (FIG. 13A) and the result of cell immunostaining for analysis of the expression of differentiation markers (MUC2, LYZ1, CHGA, VILLIN and ZO1) of the decellularized intestinal tissue-derived IEM hydrogel and MATRIGEL® (FIG. 13B) were obtained.

It can be seen from the analyses described above that there is no difference in the expression level of the specific markers between the intestinal organoids cultured in the decellularized intestinal tissue-derived IEM hydrogel and MATRIGEL®, respectively. Thus, it can be seen that the IEM hydrogel has the ability to induce proliferation and differentiation of an intestinal organoid, similarly to MATRIGEL®.

* LGR5, SOX9: intestinal stem cell marker/ECAD: intestinal epithelial marker

* MUC2: goblet cell marker/LYZ1: Paneth cell marker/CHGA: enteroendocrine cell marker/VILLIN, ZO1: enterocyte marker Test Example 2-5. Analysis of Expression of Stem Cells and Differentiation Markers of Intestinal Organoid Cultured in Scaffold Composition (Quantitative PCR)

The expression of stem cells and differentiation markers of the intestinal organoid cultured in the scaffold composition (hydrogel) prepared in Example 1-2 was analyzed by quantitative PCR.

Specifically, an mRNA sample was extracted from the intestinal organoid using an RNA extraction kit, and a cDNA sample was synthesized from the extracted mRNA using a cDNA synthesis kit. Thereafter, a quantitative PCR analysis was performed using a tissue-specific gene primer.

Figure 14A:
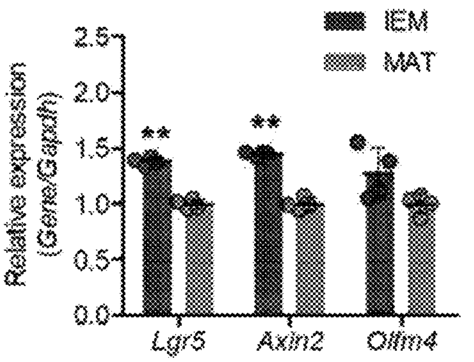
FIG. 14A shows the analysis of the expression of stem cells and differentiation markers of the intestinal organoid cultured in the decellularized intestinal tissue-derived hydrogel scaffold (gene expression analysis through quantitative polymerase chain reaction (PCR)).

As a result, as shown in FIG. 14, it can be seen from qPCR analysis data on the expression of stemness markers of the intestinal organoids cultured in the decellularized intestinal tissue-derived IEM hydrogel and MATRIGEL® that the intestinal organoid cultured in the decellularized intestinal tissue-derived IEM hydrogel scaffold exhibits a higher expression level of the stemness markers than the intestinal organoid cultured in MATRIGEL® (FIG. 14A). This shows that the intestinal organoid cultured in the IEM hydrogel is excellent in proliferative ability.

Figure 14B:
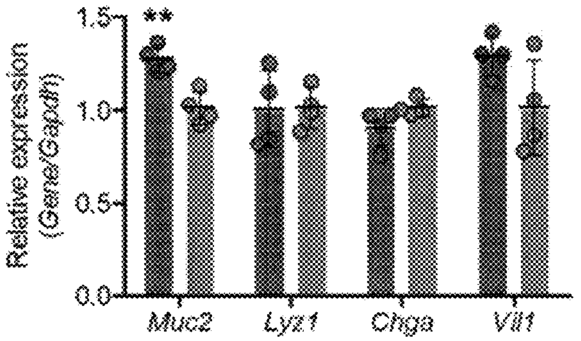
FIG. 14B shows the analysis of the expression of stem cells and differentiation markers of the intestinal organoid cultured in the decellularized intestinal tissue-derived hydrogel scaffold (gene expression analysis through quantitative polymerase chain reaction (PCR)).

Also, it can be seen from qPCR analysis data on the expression of differentiation markers of the intestinal organoids cultured in the decellularized intestinal tissue-derived IEM hydrogel and MATRIGEL® that the intestinal organoid cultured in the decellularized intestinal tissue-derived IEM hydrogel scaffold exhibits an expression level of the differentiation markers, similarly to the intestinal organoid cultured in MATRIGEL® (FIG. 14B). This shows that the IEM hydrogel scaffold can replace the commercially available MATRIGEL® scaffold in terms of its ability to induce differentiation of an organoid.

Test Example 2-6. Verification of Functionality of Intestinal Organoid Cultured in Scaffold Composition The functionality of the intestinal organoid cultured in the scaffold composition (hydrogel) prepared in Example 1-2 was verified.

Specifically, 5 μM forskolin was added to an intestinal organoid culture medium and changes in size of the organoid over time were quantified.

Figure 15A:
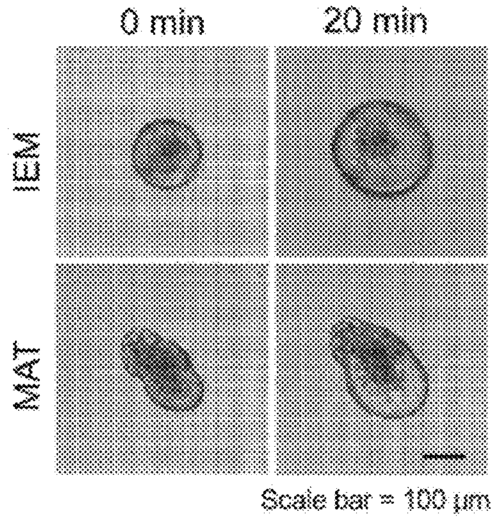
FIG. 15A verifies the functionality of the intestinal organoid cultured in the decellularized intestinal tissue-derived hydrogel scaffold.
Figure 15B:
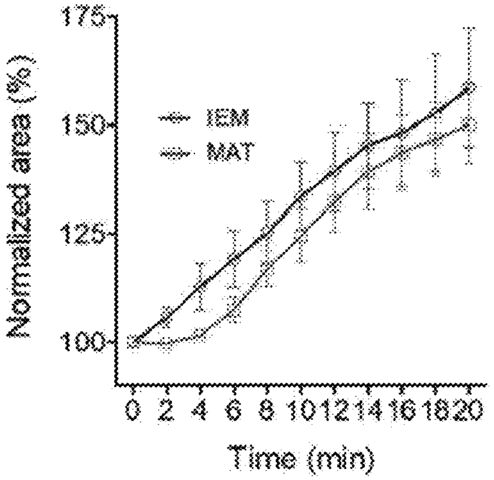
FIG. 15B verifies the functionality of the intestinal organoid cultured in the decellularized intestinal tissue-derived hydrogel scaffold.

As a result, as can be seen from FIG. 15, when the intestinal organoids respectively cultured in the decellularized intestinal tissue-derived IEM hydrogel and MATRIGEL® were treated with forskolin (a chemical that stimulates the opening of ion channels and promotes the release of water), which is an antagonist of cystic fibrosis transmembrane conductance regulator (CFTR) present in the epithelial cells of the intestinal tissue, the lumens of the intestinal organoids was swollen to a similar degree (FIG. 15A). As a result of quantitative analysis of change in area over time after the intestinal organoids respectively cultured in the decellularized intestinal tissue-derived IEM hydrogel and MATRIGEL® were treated with forskolin, it was found that intestinal organoid cultured in the decellularized intestinal tissue-derived IEM hydrogel and the intestinal organoid cultured in MATRIGEL® are similar in the degree of swelling induced by treatment with forskolin. Thus, it was confirmed that the intestinal organoid cultured in the developed IEM hydrogel scaffold has an intestinal tissue-specific functionality to regulate the secretion of electrolyte and water in a human body (FIG. 15B).

Test Example 2-7. Analysis of Gene Expression Profile of Intestinal Organoid Cultured in Scaffold Composition (1) (RNA-Sequencing Analysis)

The gene expression profile of the intestinal organoid cultured in the scaffold composition (hydrogel) prepared in Example 1-2 was analyzed.

Figure 16A:
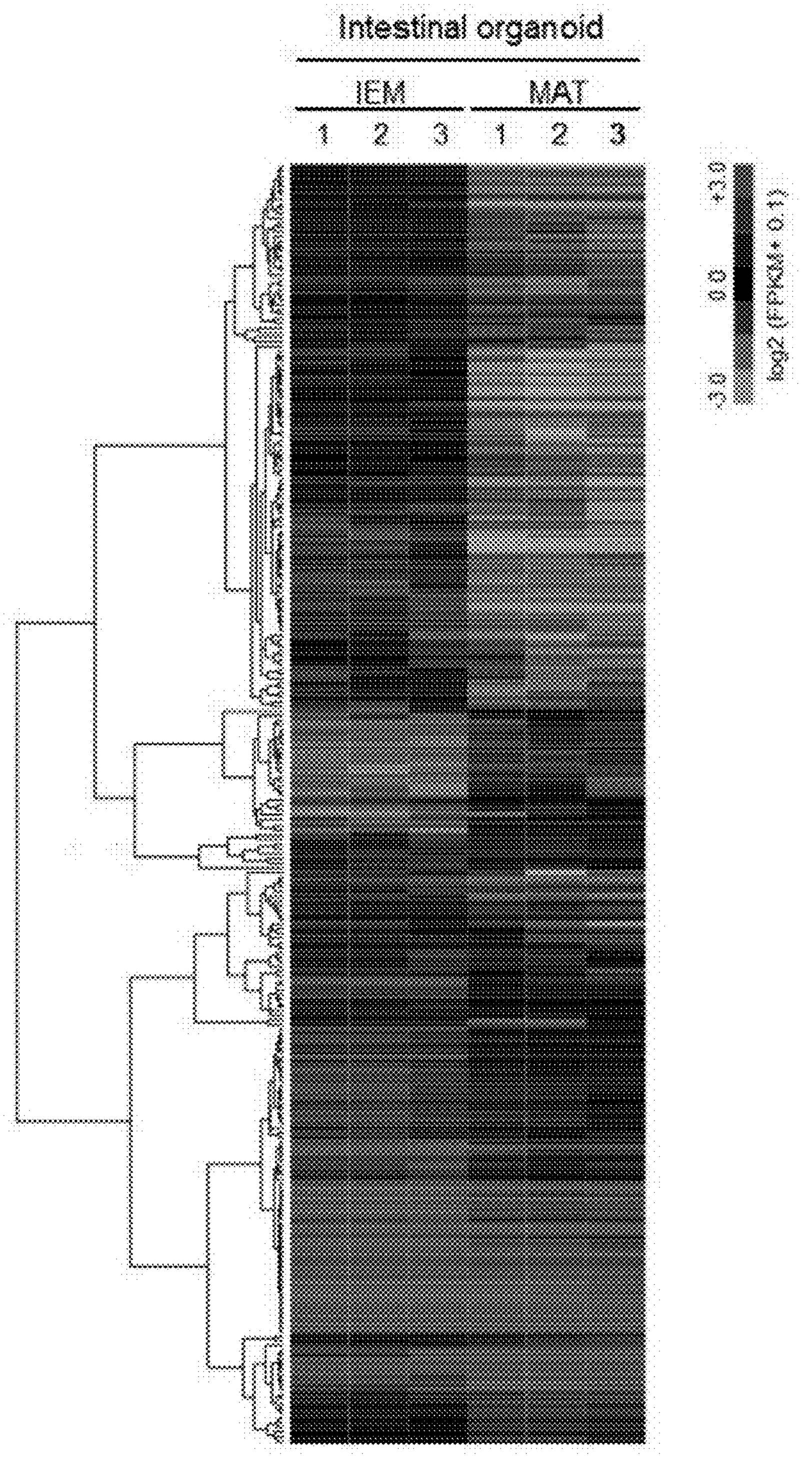
FIG. 16A shows the analysis of the gene expression profile of the intestinal organoid cultured in the decellularized intestinal tissue-derived hydrogel scaffold (RNA-sequencing analysis).

Specifically, information of genes from the organoids cultured in decellularized intestinal tissue-derived hydrogel and MATRIGEL® was classified, and from among these genes, differentially expressed genes (DEGs) were selected based on the statistical criteria of 2 fold, p-value <0.05 and FDR<0.1. As a result, 270 kinds of genes were obtained and these genes were visualized in a heatmap. Accordingly, it was confirmed that when the organoids were cultured in the respective hydrogels, the forms of the organoids were almost similar to each other, but a significant number of genes were differentially expressed (FIG. 16A).

Figure 16B:
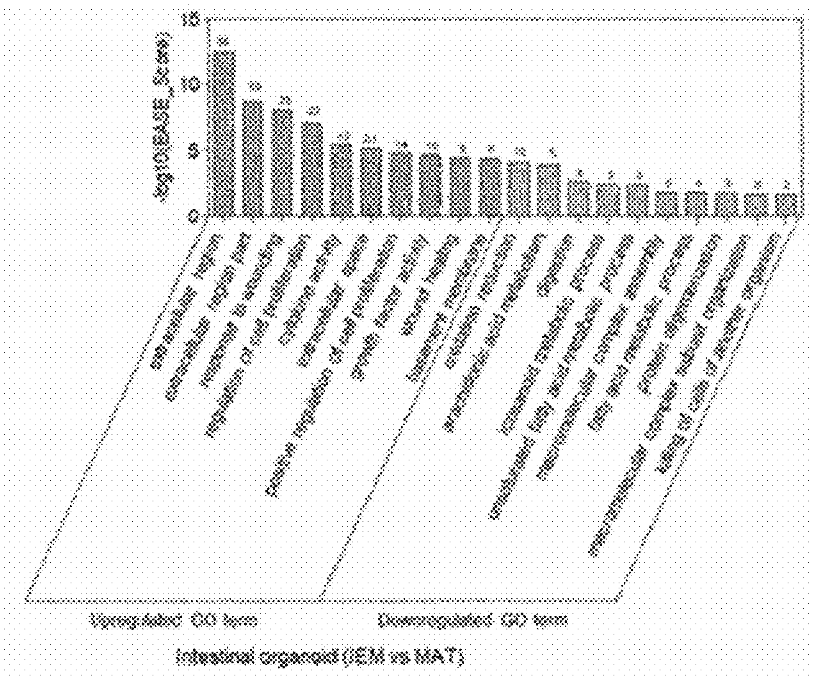
FIG. 16B shows the analysis of the gene expression profile of the intestinal organoid cultured in the decellularized intestinal tissue-derived hydrogel scaffold (RNA-sequencing analysis).

Also, the expression of 213 genes out of 270 DEGs was increased in the intestinal organoid cultured in the decellularized intestinal tissue-derived IEM hydrogel compared to the intestinal organoid cultured in MATRIGEL®, and an increase in the extracellular matrix-related genes was observed highest. The expression of 57 genes out of 270 DEGs was decreased, and a decrease in the genes related to oxidation/reduction and metabolism was observed highest (FIG. 16B).

Figure 16C:
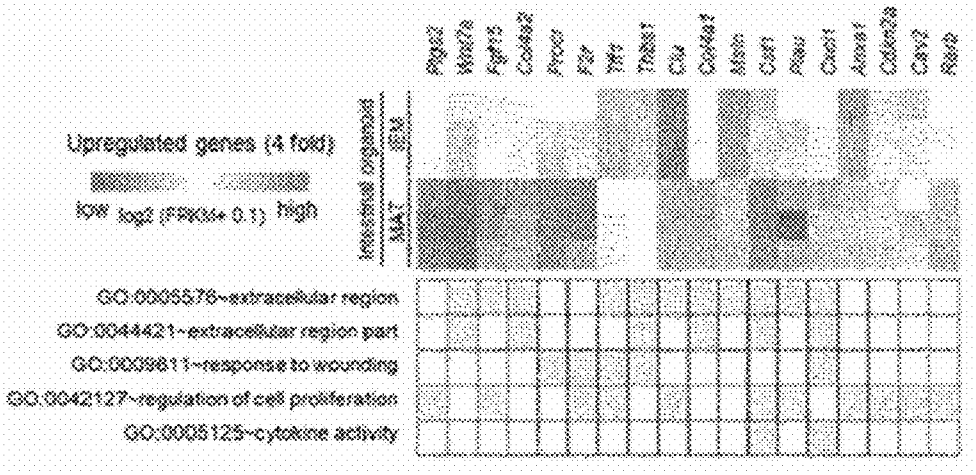
FIG. 16C shows the analysis of the gene expression profile of the intestinal organoid cultured in the decellularized intestinal tissue-derived hydrogel scaffold (RNA-sequencing analysis).

Meanwhile, it was confirmed that when genes with a 4-fold or more difference among the DEGs were selected, the expressions of the genes included in the categories related to extracellular matrix, wound healing response, cell proliferation and cytokine activity were greatly increased in the intestinal organoid cultured in the decellularized intestinal tissue-derived IEM hydrogel compared to the intestinal organoid cultured in MATRIGEL® (FIG. 16C). Accordingly, it was found that the decellularized intestinal tissue-derived IEM hydrogel greatly activated the extracellular matrix synthesis- and cell proliferation-related genes of the intestinal organoid.

Test Example 2-8. Analysis of Gene Expression Profile of Intestinal Organoid Cultured in Scaffold Composition (2) (RNA-Sequencing Analysis)

The gene expression profile of the intestinal organoid cultured in the scaffold composition (hydrogel) prepared in Example 1-2 was analyzed.

Figure 17A:
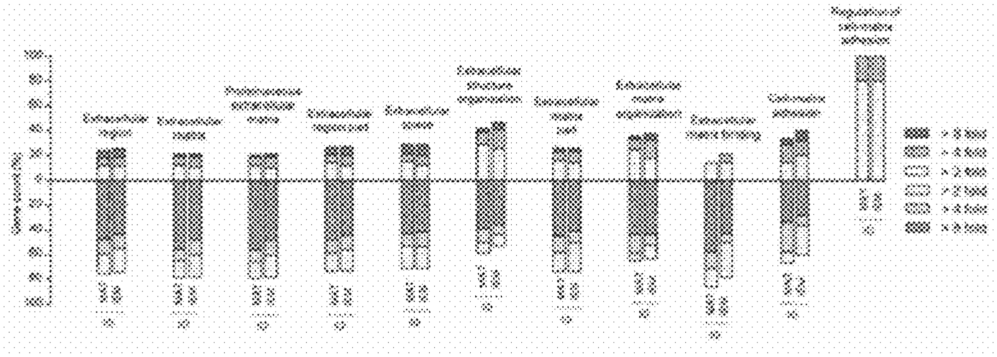
FIG. 17A shows the analysis of the gene expression profile of the intestinal organoid cultured in the decellularized intestinal tissue-derived hydrogel scaffold (RNA-sequencing analysis).

Specifically, it was confirmed that among the genes included in the gene categories related to extracellular matrix environment and cell-matrix interaction, the number of genes whose expression levels were increased is greater in organoids of a decellularized intestinal tissue-derived hydrogel group than in organoids of a MATRIGEL® group and the degree of increase is also higher in the organoids of the decellularized intestinal tissue-derived hydrogel group (FIG. 17A).

Figure 17B:
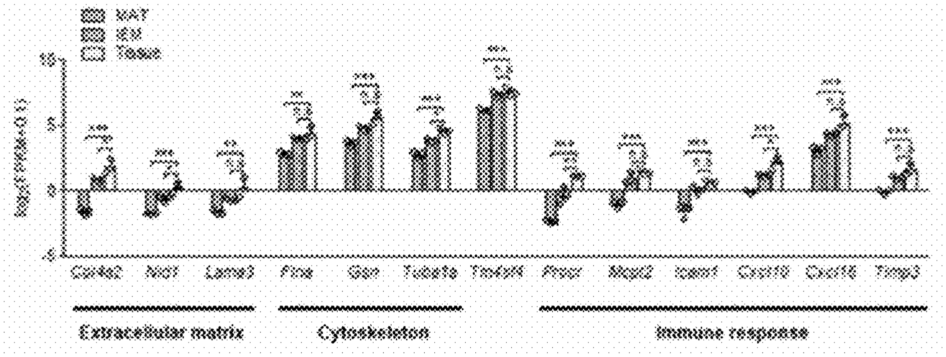
FIG. 17B shows the analysis of the gene expression profile of the intestinal organoid cultured in the decellularized intestinal tissue-derived hydrogel scaffold (RNA-sequencing analysis).

It was confirmed that the expression of extracellular matrix protein-related genes (Col4a2, Nid1, Lama3), cytoskeletal-related genes (Flna, Gsn, Tuba1) and intestinal epithelial gene (Tm4sf4) involved in thiamine absorption in the decellularized intestinal tissue-derived hydrogel group is similar to that in the native tissue. However, it was confirmed that the organoid cultured in MATRIGEL® is quite different in the expression levels of the corresponding genes from the native tissue. Also, it was confirmed that the expression of the genes (Procr, Mcpt2, Icam1, Cxcl10, Cxcl16, Timp3) related to wound regeneration, inflammation and immune response in the decellularized intestinal tissue-derived hydrogel is similar to that in the native tissue. (FIG. 17B).

These genes are involved in maintaining barrier homeostasis under physiological conditions. Accordingly, it can be seen that the hydrogel scaffold of the present disclosure well preserves the intrinsic ability of an intestinal organoid to cope with damage and maintain tissue homeostasis.

Test Example 2-9. Tissue-Specificity of Intestinal Organoid Cultured in Scaffold Composition The tissue-specific effects of the scaffold composition (hydrogel) in the intestinal organoid culture prepared in Example 1-2, specifically, survival and development of the intestinal organoid were analyzed.

Specifically, the intestinal crypt containing intestinal stem cells was encapsulated in hydrogels derived from 6 types of decellularized tissues (intestine, stomach, skin, lymph, heart and muscle) and MATRIGEL® and three-dimensionally cultured. After culture for 6 days, the formation patterns of organoids formed in the respective hydrogels were examined. The organoid formation efficiency in the hydrogels derived from 3 types of decellularized tissues (intestine, stomach and skin) and MATRIGEL® was measured, and mRNA was extracted from each organoid to analyze the expression of stem cells and differentiation markers by quantitative PCR.

Figure 18A:
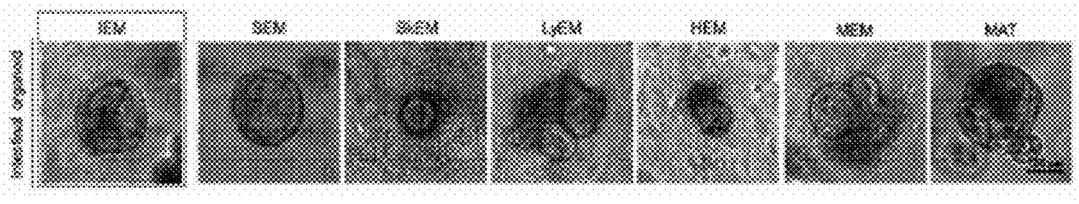
FIG. 18A shows the analysis of the survival and development of an intestinal organoid as a tissue-specific effect of an intestinal extracellular matrix scaffold.
Figure 18B:
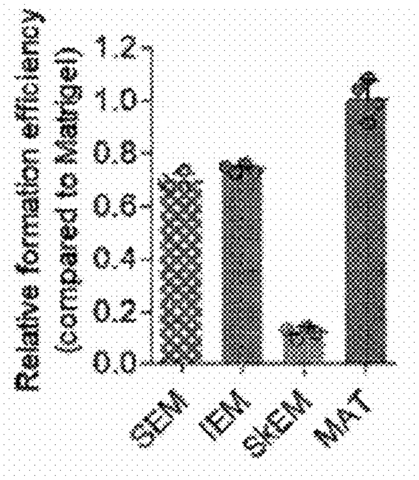
FIG. 18B shows the analysis of the survival and development of an intestinal organoid as a tissue-specific effect of an intestinal extracellular matrix scaffold.
Figure 18C:
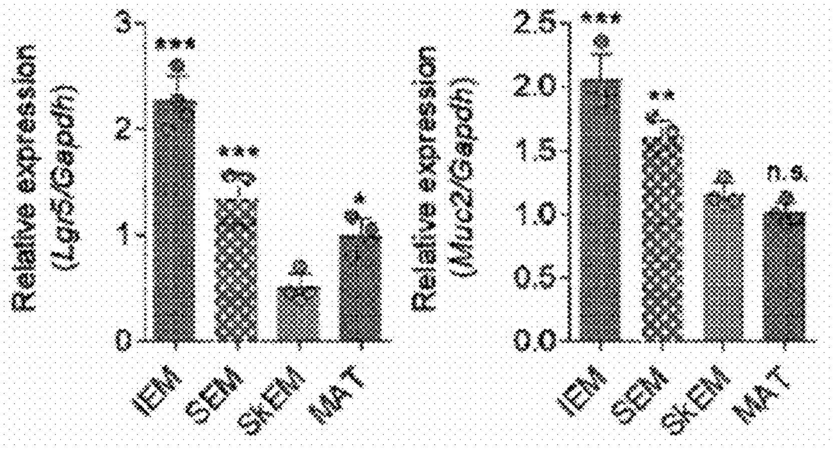
FIG. 18C shows the analysis of the survival and development of an intestinal organoid as a tissue-specific effect of an intestinal extracellular matrix scaffold.

As a result, as can be seen from FIG. 18, when the formation patterns of intestinal organoids cultured in the hydrogels derived from 6 types of decellularized tissues (intestine, stomach, skin, lymph, heart and muscle) and MATRIGEL® (all at the same concentration of 2 mg/ml) are compared, the intestinal organoids were not properly formed in the decellularized scaffolds derived from other organs (skin, lymph, heart and muscle). Also, a quantitative PCR (qPCR) analysis of the intestinal organoid formation efficiency and the stemness marker (Lgr5) and differentiation marker (Muc2) of the intestinal organoids was performed. It was confirmed that the expression levels of the stemness marker and the differentiation marker are the lowest in the intestinal organoid cultured in the decellularized skin tissue-derived hydrogel.

According to these results, it was confirmed that the formation and development of the intestinal organoid were better in the decellularized scaffold derived from intestinal tissue than in the decellularized scaffolds derived from other tissues, which verifies that the microenvironment provided by the intestinal tissue-specific extracellular matrix has an important effect on intestinal organoid culture.

* SEM: stomach extracellular matrix, SkEM: skin extracellular matrix, LyEM: lymph node extracellular matrix, HEM: heart extracellular matrix, MEM: muscle extracellular matrix

Test Example 2-10. Comparative Analysis of Tissue-Specific Extracellular Matrix Component of Decellularized Intestinal Tissue-Derived Scaffold (1)

The tissue-specific extracellular matrix components of the scaffold composition prepared in Example 1-2 were compared and analyzed.

Specifically, the extracellular matrix protein content in a decellularized skin tissue-derived scaffold (SkEM) and the decellularized intestinal tissue-derived scaffold (IEM) was compared and analyzed.

Figure 19:
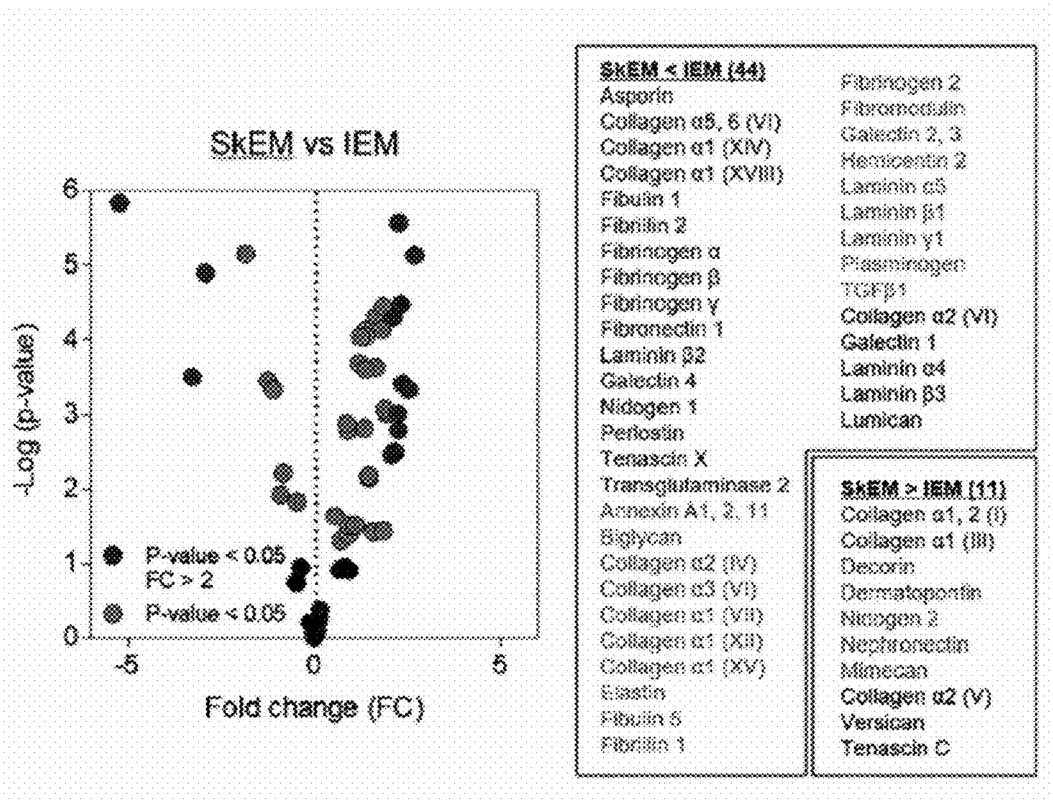
FIG. 19 shows the comparative analysis of tissue-specific extracellular matrix components of a decellularized tissue-derived scaffold.

As a result, as can be seen from FIG. 19, extracellular matrix proteins such as laminin and fibronectin are very important in the formation and development of an intestinal organoid, and the content of these particular extracellular matrix proteins is higher in the IEM than in the SkEM.

Also, collagen types 1 and 3 abound in the SkEM, and collagen types 6 and 14 abound in the IEM. Collagen type 6 is known to be an important factor regulating the interaction between intestinal epithelial cells and fibronectin.

Accordingly, it was confirmed that when a scaffold derived from decellularized intestinal tissue is applied to intestinal organoid culture, it is possible to better recapitulate the intestinal tissue-specific extracellular matrix microenvironment compared to the other tissue-derived decellularized scaffolds, and, thus, it can be applied as a more suitable matrix for intestinal organoid culture.

Test Example 2-11. Comparative Analysis of Tissue-Specific Extracellular Matrix Component of Decellularized Intestinal Tissue-Derived Scaffold (2)

The expression of stem cells and differentiation markers of the intestinal organoid cultured in the scaffold composition (hydrogel) prepared in Example 1-2 was compared and analyzed.

Specifically, small intestines were extracted respectively from 6-month-old pigs (Old) weighing 100 kg to 120 kg and 2-month-old piglets (Young) weighing 20 kg and subjected to decellularization. Then, a qPCR analysis of the expression of stemness markers (Lgr5, Axin2 and Olfm4) and differentiation markers (Lyz1, Muc2, Chga and Vil1) of the intestinal organoids cultured in the prepared IEM was performed.

Figure 20A:
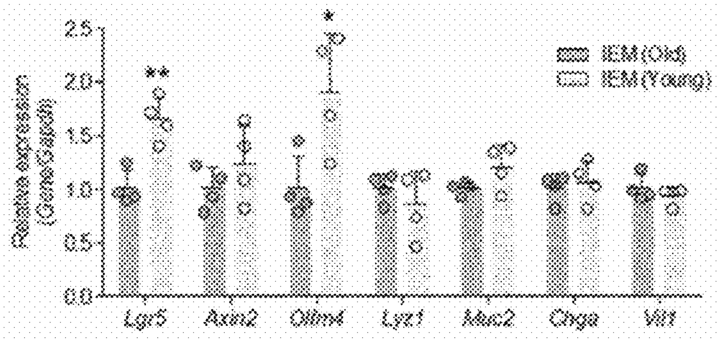
FIG. 20A shows the comparative analysis of the organoid growth pattern and extracellular matrix depending on the tissue age of a decellularized intestinal tissue-derived scaffold.

As a result, it was confirmed that stem cell-related genes of the intestinal organoids were highly expressed in the IEM scaffolds prepared from the tissues extracted from the young individuals (FIG. 20A).

Also, relative quantification and comparative analysis were performed on the extracellular matrix proteins in the decellularized tissue-derived IEM scaffolds prepared from the small intestines of 6-month-old pigs (Old) weighing 100 kg to 120 kg and 2-month-old piglets (Young) weighing 20 kg.

Figure 20B:
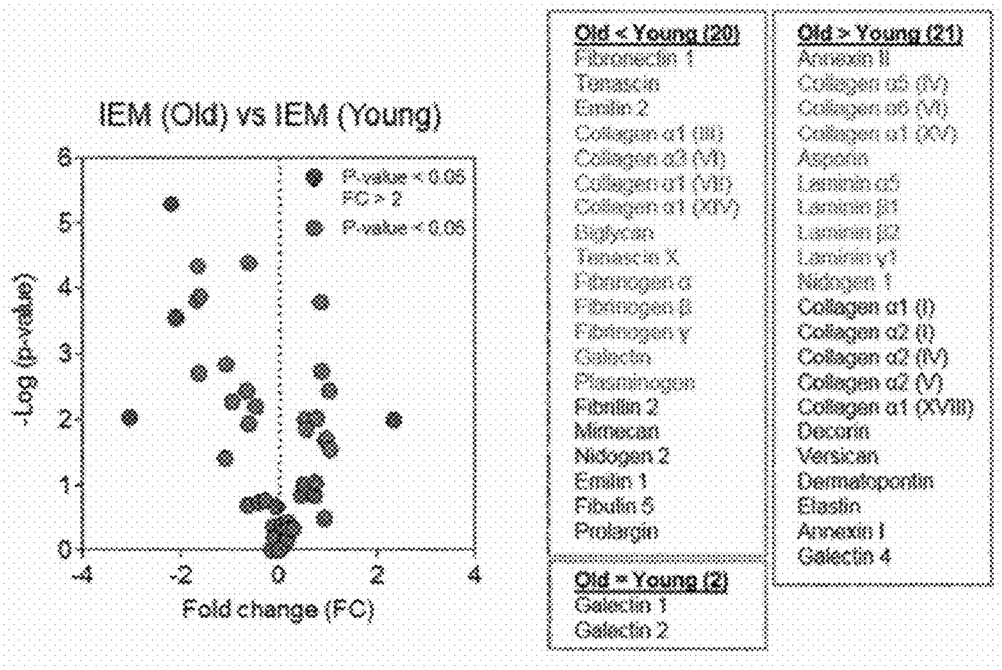
FIG. 20B shows the comparative analysis of the organoid growth pattern and extracellular matrix depending on the tissue age of a decellularized intestinal tissue-derived scaffold.

As a result, the fibronectin content was higher in the IEM scaffolds prepared from the tissues of the young individuals. Fibronectin is known to be very important for the early development of an intestinal organoid (FIG. 20B).

According to these results, it was confirmed that the extracellular matrix protein content in the tissues of the same type varies depending on age, and the decellularized scaffolds prepared using the tissues of different age groups also have a difference in the extracellular matrix protein content. Therefore, it can be seen that when a decellularized scaffold prepared using the tissue of a younger individual is applied to organoid culture, it is more advantageous for the growth of an organoid.

Test Example 3: Verification of Applicability of Intestinal Organoid Cultured in Scaffold Composition

Test Example 3-1. Verification of Long-Term Culture Maintenance Ability of Intestinal Organoid Cultured in Scaffold Composition The long-term culture maintenance ability of the intestinal organoid cultured in the scaffold composition (hydrogel) prepared in Example 1-2 was verified.

Figure 21A:
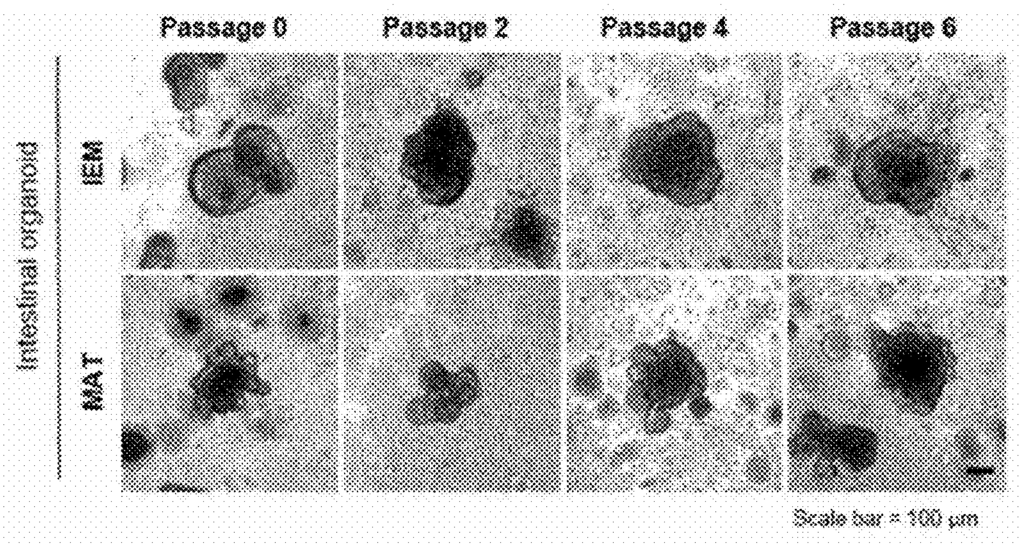
FIG. 21A verifies the ability of the decellularized intestinal tissue-derived hydrogel scaffold to maintain long-term culture of intestinal organoids.
Figure 21B:
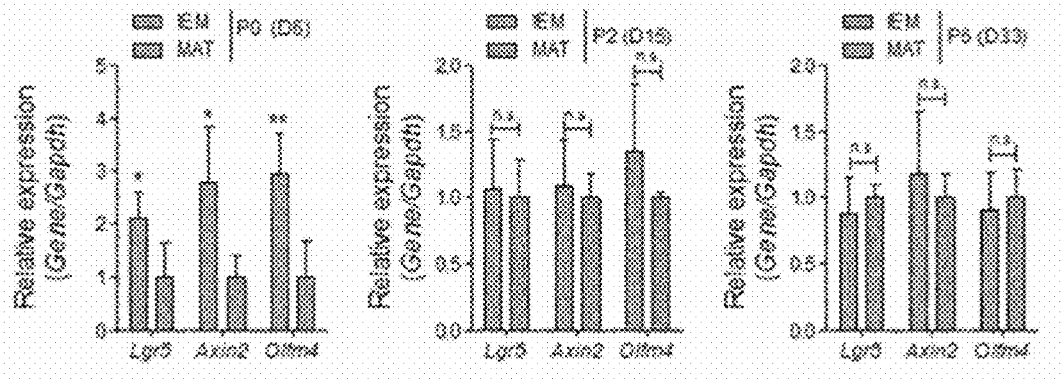
FIG. 21B verifies the ability of the decellularized intestinal tissue-derived hydrogel scaffold to maintain long-term culture of intestinal organoids.

As a result, long-term subculture data of intestinal organoids cultured in a decellularized intestinal tissue-derived IEM hydrogel and MATRIGEL® (FIG. 21A) and a qPCR analysis result of the expression of stemness markers (Lgr5, Axin2 and Olfm4) of P0 (day 6), P2 (day 15), P6 (day 33) intestinal organoids cultured in the decellularized intestinal tissue-derived IEM hydrogel and MATRIGEL® (P=passage number, D=culture day) (FIG. 21B) were obtained.

According to these results, it was confirmed that the intestinal organoid cultured in the decellularized intestinal tissue-derived IEM hydrogel scaffold does not show significant changes in cell growth or formation pattern during the long-term culture and maintains the expression of the stemness markers at a constant level, similarly to the intestinal organoid cultured in MATRIGEL®. Therefore, it was verified that the developed IEM hydrogel scaffold is suitable for stable long-term culture of an intestinal organoid.

Test Example 3-2. Verification of Possibility of Freezing Storage of Scaffold Composition for Intestinal Organoid Culture The possibility of freezing storage of the scaffold composition prepared in Example 1-2 was verified.

Figure 22A:
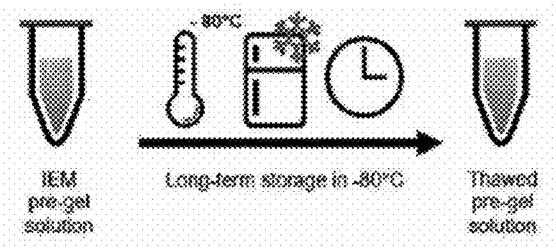
FIG. 22A verifies the possibility of long-term freezing storage of a decellularized intestinal tissue-derived biomimetic artificial scaffold.

Specifically, to confirm the possibility of long-term freezing storage of a decellularized intestinal tissue-derived IEM hydrogel pre-gel solution, the decellularized intestinal tissue-derived IEM hydrogel pre-gel solution was thawed after long-term freezing storage and used for intestinal organoid culture (FIG. 22A). An intestinal organoid cultured in an IEM hydrogel prepared immediately before culture and intestinal organoids cultured in decellularized intestinal tissue-derived IEM hydrogels prepared by thawing after freezing (−80° C.) for 1 month, 2 months and 3 months were compared in shape to an intestinal organoid cultured in MATRIGEL® (FIG. 22B).

Figure 22B:
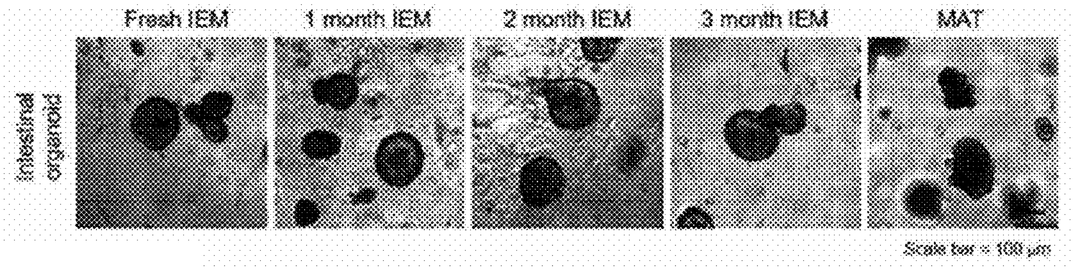
FIG. 22B verifies the possibility of long-term freezing storage of a decellularized intestinal tissue-derived biomimetic artificial scaffold.
Figure 22C:
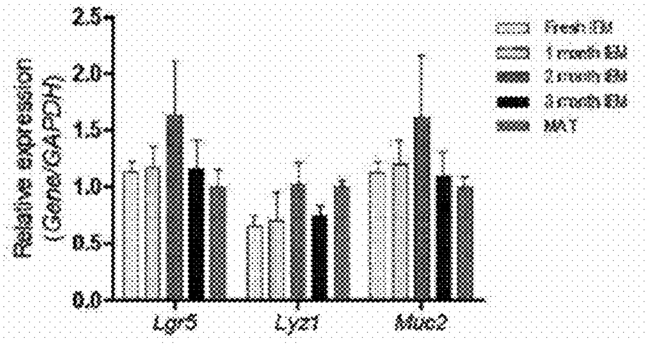
FIG. 22C verifies the possibility of long-term freezing storage of a decellularized intestinal tissue-derived biomimetic artificial scaffold.

As a result, as shown in FIG. 22, it was confirmed that the intestinal organoids were well formed even in the IEM hydrogels subjected to long-term freezing storage without any difference from the intestinal organoid in MATRIGEL® (FIG. 22B). As a result of qPCR analysis of the expression of a stemness marker (Lgr5) and differentiation markers (Lyz1 and Muc2) of the intestinal organoids cultured in an IEM hydrogel prepared immediately before culture and the intestinal organoids cultured in the decellularized intestinal tissue-derived IEM hydrogels prepared by thawing after freezing (−80° C.) for 1 month, 2 months and 3 months, it was confirmed that there is no significant difference in the expression of each marker (FIG. 22C).

According to these results, it was confirmed that the decellularized intestinal tissue-derived IEM hydrogel scaffold can be frozen for a long time after production and can be used without any abnormality in terms of ability for intestinal organoid culture even after thawing when necessary. This serves as an advantage for the commercialization of the developed hydrogel scaffold.

Test Example 3-3. Verification of Possibility of Refrigeration Storage of Scaffold Composition for Intestinal Organoid Culture The possibility of refrigeration storage of the scaffold composition prepared in Example 1-2 was verified.

Figure 23A:
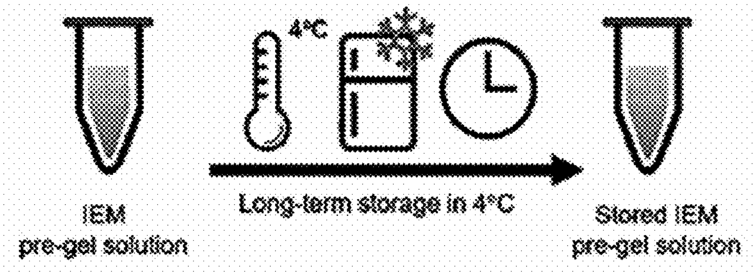
FIG. 23A verifies the possibility of long-term refrigeration storage of the decellularized intestinal tissue-derived biomimetic artificial scaffold.

Specifically, to confirm the possibility of long-term refrigeration storage of a decellularized intestinal tissue-derived IEM hydrogel scaffold, a refrigerated IEM hydrogel pre-gel solution was applied to intestinal organoid culture (FIG. 23A). An intestinal organoid cultured in an IEM hydrogel prepared immediately before culture and intestinal organoids cultured in decellularized intestinal tissue-derived IEM hydrogels refrigerated for a predetermined period of time were compared in shape to an intestinal organoid cultured in MATRIGEL® (FIG. 23B).

Figure 23B:
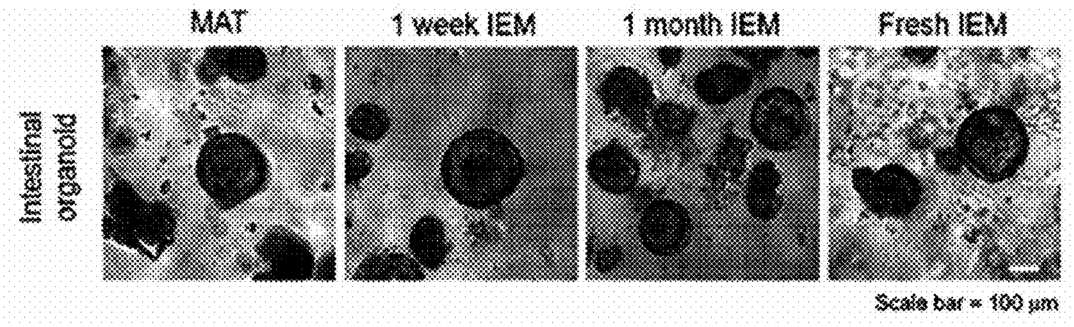
FIG. 23B verifies the possibility of long-term refrigeration storage of the decellularized intestinal tissue-derived biomimetic artificial scaffold.

As a result, as shown in FIG. 23, it was confirmed that the intestinal organoids were well formed even in the refrigerated IEM hydrogels without any difference from the intestinal organoid in MATRIGEL® (FIG. 23B).

Figure 23C:
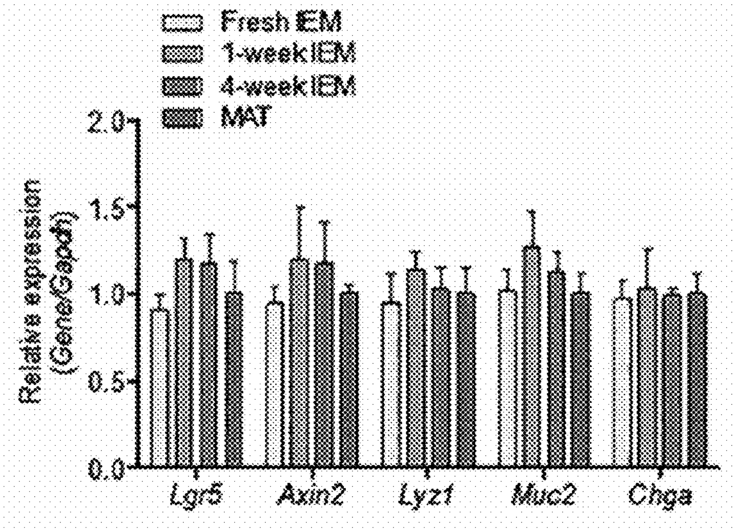
FIG. 23C verifies the possibility of long-term refrigeration storage of the decellularized intestinal tissue-derived biomimetic artificial scaffold.

In addition, stem cell (Lgr5, Axin2) and differentiation (Lyz1, Muc2, Chga) marker expression was analyzed by quantitative PCR (qPCR), it was confirmed that there was no significant difference in the expression of each marker (FIG. 23 (C)) As a result of qPCR analysis of the expression of stemness markers (Lgr5 and Axin2) and differentiation markers (Lyz1, Muc2 and Chga) of the refrigerated prepared immediately before culture and the intestinal organoids cultured in the decellularized intestinal tissue-derived IEM hydrogels refrigerated for 1 week and 4 weeks, it was confirmed that there is no significant difference in the expression of each marker (FIG. 23C).

According to these results, it was confirmed that the decellularized intestinal tissue-derived IEM hydrogel scaffold can be refrigerated for a long time after production and can be used without any abnormality in terms of ability for intestinal organoid culture even after refrigeration. This serves as an advantage for the commercialization of the developed hydrogel scaffold.

Test Example 3-4. Verification of Applicability of Scaffold Composition to Scaffold for In Vivo Transplantation of Intestinal Organoid The applicability of the scaffold composition (hydrogel) prepared in Example 1-2 to a scaffold for in vivo transplantation of an intestinal organoid was verified.

Figure 24A:
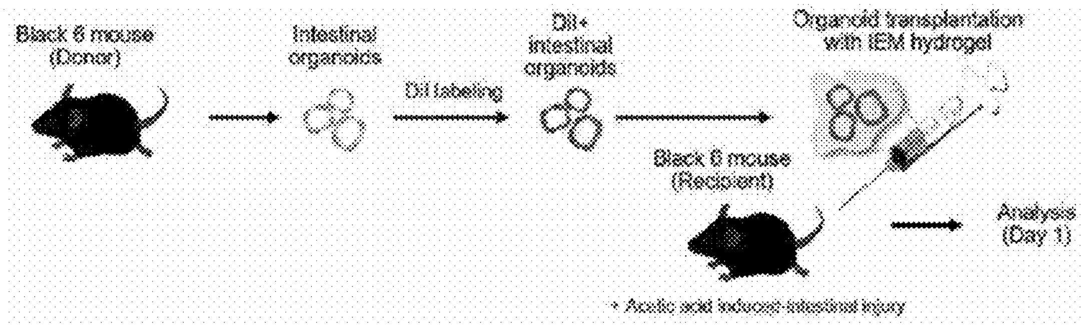
FIG. 24A shows the application of a decellularized intestinal tissue-derived hydrogel as a scaffold for in vivo transplantation of an intestinal organoid.

Specifically, in a test for transplanting an intestinal organoid labeled with a fluorescent dye Dil into an intestinal injury site of a mouse by using a decellularized intestinal tissue-derived IEM hydrogel, a part of the small intestine of the mouse was fixed with a surgical clamp and 40 μl of 1% acetic acid was injected into the site to induce tissue damage for 2 minutes. Thereafter, the organoid was mixed with a hydrogel solution for transplantation and then injected into the injury site (FIG. 24A).

Figure 24B:
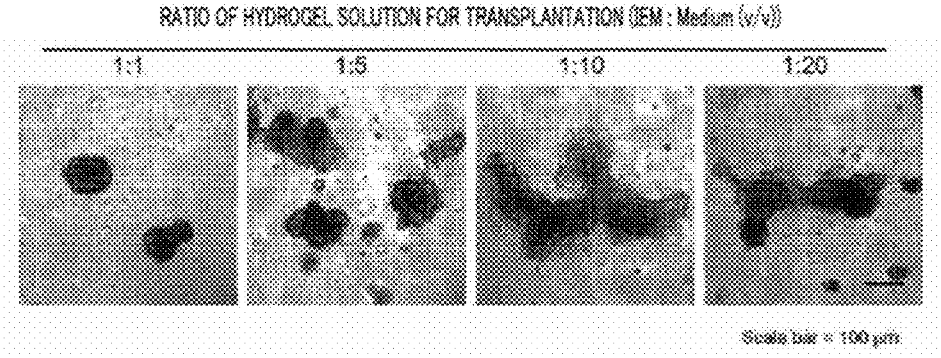
FIG. 24B shows the application of a decellularized intestinal tissue-derived hydrogel as a scaffold for in vivo transplantation of an intestinal organoid.

Also, to adjust the viscosity of the decellularized intestinal tissue-derived IEM hydrogel to be suitable for in vivo transplantation, intestinal organoid culture was performed under conditions in which the IEM hydrogel and a culture medium were mixed at various ratios (FIG. 24B).

As a result, as can be seen from FIG. 24, it was confirmed that intestinal organoids survived well under all the conditions of IEM hydrogel for transplantation. In the existing literature, when an organoid is transplanted, MATRIGEL® and a culture medium are mixed at a volume ratio of 1:20. Therefore, a mixing ratio (v/v) of 1:20 with a culture medium was applied to the conditions of IEM hydrogel for transplantation as well.

Test Example 3-5 Verification of In Vivo Transplantation and Induction of Engraftment of Intestinal Organoid Cultured in Scaffold Composition The possibility of in vivo transplantation and induction of engraftment of the intestinal organoid cultured in the scaffold composition (hydrogel) prepared in Example 1-2 was verified.

Figure 25A:
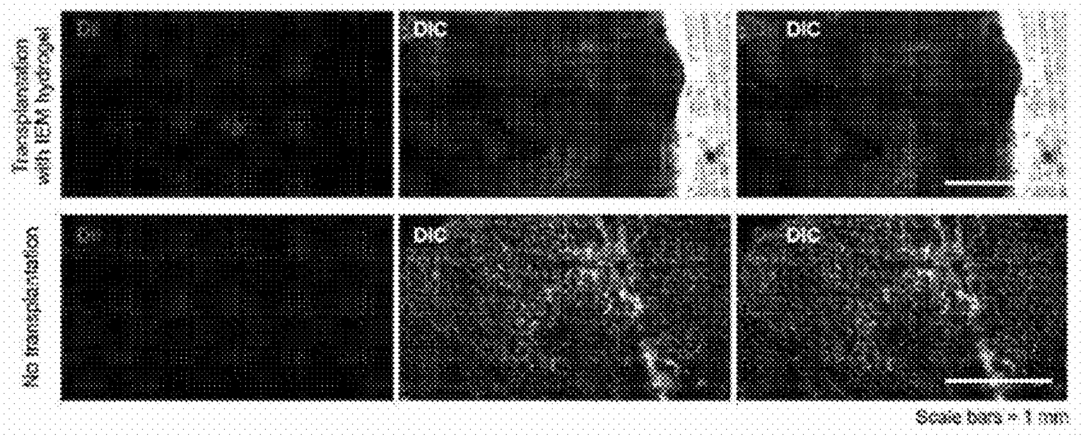
FIG. 25A shows the in vivo transplantation and induction of engraftment of the intestinal organoid using the decellularized intestinal tissue-derived hydrogel.

Specifically, a fluorescent Dil-labeled intestinal organoid was transplanted into a damaged intestinal tissue by using an IEM hydrogel solution for transplantation (IEM:medium=1:20), and a fluorescent Dil was observed at the transplanted tissue site on the next day, which confirmed that the intestinal organoid was successfully engrafted (FIG. 25A).

Figure 25B:
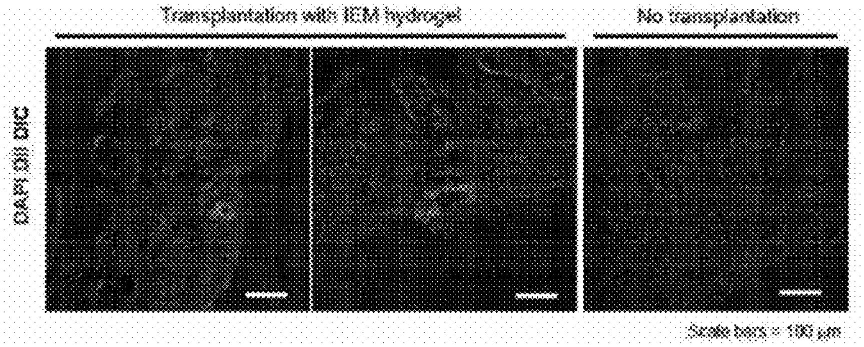
FIG. 25B shows the in vivo transplantation and induction of engraftment of the intestinal organoid using the decellularized intestinal tissue-derived hydrogel.

In addition, when the intestinal tissue was collected from the site where the intestinal organoid was transplanted and the expression of fluorescence was examined, it was confirmed that the fluorescent Dil (transplanted intestinal organoid) was present in the intestinal epithelial tissue. It was confirmed that the decellularized intestinal tissue-derived IEM hydrogel scaffold is applicable not only to ex vivo culture of an intestinal organoid but also as a material for in vivo delivery and transplantation (FIG. 25B).

Figure 26A:
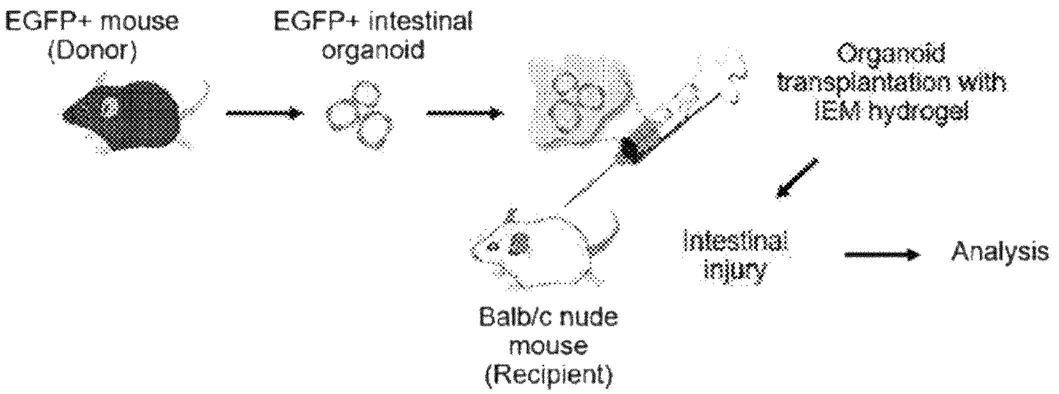
FIG. 26A shows the in vivo transplantation and induction of engraftment of the intestinal organoid using the decellularized intestinal tissue-derived hydrogel.

Meanwhile, as shown in FIG. 26A, a test was conducted in which an EGFP-expressing mouse-derived intestinal organoid was transplanted into an intestinal injury site by using a decellularized intestinal tissue-derived IEM hydrogel scaffold.

Specifically, a part of the small intestine of a mouse was fixed with a surgical clamp and 40 μl of 1% acetic acid was injected into the site to induce tissue damage for 2 minutes. Thereafter, the organoid was mixed with a hydrogel solution for transplantation and then injected into the injury site, followed by checking a day later.

Figure 26B:
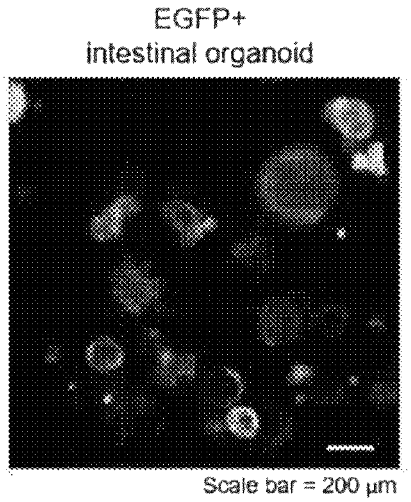
FIG. 26B shows the in vivo transplantation and induction of engraftment of the intestinal organoid using the decellularized intestinal tissue-derived hydrogel.
Figure 26C:
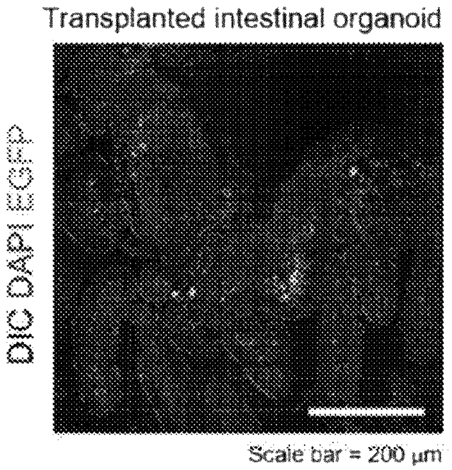
FIG. 26C shows the in vivo transplantation and induction of engraftment of the intestinal organoid using the decellularized intestinal tissue-derived hydrogel.

Before transplantation, it was confirmed that green fluorescence (EGFP) was well expressed in the whole intestinal organoid prepared by extracting intestinal stem cells from an EGFP-expressing mouse (FIG. 26B). The intestinal organoid was transplanted into the intestinal tissue by using an IEM hydrogel solution for transplantation (IEM:medium=1:20), and the transplanted site was collected and the expression of fluorescence was examined. As a result, EGFP fluorescence (transplanted EGFP-expressing intestinal organoid) was detected in the intestinal epithelial tissue (FIG. 26C).

According to these results, it was confirmed that the decellularized intestinal tissue-derived IEM hydrogel scaffold is applicable not only to ex vivo culture of an intestinal organoid but also as a material for in vivo delivery and transplantation.

Test Example 3-6. Check of Possibility of Culturing Human Induced Pluripotent Stem Cell- and Embryonic Stem Cell-Derived Intestinal Organoids in Scaffold Composition The possibility of culturing human induced pluripotent stem cell- and embryonic stem cell-derived intestinal organoids in the scaffold composition (hydrogel) of Example 1-2 was checked.

Specifically, human induced pluripotent stem cells and embryonic stem cells were seeded as single cells in a culture dish, and intestinal differentiation was initiated by adding Activin A and FBS from the time when the cells reached more than 90% confluence. Then, the cells were treated with FGF-4 and CHIR99021, and when mid-hindgut spheroids were formed, they were transferred to a decellularized intestinal tissue-derived IEM hydrogel or MATRIGEL® and three-dimensionally cultured using an intestinal organoid culture medium.

Figure 27A:
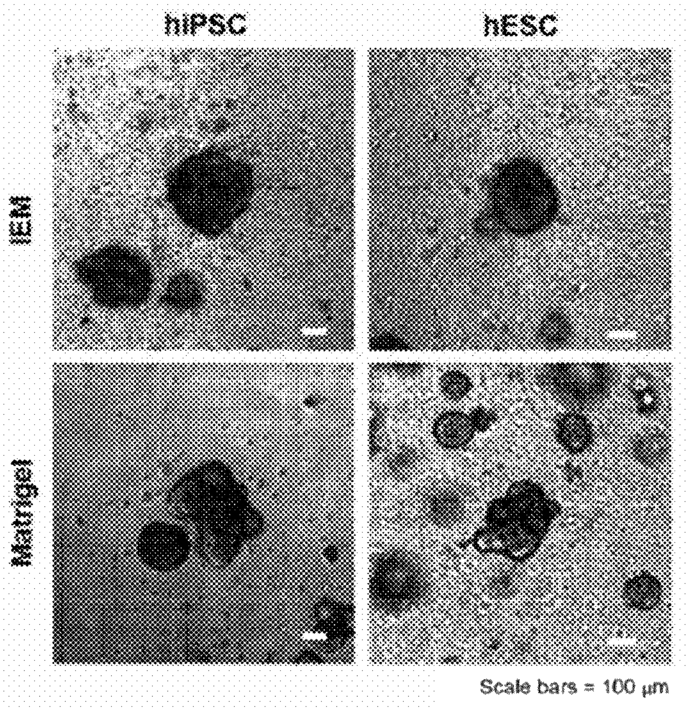
FIG. 27A confirms the possibility of culturing human induced pluripotent stem cell- and embryonic stem cell-derived intestinal organoids in the decellularized intestinal tissue-derived hydrogel scaffold.

As a result, as can be seen from FIG. 27, it was confirmed that the human induced pluripotent stem cell (hiPSC)- and human embryonic stem cell (hESC)-derived intestinal organoids can be well cultured in the decellularized intestinal tissue-derived IEM hydrogel and MATRIGEL® (images of organoid morphology on day 7 of culture) (FIG. 27A).

Figure 27B:
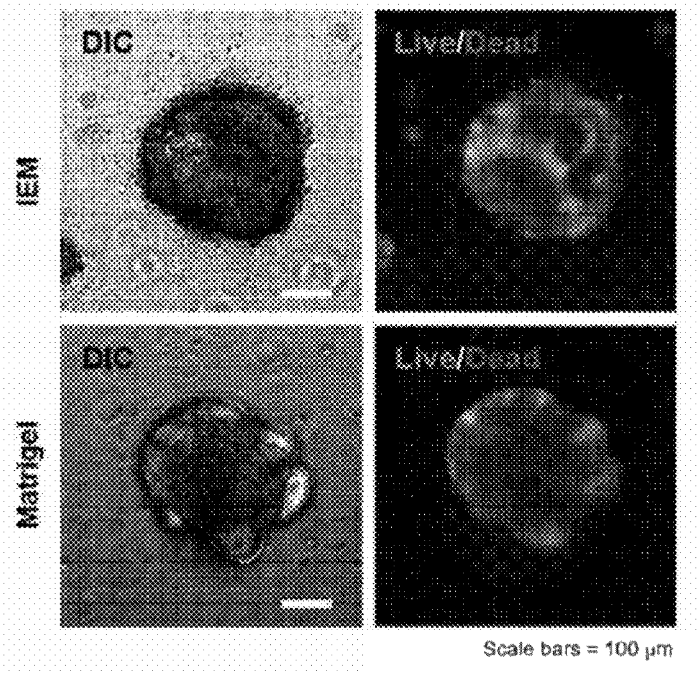
FIG. 27B confirms the possibility of culturing human induced pluripotent stem cell- and embryonic stem cell-derived intestinal organoids in the decellularized intestinal tissue-derived hydrogel scaffold.

As a result of cell viability analysis (Live/Dead analysis) of intestinal organoids differentiated from human embryonic stem cells (hESCs) in the decellularized intestinal tissue-derived IEM hydrogel and MATRIGEL®, it was confirmed that cells in the intestinal organoids were well survived when cultured for 6 days (FIG. 27B).

The decellularized intestinal tissue-derived IEM hydrogel scaffold was confirmed as a culture scaffold effective in forming, maintaining and growing not only an adult mouse intestinal stem cell-derived intestinal organoid but also an intestinal organoid differentiated from human induced pluripotent stem cells and human embryonic stem cells, which are stem cells with totipotency. Therefore, irrespective of the stem cell type, it is highly versatile as a scaffold capable of culturing various tissue and cell-derived intestinal organoids, which provides an advantage for commercialization. It was confirmed that the applicability of an IEM hydrogel as an elemental technology of a culture system for the establishment of a disease model based on a patient stem cell-derived intestinal organoid is very high.

Test Example 3-7. Check of Possibility of Forming and Culturing Three-Dimensional Colorectal Cancer-Derived Organoid in Scaffold Composition The possibility of forming and culturing a three-dimensional colorectal cancer-derived organoid in the scaffold composition (hydrogel) of Example 1-2 was checked.

Figure 28A:
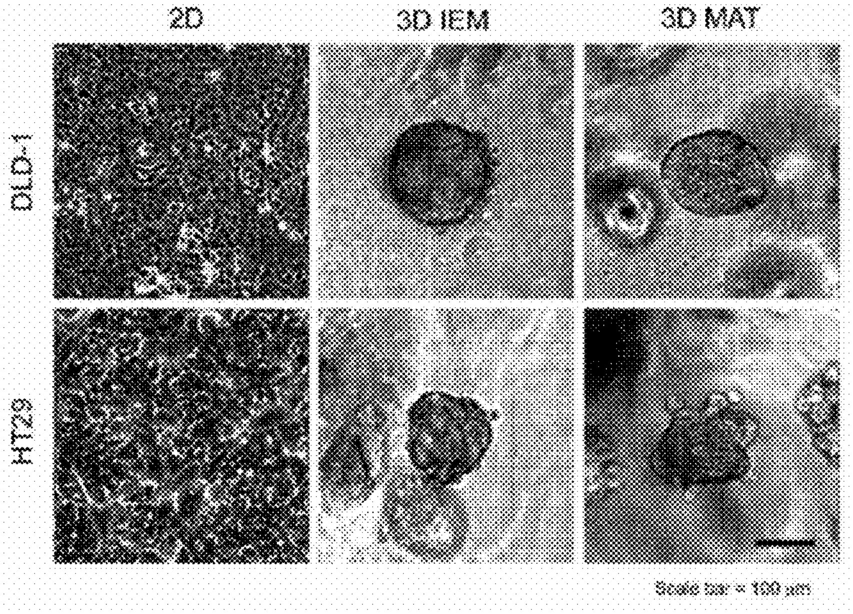
FIG. 28A shows the formation and culture of colorectal cancer-derived three-dimensional organoid in the decellularized intestinal tissue-derived hydrogel scaffold.

Specifically, as shown in FIG. 28, the formation patterns of three-dimensional cancer organoids (day 8 of culture) prepared from colorectal cancer-derived cell lines (DLD-1, HT29) in decellularized intestinal tissue-derived IEM hydrogel and MATRIGEL® were compared. As a result, it was confirmed that a colorectal cancer organoid was well formed in the IEM hydrogel without a significant difference from that in MATRIGEL® (FIG. 28A).

Figure 28B:
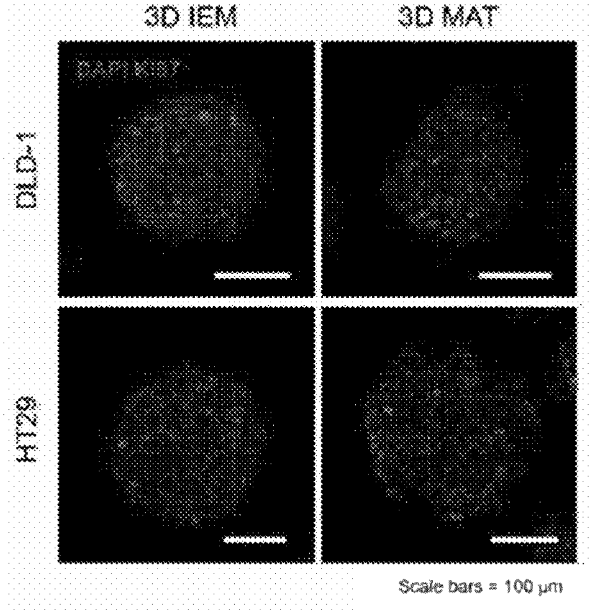
FIG. 28B shows the formation and culture of colorectal cancer-derived three-dimensional organoid in the decellularized intestinal tissue-derived hydrogel scaffold.

As a result of immunostaining analysis of Ki67, which is a cell proliferation marker of the three-dimensional cancer organoids (day 8 of culture) prepared from the colorectal cancer-derived cell lines (DLD-1, HT29) in the decellularized intestinal tissue-derived IEM hydrogel and MATRIGEL®, it was confirmed that there is no significant difference in the proliferative ability of the cells in the colorectal cancer organoids cultured in the IEM hydrogel and MATRIGEL® (FIG. 28B).

According to these results, it was confirmed that the decellularized intestinal tissue-derived IEM hydrogel scaffold was confirmed as a culture scaffold effective in forming and growing not only a stem cell-derived intestinal organoid but also a cancer organoid prepared from the colorectal cancer cell lines. The applicability of an IEM hydrogel as an elemental technology of a culture system for the construction of an in vitro colorectal cancer patient model is very high.

Test Example 3-8. Check of Possibility of Cryopreservation of Organoid Using Scaffold Composition Typical cryopreservation of an intestinal organoid is performed by removing a hydrogel (scaffold) where the organoid has been cultured and freezing only the organoid using a freezing culture medium. In this case, it is necessary to encapsulate and culture the organoid in the hydrogel again after thawing, and in this process, the function and activity of the cells in the organoid can be damaged.

The possibility of cryopreservation of an organoid using the scaffold composition (hydrogel) of Example 1-2 was checked.

Specifically, each intestinal organoid cultured in a decellularized intestinal tissue-derived IEM hydrogel and MATRIGEL® for 6 days was cryopreserved without removing each culture scaffold and then cultured without additional scaffold encapsulation after thawing.

Figure 29A:
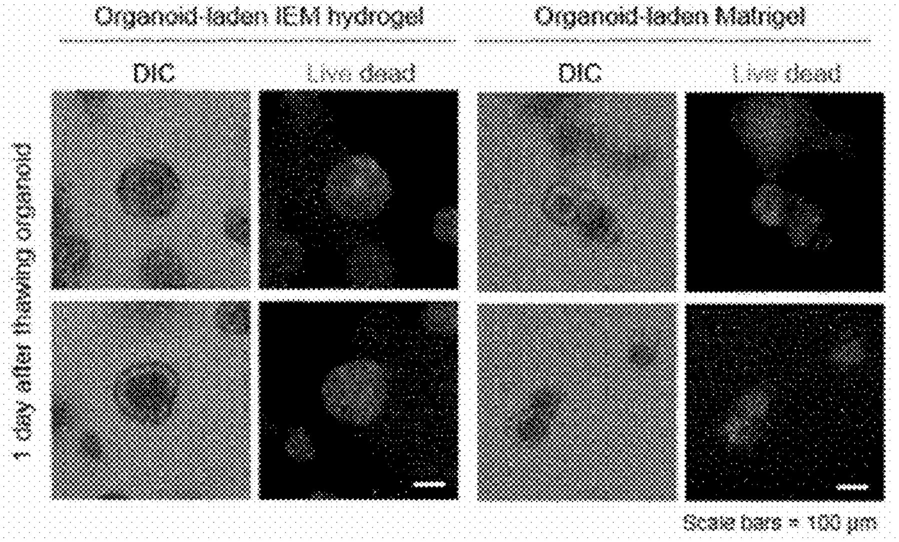
FIG. 29A shows the result confirming the possibility of cryopreservation of an organoid using the decellularized intestinal tissue-derived hydrogel scaffold.

As a result of Live/Dead staining analysis of the organoids thawed after being encapsulated and cryopreserved in the decellularized intestinal tissue-derived IEM hydrogel and MATRIGEL®, it was confirmed that most of the cells survived (green fluorescence) in the organoid thawed after being encapsulated and cryopreserved in the IEM hydrogel, and a large number of dead cells (red fluorescence) were present in the organoid thawed after being encapsulated and cryopreserved in MATRIGEL® (FIG. 29A).

Figure 29B:
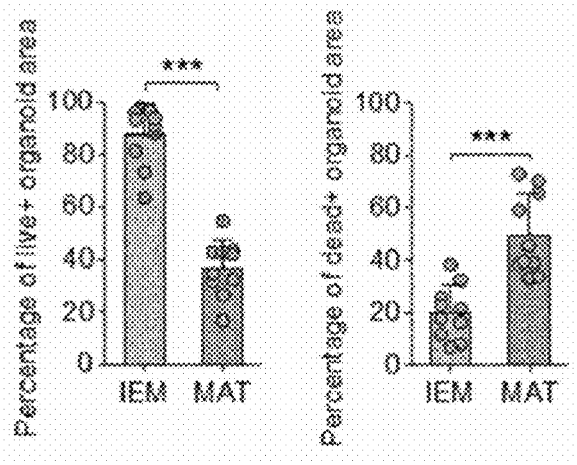
FIG. 29B shows the result confirming the possibility of cryopreservation of an organoid using the decellularized intestinal tissue-derived hydrogel scaffold.

Also, images taken after Live/Dead staining were quantitatively analyzed (Left: Comparison of the area of Live+ cell region (green fluorescence) in the organoid, Right: Comparison of the area of the Dead+ cell region (red fluorescence) in the organoid) (FIG. 29B).

Figure 29C:
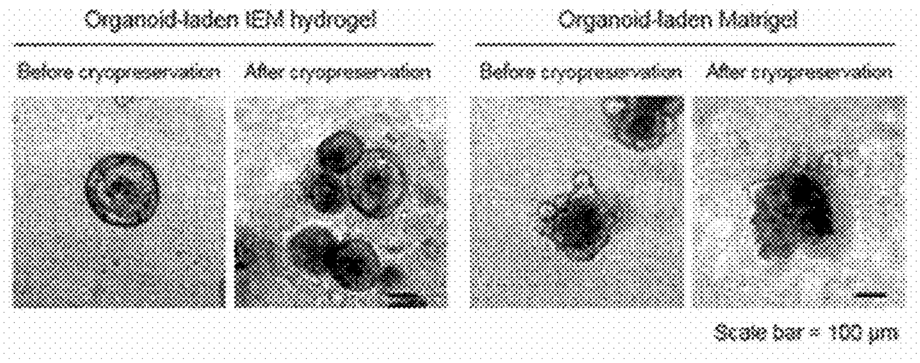
FIG. 29C shows the result confirming the possibility of cryopreservation of an organoid using the decellularized intestinal tissue-derived hydrogel scaffold.

In addition, as a result of obtaining images of the organoids before and after being encapsulated and cryopreserved in the decellularized intestinal tissue-derived IEM hydrogel and MATRIGEL®, respectively, it was confirmed that the intestinal organoid thawed after being encapsulated and cryopreserved in MATRIGEL® was structurally damaged with a large number of dead cells, whereas the intestinal organoid thawed after being encapsulated and cryopreserved in the decellularized intestinal tissue-derived IEM hydrogel was well maintained in structure and shape at almost the same level as before cryopreservation (FIG. 29C).

Figure 29D:
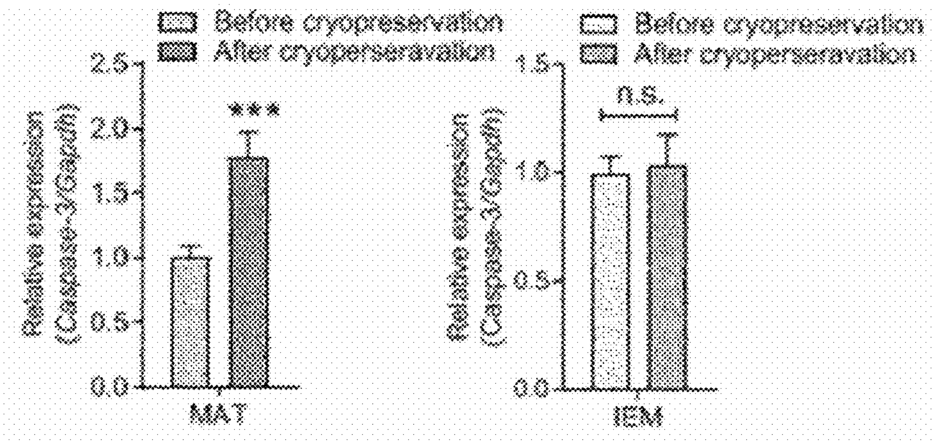
FIG. 29D shows the result confirming the possibility of cryopreservation of an organoid using the decellularized intestinal tissue-derived hydrogel scaffold.

As a result of qPCR analysis of the expression of an apoptosis gene (Caspase-3) in the organoids before and after being encapsulated and cryopreserved in the decellularized intestinal tissue-derived IEM hydrogel and MATRIGEL®, respectively, it was confirmed that the organoid encapsulated and cryopreserved in MATRIGEL® exhibited an increase in expression level of the apoptosis gene after thawing, whereas the organoid encapsulated and cryopreserved in the decellularized intestinal tissue-derived IEM hydrogel showed no difference between before and after cryopreservation (FIG. 29D).

According to these results, when the decellularized intestinal tissue-derived IEM hydrogel scaffold is used in cryopreservation of an organoid, the frozen intestinal organoid can be used for culture immediately after thawing without a cumbersome process and the organoid can be protected from damage during the freezing and thawing process. Therefore, it is very advantageous for storage of an organoid and culture of an organoid after thawing.

Test Example 3-9. Check of Possibility of Mass Culture of Intestinal Organoid Using Scaffold Composition and Microfluidic Chip The possibility of mass culture of intestinal organoids using the scaffold composition (hydrogel) of Example 1-2 and a microfluidic chip was checked.

Figure 30A:
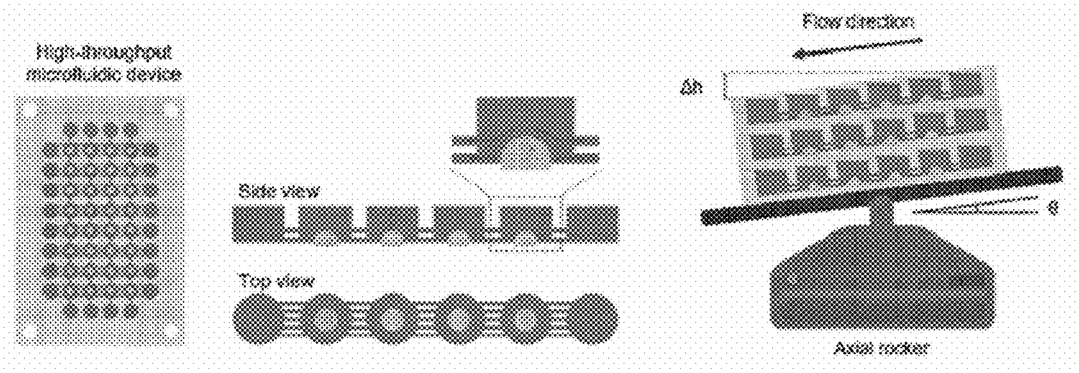
FIG. 30A shows the result confirming the possibility of mass culture of intestinal organoids using the decellularized intestinal tissue-derived hydrogel scaffold and a microfluidic chip.

Specifically, the microfluidic chip is composed of multiple organoid chambers and thus enables simultaneous mass culture of organoids and provides the organoids with a microflow of culture medium using only a simple rocker. Therefore, the microfluidic chip enables effective dynamic culture (FIG. 30A). An intestinal organoid was cultured using the scaffold of the present disclosure in this device.

Figure 30B:
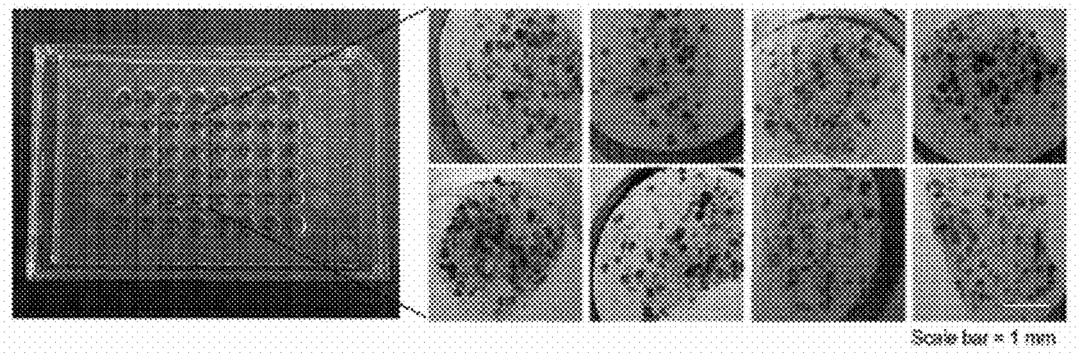
FIG. 30B shows the result confirming the possibility of mass culture of intestinal organoids using the decellularized intestinal tissue-derived hydrogel scaffold and a microfluidic chip.

As a result of culturing an intestinal organoid using the decellularized intestinal tissue-derived IEM hydrogel scaffold in the microfluidic chip capable of mass culture of organoids (day 6 of culture) (FIG. 30B), it was confirmed that a lot of intestinal organoids can be formed and cultured in each chamber.

According to these results, it can be seen that when the intestinal organoid that is three-dimensionally cultured in the decellularized intestinal tissue-derived IEM hydrogel scaffold is combined with the microfluidic chip technology, a tissue-specific extracellular matrix microenvironment is applied to a dynamic culture with a precise microfluidic flow, which enables efficient mass production of organoids.

With respect to a stomach extracellular matrix (SEM) for culture and transplantation of a gastric organoid and a method of preparing the same, the present disclosure establishes a method for mass-producing decellularized scaffolds through a simple chemical treatment on stomach tissue and the prepared decellularized stomach tissue matrix is used for gastric organoid culture.

It was confirmed that the decellularized scaffold developed in the present disclosure contains various extracellular matrices and growth factors contained in stomach tissue with all cellular components removed and thus can provide an optimal three-dimensional microenvironment for gastric organoid culture.

It was confirmed that a gastric organoid is generated and grown in the developed decellularized stomach tissue-derived hydrogel scaffold. In order to efficiently use the decellularized scaffold for gastric organoid culture, the decellularized scaffold was tested at various concentrations and the optimal concentration for gastric organoid culture was selected.

It was confirmed that gastric organoids can be cultured in a similar manner in the developed decellularized scaffold and MATRIGEL® as a control group, and can also be differentiated into various stomach tissue epithelial cells. Accordingly, the applicability of the decellularized scaffold as an alternative to MATRIGEL® was confirmed. Also, conditions that can further enhance organoid differentiation were found through appropriate mixing with MATRIGEL® when necessary. This shows that the gastric organoid cultured in the scaffold developed in the present disclosure can better mimic the stomach tissue structure and function of stomach tissue than the conventional organoids.

It was confirmed that the decellularized stomach tissue-derived hydrogel scaffold developed in the present disclosure can enhance organoid differentiation as well as acid secretion function. Accordingly, a culture technology capable of producing gastric organoids with enhanced differentiation and function beyond the limitations of the conventional gastric organoids cultured in MATRIGEL® was established. Also, it was confirmed that even during long-term culture, the organoid can maintain a similar level of stemness compared to that in MATRIGEL®.

In order to confirm a tissue-specific effect of the decellularized scaffold developed in the present disclosure, gastric organoids were cultured in decellularized scaffolds derived from stomach, intestine, skin, lymph, heart and muscle, respectively, and then compared. It was observed that the formation efficiency of a gastric organoid and the expression of stem cell-related genes in the SEM were better than those in the scaffolds derived from the other tissues such as skin, lymph, heart and muscle. Thus, it was confirmed that the developed scaffold can have a tissue-specific effect.

In the present disclosure, when a mouse gastric ulcer model was prepared and transplanted with a gastric organoid using the decellularized scaffold, it was confirmed that the gastric organoid can be engrafted and transplanted into the stomach tissue. Therefore, it was confirmed that the decellularized scaffold is highly applicable as a transplantation material In the present disclosure, it was verified that when the decellularized scaffold was used for gastric organoid culture after long-term storage in refrigerated and frozen conditions, a gastric organoid was formed, similarly to that in a newly prepared scaffold. This shows that the developed scaffold can be stored stably for the long term, suggesting a high possibility of commercialization and industrialization of the decellularized scaffold in the future.

In the present disclosure, it was confirmed that not only a stem cell-derived organoid but also a gastric cancer organoid can be successfully cultured using the decellularized scaffold. Therefore, it has high applicability as an advanced elemental technology for culture that can be applied as a personalized in vitro cancer model for anticancer drug screening and new drug development.

Hereinafter, Examples will be presented for understanding of the present disclosure. However, the following Examples are illustrative only for better understanding of the present disclosure but do not limit the present disclosure.

Figure 31A:
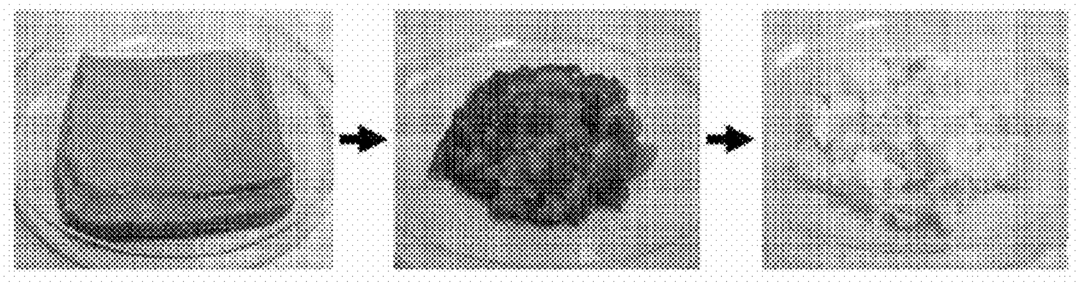
FIG. 31A shows the fabrication of a stomach extracellular matrix (SEM) for gastric organoid culture.

Example 2: Preparation of Scaffold Composition Containing Stomach Extracellular Matrix A scaffold composition containing a stomach extracellular matrix was prepared as described below (see FIG. 31A).

Example 2-1. Preparation of Stomach Extracellular Matrix (SEM)

A porcine stomach tissue was isolated and sliced, and the stomach tissue was stirred with 1% TRITON X-100™ and 0.1% ammonium hydroxide to remove only the cells of the stomach tissue and prepare a decellularized stomach tissue.

Thereafter, the decellularized stomach tissue was lyophilized and ground to prepare a stomach extracellular matrix (SEM).

Figure 31B:
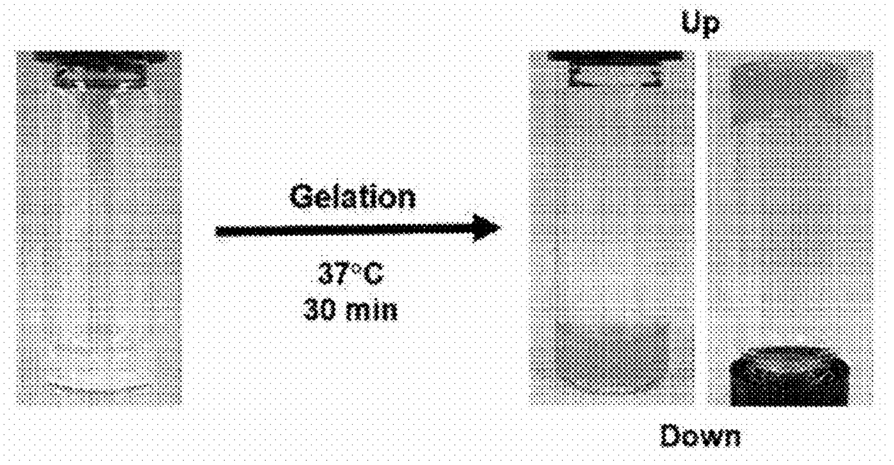
FIG. 31B shows the fabrication of a stomach extracellular matrix (SEM) for gastric organoid culture.

Example 2-2. Preparation of Scaffold Composition 10 mg of the SEM was dissolved in a 4 mg/ml pepsin solution (a solution of 4 mg of pepsin powder derived from porcine gastric mucosa in 1 ml of 0.02 M HCl) for 48 hours. Gelation was performed at a temperature of 37° C. for 30 minutes after setting a neutral pH in an electrolyte state of 1×PBS buffer by using 10×PBS and 1 M NaOH with uniform blending to prepare a scaffold composition in the form of a hydrogel (FIG. 31B).

Test Example 4: Analysis of SEM

The SEM of Example 2-1 was analyzed as follows.

Test Example 4-1. Analysis of Mechanical Properties of SEM

The mechanical properties of the SEM prepared in Example 2-1 were analyzed.

Figure 32A:
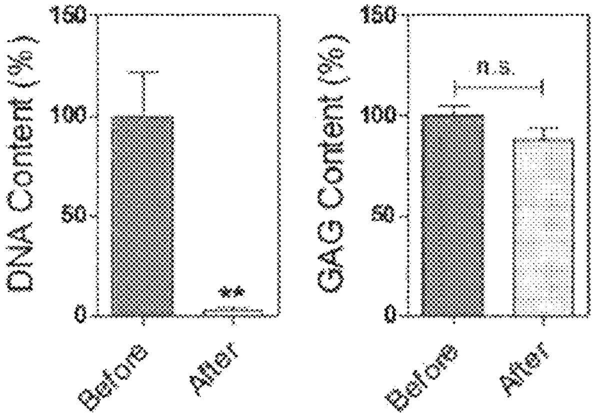
FIG. 32A shows the analysis of mechanical properties; elastic modulus of the fabricated SEM.

In order to check whether cells were sufficiently removed from the prepared SEM scaffold, the amounts of DNAs before and after decellularization were compared. Also, in order to check whether the extracellular matrix components remained, the amounts of glycosaminoglycans (GAGs) as a representative extracellular matrix component were quantitatively compared. As a result, it was confirmed that after decellularization, all the cells were removed and GAGs were maintained at a level similar to that in the stomach tissue (FIG. 32A).

Figure 32B:
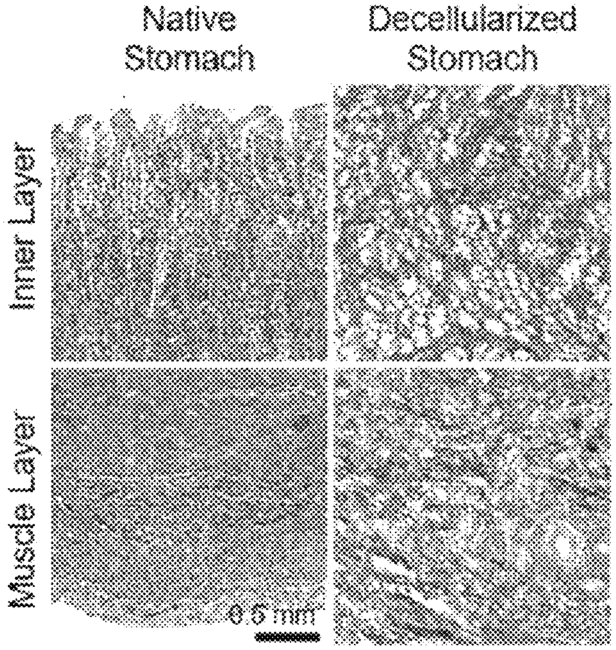
FIG. 32B shows the analysis of properties of the fabricated SEM.

Also, in order to check whether all the cells were removed and a matrix structure of the stomach tissue was well maintained after decellularization, an analysis was performed through H&E staining. As a result, no cell nucleus was observed, which confirmed that most of the cells were removed (FIG. 32B).

Figure 32C:
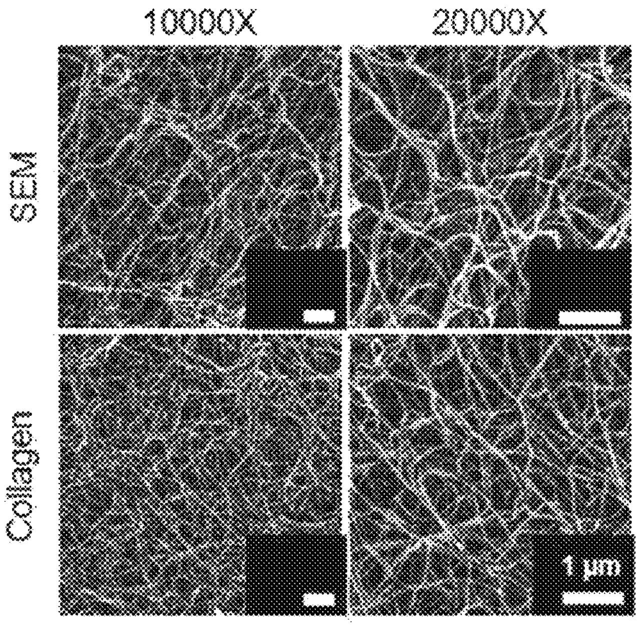
FIG. 32C shows the analysis of properties of the fabricated SEM.

Meanwhile, in order to confirm that the matrix structure of the entire stomach tissue remained, a hydrogel was formed with the prepared SEM and then the structure inside the hydrogel was checked through scanning electron microscopy (SEM). As a result, it was observed that the SEM hydrogel was observed to have a nanofibrous structure similar to a collagen hydrogel, confirming that it had an internal structure suitable for the attachment and growth of a gastric organoid (FIG. 32C).

Test Example 4-2. Analysis of Mechanical Properties Depending on Concentration of SEM The mechanical properties depending on concentration of the SEM of Example 2-1 were analyzed.

After a hydrogel was formed using a scaffold composition for each concentration of the SEM, changes in elastic modulus; mechanical properties depending on four concentrations of the SEM were measured by rheological analysis.

Figure 33:
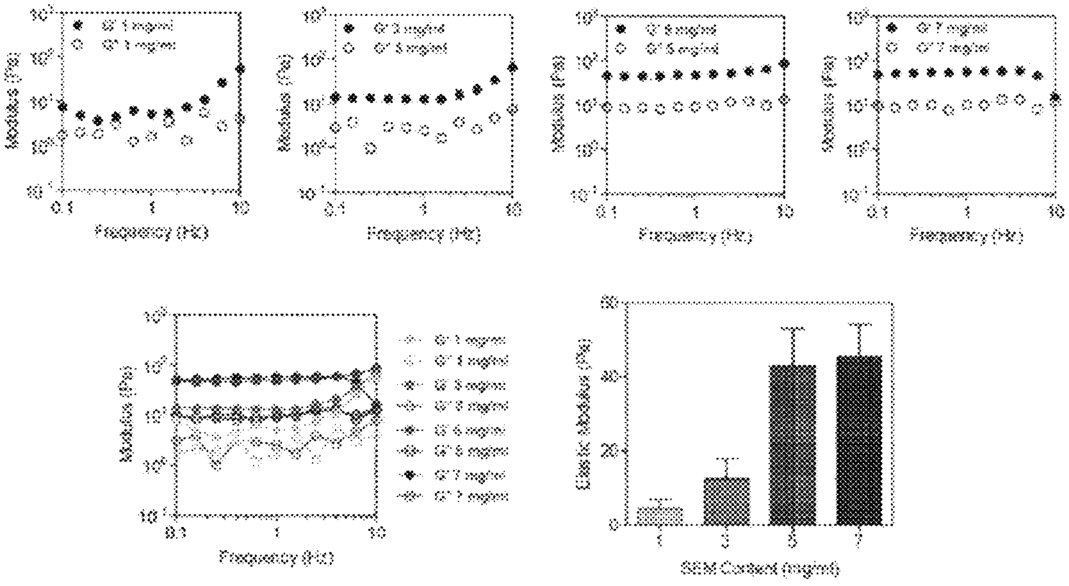
FIG. 33 shows the elastic modulus of the fabricated SEM depending on concentration.

As a result, as can be seen from FIG. 33, it was confirmed that a storage modulus G' was consistently higher than a loss modulus G" at all concentrations, and, thus, a stable polymer network was formed through crosslinking in the hydrogel. It was confirmed that as the SEM concentration increased, the mechanical properties (modulus) also increased.

Test Example 4-3. Comparative Analysis Based on Decellularization Condition

A test was conducted to compare the decellularization method established in the present disclosure (Protocol 1) and the decellularization method (Protocol 2) previously reported in the prior art document.

In the prior art document, DNA was removed using DNase I after treatment with 4% sodium deoxycholate (SDC) for 4 hours, and in the present disclosure, only a mixed solution of non-ionic 1% TRITON X-100™ and 0.1% ammonium hydroxide was used for more mild conditions to minimize damage to proteins in tissue.

Figure 34A:
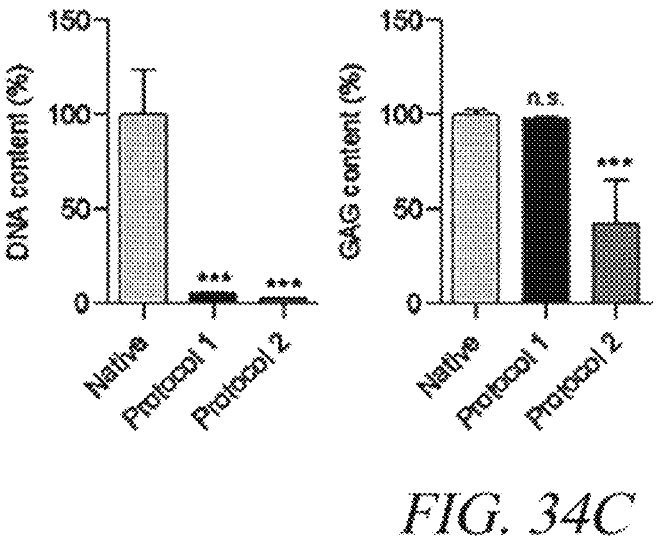
FIG. 34A shows the result of comparative analysis of decellularization methods of stomach tissue.

As a result of comparing the amount of DNA remaining after decellularization, it was confirmed that DNA was successfully removed according to both protocols. As a result of comparing the remaining extracellular matrix components by GAG quantification, it was confirmed that GAG components were well preserved in the tissue treated according to Protocol 1, whereas GAG components were significantly decreased in the tissue treated according to Protocol 2 (FIG. 34A).

Figure 34B:
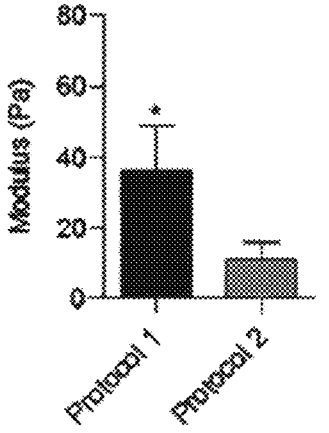
FIG. 34B shows the result of comparative analysis of decellularization methods of stomach tissue.

Also, after hydrogels were fabricated using the prepared decellularized matrices, the mechanical properties (modulus) thereof were measured. It was confirmed that the mechanical properties of the hydrogel prepared according to Protocol 1 were significantly high (FIG. 34B).

Figure 34C:
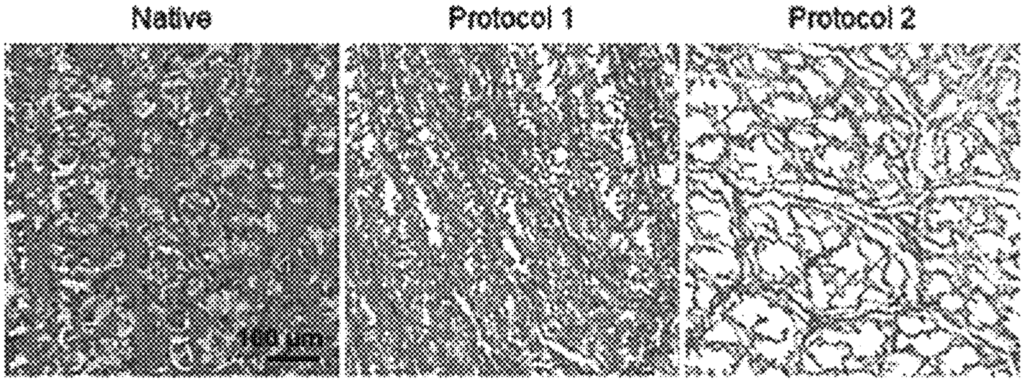
FIG. 34C shows the result of comparative analysis of decellularization methods of stomach tissue.

As a result of comparison by H&E histological analysis, it was confirmed that cells were well removed according to both methods, but the extracellular matrix components were better preserved according to Protocol 1 (FIG. 34C).

Figure 34D:
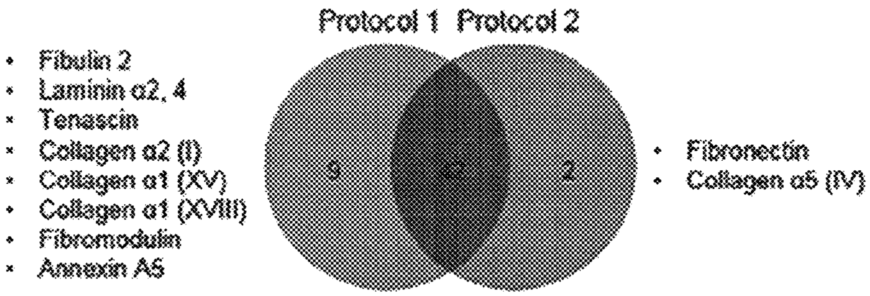
FIG. 34D shows the result of comparative analysis of decellularization methods of stomach tissue.

Proteomic analysis of the matrices prepared by the decellularization methods was performed. It was confirmed that Protocol 1 is more effective in preserving a greater number of stomach tissue-specific extracellular matrix proteins than Protocol 2 (FIG. 34D).

According to this result, the decellularization protocol established in the present disclosure can better preserve the extracellular matrix components of stomach tissue than the conventional method. Therefore, it can be predicted that the decellularization protocol established in the present disclosure can be more effective for gastric organoid culture.

Meanwhile, a test was conducted to compare the decellularization method established in the present disclosure (Protocol 1) and the conventional decellularization method (Protocol 3).

Specifically, according to Protocol 3, treatment with 3% sodium dodecyl sulfate (SDS), which is often used as a decellularization reagent, was performed for 24 hours in addition to the decellularization protocol 1 established in the present disclosure.

Figure 35A:
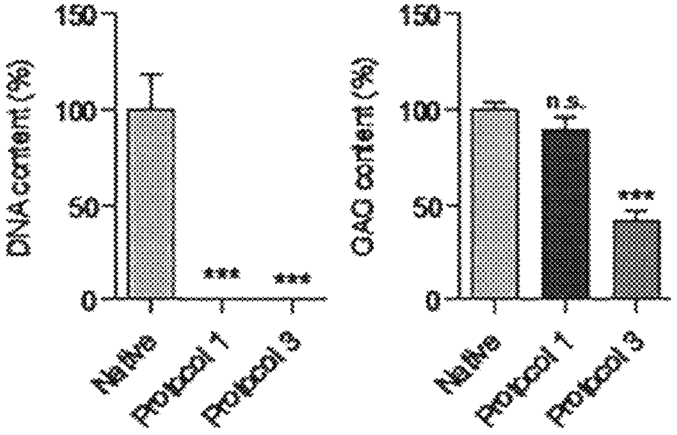
FIG. 35A shows the result of comparative analysis of decellularization methods of stomach tissue.

As a result of comparing the amounts of DNAs remaining after decellularization, it was confirmed that DNAs were successfully removed according to the two protocols. However, as a result of comparing the remaining extracellular matrix components by GAG quantification, it was confirmed that GAG components were significantly decreased in the tissue treated according to Protocol 3 (FIG. 35A).

Figure 35B:
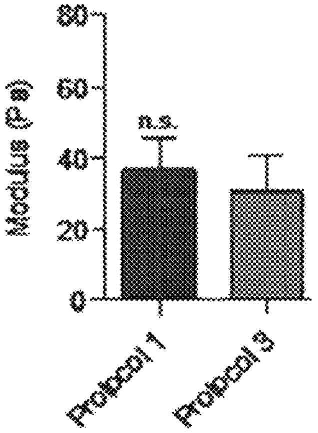
FIG. 35B shows the result of comparative analysis of decellularization methods of stomach tissue.

Also, after hydrogels were fabricated using the prepared decellularized matrices, the mechanical properties (modulus) thereof were measured. It was confirmed that the hydrogels prepared according to the respective protocols were not much different in mechanical properties (FIG. 35B).

Figure 35C:
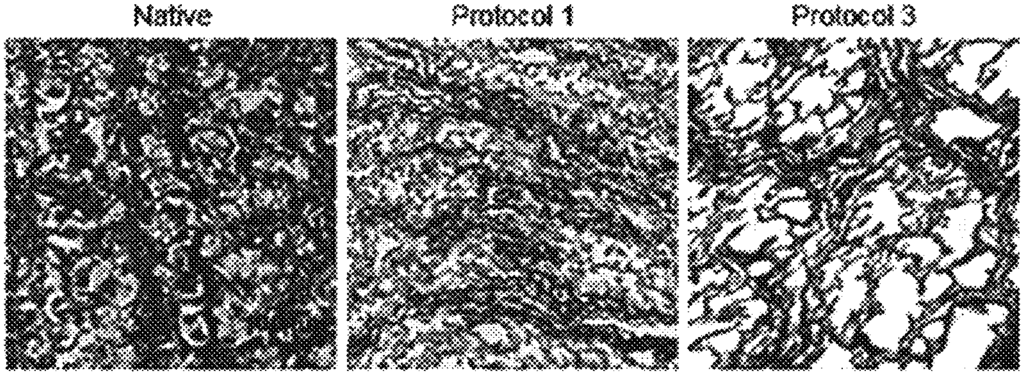
FIG. 35C shows the result of comparative analysis of decellularization methods of stomach tissue.

As a result of comparison by H&E histological analysis, it was confirmed that cells were well removed according to both methods, but the extracellular matrix components were better preserved according to Protocol 1 (FIG. 35C).

Figure 35D:
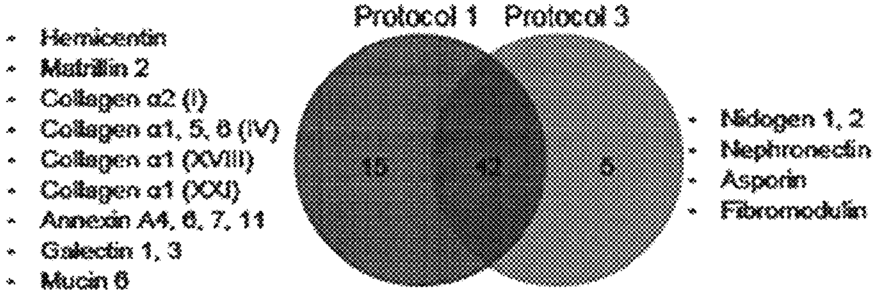
FIG. 35D shows the result of comparative analysis of decellularization methods of stomach tissue.

Proteomic analysis of the matrices prepared by the respective decellularization methods was performed. It was confirmed that Protocol 1 is more effective in preserving a greater number of stomach tissue-specific extracellular matrix proteins than Protocol 3 (FIG. 35D).

According to these results, the decellularization protocol established in the present disclosure can better preserve the extracellular matrix components of stomach tissue than the method using SDS. Therefore, it can be predicted that the decellularization protocol established in the present disclosure can be more effective for gastric organoid culture.

Test Example 4-4. Check of Difference in Gastric Organoid Growth Pattern Based on Decellularization Condition A test was conducted to compare the decellularization method established in the present disclosure (Protocol 1) and the conventionally used decellularization method (Protocol 3) in the decellularization process for preparing a gastric organoid culture matrix.

Specifically, gastric organoids were cultured in the decellularized matrix hydrogels fabricated according to the respective protocols and then, the formation efficiency and gene expression were analyzed.

Figure 36A:
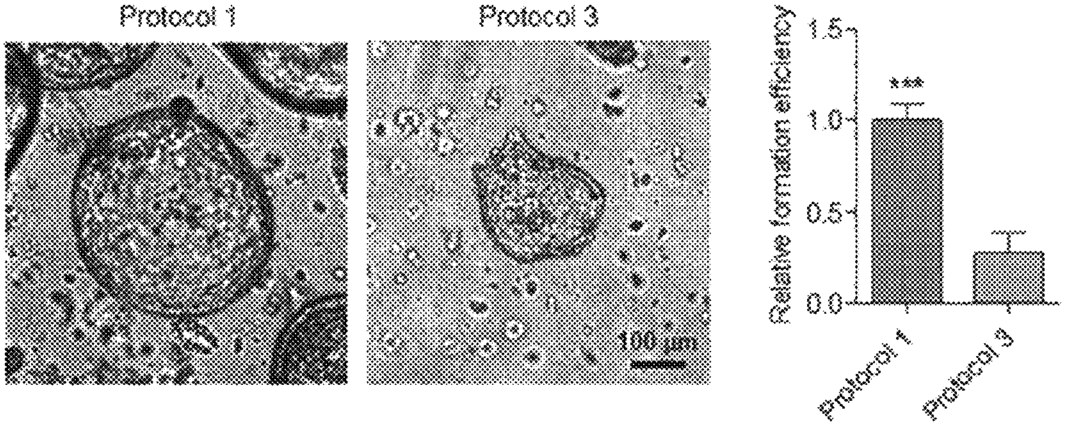
FIG. 36A shows the result of comparison of gastric organoid growth patterns depending on the decellularization method of stomach tissue.

As a result of organoid morphology analysis on day 5 of culture, it was confirmed that the gastric organoid cultured in the decellularized matrix prepared according to Protocol 1 was larger in size than the organoid cultured in the decellularized matrix prepared according to Protocol 3 and well maintained the spherical structure. Also, as a result of quantifying the formation efficiency, it was confirmed that the formation efficiency according to Protocol 1 was significantly high (FIG. 36A).

Figure 36B:
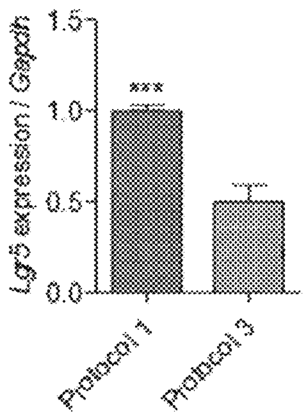
FIG. 36B shows the result of comparison of gastric organoid growth patterns depending on the decellularization method of stomach tissue.

As a result of comparing the expression of Lgr5 gene, which is important for stemness, through quantitative qPCR on day 5 of culture, it was confirmed that the gastric organoid formed in the decellularized stomach tissue-derived matrix prepared according to Protocol 1 showed a significantly high expression level of Lgr5 gene (FIG. 36B).

Accordingly, it was verified that the decellularization protocol established in the present disclosure is more suitable for gastric organoid culture than the conventional method.

Test Example 4-5. Proteomics of SEM

The fabricated SEM scaffold contains various stomach tissue-specific proteins present in the stomach tissue. Therefore, proteomic analysis was performed on the SEM scaffold to identify detailed components, and it was confirmed that various extracellular matrix-related proteins (glycoproteins, proteoglycans, collagens, secreted factors, etc.) are contained in the decellularized matrix.

As a result, as can be seen from FIG. 37, the fabricated SEM scaffold contained various stomach tissue-specific proteins present in the stomach tissue. When SEM samples from four different tissue batches were analyzed, these extracellular matrix components were almost commonly observed. Therefore, it can be inferred that gastric organoids can be produced at a uniform level through culture using an SEM hydrogel scaffold that has been subjected to decellularization.

Test Example 4-6. Type of Protein of SEM and Quantitative Analysis

The types of proteins of the extracellular matrix of the present disclosure were identified and quantitative analysis was performed.

Specifically, the decellularized stomach tissue was solubilized using a lysis buffer [4% sodium dodecyl sulfate (SDS), 0.1 M Tris-HCl (pH 7.6), and 1× protease inhibitor], and protein components were extracted and degraded to the peptide level. Then, the types and relative values of the peptides were detected using a mass spectrometer and MaxQuant software. Thereafter, a detailed classification, such as into matrisome, was performed using the existing library.

As a result, the matrisome proteins included in MATRIGEL® and the SEM were detected through proteomics and classified by type. It can be seen that the number of matrisome proteins detected from the SEM is greater than that from MATRIGEL® (FIG. 38A).

Figures 38B, 39A:
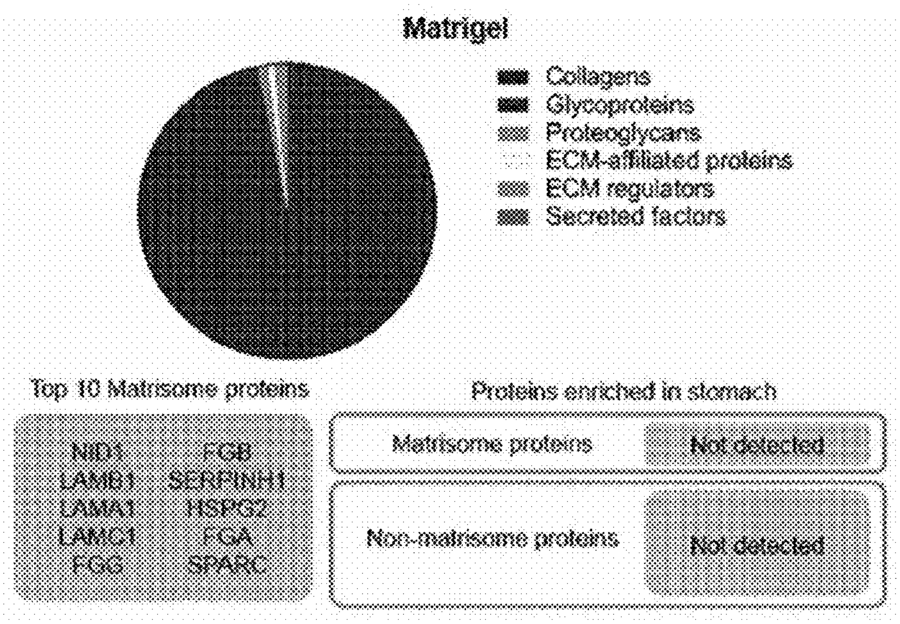
FIG. 38B shows the types of matrisome proteins contained in the SEM and the result of quantitative analysis.
FIG. 39A shows the types of matrisome proteins contained in the SEM and the result of quantitative analysis.

Further, as a result of relative quantification and numerical expression of the matrisome proteins in MATRIGEL® and SEM, it was confirmed that MATRIGEL® is composed of more than 96% glycoproteins, and the SEM is composed of evenly distributed matrisome proteins including 40% collagens and 35% proteoglycans and 15% glycoproteins (FIG. 38B).

Therefore, it can be expected that the SEM scaffold can provide a more suitable microenvironment for gastric organoid culture because it contains much more various types of extracellular matrix components than the conventional MATRIGEL®.

As a result of relative quantification of the matrisome proteins, it was confirmed that glycoproteins account for more than 95% of the proteins in MATRIGEL®. As a result of identifying the top 10 most abundant matrisome proteins, it was found that laminin, which is a representative glycoprotein, accounts for a very high percentage. Also, none of the proteins known to be highly expressed specifically in stomach tissue were detected (FIG. 39A).

Figure 39B:
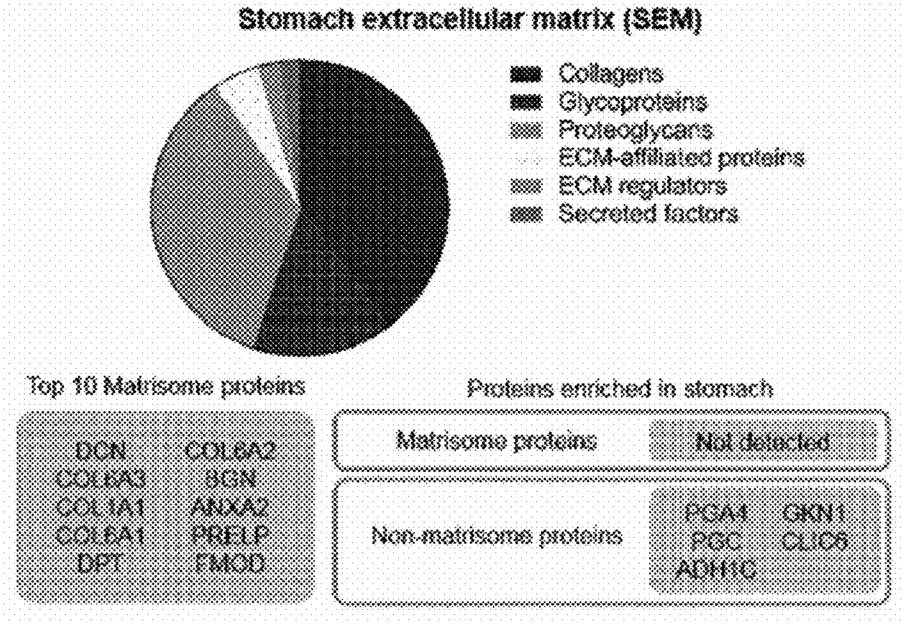
FIG. 39B shows the types of matrisome proteins contained in the SEM and the result of quantitative analysis.

Similarly, when relative quantification of the matrisome proteins in the SEM was performed, it was confirmed that the SEM contains a lot of matrisome proteins in the order of collagens, proteoglycans and glycoproteins and that they are evenly distributed. Also, when the top 10 most abundant matrisome proteins were examined, it was confirmed that the SEM contains a lot of collagens, unlike MATRIGEL®. Further, 5 types of non-matrisome proteins known to be highly expressed specifically in stomach tissue were detected from the SEM. These stomach tissue-specific components are also expected to have a positive effect on the growth and development of a gastric organoid (FIG. 39B).

Therefore, it is expected that the SEM scaffold with this proteomic composition can be applied as a hydrogel more suitable for gastric organoid culture than the conventional MATRIGEL®.

Test Example 4-7. Analysis of Non-Matrisome Protein in Decellularized Stomach Tissue The non-matrisome proteins detected in the decellularized stomach tissue of the present disclosure were compared and analyzed with those in MATRIGEL®.

The decellularized stomach tissue was solubilized using a lysis buffer [4% sodium dodecyl sulfate (SDS), 0.1 M Tris-HCl (pH 7.6), and 1× protease inhibitor], and protein components were extracted and degraded to the peptide level. Then, the types and relative values of the peptides were detected using a mass spectrometer and MaxQuant software. Thereafter, a detailed classification, such as into matrisome, was performed using the existing library.

Figure 40A:
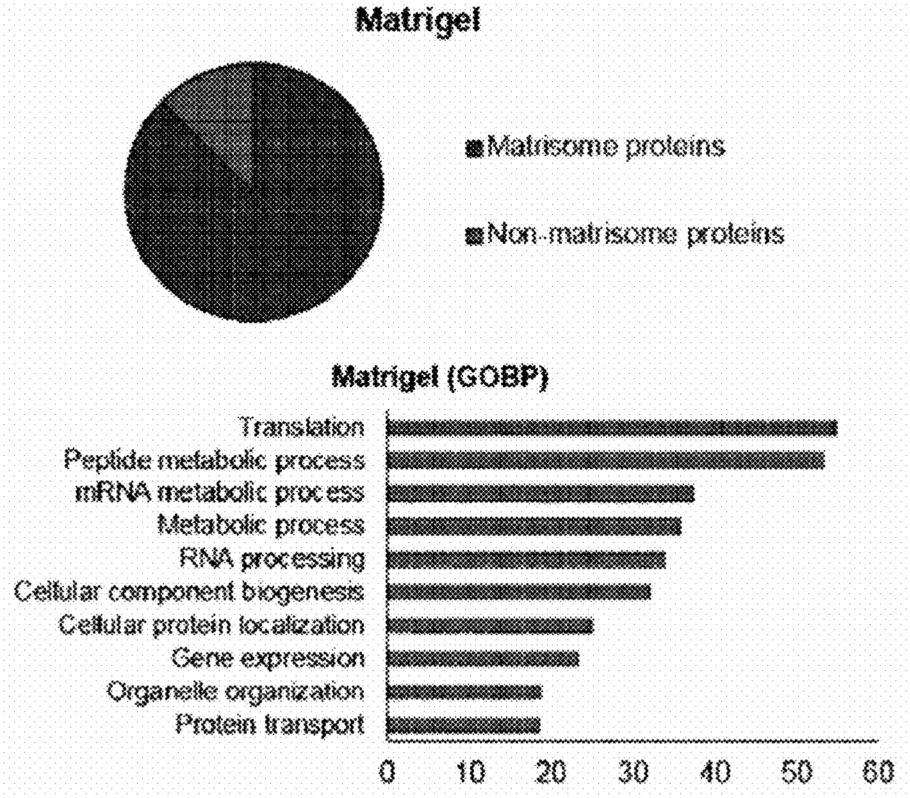
FIG. 40A shows the result of analysis of non-matrisome proteins contained in the SEM.

As a result, as can be seen from FIG. 40, it was confirmed that most of the constituent proteins of MATRIGEL® are matrisome proteins. Also, non-matrisome proteins, not matrisome proteins, among the constituent proteins of MATRIGEL® were analyzed by a gene ontology biological process (GOBP) to analyze which biological processes are involved with the proteins. It was confirmed that MATRIGEL® contains a lot of proteins involved in translation or metabolism (FIG. 40A).

Figure 40B:
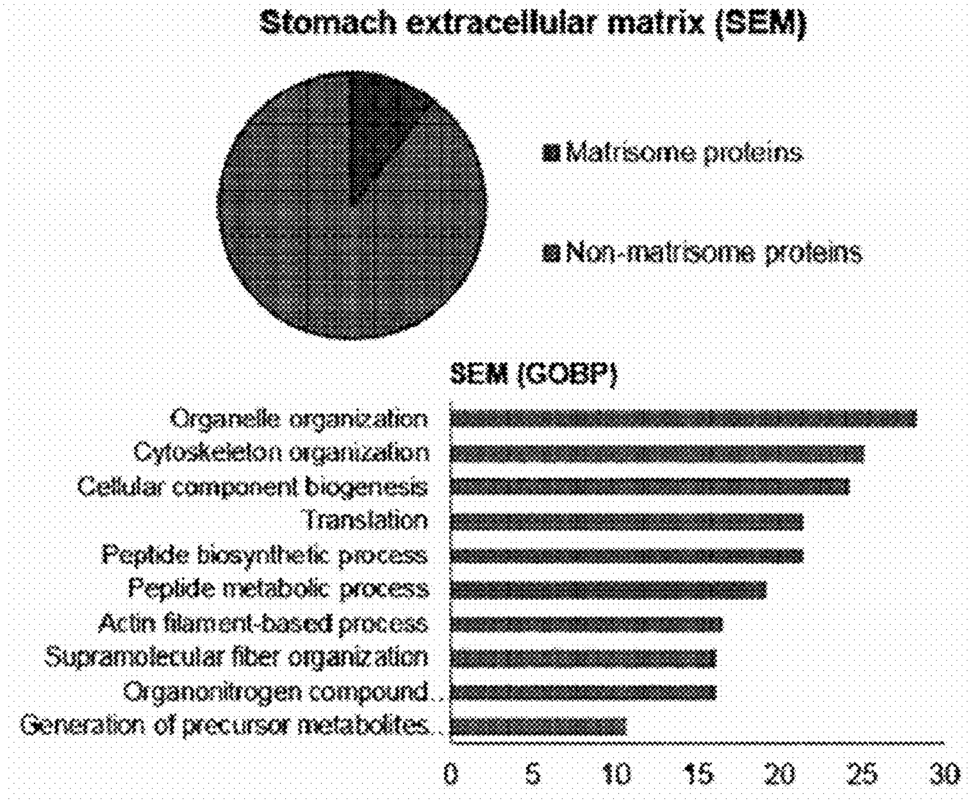
FIG. 40B shows the result of analysis of non-matrisome proteins contained in the SEM.

It was confirmed that the SEM contains relatively more non-matrisome proteins. As a result of analyzing the roles of these proteins by the GOBP, it was confirmed that the SEM particularly contains a lot of proteins involved in the formation of cells and tissues such as organelle organization and cytoskeleton organization (FIG. 40B).

Therefore, it can be expected that the SEM scaffold containing these non-matrisome proteins can be applied as a hydrogel more suitable for gastric organoid culture than the conventional MATRIGEL®.

Test Example 5: Analysis of Scaffold Composition Containing SEM

Test Example 5-1. Selection of Optimal Concentration of SEM in Scaffold Composition With respect to the scaffold composition (hydrogel) prepared in Example 2-2, the optimal concentration of the SEM was selected.

Specifically, to select the optimal hydrogel concentration when applying a decellularized stomach tissue-derived scaffold to organoid culture, hydrogels were prepared at respective SEM concentrations (1, 3, 5 and 7 mg/mL) and gastric organoids were cultured. The gastric gland, which is the most functional unit, was extracted from the stomach tissue of a mouse and three-dimensionally cultured in each hydrogel to induce formation of a gastric organoid. The morphology and formation efficiency of the gastric organoids formed at the respective SEM concentrations on day 5 of culture were compared with those of a gastric organoid formed in MATRIGEL®.

Figure 41A:
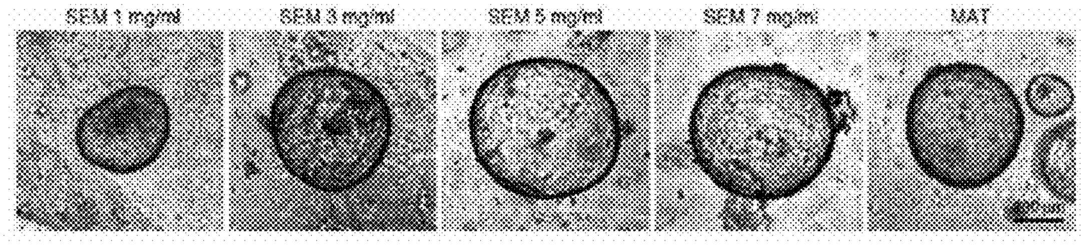
FIG. 41A shows the optimal concentration of a decellularized stomach tissue-derived hydrogel scaffold for gastric organoid culture.
Figure 41B:
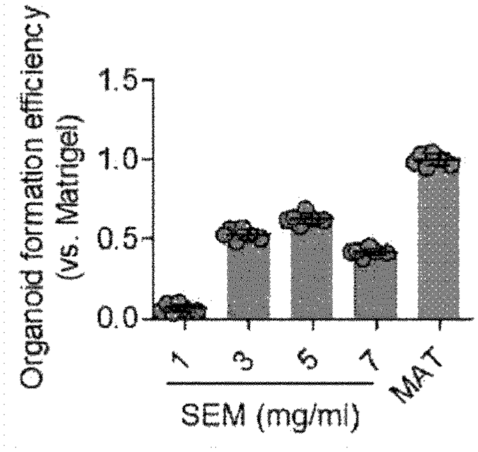
FIG. 41B shows the optimal concentration of a decellularized stomach tissue-derived hydrogel scaffold for gastric organoid culture.

As a result, as can be seen from FIG. 41, it was confirmed that the gastric organoids cultured in the SEM hydrogels of all concentrations were formed into a spherical shape similar to the organoid cultured in MATRIGEL® used as a control group. At a concentration of 1 mg/ml, an organoid having a relatively small size was formed (FIG. 41A). As a result of comparing the organoid formation efficiency for each SEM concentration, the organoid formation efficiency of the SEM hydrogel was lower at most concentrations than that of MATRIGEL®, but the SEM hydrogel of 5 mg/ml exhibited the highest formation efficiency among all the SEM hydrogels (FIG. 41B).

Test Example 5-2. Comparison of Growth Patterns of Gastric Organoids Cultured in Scaffold Compositions Depending on Concentration of SEM With respect to the scaffold composition (hydrogel) prepared in Example 2-2, gastric organoid growth patterns were compared depending on the concentration of the SEM.

Specifically, to select the optimal SEM hydrogel concentration when applying a decellularized stomach tissue-derived scaffold to gastric organoid culture, gastric organoids were cultured in hydrogels prepared at respective SEM concentrations (1, 3, 5 and 7 mg/ml). MATRIGEL® was used as a control group.

Figure 42A:
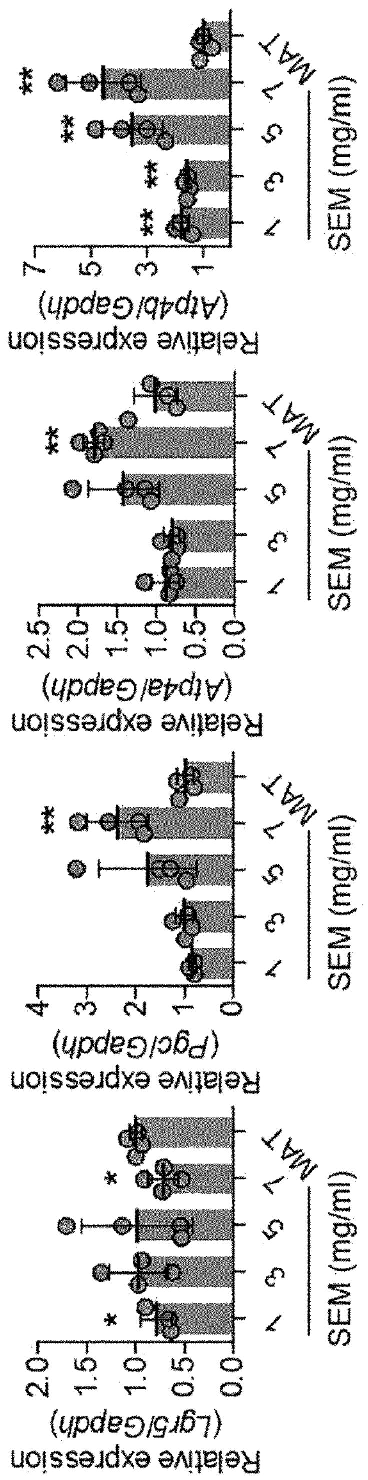
FIG. 42A compares gastric organoid growth patterns depending on the concentration of the decellularized stomach tissue-derived hydrogel scaffold.

As a result of comparing the mRNA expression levels of gastric organoids cultured for 5 days in the SEM hydrogels prepared at respective concentrations by quantitative PCR (q-PCR), it was confirmed that Lgr5, a gene related to stemness, significantly decreases at a concentration of 1 mg/ml and a concentration of 7 mg/ml. Also, the expression of Pgc (chief cell), Atp4a, and Atp4b (parietal cell), genes expressed in specific types of cells of stomach tissue, tends to increase as the concentration increases. Overall, it is determined that 5 mg/ml SEM is a suitable concentration for promoting differentiation into various stomach tissue-specific cell types while maintaining stemness (Lgr5 expression) compared to the control group MATRIGEL® (FIG. 42A).

Figure 42B:
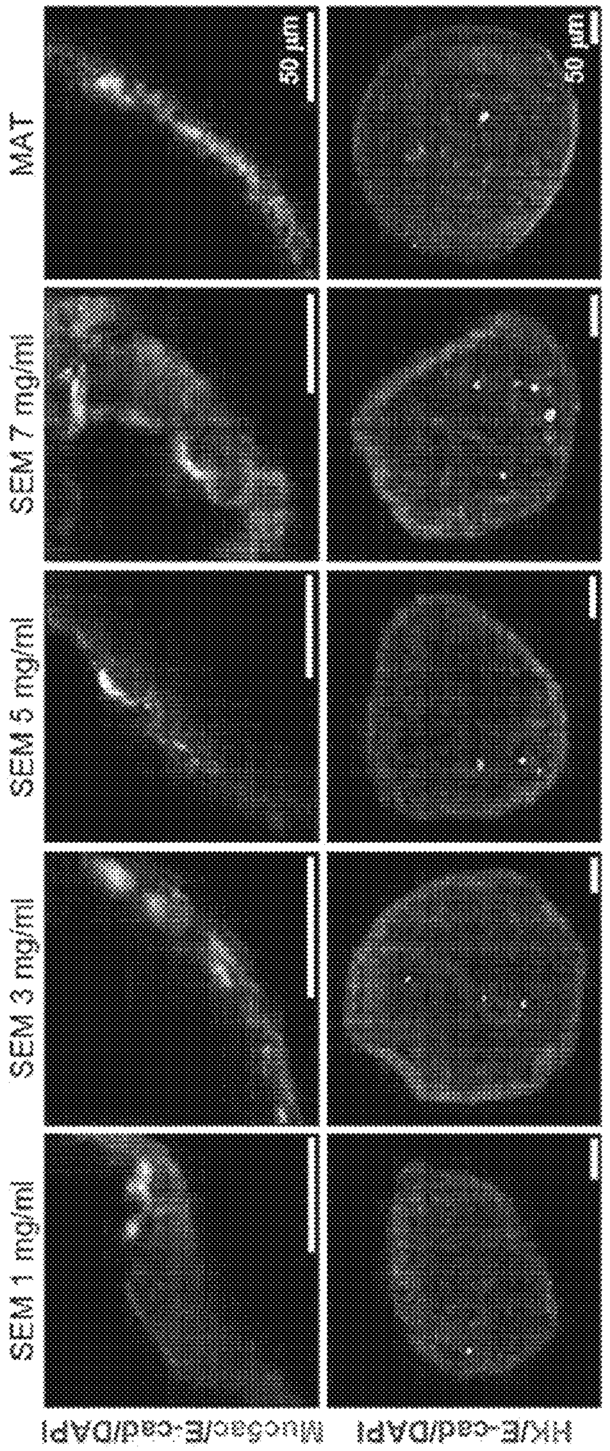
FIG. 42B compares gastric organoid growth patterns depending on the concentration of the decellularized stomach tissue-derived hydrogel scaffold.

In addition, as a result of comparing the expression levels of stomach tissue cell markers Muc5ac (gastric pit cell) and HK (parietal cell) by immunostaining on the same 5th day, it was confirmed that the overall stomach tissue-specific marker protein expression level increases as the SEM hydrogel concentration increases (FIG. 42B). Through concentration screening of the SEM hydrogels, subsequent tests were conducted at an SEM concentration of 5 mg/ml at which both the proliferation and differentiation effects of gastric organoids can be expected.

Test Example 5-3. Comparison of Growth Patterns of Gastric Organoids Cultured in SEM Scaffold Composition and Conventional Culture Scaffold Growth patterns of gastric organoids cultured in the scaffold composition of the present disclosure and the conventional culture scaffold (MATRIGEL®) were compared.

Specifically, a gastric organoid cultured in MATRIGEL®, which is the most widely used scaffold for organoid culture, was compared with a gastric organoid cultured in the decellularized stomach tissue-derived SEM hydrogel (5 mg/ml) scaffold.

Figure 43:
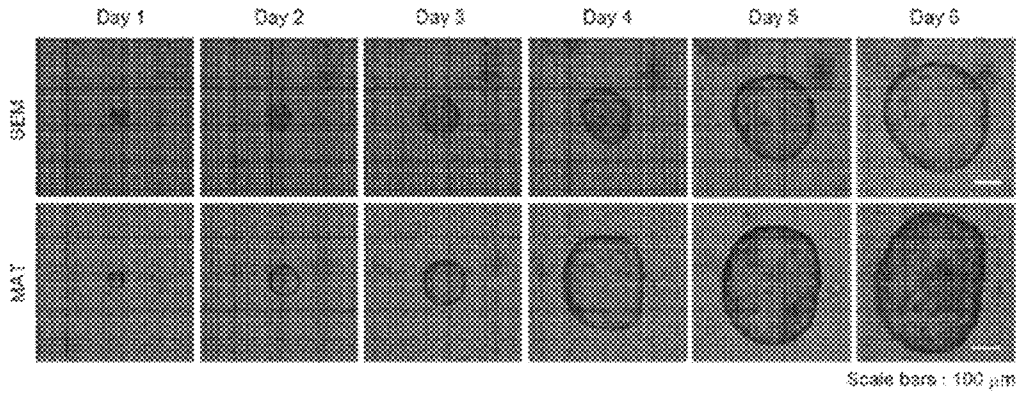
FIG. 43 compares the growth of gastric organoids formed in the decellularized stomach tissue-derived hydrogel scaffold and a conventional culture scaffold (MATRIGEL®).

As a result, as shown in FIG. 43, it was confirmed that all the gastric organoids formed in the respective scaffolds continued to increase in size and cultured well until 5 to 6 days immediately before subculture.

Test Example 5-4. Comparison of Gastric Organoids Cultured in SEM Scaffold Composition and Conventional Culture Scaffold A gastric organoid cultured in MATRIGEL®, which is the most widely used scaffold for organoid culture, was compared and analyzed with a gastric organoid cultured in the decellularized stomach tissue-derived SEM hydrogel (5 mg/ml) scaffold in various terms.

Specifically, the gene expression and protein expression of the gastric organoids cultured in the respective culture scaffolds were compared on day 5 of culture.

Figure 44A:
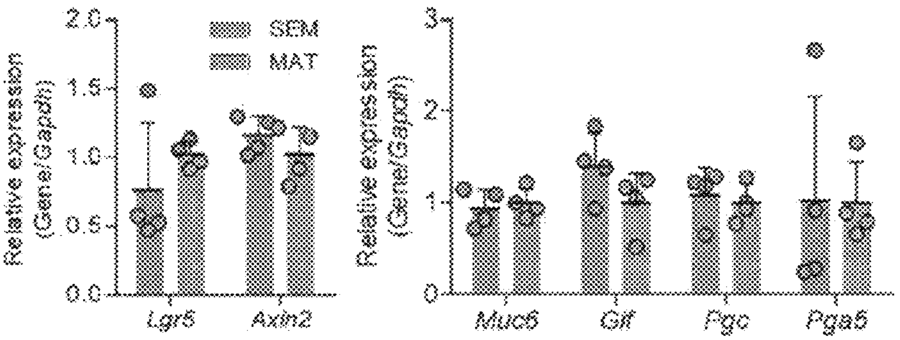
FIG. 44A compares gastric organoids formed in the decellularized stomach tissue-derived hydrogel scaffold and the conventional culture scaffold (MATRIGEL®).

As a result of comparing the expression of markers of the gastric organoids cultured in the decellularized SEM hydrogel scaffold and MATRIGEL® at the mRNA level, it was confirmed that the stem cell markers, Lgr5 and Axin2, showed similar levels. Also, it was confirmed that Muc6 (neck cell), Gif (parietal cell), Pgc and Pga5 (chief cell), genes expressed in various types of gastric cells, showed similar levels (FIG. 44A).

Figure 44B:
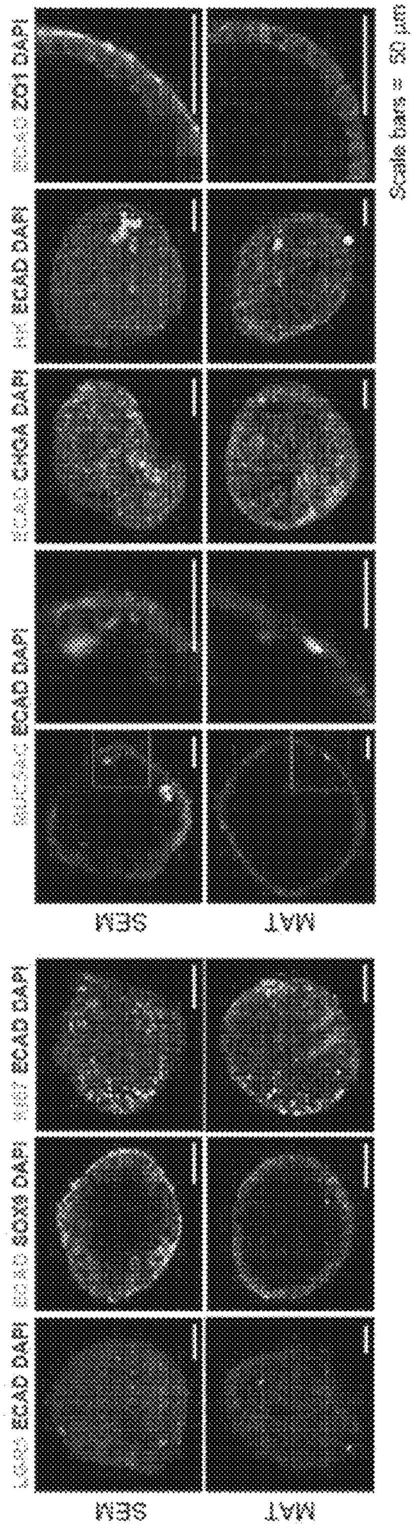
FIG. 44B compares gastric organoids formed in the decellularized stomach tissue-derived hydrogel scaffold and the conventional culture scaffold (MATRIGEL®).

Further, as a result of comparing the protein expression by immunostaining, it was confirmed that LGR5, SOX9 and KI67 related to stemness and proliferation and MUC5AC (gastric pit cell), CHGA (endocrine cell) and HK (parietal cell) related to differentiation were all well expressed at a similar level in the organoids of both groups. Also, in each organoid, ECAD and ZO1 related to cell-cell interaction or tight junction were well expressed. Morphologically, it was confirmed that the organoid is composed of stomach tissue epithelial cells and well maintains the shape of epithelium (FIG. 44B).

Therefore, it was confirmed that the decellularized stomach tissue-derived SEM hydrogel is a scaffold capable of culturing a gastric organoid at a level similar to that in MATRIGEL®, which is a conventional culture scaffold.

Test Example 5-5. Comparative Analysis of Acid Secretion by Gastric Organoids Cultured in SEM Scaffold Composition and Conventional Culture Scaffold The functionality of a gastric organoid cultured for 5 days in the hydrogel scaffold of the present disclosure was compared and analyzed with that of a gastric organoid cultured for the same period of time in MATRIGEL®.

Specifically, acid secretion, which is one of the important functions of stomach, was checked by Acridine Orange staining.

Figure 45:
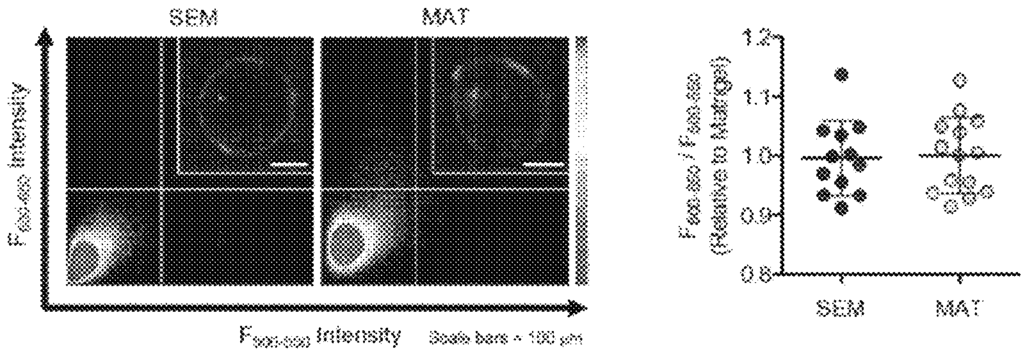
FIG. 45 shows the comparative analysis of the acid secretion of gastric organoids cultured in the decellularized stomach tissue-derived hydrogel scaffold and MATRIGEL®.

As can be seen from FIG. 45, as acidity increased, a green fluorescence ($F_{500-550}$) intensity decreased and a red fluorescence ($F_{600-650}$) intensity increased. After the Acridine Orange staining, the expression of fluorescence was compared between the groups. It was confirmed that the gastric organoid cultured in the SEM hydrogel showed a similar level of acid secretion to the gastric organoid cultured in MATRIGEL®. Therefore, it seems that a gastric organoid cultured using a decellularized stomach tissue-derived scaffold has no functional problem in replacing an organoid cultured in the conventional MATRIGEL®.

Test Example 5-6. Effect of Promoting Differentiation of Organoid by Mixing SEM Scaffold Composition and Conventional Culture Scaffold The effect of promoting the differentiation of an organoid by mixing the hydrogel scaffold composition of the present disclosure and the conventional culture scaffold was checked.

Specifically, to construct a culture system that can further promote the differentiation of a gastric organoid while maximally replacing MATRIGEL®, which is a conventional gastric organoid culture scaffold, the SEM hydrogel and MATRIGEL® were mixed at 9:1 (v/v) and tested as a new culture scaffold. A MATRIGEL® group was used as a control group.

Figure 46A:
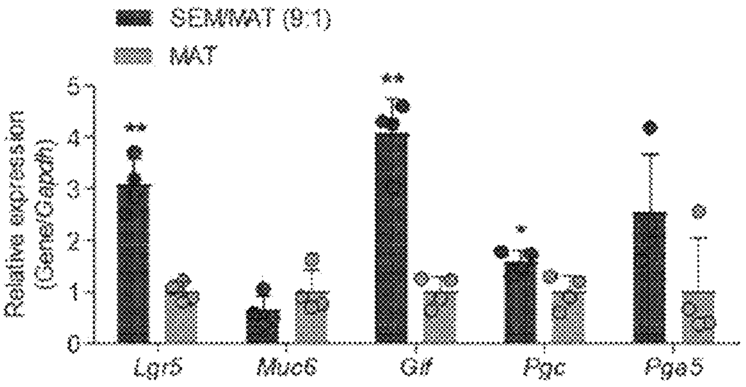
FIG. 46A shows the effect of improving gastric organoid differentiation by mixing the decellularized stomach tissue-derived hydrogel scaffold and MATRIGEL®.

As a result of comparing the mRNA expression level for each marker of the gastric organoids cultured for 5 days in the SEM/MAT (9:1) hydrogel and MATRIGEL®, respectively, the expression level of Lgr5 related to stemness significantly increased and the expression levels of various differentiation markers Gif (parietal cell) and Pgc (chief cell) expressed in specific stomach tissue epithelial cells also significantly increased. The expression level of Pga5 (chief cell) also increased compared to an organoid cultured in MATRIGEL® (FIG. 46A).

Figure 46B:
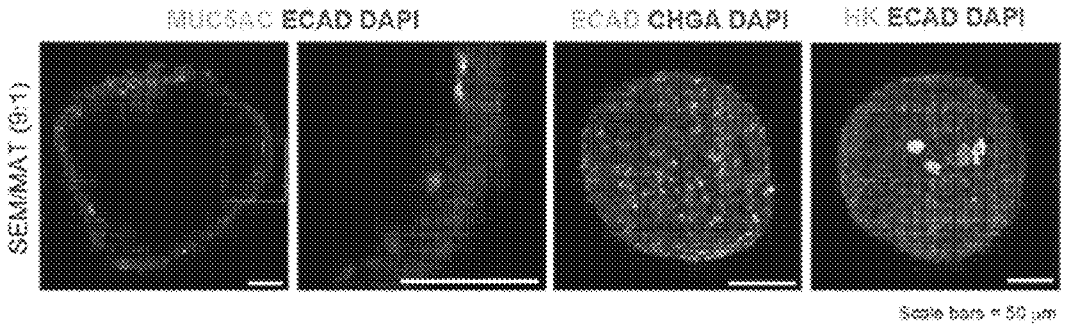
FIG. 46B shows the effect of improving gastric organoid differentiation by mixing the decellularized stomach tissue-derived hydrogel scaffold and MATRIGEL®.

Also, as a result of checking the expression of various marker proteins by immunostaining of the gastric organoid cultured for 5 days in the SEM/MAT (9:1) hydrogel scaffold, the gastric organoid was well formed and its differentiation was promoted through the expression of MUC5AC (gastric pit cell), CHGA (endocrine cell), HK (parietal cell) and ECAD (epithelial cell) (FIG. 46B).

According to these results, it can be seen that a culture scaffold capable of promoting the proliferation and differentiation of a gastric organoid can be prepared by mixing a small amount of MATRIGEL® with the SEM-based hydrogel.

Test Example 5-7. Effect of Enhancing Effect of Organoid by Mixing SEM Scaffold Composition and Conventional Culture Scaffold The effect of enhancing the function of an organoid by mixing the hydrogel scaffold composition of the present disclosure and the conventional culture scaffold was checked.

Specifically, the degree of functional enhancement of a gastric organoid cultured for 5 days in a SEM/MAT (9:1) hydrogel scaffold was analyzed. Acid secretion, which is one of the important functions of stomach, was checked by Acridine Orange staining. A MATRIGEL® group was used as a control group.

Figure 47:
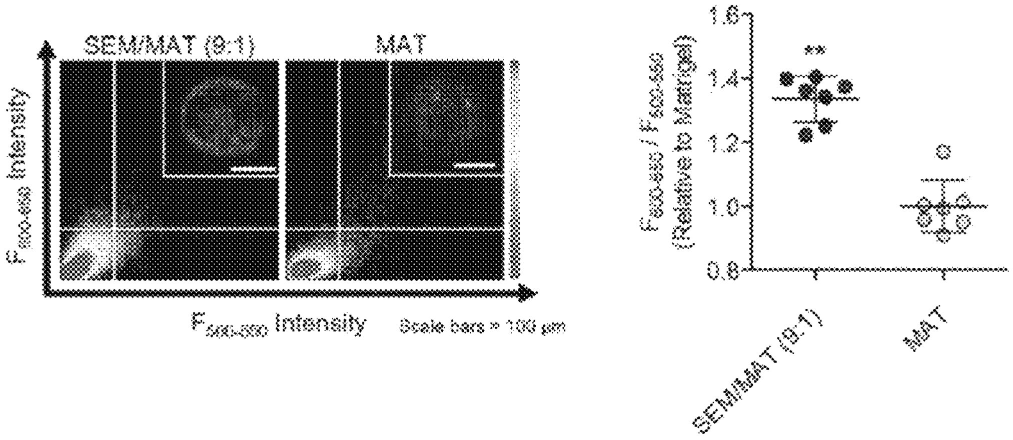
FIG. 47 shows the effect of improving the gastric organoid functionality by mixing the decellularized stomach tissue-derived hydrogel scaffold and MATRIGEL®.

As a result, as shown in FIG. 47, after Acridine Orange staining, the expression of fluorescence was compared between the groups. It was confirmed that the gastric organoid cultured in the SEM/MAT (9:1) hydrogel showed a significant increase in acid secretion compared to the gastric organoid cultured in MATRIGEL®. This test confirmed the possibility of fabricating a functionally superior gastric organoid by mixing a decellularized stomach tissue-derived SEM hydrogel scaffold.

Test Example 5-8. Check of Tissue-Specific Effect of SEM Scaffold Composition

In order to check whether stomach-specific extracellular matrix components in a decellularized stomach tissue-derived scaffold has a tissue-specific effect on gastric organoid culture, a test was conducted in which gastric organoids were cultured in other organ-derived decellularized scaffolds and compared to each other.

Specifically, gastric organoids were cultured for 5 days in decellularized scaffolds derived from respective tissues and then various analyses were performed.

Figure 48A:
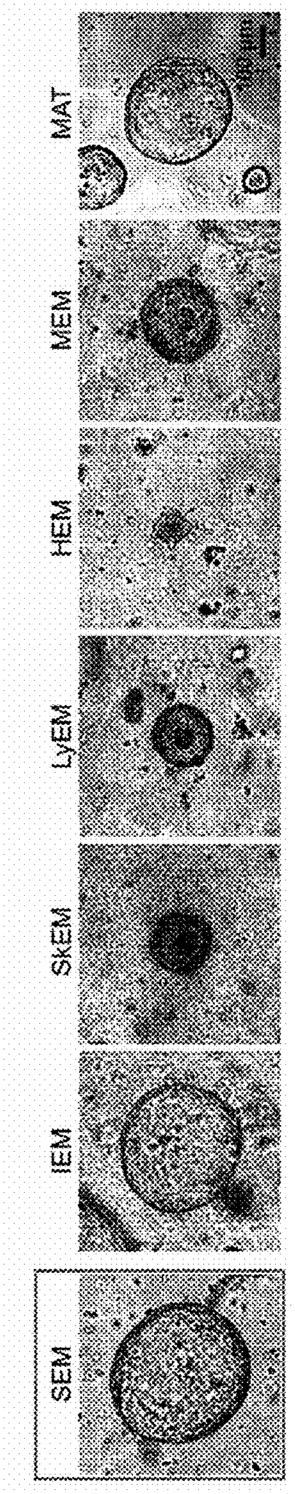
FIG. 48A confirms the tissue-specific effect of the decellularized stomach tissue-derived hydrogel scaffold for gastric organoid culture.

As a result of culturing using decellularized scaffolds derived from stomach, intestine, skin, lymph, heart and muscle, gastric organoids were well formed in the decellularized scaffolds derived from stomach and intestine. Also, a gastric organoid was not properly formed in the decellularized scaffold derived from skin (FIG. 48A).

Figure 48B:
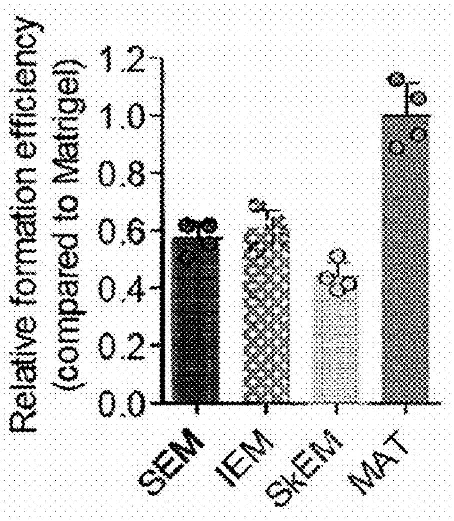
FIG. 48B confirms the tissue-specific effect of the decellularized stomach tissue-derived hydrogel scaffold for gastric organoid culture.

As a result of quantitative analysis of the organoid formation efficiency, the stomach and intestinal-derived decellularized scaffolds exhibited similar formation efficiency, whereas the skin tissue-derived decellularized scaffold showed a decrease in formation efficiency (FIG. 48B).

Figure 48C:
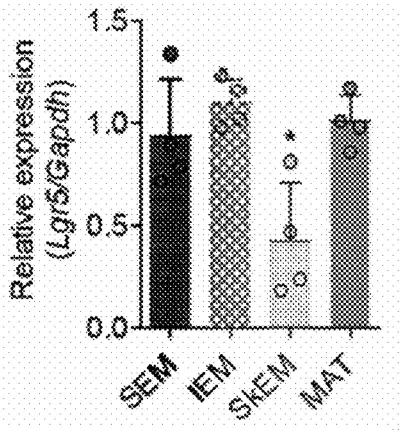
FIG. 48C confirms the tissue-specific effect of the decellularized stomach tissue-derived hydrogel scaffold for gastric organoid culture.

As a result of comparing the expression of marker mRNA of the gastric organoids cultured for 5 days in the respective organ-derived decellularized scaffolds, the expression level of Lgr5 related to stemness significantly decreased in the organoids cultured in the skin tissue-derived scaffold (FIG. 48C).

This test confirmed the tissue-specific effect of the decellularized stomach tissue-derived scaffold in gastric organoid culture. Also, it was confirmed that a decellularized scaffold derived from the intestine, which is the digestive tissue similar to the stomach, also exhibited a similar effect.

Meanwhile, relative quantification of ECM proteins contained in an SEM and a SkEM was performed to confirm the tissue-specific effect of the SEM.

Figure 49:
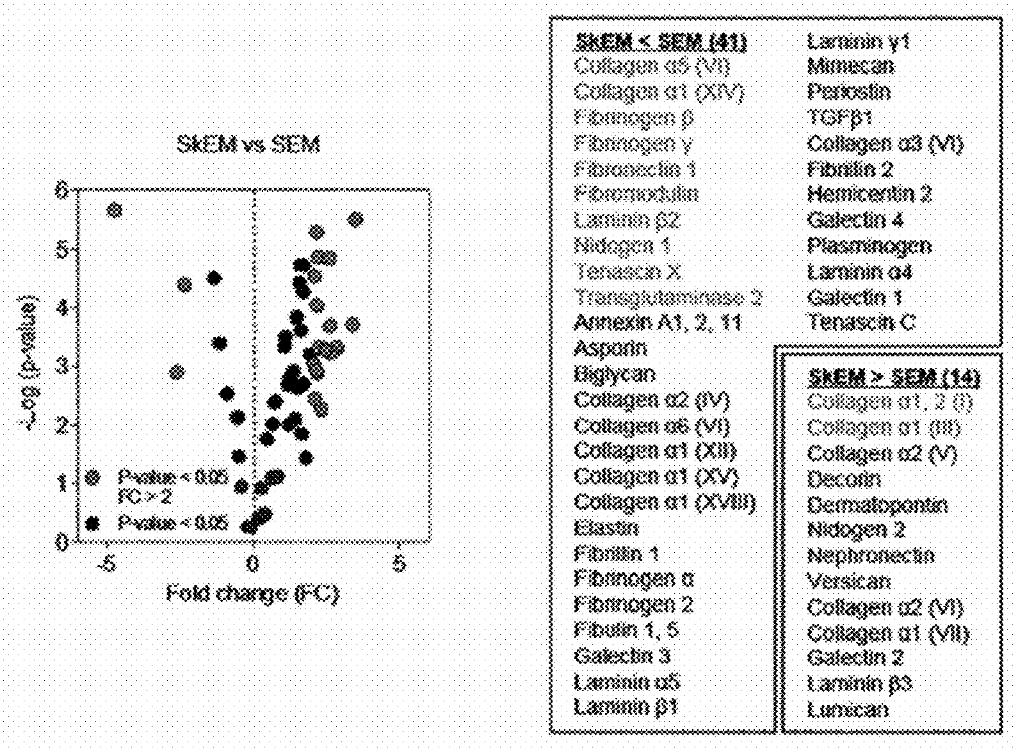
FIG. 49 shows the result confirming the difference in extracellular matrix components between skin tissue and stomach tissue.

As can be seen from FIG. 49, as a result of comparing a total of 55 extracellular matrix proteins detected in the SEM and SkEM, it can be seen that 41 extracellular matrix proteins are contained more in the SEM than in the SkEM. Particularly, major extracellular matrix components such as fibronectin and laminin, which are known to be important for organoid development, are contained more in the SEM. Thus, the SEM is regarded as more suitable for gastric organoid culture.

Test Example 5-9. Analysis of Difference in Extracellular Matrix Component Depending on Tissue Age of SEM Scaffold Composition The difference in extracellular matrix component depending on the tissue age of the scaffold composition of the present disclosure was analyzed.

Specifically, when gastric organoids were cultured in an SEM hydrogel derived from piglet stomach tissue (Piglet) and an SEM hydrogel derived from adult pig stomach tissue (adult pig), the difference in the gene expression of the gastric organoids and the difference in extracellular matrix protein components in each hydrogel were analyzed.

Figure 50A:
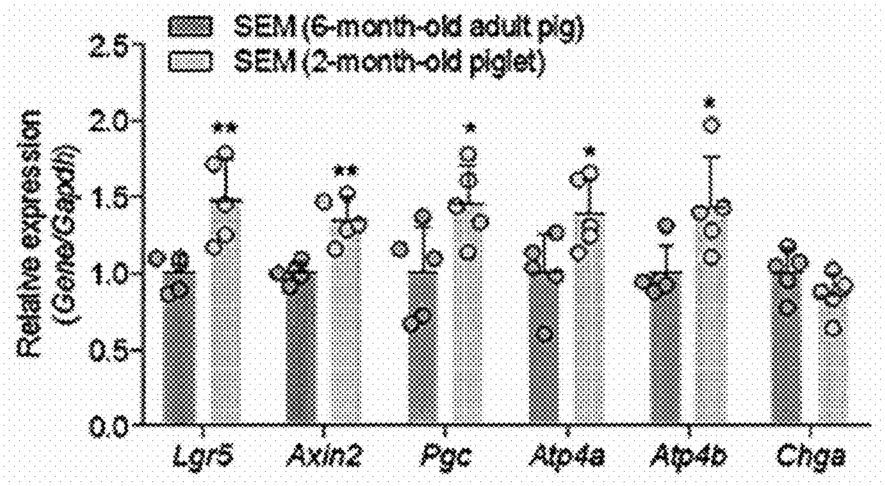
FIG. 50A shows the result of analysis of the difference in extracellular matrix components depending on the tissue age of the SEM.

As a result of analyzing the difference in the gene expression of the gastric organoids cultured in the respective hydrogels through a qPCR test, the gastric organoid cultured in the scaffold derived from the piglet stomach tissue showed an overall increase in the expression of stem cells and differentiation markers compared to the gastric organoid cultured in the scaffold derived from the adult pig stomach tissue (FIG. 50A).

Figure 50B:
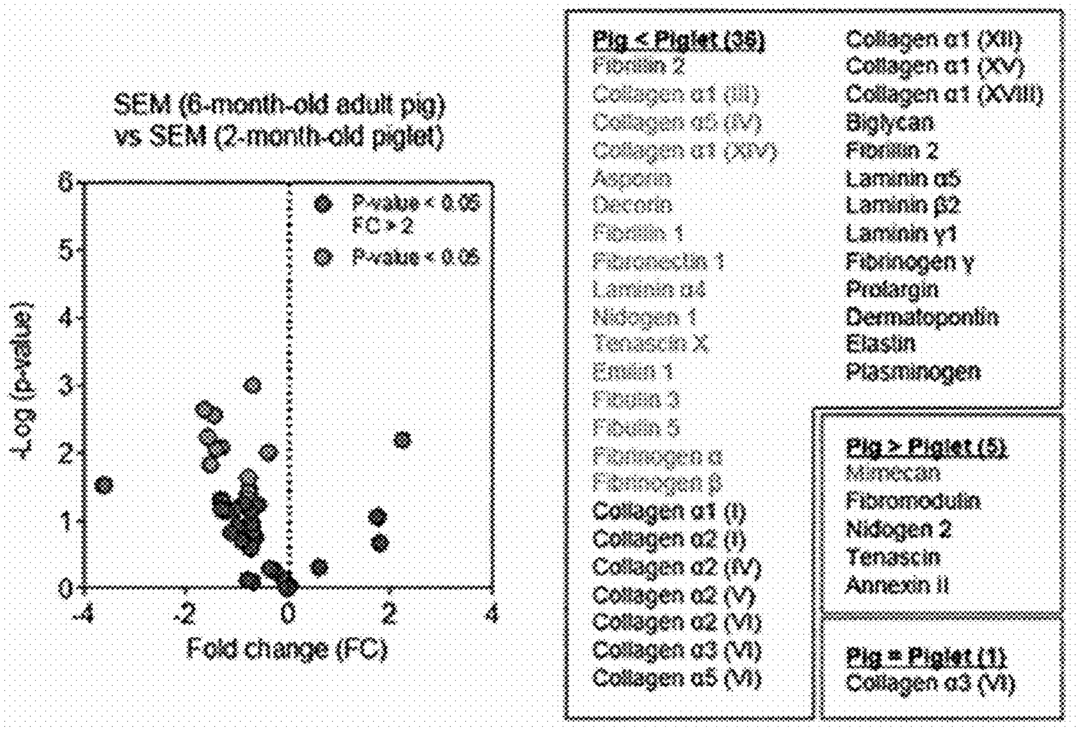
FIG. 50B shows the result of analysis of the difference in extracellular matrix components depending on the tissue age of the SEM.

As a result of relative quantitative comparison of the extracellular matrix protein components in each hydrogel, it was confirmed that the scaffold derived from the piglet stomach tissue contains a greater amount of extracellular matrix protein than the scaffold derived from the adult pig stomach tissue. In particular, since major extracellular matrix components such as fibronectin and laminin are more abundantly contained in the piglet tissue-derived scaffold, it can be seen that a scaffold prepared from the tissue of a younger individual is more effective in the formation and differentiation of a gastric organoid (FIG. 50B).

Test Example 5-10. Optimization of Culture Medium Condition for Long-Term Culture of Gastric Organoid in SEM Scaffold Composition Optimal culture medium conditions for long-term culture of a gastric organoid in the scaffold composition of the present disclosure were selected.

Figure 51A:
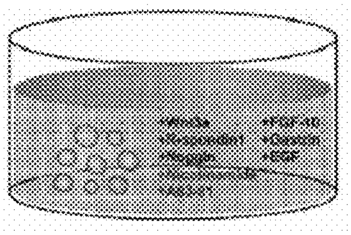
FIG. 51A shows the optimization of culture medium conditions for long-term culture of a gastric organoid in the decellularized stomach tissue-derived hydrogel scaffold.

Specifically, as shown in FIG. 51A, a test was conducted while adjusting a factor (reagent in red) added in addition to a conventional culture medium composition (reagent in black).

Figure 51B:
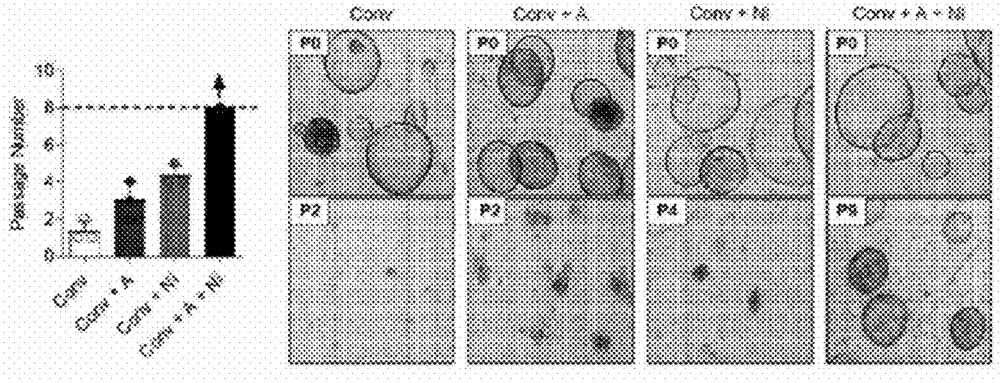
FIG. 51B shows the optimization of culture medium conditions for long-term culture of a gastric organoid in the decellularized stomach tissue-derived hydrogel scaffold.

As a result, as shown in FIG. 51B, a long-term culture of a gastric organoid was attempted in each of a conventional culture medium composition (Conv), a composition added with A83-01 (Conv+A), a composition added with nicotinamide (Conv+Ni) and a composition added with both of them (Conv+A+Ni). The maximum number of times of subculture was checked and organoid morphology was analyzed. As a result, a long-term subculture was not possible in the conventional culture medium condition and the culture medium conditions added with only one additional factor. However, it was confirmed that a subculture was possible at least 8 times in the improved culture medium condition added with both A83-01 and nicotinamide.

Test Example 5-11. Long-Term Culture of Gastric Organoid in SEM Scaffold Composition A long-term culture of a gastric organoid was attempted in the SEM and various stemness markers were analyzed under the culture medium conditions established in the above test example. A MATRIGEL® group was used as a control group.

Figure 52A:
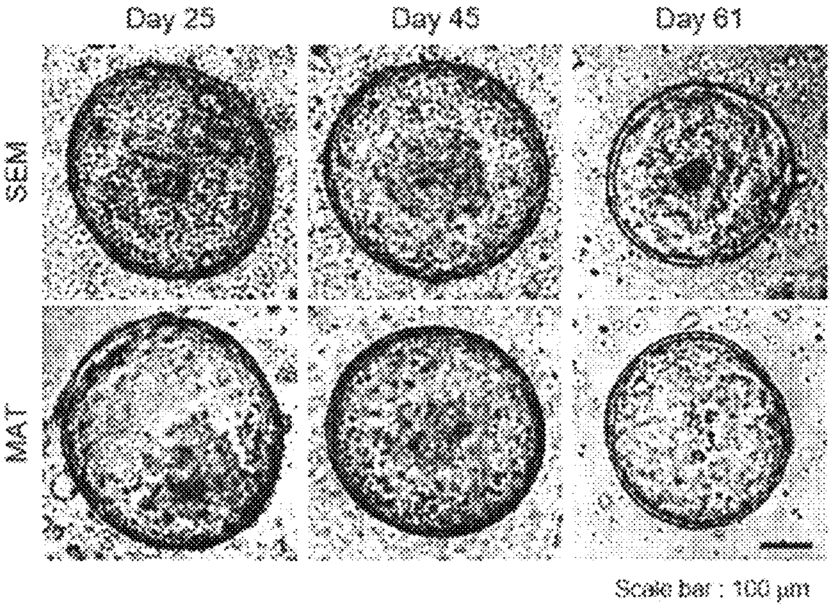

As can be seen from images of gastric organoid morphology when the organoid was subcultured in the SEM hydrogel for about 2 months (61 days), it was formed in a spherical shape with similar size to the gastric organoid cultured in MATRIGEL® (FIG. 52A).

Figure 52B:
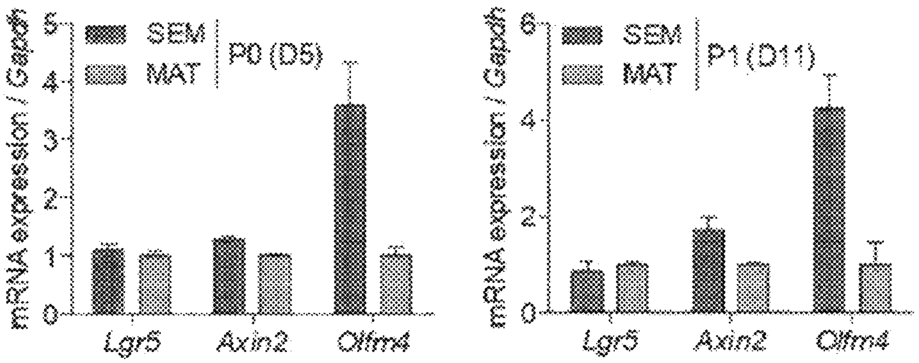

The stemness-related mRNA expression patterns of the gastric organoids cultured in the SEM hydrogel and MATRIGEL® on day 5 and day 11 of culture were compared. It was confirmed that the expression levels of Lgr5, Axin2 and Olfm4 genes related to stemness were maintained similar or higher in the SEM hydrogel group compared to the MATRIGEL® group (FIG. 52B).

Figure 52C:
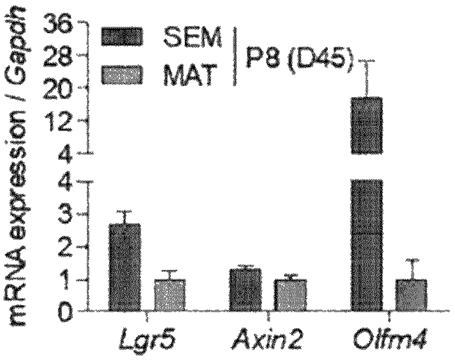

On day 45 after each subculture 8 times, the expression levels of Lgr5, Axin2 and Olfm4 in the SEM hydrogel group and the MATRIGEL® group were compared. It was also confirmed that the expression levels were maintained similar or higher in the gastric organoid cultured in the SEM hydrogel (FIG. 52C).

Accordingly, it was confirmed that the gastric organoid can be cultured for at least 2 months in the decellularized stomach tissue-derived hydrogel scaffold and has a similar or improved level of stemness compared to the organoid cultured for the same period of time in MATRIGEL®.

Test Example 5-11. Analysis of Transcriptome Expression of Gastric Organoid Cultured in SEM Scaffold Composition The transcriptome expression of a gastric organoid cultured in the scaffold composition of the present disclosure was analyzed.

Specifically, the gene expression of the gastric organoid cultured in the SEM hydrogel was checked by RNA-sequencing analysis, and the gastric organoid was compared to an organoid cultured in MATRIGEL® in terms of transcript expression level. Differentially expressed genes (DEGs) when comparing the two groups were selected and analyzed by gene ontology.

Figure 53A:
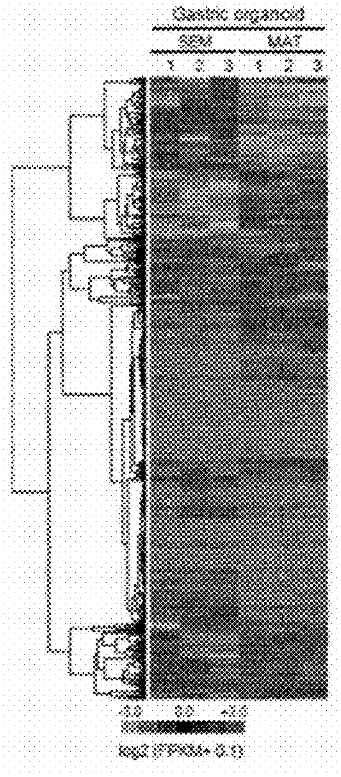

Among the genes expressed in all of the gastric organoids cultured in the SEM hydrogel and MATRIGEL®, respectively, 590 DEGs were selected based on the statistical criteria of 2-fold, p-value <0.05 and FDR<0.1 and visualized in a heatmap. As a result of comparing the two organoids, it was confirmed that, the forms of the organoids were similar to each other, but a significant number of genes were differentially expressed (FIG. 53A).

Figure 53B:
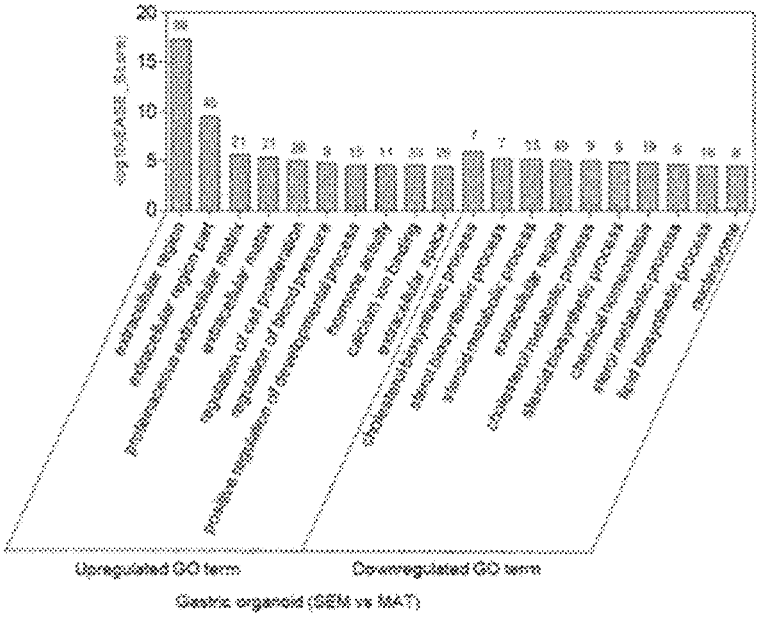

Gene ontology analysis was performed to analyze each of an upregulated gene category (orange) and a downregulated gene category (green) in the SEM hydrogel group. The expression of genes belonging to categories related to extracellular matrix, such as extracellular region, extracellular region part, proteinaceous extracellular matrix and extracellular matrix, was significantly increased. Meanwhile, the expression of genes related to fat metabolisms such as cholesterol biosynthetic process, sterol biosynthetic process and steroid metabolic process was most decreased (FIG. 53B).

Figure 53C:
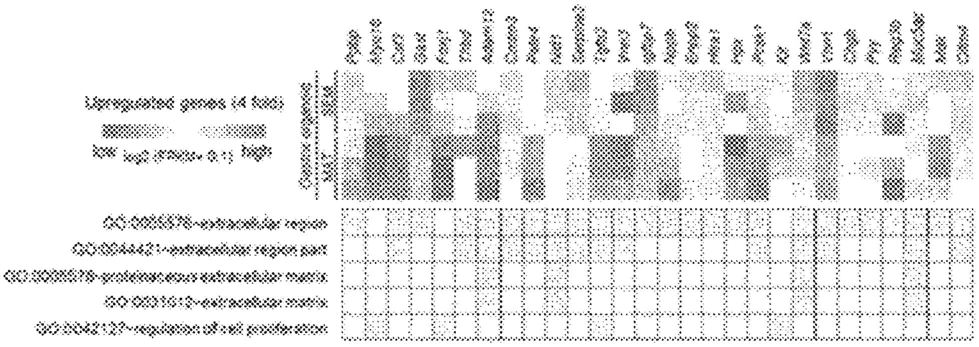

When a total of 28 DEGs whose expression levels were increased 4-fold or more in the SEM group compared to the MATRIGEL® group were selected, it was confirmed that most of the genes belonged to the extracellular matrix-related gene category, and, thus, the expression of extracellular matrix-related genes was significantly increased. In particular, it was confirmed that 25 of the 28 upregulated genes belonged to the extracellular region category and were most increased. Also, it was confirmed that 14 genes related to the extracellular region part, 4 genes related to the proteinaceous extracellular matrix, 4 genes related to the extracellular matrix and 4 genes related to the regulation of cell proliferation were contained in the SEM hydrogel, and, thus, the SEM hydrogel significantly increased the expression of the extracellular matrix and cell proliferation-related genes of the gastric organoid compared to MATRIGEL® (FIG. 53C).

Meanwhile, a transcriptome of mouse stomach tissue was checked by RNA-sequencing analysis and then compared and analyzed with transcriptomes of the gastric organoids cultured in the respective hydrogels.

Figure 54A:
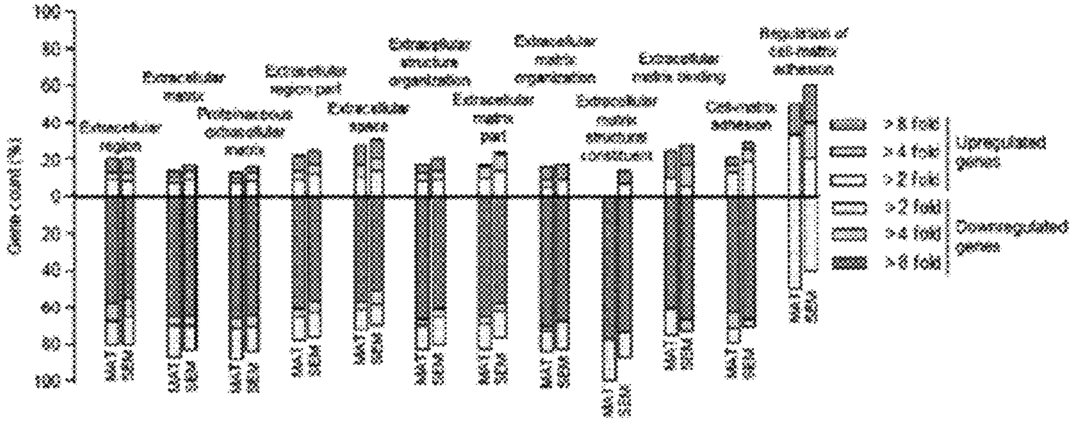

According to the result of comparing the transcriptomes of the gastric organoids cultured in the respective hydrogels with that of the mouse stomach tissue, the ratios of upregulated genes and downregulated genes were represented for respective ontologies. An analysis was performed by selecting words related to the extracellular matrix and cell-matrix interactions as the ontologies. Although the gastric organoids had lower expression levels than the stomach tissue in most of the categories, it was confirmed that the gastric organoid cultured in the SEM hydrogel contained a greater number of upregulated genes than the gastric organoid cultured in MATRIGEL® (FIG. 54A).

Figure 54B:
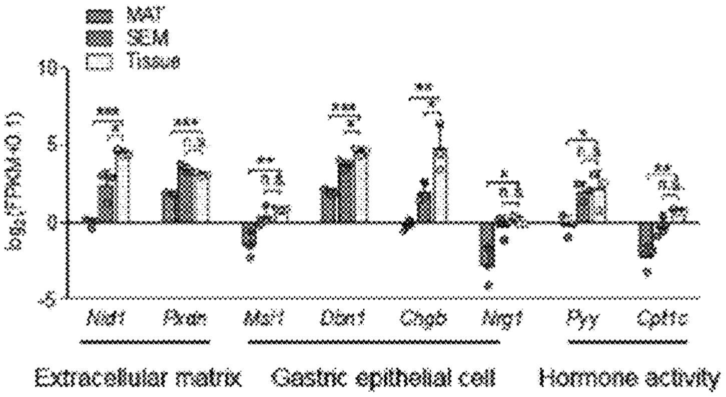

As a result of comparing individual genes, it was confirmed that the expression levels of Nid1 and Pxdn related to the extracellular matrix, Msi1, Dbn1, Chgb and Nrg1 related to gastric epithelial cells, and pyy and Cpt1c related to hormone activities are higher in the gastric organoid cultured in the SEM hydrogel than in the gastric organoid cultured in MATRIGEL®, and close to the expression levels in the stomach tissue (FIG. 54B).

Through this transcriptome analysis, it was confirmed that the gastric organoid cultured in the SEM hydrogel is closer to the stomach tissue than the gastric organoid cultured in MATRIGEL®.

Test Example 6: Verification of Applicability of Scaffold Composition

Test Example 6-1. In Vivo Transplantation of Gastric Organoid Using SEM Composition Animal tests were conducted to apply the hydrogel scaffold of the present disclosure as a material for transplantation of a gastric organoid, and a histological analysis was performed.

Figure 55A:
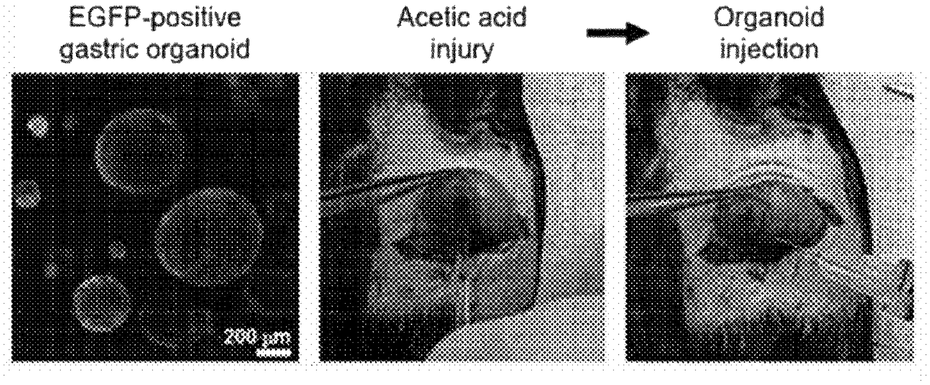

Specifically, a gastric organoid was transplanted using an SEM hydrogel to efficiently deliver and engraft the gastric organoid in a damaged stomach tissue of a mouse gastric ulcer model. The SEM hydrogel was prepared by mixing the SEM and a culture medium at a ratio of 1:20 (v/v) to tune a hydrogel viscosity for its easy injection during transplantation. In order to trace an organoid transplanted in vivo, a gastric organoid prepared from stem cells extracted from an EGFP-expressing mouse tissue was used for transplantation. Also, gastric ulcer was induced in the mouse model by treating the mouse stomach wall with 100% acetic acid using a capillary tube for 30 seconds, and the gastric organoid was transplanted into the injured stomach tissue using the SEM hydrogel. Then, the degree of engraftment of the organoid was observed (FIG. 55A).

Figure 55B:
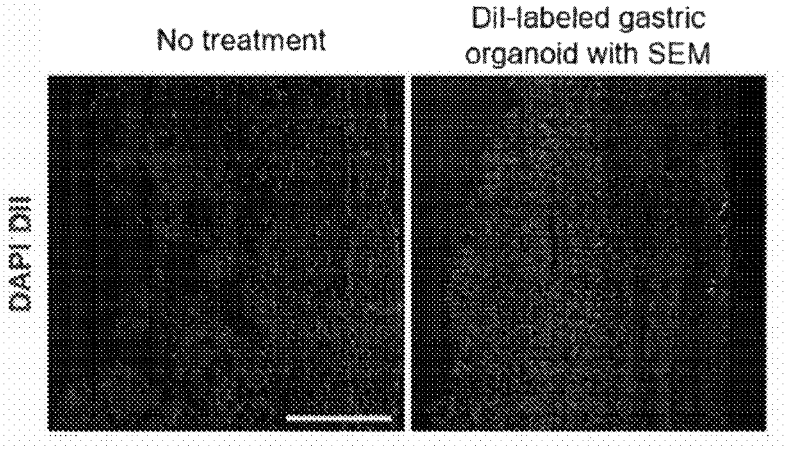

A gastric organoid labeled with a fluorescent dye Dil was transplanted into a mouse gastric ulcer model using a decellularized SEM hydrogel scaffold, and engraftment was observed through fluorescence expression one day after the transplantation. The transplanted organoid was present overall in the gastric gland. No fluorescence was observed in the damaged stomach tissue in which the organoid was not transplanted (FIG. 55B).

Figure 55C:
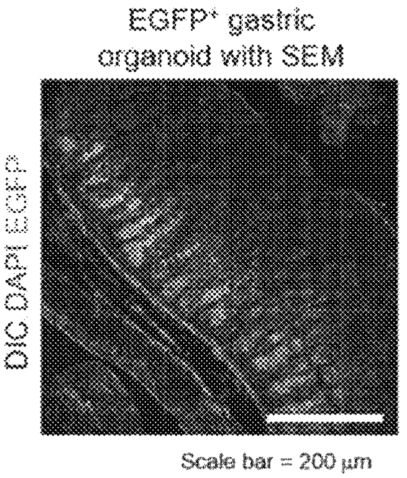

A gastric organoid expressing EGFP was transplanted into a mouse gastric ulcer model using a decellularized SEM hydrogel scaffold, and engraftment was observed through fluorescence expression a day later. The transplanted organoid was well engrafted in the damaged tissue (FIG. 55C).

Test Example 6-2. Verification of Possibility of Culturing Gastric Organoid Using Long-Term Stored Scaffold Composition The possibility of culturing a gastric organoid in the long-term stored scaffold composition of the present disclosure was verified.

Specifically, an SEM solution was cryopreserved at −80° C. for a long time, and an SEM hydrogel was prepared by thawing the cryopreserved SEM solution. The SEM hydrogel was used for gastric organoid culture to check whether it can be stored stably for a long term (FIG. 56A).

As a result, as can be seen from FIG. 56B, it was confirmed that the gastric organoid was well cultured even in the SEM hydrogel thawed after long-term cryopreservation (images of the organoid on day 5 of culture), and the organoid formation efficiency was also maintained similar to those of an SEM hydrogel prepared immediately before culture and MATRIGEL®. Also, there was no significant difference in mRNA expression levels of stem cell markers and differentiation markers. Accordingly, it was confirmed that the decellularized stomach tissue-derived scaffold can be stably maintained without denaturation even after storage for a long period of time up to at least 6 months under cryopreservation conditions (−80° C.) and can be used for gastric organoid culture. This verified that it can be developed into a product with a long shelf life.

Meanwhile, the SEM solution was cold-stored at 4° C., and it was used for gastric organoid culture to check the possibility of long-term storage, denaturation and stability (FIG. 57A).

As a result, as can be seen from FIG. 57B, a gastric organoid was well formed, maintained and cultured even in an SEM hydrogel prepared from the cold-stored SEM solution at a similar level to those in an SEM hydrogel prepared immediately before culture and MATRIGEL®(images of the organoids on day 5 of culture). Accordingly, it was confirmed that the decellularized stomach tissue-derived scaffold can be stably maintained without denaturation for at least 1 month even after cold storage of the SEM in the form of a solution at 4° C., and can be used for gastric organoid culture after cold storage. This verified that it can be developed into a product with a long shelf life.

Test Example 6-3. Verification of Possibility of Culturing Gastric Cancer Organoid in Scaffold Composition The possibility of culturing a gastric cancer organoid using the scaffold of the present disclosure was checked.

Specifically, it was confirmed that cancer organoids were formed when gastric cancer cell lines MKN-74 and NCI-N87 were three-dimensionally cultured in SEM hydrogels (images of the organoids and immunostaining analysis of day 10 of culture).

As a result, as can be seen from FIG. 58, it was confirmed that organoids were well formed from the two types of gastric cancer cell lines in the SEM hydrogels through optical microscopy. Also, a protein Ki67 related to cell proliferation was stained by immunostaining, and it was confirmed that cell proliferation actively occurred in the organoids.

The present test verified that the decellularized stomach tissue-derived SEM hydrogel scaffold can be used for culturing not only a stem cell-derived gastric organoid but also a gastric cancer organoid. Thus, it was confirmed that the SEM hydrogel can be applied as an elemental technology of a culture platform for the construction of an in vitro gastric cancer model.

Test Example 6-4. Check of Possibility of Mass Culture of Gastric Organoid Using Scaffold Composition and Microfluidic Chip The possibility of constructing a gastric organoid culture platform based on an SEM hydrogel was checked in a microfluidic chip capable of mass culture of organoids and multi-drug screening. The microfluidic chip can provide an organoid with a microflow of culture medium in a simple manner using a rocker. Also, the microfluidic chip includes a large number of chambers and thus enables mass production of organoids (FIG. 59A).

A gastric organoid was cultured using the scaffold of the present disclosure in this device.

As a result of culturing the SEM hydrogel sealing the gastric organoid in the microfluidic chip, the gastric organoid was well cultured to a size of about 1 mm when a microflow of culture medium was provided to an organoid culture chamber for 5 days (FIG. 59B).

According to these results, it can be seen that when the gastric organoid that is three-dimensionally cultured in the decellularized stomach tissue-derived hydrogel scaffold is combined with the microfluidic chip technology, a tissue-specific extracellular matrix microenvironment is applied to a dynamic culture with a precise microfluidic flow, which enables efficient mass production of organoids.

With respect to a liver extracellular matrix (LEM) for culture and transplantation of liver organoids and a method of preparing the same, in the present disclosure, liver tissue was decellularized by removing all cellular components to prepare a decellularized liver tissue with liver-specific extracellular matrix components, and a three-dimensional hydrogel based on the decellularized liver tissue was applied to liver organoid culture.

The LEM developed in the present disclosure is composed of pure extracellular matrix components from which cellular antigens have been removed. Thus, it does not cause inflammatory reaction and immune rejection of tissue during transplantation and has excellent biocompatibility. The LEM is easy to produce and cheap. Thus, it can be applied as a culture and transplantation material with higher economic efficiency and higher safety than MATRIGEL®.

Through proteomic analysis, it was confirmed that the LEM contains various extracellular matrices and factors specific to liver tissue. It was confirmed that a stem cell-derived liver organoid is generated and grown in the prepared decellularized liver tissue-derived hydrogel scaffold. Also, the decellularized liver tissue scaffold was tested at various concentrations and the optimal hydrogel concentration for liver organoid culture was selected.

When the liver organoid cultured in the developed LEM was compared to an organoid cultured in MATRIGEL® as a control group, it was confirmed that the differentiation ability and liver function (albumin secretion, cytochrome activity, urea synthesis, etc.) were similarly maintained or improved. Accordingly, it was verified that the LEM can replace the conventional MATRIGEL® for liver organoid culture.

According to this series of results, it was confirmed that the liver organoid cultured in the scaffold developed in the present disclosure can better recapitulate the structure and function of actual liver tissue than the organoid cultured in the conventional matrix (MATRIGEL®).

In the present disclosure, it was confirmed that when liver damage was induced in a mouse model and liver organoids were transplanted using the decellularized liver tissue-derived hydrogel scaffold, organoids were engrafted in the damaged site and efficient transplantation was possible. Also, the possibility of applying the liver organoid as a transplantation material was confirmed.

Hereinafter, Examples will be presented for understanding of the present disclosure. However, the following Examples are illustrative only for better understanding of the present disclosure but do not limit the present disclosure.

Example 3: Preparation of Scaffold Composition Containing Liver Extracellular Matrix A scaffold composition containing a liver extracellular matrix was prepared as described below (see FIG. 60A).

Example 3-1. Preparation of Liver Extracellular Matrix (LEM)

A porcine liver tissue was isolated and sliced, and the liver tissue was stirred with 1% TRITON X-100™ and 0.1% ammonium hydroxide to remove only the cells of the liver tissue and prepare a decellularized liver tissue.

Thereafter, the decellularized liver tissue was lyophilized and ground to prepare a liver extracellular matrix (LEM).

Example 3-2. Preparation of Scaffold Composition 10 mg of the LEM was dissolved in a 4 mg/ml pepsin solution (a solution of 4 mg of pepsin powder in 1 ml of 0.02 M HCl) for 48 hours. Gelation was performed at a temperature of 37° C. for 30 minutes after setting a neutral pH in an electrolyte state of 1×PBS buffer by using 10×PBS and 1 M NaOH with uniform blending to prepare a scaffold composition in the form of a hydrogel (FIG. 60B).

Test Example 7: Analysis of LEM

Example 3-1. The LEM of Example 3-1 was analyzed as follows.

Test Example 7-1. Analysis of Mechanical Properties of LEM

The mechanical properties of the LEM prepared in Example 3-1 were analyzed.

Specifically, DNAs were extracted from the decellularized liver tissue scaffold and the liver tissue that was not subjected to decellularization for quantitative comparison, and the GAG content in the scaffold was measured by dye binding analysis with chondroitin sulfate and dimethylmethylene blue (FIG. 61A).

In case of H&E staining, the decellularized liver tissue scaffold and the tissue that was not subjected to decellularization were sliced and the cell nuclei were stained with hematoxylin and the cytoplasms were stained with eosin to analyze the degree of cell nucleus removal in the decellularized liver tissue scaffold (FIG. 61B).

A decellularized liver tissue scaffold was prepared for each concentration, and an internal structure of the hydrogel was analyzed through a scanning electron microscope that produces images of an object by scanning the object with an electron beam (FIG. 61C).

It was confirmed that most of the cellular components were removed by decellularization through quantitative comparison of DNAs before and after decellularization of the liver tissue. Through quantitative analysis of glycosaminoglycans (GAGs) as a representative extracellular matrix component, it was confirmed that GAGs were well preserved in the decellularized liver tissue (FIG. 61A).

It was confirmed from H&E staining that the structure of the decellularized liver tissue matrix was well maintained and all cellular components were removed (FIG. 61B).

Through scanning electron microscopy (SEM), it was confirmed that the decellularized liver tissue-derived hydrogel scaffold prepared for each concentration had an internal structure in the form of a nanofiber bundle (FIG. 61C). Therefore, it was confirmed that the decellularized liver tissue-derived hydrogel scaffold can provide a three-dimensional microenvironment suitable for liver organoid culture.

Test Example 7-2. Analysis of Mechanical Properties Depending on Concentration of LEM In order to investigate the difference in mechanical properties of the LEM depending on concentration, the formation of hydrogels was induced at four concentrations (2, 4, 6 and 8 mg/ml) and then the mechanical properties thereof were measured by rheological analysis.

As a result, as can be seen from FIG. 62, it was confirmed that a storage modulus G' was consistently higher than a loss modulus G" at all concentrations of the LEM scaffold, and, thus, a stable polymer network was formed through cross-linking in the hydrogel. It was confirmed that as the LEM concentration increased, the mechanical properties (modulus) also increased. Also, it was confirmed that the overall mechanical properties were lower than those of MATRIGEL® (MAT) which is a control group. High concentration (8 mg/ml) LEM hydrogel has similar mechanical properties to MATRIGEL®.

Test Example 7-3. Proteomics of LEM

Proteomic analysis using a mass spectrometer was performed to identify the components of the LEM. Thus, it was confirmed that various extracellular matrices (collagens, ECM glycoproteins, proteoglycans) and growth factor proteins specific to liver tissue are detected in the LEM.

As a result, as can be seen from FIG. 63, MATRIGEL® (MAT), the commercially available scaffold, is mostly composed of ECM glycoproteins, whereas LEM is mostly composed of collagens and ECM glycoproteins, as well as other components including proteoglycans and ECM regulators. Among LEM is mostly composed of collagens and ECM glycoproteins, as well as other components including proteoglycans and ECM regulators, biglycan (BGN), lumican (LUM) and asporin (ASPN), which are specifically present in the LEM, are major proteins involved in ECM remodeling during liver tissue development, and PRELP is known as a protein that is important in maintaining the structure of a normal hepatocyte. Accordingly, it was confirmed that the fabricated LEM scaffold contains various extracellular matrix proteins present in the liver tissue which are important in the structure, development and function of liver compared to MATRIGEL®.

Also, as can be seen from FIG. 64, as a result of comparing proteins known to be enriched in liver tissue that are identified in MATRIGEL® (MAT) and the decellularized liver tissue-derived scaffold (LEM), much more matrisome and non-matrisome proteins related to liver tissue were detected in the LEM than in MATRIGEL® (FIG. 64A).

As a result of gene ontology analysis that was performed to investigate the functions of protein components except for the extracellular matrix (ECM) in each matrix, it was confirmed that the non-matrisome components in MATRIGEL® are mainly involved in the functions of biosynthesis of peptide or amide and metabolism, whereas the non-matrisome components contained in the LEM scaffold prepared in the present disclosure are mainly involved in the functions related to small molecules, various organic acids and cellular metabolism (FIG. 64B).

That is, the non-matrisome protein components other than the ECM in the LEM scaffold are regarded as playing an important role in the formation of a highly functional liver organoid with enhancement of organic acid metabolism and various cellular metabolisms, which are important functions of hepatocytes.

Test Example 8: Analysis of Scaffold Composition Containing LEM

Test Example 8-1. Culture and Concentration Selection of Liver Organoid (Cholangiocyte-Derived Liver Organoid (CLO)) Depending on Concentration of Decellularized Liver Tissue-Derived Hydrogel Scaffold Hydrogels were prepared at respective concentrations of the decellularized liver tissue-derived LEM and liver organoids (CLOs) were cultured. The formation efficiency thereof was compared to select a concentration suitable for organoid culture. A commercially available culture scaffold, MATRIGEL®, was used as a control group. The CLOs were prepared using bile ductal cells extracted from mouse liver tissue.

As shown in FIG. 65, when the decellularized liver tissue-derived LEM hydrogel was applied at various LEM concentrations for liver organoid culture, it was confirmed that liver organoids were well formed into a well formed in a similar morphology to that of liver organoids in MATRIGEL®, a control group, at all concentrations in MATRIGEL® as a control group at all concentrations (2, 4, 6 and 8 mg/ml) (FIG. 65A). As a result of comparing the liver organoid formation efficiency depending on the concentration of the decellularized liver tissue-derived LEM hydrogel scaffold on day 7 of culture, it was confirmed that the formation efficiency was the highest at concentrations of 4 mg/ml and 6 mg/ml (FIG. 65B).

Test Example 8-2. Analysis of Difference in Differentiation Ability of Liver Organoid (Cholangiocyte-Derived Liver Organoid (CLO)) Depending on LEM Concentration of Decellularized Liver Tissue-Derived Hydrogel Scaffold Decellularized liver tissue-derived LEM hydrogel scaffolds were prepared at respective concentrations and applied to mouse liver organoid culture, and the differentiation-related gene expression of organoids cultured for 7 days at respective concentrations was compared and analyzed by quantitative PCR (qPCR). A commercially available culture scaffold, MATRIGEL® (MAT), was used as a control group.

As shown in FIG. 66, as a result of comparing the gene expression for each LEM concentration, the expression of a stemness-related gene (LGR5) was slightly decreased but the expression of hepatic differentiation-related markers (Krt19, Krt18, Hnf4a, Hnf1b and Foxa3) showed a tendency to increase in the liver organoids cultured in the LEM hydrogels. Considering that an LEM hydrogel with a concentration of 6 mg/ml did not much differ from MATRIGEL® in liver organoid formation efficiency and increased in expression of hepatic differentiation markers, the LEM hydrogel concentration was set to 6 mg/ml, which was applied to subsequent liver organoid tests.

Test Example 8-3. Analysis of Liver Organoid (Cholangiocyte-Derived Liver Organoid (CLO)) Cultured in Decellularized Liver Tissue-Derived Hydrogel Scaffold Immunostaining of liver organoids cultured in MATRIGEL®, which is the most widely used for organoid culture, and a decellularized liver tissue-derived LEM hydrogel (6 mg/ml) scaffold was performed. The liver organoids were prepared using bile ductal cells extracted from mouse liver tissue and compared by immunostaining on day 7 of culture.

As shown in FIG. 67, as a result of comparison with the liver organoid cultured in the control group MATRIGEL® by immunostaining for liver-specific markers, it was confirmed that liver tissue-specific markers were well expressed in the CLO-type liver organoid cultured in the decellularized liver tissue-derived LEM hydrogel scaffold at a level similar to that in the MATRIGEL® group. * KRT19 (cholangiocyte marker), ECAD (cell-cell junction marker), SOX9 (cholangiocyte progenitor marker), Ki67 (proliferative cell marker), ALB (mature hepatocyte marker).

Test Example 8-4. Analysis of Functionality of Liver Organoid (Cholangiocyte-Derived Liver Organoid (CLO)) Cultured in Decellularized Liver Tissue-Derived Hydrogel Scaffold A cholangiocyte-derived liver organoid was cultured, and the hepatic functionality thereof was evaluated on day 7 of culture. A commercially available culture scaffold, MATRIGEL®, was applied as a control group, and an LEM hydrogel with a concentration of 6 mg/ml was used.

As shown in FIG. 68, through PAS staining that was performed to analyze the storage capacity of polysaccharides such as glycogen, it was confirmed that the liver organoid cultured in the LEM hydrogel had a polysaccharide storage capacity similar to that of the control (MAT) group (FIG. 68A). As a result of analysis of various hepatic functions (albumin secretion, urea synthesis and cytochrome activity), it was confirmed that the CLO-type liver organoid cultured in the LEM hydrogel showed a similar functionality to the liver organoid cultured in MATRIGEL® (FIG. 68B).

Test Example 8-5. Long-Term Culture of Liver Organoid (Cholangiocyte-Derived Liver Organoid (CLO)) Using Decellularized Liver Tissue-Derived Hydrogel Scaffold A long-term culture of mouse cholangiocyte-derived liver organoid was attempted in the decellularized liver tissue-derived LEM hydrogel scaffold established as described above, and liver-specific differentiation markers were analyzed. A MATRIGEL® group was used as a control group.

As shown in FIG. 69, It can be seen from the liver organoid morphology images that when the organoid was subcultured in the LEM hydrogel for 1 month, it was cultured in a morphology and size similar to that of liver organoid cultured in MATRIGEL® (FIG. 69A). Even when the liver organoids were cultured for more than 1 month, it was confirmed that the expression of hepatic differentiation markers increased in the liver organoids cultured in the decellularized liver tissue-derived LEM hydrogel scaffold than in the MATRIGEL®-based organoids. It was found that organoid differentiation in the LEM hydrogel is further enhanced over the culture time (FIG. 69B).

Test Example 8-6. Culture and Analysis of Human Liver Organoid (Human Cholangiocyte-Derived Liver Organoid (hCLO)) Using Decellularized Liver Tissue-Derived Hydrogel Scaffold It was confirmed whether human liver tissue-derived liver organoids can be cultured using decellularized liver tissue-derived LEM hydrogel scaffold (6 mg/ml). Bile ductal cells were isolated from liver to generate a human cholangiocyte-derived liver organoid. MATRIGEL® was used as a control group.

As shown in FIG. 70, it was confirmed that similar to MATRIGEL® (MAT), a human-derived liver organoid was well formed in the decellularized liver tissue-derived LEM hydrogel scaffold, and a long-term subculture was possible for 50 days or more (FIG. 70A). When the expression of liver tissue markers was analyzed by quantitative PCR on day 7 of culture, the expression of a stemness-related gene (LGR5) and hepatic differentiation-related genes (HNF4A, SOX9 and FOXA2) in the liver organoid cultured in the LEM hydrogel was similar to that of the organoid cultured in MATRIGEL® or showed a tendency to increase (FIG. 70B).

Also, decellularized liver tissue-derived LEM hydrogel scaffolds of respective concentrations were prepared and applied to human liver organoid culture, and the expression of differentiation-related genes in organoids cultured for 14 days at respective concentrations was compared and analyzed by quantitative PCR (qPCR). A commercially available culture scaffold, MATRIGEL® (MAT), was used as a control group.

As can be seen from FIG. 71, as a result of comparing the gene expression for each LEM concentration, the expression of a stemness-related gene (LGR5) and hepatic differentiation-related genes (SOX9, HNF4A, KRT19 and FOXA2) was similar in the LEM hydrogel and MATRIGEL® (MAT) without a significant difference. Considering that an LEM hydrogel with a concentration of 6 mg/ml showed a good formation efficiency and the expression of differentiation markers KRT19 and HNF4A also slightly increased, the LEM hydrogel concentration was set to 6 mg/ml, which was applied to subsequent liver organoid tests.

Then, immunostaining of liver organoids cultured in MATRIGEL® (MAT) and the decellularized liver tissue-derived LEM hydrogel (6 mg/ml) scaffold was performed. The liver organoids were prepared using bile ductal cells extracted from human liver tissue and compared by immunostaining on day 14 of culture.

As a result of comparison with the liver organoid cultured in the control group MATRIGEL® (MAT) by immunostaining for liver-specific markers, it was confirmed that liver tissue-specific markers were well expressed in the liver organoid cultured in the decellularized liver tissue-derived LEM hydrogel scaffold at a level similar to that in the MATRIGEL® group (FIG. 72A).

As a result of analysis of hepatic functions (urea synthesis and albumin secretion), it was confirmed that the human liver organoid cultured in the LEM hydrogel showed a similar or slightly higher functionality than the liver organoid cultured in MATRIGEL® (FIG. 72B).

* KRT19 (cholangiocyte marker), ECAD (cell-cell junction marker), SOX9 (cholangiocyte progenitor marker), Ki67 (proliferative cell marker), F-actin (filamentous actin marker)

Test Example 8-7. Culture and Optimal Concentration Selection of Liver Organoid (Hepatocyte-Derived Liver Organoid (HLO)) Depending on Concentration of Decellularized Liver Tissue-Derived Hydrogel Scaffold Hydrogels were prepared at respective concentrations of a decellularized liver scaffold to culture liver organoids, and the formation efficiency and gene expression were compared and analyzed. A commercially available culture scaffold, MATRIGEL®, was used as a control group. The liver organoids were prepared using pure hepatocytes extracted by perfusion of mouse liver tissue.

As shown in FIG. 73, when a hepatocyte-derived liver organoid was cultured for 14 days in the decellularized LEM hydrogel scaffold, the liver organoid was formed in a morphology similar to that in the control group (MAT) (FIG. 73A). The formation efficiency of liver organoids depending on the concentration of a decellularized scaffold was compared to that of the control group (MAT) on day 7 of culture (FIG. 73B). As results of quantitative PCR analysis of liver tissue-specific marker expression in organoids cultured in LEM hydrogels prepared at each concentration, the expression of hepatic differentiation markers (Krt18, Hnf4a and Cdh1) was higher in the decellularized LEM scaffold group (FIG. 73C). The formation efficiency was stable and the expression levels of the hepatic differentiation markers increased at a concentration of 4 mg/ml, which was regarded as an appropriate condition and applied to subsequent HLO culture.

Test Example 8-8. Comparison of Growth of Liver Organoids (HLO) Formed in Decellularized Liver Tissue-Derived Hydrogel Scaffold (LEM) and Conventional Culture Scaffold (MAT)

Liver organoids were prepared using pure hepatocytes extracted by perfusion of mouse liver tissue and cultured in a decellularized LEM scaffold (4 mg/ml) and a commercially available culture scaffold, MATRIGEL®. Then, the growth rate of liver organoids was compared.

As shown in FIG. 74, as a result of comparing the mouse liver tissue-derived liver organoids cultured in MATRIGEL®, which is the most widely used for organoid culture, and the decellularized liver tissue-derived LEM hydrogel (4 mg/ml) scaffold, it was confirmed that all of the liver organoids formed on the respective scaffolds continued to increase in size and were well subcultured.

Test Example 8-9. Analysis of Hepatocyte-Derived Liver Organoid (HLO) Cultured in Decellularized Liver Tissue-Derived Hydrogel Scaffold (LEM)

Liver organoids were cultured for 20 days using a decellularized liver scaffold hydrogel (4 mg/ml), and immunostaining and a hepatic functionality analysis was performed. A commercially available culture scaffold, MATRIGEL®, was used as a control group. The liver organoids were prepared using pure hepatocytes extracted by perfusion of mouse liver tissue.

As shown in FIG. 75, as a result of comparison with the organoid cultured in the control group MATRIGEL® (MAT) in terms of expression of various markers by immunostaining, it was confirmed that liver tissue-specific markers were well expressed even in the decellularized LEM scaffold group (FIG. 75A).

* ALB (hepatocyte marker), ECAD (tight junction marker), F-actin (cytoskeleton marker)

Through PAS (Periodic Acid Schiff) staining to determine the storage capacity of polysaccharides such as glycogen, the glycogen storage capacity of each of the two groups was compared (FIG. 75B). As a result of comparing the urea synthesis ability and the amount of albumin secretion, it was confirmed that the decellularized LEM scaffold group showed a higher functionality than the control group (MAT) (FIG. 75C).

Test Example 9: Check of Applicability of Decellularized Liver Tissue-Derived Hydrogel Scaffold

Test Example 9-1. Culture of Human Induced Pluripotent Stem Cell (hiPSC)-Derived Liver Organoid Using Decellularized Liver Tissue-Derived Hydrogel Scaffold In order to control the mechanical properties of a hydrogel suitable for the formation of a liver organoid from human induced pluripotent stem cells, a hydrogel layer was prepared by mixing the LEM and a culture medium at a ratio of 1:1 (v/v), and cells (human induced pluripotent stem cell-derived hepatic endoderm cells, vascular endothelial cells, mesenchymal stem cells) necessary for the formation of a liver organoid were applied thereon. Within 72 hours, the cells were formed into a liver organoid through self-organization. The protein expression was compared and analyzed by immunostaining of the liver organoid cultured in the decellularized liver scaffold hydrogel (LEM). A commercially available culture scaffold, MATRIGEL® (MAT), was used as a control group.

As shown in FIG. 76, when human induced pluripotent stem cell-derived hepatic endoderm cells, vascular endothelial cells and mesenchymal stem cells were cultured in MATRIGEL® (MAT) and the decellularized liver tissue-derived hydrogel (LEM) layer, the cells were aggregated over time into three-dimensional organoids within 72 hours in both groups (FIG. 76A). As a result of immunostaining, it was confirmed that liver-related markers (ALB and AFP) and a vascular cell marker (CD31) were well expressed in both groups (FIG. 76B).

* ALB (mature hepatocyte marker), AFP (early hepatocyte marker), CD31 (vascular endothelial marker).

Test Example 9-2. Analysis of Human Induced Pluripotent Stem Cell-Derived Liver Organoid (hiPSC-LO) Cultured in Decellularized Liver Tissue-Derived Hydrogel Scaffold Human induced pluripotent stem cell-derived liver organoids were cultured for 7 days using a decellularized liver scaffold hydrogel, and the functionality and gene expression were compared and analyzed. A commercially available culture scaffold, MATRIGEL® (MAT), was used as a control group. The liver organoids were prepared through self-organization of human induced pluripotent stem cells-derived hepatic endoderm cells, vascular endothelial cells and mesenchymal stem cells.

As shown in FIG. 77, through PAS staining related to hepatic functionality, it was confirmed that glycogen storage was well performed in both the MATRIGEL® group and the LEM hydrogel group. It was confirmed that the urea synthesis ability was higher in the organoid cultured in the decellularized matrix (FIG. 77A). As a result of analysis of the expression of liver tissue-related markers by quantitative PCR, it was confirmed that the expression of a gene OCT4, which is a pluripotency-related marker, of the liver organoid cultured in the LEM hydrogel decreased slightly, but the expression of hepatic differentiation-related genes (SOX17 and HNF4A) and endothelial cell-related genes (PECAM1 and CD34) of the liver organoid cultured in the LEM hydrogel showed a tendency to increase compared to the organoid cultured in MATRIGEL® (FIG. 77B).

Test Example 9-3. Construction of Liver Fibrosis Model Using Liver Organoid (CLO) Cultured in Decellularized Liver Tissue-Derived Hydrogel Scaffold (LEM)

For disease modeling using an LEM-based liver organoid, TGF-beta was screened at each concentration and the possibility of inducing liver fibrosis was checked. A model was induced using mouse cholangiocyte-derived liver organoids (CLOs) cultured for 7 days. To construct a liver fibrosis model, the organoids were treated with TGF-β at each concentration for 48 hours and observed.

As shown in FIG. 78, it was confirmed that, unlike the liver organoids that were not treated with TGF-β, all liver organoids treated with TGF-β were changed in morphology and did not grow well (Scale bars=100 μm) (FIG. 78A). To evaluate liver fibrosis, SMA (Smooth Muscle Actin) and COL1A1 were stained to determine the accumulated extracellular matrix (ECM) around the organoids (Scale bars=100 μm) (FIG. 78B). A quantitative PCR analysis showed that the expression of liver fibrosis markers was highest in the group treated with 4 ng/ml TGF-β (FIG. 78C). Under normal conditions without TGF-β treatment, the expression of a liver fibrosis marker (Col1a1) decreased and the expression of a cholangiocyte marker (Krt19) increased in the LEM group than in the control group MATRIGEL®. However, when liver organoids cultured in LEM were treated with TGF-β to induce fibrosis, the expression of the fibrosis marker greatly increased and the expression of the cholangiocyte marker significantly decreased (FIG. 78D). Through this experiment, it was verified that a fibrosis model can be constructed using a liver organoid cultured in the LEM scaffold.

Meanwhile, for disease modeling using human cholangiocyte-derived liver organoids (hCLOs) cultured in the LEM, TGF-β was tested at each concentration and the organoids were treated with the most appropriate concentration of TGF-β (80 ng/ml). Then, the possibility of inducing liver fibrosis was checked.

As shown in FIG. 79, the organoids were treated with TGF-β at respective concentrations to fabricate a liver fibrosis model and observed 3 days later. It was confirmed that the liver organoid that was not treated with TGF-β grew for 3 days, but all liver organoids treated with TGF-β were deformed in morphology and did not grow well (FIG. 79A). To verify a liver fibrosis model, SMA (Smooth Muscle Actin) was used for staining to determine the accumulated extracellular matrix (ECM) around the organoids. Through this experiment, it was verified that a human liver fibrosis model can be constructed using a liver organoid cultured in the LEM scaffold (FIG. 79B).

Test Example 9-4. In Vivo Transplantation of Liver Organoid Using Decellularized Liver Tissue-Derived Hydrogel Scaffold Animal tests were performed to utilize a decellularized liver tissue-derived LEM hydrogel scaffold as a material for liver organoid transplantation, and a histological analysis was performed. In order to efficiently deliver and engraft liver organoids to liver tissue of a mouse hepatotoxicity injury model, liver organoids were transplanted using an LEM hydrogel. The LEM hydrogel was prepared by mixing the LEM and a culture medium at a ratio of 1:10 (v/v) to tune the hydrogel adjust the hydrogel viscosity for its efficient injection during transplantation As shown in FIG. 80, a liver injury model was induced by intraperitoneal injection of acetaminophen (24 hours), and the injury model was investigated by H&E histological analysis (FIG. 80A). Cholangiocyte-derived liver organoids (CLO) labeled with a fluorescence dye Dil were transplanted into a mouse liver injury model. Liver organoids were transplanted using MATRIGEL® and a decellularized LEM hydrogel as a scaffold for transplantation, and engraftment was checked through fluorescence expression one day after transplantation. The potential of the LEM hydrogel as a biomaterial for organoid transplantation was demonstrated by confirming that liver organoids transplanted into the injured site survived well and were engrafted in the liver tissue (FIG. 80B)

Test Example 9-5. Verification of Possibility of Long-Term Storage of Decellularized Liver Tissue-Derived Hydrogel A decellularized liver tissue-derived LEM hydrogel was cryopreserved at −80° C. for a long time and then used for culturing a cholangiocyte-derived liver organoid (CLO). MATRIGEL® was used as a control group.

As a result, as shown in FIG. 81, when liver organoids were cultured using the control group MATRIGEL®, a LEM hydrogel prepared immediately before organoid culture, and the LEM hydrogel cryopreserved at −80° C. for a long time, the organoids were well formed in all groups (FIG. 81A).

It was confirmed that liver organoids were stably cultured not only in MATRIGEL® and LEM hydrogel prepared just before liver organoid culture, but also in hydrogel prepared from LEM solution cryopreserved for 1 month or 2 months, and the expression levels of all hepatic differentiation markers were increased compared to the MATRIGEL® group, and similar expression levels were shown without significant difference between the decellularized LEM hydrogels (FIG. 81B).

Further, a decellularized liver tissue-derived LEM hydrogel was cold-stored at 4° C. for a long time and then used for culturing a human cholangiocyte-derived liver organoid (hCLO). MATRIGEL® was used as a control group.

As a result, as can be seen from FIG. 82, the human liver organoids were stably cultured not only in the MATRIGEL® and the LEM hydrogel prepared immediately before culture, but also in the hydrogel prepared from the LEM solution cold-stored for 2 months, and all hepatic differentiation markers and stemness markers showed similar or higher expression levels compared to the MATRIGEL® group (FIG. 82A).

As a result of analysis of hepatic functions (urea synthesis and albumin secretion), it was confirmed that human liver organoids maintained hepatic functions well in the long-term stored LEM hydrogel, and showed a similar or slightly higher functionality than the liver organoids cultured in the MATRIGEL® group (FIG. 82B).

Accordingly, it was confirmed that the decellularized liver tissue-derived LEM hydrogel scaffold can be stably maintained without denaturation even after cold storage in the form of a solution at 4° C. for 2 months or more and can be used for liver organoid culture.

Test Example 9-6. Culture of Liver Cancer Organoid Using Decellularized Liver Tissue-Derived Hydrogel Scaffold The possibility of culturing a human liver cancer organoid using a decellularized liver tissue-derived LEM hydrogel scaffold was checked. Human liver organoids derived from normal liver tissue and liver organoids derived from a hepatocellular carcinoma (HCC) patient's tissue were cultured in MATRIGEL® and a decellularized liver tissue-derived LEM hydrogel for 20 days, and then analyzed.

As a result, as can be seen from FIG. 83, it was confirmed that all normal liver organoids and liver cancer organoids were similarly formed in the MATRIGEL® group and the decellularized liver tissue-derived LEM hydrogel scaffold (FIG. 83A). As a result of immunostaining of the liver cancer organoid cultured in MATRIGEL® and the liver cancer organoid cultured in the LEM hydrogel, it was confirmed that liver cancer-related marker proteins (SMA and AFP) were stained in both groups (FIG. 83B). As a result of comparing the gene expression of the normal liver organoid and the liver cancer organoid cultured in the decellularized liver tissue-derived LEM hydrogels by qPCR analysis, it was confirmed that a stemness-related LGR5 expression level in the liver cancer organoid decreased and the expression of inflammatory response-related markers TNFa and HES1 and liver cancer-related markers AFP and PLIN2 increased (FIG. 83C).

Accordingly, it was verified that the decellularized liver tissue-derived LEM hydrogel scaffold can be used for culturing not only a normal liver organoid but also a liver cancer organoid. Thus, it was confirmed that the LEM hydrogel can be applied as a culture platform for the construction of an in vitro liver cancer model.

Test Example 9-7. Verification of Superiority of LEM Constructed in the Present Disclosure by Comparison Between Liver Tissue Decellularization Protocols The decellularization method (Protocol 1) developed in the present disclosure was compared with the decellularization method (Protocol 2) previously reported in the prior art document. In the method of Protocol 2, DNA was removed using DNase I (3 hours) after treatment with 4% sodium deoxycholate for 4 hours, and in the decellularization method developed in the present disclosure, decellularization was induced using only a mixed solution of 1% TRITON X-100™ and 0.1% ammonium hydroxide under more mild conditions to reduce damage to proteins in tissue.

As can be seen from FIG. 84, as a result of H&E histological analysis, it was confirmed that cells were effectively removed according to both methods, but more ECM components were preserved in the tissue treated according to Protocol 1 (FIG. 84A).

After decellularization, the amount of DNA was significantly decreased in the tissues treated according to the respective protocols, but a GAG quantitative analysis confirmed that GAG components remaining in the tissue treated according to Protocol 2 were significantly less than those in the tissue treated according to Protocol 1. When the mechanical properties (elastic modulus) of the decellularized liver tissue-derived hydrogels prepared according to the respective protocols were measured, the hydrogel derived from the decellularized tissue according to Protocol 2 had lower mechanical properties (FIG. 84B).

According to these results, it can be seen that Protocol 1 is a more efficient way to not only induce efficient decellularization, but also reduce damage to an extracellular matrix (ECM).

In addition, the decellularization method (Protocol 1) developed in the present disclosure was compared with the conventionally used decellularization method (Protocol 3). According to Protocol 3, treatment with a 3% sodium dodecyl sulfate was performed for 24 hours in addition to the decellularization method established in the present disclosure.

As can be seen from FIG. 85, as a result of H&E histological analysis, it was confirmed that cells were effectively removed according to both methods, but more ECM components were preserved in the tissue treated according to Protocol 1 (FIG. 85A).

After decellularization, the amount of DNA was significantly decreased in the tissues treated according to the respective protocols, but a GAG quantitative analysis confirmed that GAG components remaining in the tissue treated according to Protocol 2 were significantly less than those in the tissue treated according to Protocol 1. When the mechanical properties (elastic modulus) of the decellularized liver tissue-derived hydrogels prepared according to the respective protocols were measured, there was no significant difference in mechanical properties of the hydrogels prepared according to the respective protocols (FIG. 85B).

When proteomic analysis of the liver tissue-derived LEM scaffolds prepared according to the respective decellularization protocols was performed, liver tissue-specific proteins collagen α1 (XVIII) and kininogen 1 were detected in the LEM scaffold prepared according to Protocol 1 and more extracellular matrix proteins were also detected (FIG. 85C).

Therefore, it can be seen that Protocol 1 can induce more efficient decellularization while reducing damage to liver tissue-specific extracellular matrix components than Protocol 3.

Test Example 9-8. Verification of Superiority of LEM Constructed in Present Disclosure by Comparison Between Liver Tissue Decellularization Protocols (Organoid Culture Test)

Mouse cholangiocyte-derived liver organoids (CLOs) were cultured using decellularized liver tissue-derived hydrogels prepared according to the decellularization method (Protocol 1) constructed in the present disclosure, the decellularization method (Protocol 2) previously reported in the prior art document and the conventionally used decellularization method (Protocol 3), respectively, and then compared.

It was confirmed that the liver organoids were well formed in all of the decellularized liver tissue-derived LEM hydrogels prepared according to Protocols 1, 2 and 3, respectively (Day 7) (FIG. 86A). As a result of comparing the gene expression of the liver organoids cultured in the LEM hydrogels prepared according to the respective protocols by quantitative PCR (qPCR) on day 7, it was confirmed that the expression of a stemness marker (Lgr5) and hepatic differentiation markers (Afp and Foxa3) significantly decreased in the liver organoids cultured in the hydrogel prepared according to Protocols 2 and 3 compared to Protocol 1 (FIG. 86B). As a result of comparing the formation efficiency of a liver organoid in MATRIGEL® (MAT), which is a conventional culture scaffold, and the LEM hydrogels prepared according to the respective decellularization protocols, it was confirmed that the liver organoid formation efficiency decreased slightly in Protocol 1 group, but the liver organoid formation efficiency significantly decreased in the hydrogels prepared according to Protocols 2 and 3 (FIG. 86C).

According to these results, it can be seen that the LEM hydrogel prepared according to Protocol 1 is more efficient to form to generate liver organoids and can provide a more favorable environment for the growth and differentiation of liver organoids. That is, it can be seen that the LEM prepared according to Protocol 1 constructed in the present disclosure is a much superior scaffold for liver organoid culture.

Test Example 9-9. Cross-Species Comparative Analysis of Decellularized Liver Tissue-Derived Hydrogel Scaffold (Pig Vs Human)

Proteomic analysis of MATRIGEL®, a decellularized porcine liver tissue-derived hydrogel scaffold (Porcine LEM) and a decellularized human liver tissue-derived hydrogel scaffold (Human LEM) prepared by decellularizing human liver tissue was performed. By comparing the three types of hydrogels through proteomic analysis, the suitability of Porcine LEM developed in the present disclosure for human liver organoid culture was verified.

An extracellular matrix component of the control group MATRIGEL® is mostly composed of ECM glycoproteins, and followed by ECM regulators and proteoglycans. However, proteoglycans are most abundant in the porcine and human decellularized liver tissue-derived LEM scaffolds, and collagens and ECM glycoproteins are detected at similar levels. It was confirmed that most of the top 10 most abundant ECM proteins detected in Porcine LEM and Human LEM are similar, and they are significantly different from those in the control group MATRIGEL®. Therefore, it can be seen that the decellularized porcine liver tissue-derived hydrogel scaffold can provide a microenvironment similar to that of human liver tissue and thus is more suitable for human liver organoid culture than MATRIGEL®. When extracellular matrix protein components specifically present only in the respective culture matrices were analyzed, the highest number of ECM proteins was detected in the human liver tissue-derived LEM scaffold, and the greater number of ECM proteins was detected in the porcine liver tissue-derived LEM scaffold than the control group MATRIGEL® (FIG. 87A).

As a result of gene ontology analysis that was performed to investigate the functions of non-matrisome protein components except for the extracellular matrix (ECM) in each scaffold, it was confirmed that the non-matrisome components contained in MATRIGEL® are mainly involved in the functions of biosynthesis of peptide or amide and metabolism, whereas the non-matrisome components contained in the human and porcine LEM scaffolds are mainly involved in the functions related to small molecules, various organic acids and cellular metabolism (FIG. 87B). That is, the non-matrisome protein components other than the ECM in the human and porcine LEM scaffolds are regarded as playing an important role in the formation of a functionally mature liver organoid with enhanced organic acid metabolism and various cellular metabolisms, which are important functions of hepatocytes.

Test Example 9-10. Comparison of Human Liver Organoids (Human Cholangiocyte-Derived Liver Organoids (hCLOs)) Cultured in Human and Porcine Decellularized Liver Tissue-Derived Hydrogel Scaffolds Human liver organoids were cultured in MATRIGEL® (MAT) and the decellularized human and porcine liver tissue-derived LEM hydrogel scaffolds prepared as described above. The liver organoids were prepared using bile ductal cells extracted from human liver tissue and compared in terms of urea synthesis ability and gene expression by qPCR on day 14 of culture.

As a result of comparison with the liver organoid cultured in the control group MATRIGEL® (MAT), it was confirmed that the liver organoids were stably formed in the decellularized liver tissue-derived LEM hydrogel scaffolds derived from two different species at a level similar to that in the MATRIGEL® group (FIG. 88A)

As a result of comparing the gene expression of the liver organoids cultured in the respective matrices by qPCR analysis, it was confirmed that a stemness-related marker (LGR5) was maintained at a similar level and the expression of differentiation markers (KRT19, KRT7 and SOX9) increased in the decellularized liver tissue LEM hydrogel group. Also, as a result of analysis of the hepatic functionality (urea synthesis ability), it was confirmed that liver organoids cultured in the human and porcine liver tissue-derived LEM hydrogels showed a similar or slightly higher functionality than the liver organoid cultured in MATRIGEL® (FIG. 88B).

Accordingly, it can be seen that the porcine tissue-derived LEM scaffold has the same performance as the human tissue-derived LEM scaffold, and, thus, it can replace MATRIGEL® and a human tissue-derived matrix for liver organoid culture.

With respect to a lung extracellular matrix for culture and transplantation of a lung organoid and a method of preparing the same, in the present disclosure, porcine lung tissue was chemically treated to obtain a large amount of decellularized tissue, and a hydrogel scaffold was prepared based on the decellularized lung tissue and applied to lung organoid culture. The newly developed decellularized culture scaffold can be manufactured at low cost by a simple process and low cost, which results in high economic efficiency, and, thus, it is advantageous for commercialization. Also, in the developed decellularized scaffold, all immunogenic cells have been removed and lung tissue-specific intrinsic extracellular matrix components and various factors are contained. Therefore, it is possible to improve lung organoid culture.

In order to find the optimal conditions for lung organoid culture, organoid culture tests were performed in decellularized lung tissue-derived hydrogel scaffolds at various concentrations. It was confirmed that a lung organoid cultured in the optimized decellularized lung tissue scaffold showed enhanced differentiation. As a result of comparison with a commercially available scaffold MATRIGEL®, the expression of various lung tissue cell-specific proteins was similarly observed. Further, it was confirmed that long-term culture over several passages is possible. Accordingly, it was confirmed that the prepared decellularized scaffold can replace MATRIGEL® as a lung organoid culture matrix.

In the present disclosure, it was confirmed that not only a mouse-derived lung organoid but also a human-derived lung organoid can be cultured using the decellularized lung tissue scaffold. It was confirmed that a human lung organoid cultured in the decellularized scaffold also shows high expression levels of lung tissue cell-specific proteins and can be long-term cultured.

In the present disclosure, a method of culturing a lung organoid without a culture scaffold by adding a decellularized scaffold in the form of a solution to a culture medium as well as a method of three-dimensional culturing a lung organoid in a decellularized scaffold were constructed. When the decellularized scaffold solution was added to the culture medium, the organoid formation efficiency was greatly increased and the differentiation into alveolus-specific cells was enhanced. If an organoid can be cultured without a hydrogel scaffold, desired factors or stimuli can be applied directly to the organoid, unlike a conventional method of culturing organoids within a scaffold, and it is easy to separate and collect samples, which has many advantages for organoid research.

Furthermore, in the present disclosure, the possibility of making a disease model using a lung organoid was confirmed. By adding particulate matter particles at each concentration, a lung organoid model was prepared for research on harmfulness of particulate matter. Also, it was shown that lung fibrosis disease can be modeled through treatment with a drug that induces pulmonary fibrosis. Such a disease model platform is expected to be utilized for lung fibrosis-related research and drug screening.

In the present disclosure, a technology for culturing an alveolus-specific organoid was additionally constructed. The alveolus is one of the most important constituent tissues of the lung as a unit that exchanges gases in the lung. The use of lung alveolar organoid is expected to enable more diverse studies on lung diseases.

Hereinafter, Examples will be presented for understanding of the present disclosure. However, the following Examples are illustrative only for better understanding of the present disclosure but do not limit the present disclosure.

Example 4: Preparation and Analysis of Lung Extracellular Matrix (LuEM) for Lung Organoid Culture

Example 4-1. Preparation of LuEM

A lung tissue was cut into small pieces and then treated with a decellularization solution including 1% TRITON X-100™ and 0.1% ammonium hydroxide under refrigerated conditions for 48 hours. Thereafter, a decellularized lung tissue extracellular matrix in the form of powder was prepared through lyophilization.

Example 4-2. Preparation of Scaffold Composition

The dried tissue in the form of powder can be stored for a long time. The dried tissue was dissolved in a 4 mg/ml pepsin solution (a solution of 4 mg of pepsin powder derived from porcine gastric mucosa in 1 ml of 0.02 M HCl) for 48 hours. Gelation was performed at a temperature of 37° C. for 30 minutes after setting a neutral pH in an electrolyte state of 1×PBS buffer by using 10×PBS and 1 M NaOH with uniform blending to prepare a scaffold composition in the form of a hydrogel.

Test Example 10: Analysis of LuEM

Test Example 10-1. Analysis of Mechanical Properties of LuEM

An LuEM was prepared from a porcine lung tissue and its mechanical properties were analyzed.

Specifically, in order to check whether cells were sufficiently removed from the prepared LuEM and sufficient extracellular matrix components remained, DNAs and GAGs (glycosaminoglycans) were quantified. It was confirmed that after decellularization, most of the DNAs were removed and the GAGs were maintained at a level similar to that in the lung tissue ( $p<0.01$ versus Before) (FIG. 89**A).

Also, as a result of H&E histological analysis after decellularization, it was confirmed that most of the cell nuclei stained in purple were removed and the characteristic structure of the lung tissue was maintained (FIG. 89B).

Further, as a result of analysis of the internal structure of a three-dimensional hydrogel prepared based on the decellularized lung tissue-derived extracellular components through scanning electron microscopy (SEM), it was confirmed that the hydrogel has an extracellular matrix nanofiber-based porous structure and thus has structural characteristics and environment suitable for material exchange for organoid culture (FIG. 89C).

Test Example 10-2. Analysis of Mechanical Properties of LuEM for Lung Organoid Culture A test was conducted to check whether the LuEM has suitable mechanical properties for lung organoid culture.

Specifically, hydrogels were prepared based on decellularized lung tissue extracellular matrix components of various concentrations and their mechanical properties were measured by rheological analysis.

As a result, as can be seen from FIG. 90, the elastic moduli tend to increase as the LuEM concentration increases. MATRIGEL®, which is widely used as a conventional culture scaffold, was also reported to have an elastic modulus of 100 Pa or less, which confirms that the mechanical property of the LuEM hydrogel are suitable for lung organoid culture.

Test Example 10-3. Proteomics of LuEM for Lung Organoid Culture

In order to investigate extracellular matrix component in the decellularized lung tissue-derived LuEM scaffold, proteomic analysis was performed using a mass spectrometer.

As a result, as can be seen from FIG. 91, it was confirmed that many extracellular matrix proteins and glycoproteins such as various collagens, proteoglycans and glycoproteins are detected in the decellularized lung tissue-derived LuEM scaffold. Accordingly, it is expected that these lung tissue-specific factors present in the lung tissue can have a positive role in culturing lung organoids.

Test Example 10-4. Type of Matrisome Protein of LuEM and Quantitative Analysis Matrisome proteins in the LuEM were detected by proteomic analysis using a mass spectrometer and classified by type. Also, a relative quantification was performed.

As a result, it was confirmed that various types of extracellular matrix such as collagens, glycoproteins and proteoglycans were evenly present in amount in the LuEM scaffold, and it is expected that these components in the lung tissue can promote the formation and development of a lung organoid (FIG. 92A and FIG. 92B).

When the top 10 most abundant matrisome proteins in the LuEM scaffold were identified by relative quantification of proteins, the LuEM scaffold contained various types of proteins such as collagen, decorin, elastin, fibrinogen (alpha) and biglycan. Also, when the matrisome proteins known to be highly expressed specifically in the lung tissue were checked in the LuEM scaffold, the LuEM scaffold contained four of these proteins (FIG. 92C). It is predicted that these various matrisome components contained in the LuEM can promote the formation, development and differentiation of a lung organoid.

Therefore, it is predicted that LuEM hydrogel with this proteomic composition can provide a lung tissue-specific extracellular microenvironment and thus can be applied as an effective scaffold for lung organoid culture.

Test Example 10-5. Analysis of Non-Matrisome Protein of LuEM

The non-matrisome proteins of the lung extracellular matrix (LuEM) of the present disclosure were analyzed.

As a result, it was confirmed that the LuEM contains a large amount of non-matrisome proteins as well as matrisome proteins (FIG. 93A). Also, when the non-matrisome proteins known to be highly expressed specifically in the lung tissue were checked, 7 types of various non-matrisome proteins were detected in the LuEM (FIG. 93B).

Meanwhile, the non-matrisome proteins were analyzed by a gene ontology biological process (GOBP) to analyze which biological processes are involved with the proteins.

As a result, it was confirmed that the LuEM particularly contains a lot of proteins involved in the formation and development of tissues, such as cellular component organization or biogenesis, organelle organization and cytoskeleton organization (FIG. 93C).

Therefore, it is predicted that the LuEM scaffold containing these non-matrisome proteins can improve the formation and development of a lung organoid.

Test Example 10-6. Comparative Analysis of Lung Tissue Decellularization Protocol A test was conducted to compare the decellularization method (Protocol 1) of the present disclosure and the decellularization method (Protocol 2) previously reported in the prior art document. In the prior art document, DNA was removed using DNase I (3 hours) after treatment with 4% sodium deoxycholate for 4 hours. In the present disclosure, only a mixed solution of 1% TRITON X-100™ and 0.1% ammonium hydroxide under more mild conditions was used to minimize damage to proteins in tissue.

As a result of comparing the amount of DNA remaining after decellularization, it was confirmed that DNA was successfully removed according to both protocols. As a result of comparing remaining extracellular matrix components by GAG quantification, it was confirmed that GAG components were well preserved in the tissue treated according to Protocol 1, whereas GAG components were significantly decreased in the tissue treated according to Protocol 2 (FIG. 94A).

Also, after hydrogels were fabricated using the prepared decellularized lung tissue-derived LuEM, the mechanical properties thereof were measured. It was confirmed that the elastic modulus of the hydrogel prepared using the decellularized tissue-derived LuEM treated according to Protocol 2 was slightly decreased (FIG. 94B).

Also, as a result of comparison by H&E histological analysis, it was confirmed that cells were well removed according to both methods, but more ECM proteins remained in the tissue treated according to Protocol 1 (FIG. 94C).

Further, proteomic analysis of the LuEM scaffolds prepared according to the respective decellularization protocols was performed. As a result, it was confirmed that the tissue treated according to Protocol 1 contains a greater number of extracellular matrix proteins than the tissue treated according to Protocol 2 (FIG. 94D).

According to these results, the decellularization method established in the present disclosure is more effective in preserving the extracellular matrix proteins in the lung tissue than the conventional method. Therefore, it is expected that the LuEM hydrogel prepared according to Protocol 1 can be applied as a more suitable scaffold for lung organoid culture.

A test was conducted to compare the decellularization method (Protocol 1) of the present disclosure and the conventionally used decellularization method (Protocol 3). Specifically, according to Protocol 3, treatment with a 3% sodium dodecyl sulfate, which is often used as a decellularization reagent, was performed for 24 hours in addition to the decellularization method of the present disclosure.

As a result of comparing the amount of DNA remaining after decellularization, it was confirmed that DNA was successfully removed according to both protocols. As a result of comparing remaining extracellular matrix components by GAG quantification, it was confirmed that GAG components were well preserved in the tissue treated according to Protocol 1, whereas GAG components were significantly decreased in the tissue treated according to Protocol 3 (FIG. 95A).

Also, after hydrogels were fabricated using the prepared decellularized lung tissue-derived LuEM, the mechanical properties thereof were measured. It was confirmed that the hydrogels prepared according to the respective protocols were not much different in mechanical properties (FIG. 95B).

Also, as a result of comparison by H&E histological analysis, it was confirmed that cells were well removed according to both methods, but more ECM proteins remained in the tissue treated according to Protocol 1 (FIG. 95C).

Further, proteomic analysis of the LuEM scaffolds prepared according to the respective decellularization protocols was performed. As a result, it was confirmed that the tissue treated according to Protocol 1 contains a slightly greater number of extracellular matrix proteins than the tissue treated according to Protocol 3 (FIG. 95D).

According to these results, the decellularization method established in the present disclosure is more effective in preserving the extracellular matrix proteins in the lung tissue than the method using the sodium dodecyl sulfate (SDS). Therefore, it is expected that the LuEM hydrogel prepared according to Protocol 1 can be applied as a more suitable scaffold for lung organoid culture.

Test Example 11: Analysis of Scaffold Composition Containing Decellularized Lung Tissue-Derived Extracellular Matrix

Test Example 11-1. Analysis of Formation of Mouse Lung Organoid Depending on Concentration of LuEM Decellularized lung tissue-derived hydrogels were prepared based on various concentrations of LuEM components and lung organoids were cultured. On day 7 of culture, the formation efficiency of the lung organoids at each concentration was compared and analyzed. A commercially available culture scaffold, MATRIGEL® (MAT), was used as a control group, and the lung organoids were prepared using stem cells extracted from mouse lung tissue.

Lung organoids were cultured in four concentrations of LuEM hydrogel. It was confirmed that organoids were formed into a shape similar to an organoid in MAT at a concentration of 3 mg/ml or more, but at a concentration of 1 mg/ml, most of the organoids subsided and grew and attached to the bottom of a culture dish due to low mechanical properties (FIG. 96A). Therefore, it was confirmed that an LuEM concentration of 1 mg/ml was not appropriate as a lung organoid culture scaffold, and, thus, a concentration of 1 mg/ml was excluded in the subsequent tests.

As a result of comparing the formation efficiency under each hydrogel condition, it was confirmed that the formation efficiency was somewhat lower in the hydrogels with an LuEM concentration of 3 mg/ml than that in the control group MATRIGEL®. However, it was verified that LuEM hydrogel can be applied to lung organoid culture without problems by inducing an organoid formation efficiency of 75% or more under most of the LuEM conditions ( $p<0.01$ versus MAT) (FIG. 96**B).

Test Example 11-2. Analysis of Degree of Differentiation of Mouse Lung Organoid Depending on Concentration of LuEM Decellularized lung tissue-derived hydrogels were prepared based on various concentrations of LuEM components and lung organoids were cultured. On day 7 of culture, the expression of four types of genes related to the lung bronchiolar tissue was compared and analyzed. A commercially available culture scaffold, MATRIGEL® (MAT), was used as a control group.

As a result, as shown in FIG. 97, it was confirmed that Krt5, a basal cell-related gene, showed a significantly higher expression level in the lung organoids cultured in the LuEM hydrogels than in the control group. There was no significant difference in expression level among the 3, 5, and 7 mg/ml LuEM hydrogel groups.

Also, it was confirmed that Muc5ac, a goblet cell-related gene, and Scgb1a1, a gene expressed in club cell, have the highest expression levels in the LuEM hydrogel with a concentration of 7 mg/ml.

It was confirmed that ciliated cell-related gene Foxj1 has similar expression levels in all the hydrogel conditions including the control group (*$p<0.05$ and ** $p<0.01$ versus MAT).

Therefore, it was confirmed that the expression of genes related to the lung bronchiolar tissue is enhanced or maintained at a similar level by the lung organoid culture in the LuEM hydrogel. Particularly, the LuEM hydrogel group with a concentration of 7 mg/ml showed the highest level of gene expression overall. Therefore, it is expected that the LuEM hydrogel with a concentration of 7 mg/ml can be used as a scaffold that further enhances the differentiation of the organoid into the lung bronchiolar tissue compared to the conventional MATRIGEL®. Thus, the LuEM concentration was set to 7 mg/ml, which was applied to the subsequent tests.

Test Example 11-3. Comparative Analysis of Expression of Specific Marker Protein in Mouse Lung Organoids Cultured in LuEM and MATRIGEL®

The expression of various lung tissue-specific proteins in a lung organoid cultured in a decellularized lung tissue-derived LuEM hydrogel was analyzed by immunostaining.

Specifically, it was compared with a lung organoid cultured in MATRIGEL®, which is a conventional culture scaffold, on day 7 of culture. In the present test, an LuEM hydrogel with a concentration of 7 mg/ml previously confirmed as the most suitable condition was used, and MATRIGEL® was used as a control group.

As a result, as can be seen from FIG. 98, it was confirmed that various types of cells, club cell (CC10), goblet cell (MUC5AC) and basal cell (P63), present in the lung tissue are all expressed in the organoids cultured under the both conditions, and KI67, a cell proliferation-replated protein, and Sox9, a protein expressed in the lung progenitor cell, are also expressed in the organoids under the both conditions, which confirms that cells in the lung organoids actively proliferate. Also, as a result of staining of E-cadherin (ECAD) and F-actin related to cell-cell interaction and cytoskeleton, it was confirmed that the cells are organically connected and constitute an organoid.

Test Example 11-4. Analysis of Functionality of Mouse Lung Organoids Cultured in LuEM and MATRIGEL®

The functionality of a lung organoid cultured in a decellularized lung tissue-derived LuEM hydrogel was compared and analyzed by observing drug-induced swelling. The lung organoid was treated with forskolin (a chemical material that stimulates ion channels to be opened and promotes release of water) which is a cystic fibrosis transmembrane conductance regulator (CFTR) antagonist. The degree of swelling of the lung organoid over time was observed. MATRIGEL® was used as a control group.

As a result, as can be seen from FIG. 99, it was confirmed that the lung organoid cultured in the LuEM hydrogel scaffold swells over time after treatment with forskolin and it swells more than the lung organoid cultured in MATRIGEL®. Accordingly, it can be seen that the lung organoid cultured in the LuEM hydrogel has a similar level of functionality to the lung organoid cultured in MATRIGEL®.

Test Example 11-5. Analysis of Long-Term Cultured Mouse Lung Organoid Cultured in LuEM A mouse lung organoid cultured for a long time in the LuEM of the present disclosure was analyzed.

Specifically, as can be seen from images of organoid morphology obtained during long-term culture of lung organoids for up to 93 days in the decellularized LuEM hydrogel and MATRIGEL® (FIG. 100A), the organoid initially has a hollow structure and then eventually fills up as it is cultured. MATRIGEL® was used as a control group.

As a result of immunostaining analysis of CC10 (club cell), acetylated α-tubulin (ciliated cell) and P63 (basal cell) to check the cell distribution in the lung organoids long-term cultured for up to 150 days while being subcultured up to 17 times in the respective culture scaffolds, it was confirmed that various lung tissue cell compositions were maintained up to day 150 in the lung organoid cultured in the LuEM hydrogel. Further, it was confirmed that F-actin, a cytoskeleton marker, was also well expressed (FIG. 100B).

As a result of comparing the expression of Krt5 (basal cell) and Muc5ac (goblet cell) by qPCR on day 150 of culture, it was confirmed that the lung organoid cultured in the LuEM hydrogel showed significantly higher levels of expression than the organoids cultured in MATRIGEL® (* $p<0.05$ and * $p<0.001$ versus MAT) (FIG. 100**C).

According to these results, it was confirmed that the LuEM hydrogel can culture a mouse lung organoid at a level similar to or superior to that of the conventional MATRIGEL®, which verifies that the LuEM hydrogel can replace MATRIGEL®.

Also, when the lung organoids subjected to subculture 1, 3 and 7 times in the LuEM hydrogels, respectively, were compared in terms of expression of Krt5 (basal cell), Muc5ac (goblet cell) and Scgb1a1 (club cell), the expression of each marker increased as the subculture continued. Accordingly, it was confirmed that as the culture continued, the differentiation of the lung organoids in the respective LuEM hydrogels was further enhanced (FIG. 101).

According to these results, it was confirmed that the LuEM hydrogel can enhance the differentiation of specific cells as the culture continues, which confirms that the LuEM hydrogel can produce a better lung organoid than the conventional culture scaffold.

Test Example 11-6. Check of Tissue-Specific Effect of LuEM

In order to check whether tissue-specific proteins contained in an LuEM hydrogel have tissue-specific effects in culturing a lung organoid, lung organoids were also cultured in decellularized scaffolds derived from other organs and compared. After the lung organoids were cultured in the respective tissue-derived hydrogels for 7 days, an analysis was performed.

Specifically, lung organoids were cultured using decellularized scaffolds derived from lung, muscle and kidney. It was confirmed that in the lung and muscle-derived decellularized scaffolds, the organoids were well formed to a similar size to that in the MATRIGEL® group, which is a control group, but in the kidney-derived decellularized scaffold, the organoid was formed smaller (FIG. 102A).

As a result of quantitative analysis of the formation efficiency, it was confirmed that the formation efficiency was similar in the lung and muscle-derived decellularized scaffolds, whereas the formation efficiency was lower in the kidney-derived decellularized scaffold than in the other decellularized scaffolds ( $p<0.01$ versus MAT) (FIG. 102**B).

As a result of comparing the expression of Krt5 (basal cell), Muc5ac (goblet cell) and Scgb1a1 (club cell) in the lung organoids cultured for 7 days in the decellularized scaffolds derived from the respective organs, it was confirmed that the expression of basal cells was highest in the lung-derived decellularized scaffold and the expression of club cells was significantly decreased in the muscle-derived decellularized scaffold ( $p<0.01$ versus NT) (FIG. 102**C).

According to the present test, it was confirmed that the LuEM hydrogel is superior for lung organoid culture compared to the decellularized scaffolds derived from the other organs and has tissue-specific effects.

Test Example 11-7. Culture of Human Lung Organoid Using LuEM

A test was conducted to check whether not only a mouse lung organoid but also a human lung organoid can be cultured using a decellularized lung tissue-derived LuEM hydrogel.

Specifically, stem cells were extracted from human lung tissue and a lung organoid was cultured in a decellularized LuEM hydrogel scaffold. As a result, it was confirmed that a human lung organoid was well formed and grown in the LuEM hydrogel. Although it grew relatively slowly compared to a mouse lung organoid, it was confirmed that subculture and long-term culture were also possible (FIG. 103A).

As a result of checking the expression of lung tissue marker proteins in the cultured human lung organoid by immunostaining, when immunostaining of P63, a protein expressed in basal cells, and MUC5AC, a protein expressed in goblet cells, was performed, cells expressing the proteins P63 and MUC5AC were observed in the lung organoid. Also, it can be seen that the lumen of the lung organoid is well-formed by the expression of ZO-1 and F-actin, and the structures are organically well connected (FIG. 103B).

As a result of functional analysis to check a swelling response induced by forskolin in the human lung organoid, it was confirmed that the lung organoid was swollen over time after drug treatment and functioned normally (FIG. 103C).

According to the present test, it was confirmed that the human lung organoid can also be cultured using the LuEM.

Test Example 12: Check of Applicability of Scaffold Composition of the Present Disclosure Test Example 12-1. Construction of Lung Fibrosis Model Using Mouse Lung Organoid Cultured in LuEM For lung disease modeling using a lung organoid, a mouse lung organoid was treated with TGF-β and the possibility of inducing lung fibrosis was checked.

Specifically, lung organoids were treated for 3 days at respective concentrations on day 4 of culture and analyzed on day 7. A lung organoid that was not treated with TGF-β (NT, No treatment) was used as a control group.

As a result, when the lung organoids were treated with TGF-β at respective concentrations to fabricate a lung fibrosis model and observed 3 days later, the lung organoid that was not treated with TGF-β grew well for 3 days, but all the lung organoids treated with TGF-β were changed in shape and did not grow well (FIG. 104A).

As a result of checking the expression of Col1a2, a lung fibrosis-related marker, it was confirmed that the expression of Col1a2 increases as the TGF-β treatment concentration increases. It was confirmed that at a concentration of 40 ng/ml, the expression of Col1a2 increased statistically significantly (* $p<0.05$ versus NT) (FIG. 104B).

As a result of checking the expression of fibrosis-related proteins, smooth muscle actin (SMA) and collagen type 1 (Col1), by immunostaining, it was confirmed that the expression levels of the fibrosis markers increase as the TGF-β treatment concentration increases (FIG. 104C).

According to the present test, it was confirmed that a lung fibrosis model can be fabricated based on the lung organoid cultured in the LuEM hydrogel scaffold.

Test Example 12-2. Construction of Human Lung Fibrosis Model Using Human Lung Organoid Cultured in LuEM To fabricate a lung fibrosis model using a human lung organoid cultured in a decellularized LuEM hydrogel scaffold, a human lung organoid was treated with TGF-β and the possibility of inducing lung fibrosis was checked.

Specifically, human lung organoids cultured in respective scaffolds were treated with TGF-β for 3 days and then analyzed.

As a result of checking the expression of lung fibrosis markers ACTA2, COL1A2 and TNF-α by quantitative PCR, it was confirmed that the expression significantly increased in the organoids treated with TGF-β (* $p<0.05$ and  $p<0.01$). versus NT) (FIG. 105**A).

As a result of checking the expression of lung fibrosis markers smooth muscle actin (SMA), collagen type 1 (COL1) and vimentin (VIM) by immunostaining on 3 days after treatment with TGF-β, it was confirmed that the expression of all the markers increased in the lung organoids treated with TGF-β (FIG. 105B).

According to the present test, it was confirmed that a human lung fibrosis model can be fabricated based on the human lung organoid cultured in the LuEM scaffold.

Test Example 12-3. Analysis of Functionality of Human Lung Fibrosis Model Constructed in LuEM A lung fibrosis model was fabricated by treating a human lung organoid cultured in a decellularized LuEM hydrogel scaffold with TGF-β, and the functionality was checked by analyzing the degree of swelling induced by a drug forskolin.

As a result, as can be seen from FIG. 106, it was confirmed that the normal organoid was normally swollen due to the drug, but when lung fibrosis was induced, even the drug-treated lung organoid was not swollen.

According to the present test, it was confirmed that the functionality of a human lung fibrosis model cultured in the LuEM scaffold decreases.

Test Example 12-4. Construction of Particulate Matter Disease Model Using Mouse Lung Organoid Cultured in LuEM The effect of particulate matter on a lung organoid was analyzed by treating a lung organoid cultured in a decellularized LuEM scaffold with particulate matter.

Specifically, when a hydrogel was prepared from a decellularized lung tissue-derived LuEM component, particulate matter with a size of about 10 μm (PM10) was mixed in order for the particulate matter to effectively contact with the lung organoid cultured in the hydrogel. On day 3 of culture of the organoid with the particulate matter, the gene expression was analyzed.

According to images of the lung organoid cultured for 3 days in the LuEM scaffold treated with the particulate matter, it was confirmed that black materials (arrows) presumed as particulate matter were observed (FIG. 107A).

In the lung organoid treated with the particulate matter, the expression of iNOS, a gene related to inflammatory response, increased when the particulate matter was treated at a concentration of 4 mg/ml (FIG. 107B).

According to the present test, it was confirmed that lung diseases caused by particulate matter can be modeled by adding particulate matter while the lung organoid is cultured in the decellularized LuEM hydrogel scaffold.

Test Example 12-5. Verification of Possibility of Long-Term Storage of LuEM

A decellularized lung tissue-derived LuEM solution was cold-stored at 4° C. for a long time, and it was used for culturing a mouse lung organoid to check the possibility of long-term storage and stability of an LuEM hydrogel (FIG. 108A).

It was confirmed that lung organoids were well formed and cultured even in LuEM hydrogels prepared from the cold-stored LuEM for 7 days and 31 days, respectively, at a similar level to those in an LuEM hydrogel (Fresh LuEM) prepared immediately before culture and MATRIGEL® (images of the organoids on day 7 of culture). Also, as a result of comparing the mRNA expression levels of various lung-specific markers by qPCR analysis of day 7 of culture, the organoids showed higher expression than an organoid cultured in MATRIGEL® (MAT group) and a similar level of expression to an organoid cultured in the newly prepared LuEM hydrogel (Fresh group) (FIG. 108B).

Accordingly, it was confirmed that the LuEM can be stably maintained without denaturation for at least 1 month even after cold storage of the LuEM in the form of a solution at 4° C., and can be used for lung organoid culture after cold storage. This verified that it can be developed into a product with a long shelf life.

Test Example 12-6. Check of Possibility of Forming Lung Organoid Under Scaffold-Free Culture Conditions by Using LuEM Components A test was conducted to check the possibility of forming a lung organoid without a culture scaffold under the condition that an LuEM solution was added to a culture medium.

Specifically, when stem cells separated from mouse lung tissue were cultured, an LuEM solution of each concentration was added to a culture medium.

When observed on day 7 of culture, the organoids were formed to a larger size as the LuEM concentration increased. However, in the organoids cultured at a high LuEM concentration (0.1 mg/ml), some crosslinked LuEM hydrogel-like materials were observed attached to the organoids (FIG. 109A).

As a result of quantification of the number and size of lung organoids formed on day 7 of culture, it was confirmed that the number of organoids formed increased as the LuEM concentration increased and the lung organoid cultured at a medium LuEM concentration (0.01 mg/ml) had the largest size on average (FIG. 109B).

According to these results, it was confirmed that a lung organoid can be cultured simply by adding an LuEM solution to a culture medium without MATRIGEL® or a hydrogel scaffold, which is essential for the formation and maintenance of a lung organoid. According to this method, a lung organoid can be cultured more easily and efficiently and it becomes much easier to process various factors and handle the organoid. Therefore, the scope of application of organoids can be expanded.

Test Example 12-7. Analysis of Gene and Protein Expression in Mouse Lung Organoid Formed without Culture Scaffold The expression of lung tissue-specific markers in lung organoids cultured for 7 days at various LuEM treatment concentrations was compared.

Specifically, the expression of four types of genes related to the differentiation of lung bronchiolar tissue and alveolus-related genes was compared in each group. As a result, it was confirmed that a suspension group with a concentration of 0.1 mg/ml showed a similar expression level to an organoid cultured in a gel. However, it was confirmed that the expression of ciliated cells (Foxj1) and club cells (Scgb1a1) significantly increased in the No treatment group and the suspension groups with concentrations of 0.001 and 0.01. Also, it was confirmed that the expression of goblet cells (Muc5ac) was similar in the LuEM hydrogel and the expression of basal cells (Krt5) significantly decreased. Accordingly, it can be seen that differentiation from basal cells into various cells is further promoted when an organoid is cultured in suspension conditions (*$p<0.05$ and  $p<0.01$ versus No treatment, #$p<0.05$ and ##$p<0.01$ versus LuEM 7 mg/ml) (FIG. 110**A).

The expression of various cells such as ciliated cell (acetylated α-tubulin) and basal cell (P63) was checked by immunostaining. Also, when an organoid was cultured without a culture scaffold, polarization occurred, which caused the organoid to be cultured inside out. As a result, it was confirmed that at a high hydrogel concentration of 0.1 mg/ml, polarization does not occur as in the gel condition and a lumen is present inside the organoid, and the outside is recognized as a lumen in the other groups (FIG. 110B).

Based on the results of the present test, a technique of effectively fabricating a lung organoid through treatment with an LuEM solution without a culture scaffold was established. Also, it was confirmed that in the fabricated organoid, unlike an organoid cultured in a conventional scaffold, polarization occurs similarly to that under in vivo conditions, and, thus, the organoid is formed inside out.

Test Example 12-8. Analysis of Protein Expression in Human Lung Organoid Formed without Culture Scaffold Human lung organoids were cultured for 7 days under culture conditions (final concentration of 0.01 mg/ml) in which an LuEM solution with a concentration of 10 mg/ml was added at a ratio of 1:1000 (relative to the volume of a culture medium). The expression of lung tissue-specific markers in the human lung organoids was compared. A group (No treatment) that was not treated with anything and a group (MAT) treated with MATRIGEL® at a ratio of 1:100 (relative to the volume of a culture medium) were used as control groups.

As a result, as can be seen from FIG. 111, it was confirmed that at an appropriate treatment concentration of the LuEM, several organoids were combined with each other to form a larger organoid. Also, it was confirmed that the organoids were formed inside out and all of ciliated cells (acetylated α-tubulin), basal cells (P63) and goblet cells (MUC5AC) were well expressed.

Based on the results of the present test, a technique of fabricating a human lung organoid with a greater size at the tissue level through treatment with an LuEM solution without a culture scaffold was established.

Test Example 12-9. Analysis of Protein Expression in Human Lung Organoid Formed without Culture Scaffold When a human lung organoid cultured in an LuEM hydrogel scaffold was changed to a condition without a culture scaffold, the organoid was cultured inside out. Also, it was confirmed that angiotensin-converting enzyme 2 (ACE2), transmembrane protease and serine 2 (TMPRSS2), known as cell-surface proteins important for intracellular infection of COVID-19, were mainly expressed outside the organoid, and were cultured to be optimized for virus infection tests (FIG. 112).

According to the present test, it was confirmed that a lung organoid cultured without a culture scaffold can be used for infection studies.

Test Example 12-10. Particulate Matter Test on Mouse Lung Organoid Formed without Culture Scaffold Lung organoids formed only through treatment with an LuEM solution without a culture scaffold were treated with particulate matter of four concentrations, and the effect thereof was observed. The test was conducted under the condition that an LuEM solution with a concentration of 0.01 mg/ml at which the best effect was achieved in the above-described test example was included in a culture medium. In this test, when the culture medium is treated with particulate matter, which is an external material, the organoids can directly react to the particulate matter, which enables a more accurate analysis of the effect of the particulate matter.

As a result of treating the culture medium with particulate matter with a size of about 10 μm (PM10) at various concentrations of 20, 100 and 500 μg/ml, more particulate matter that appeared black in the culture medium (arrows) was observed as the concentration of the particulate matter increased. Also, it was confirmed that the particulate matter was directly attached to the organoids or a large amount of particulate matter was distributed around the organoid (FIG. 113A).

Live/Dead staining was performed to analyze cell viability, and as a result, it was confirmed that the number of dead cells increased as the concentration of the particulate matter (arrows) increased. Particularly, it was confirmed that at a high concentration (500 μg/ml), the organoid was disassembled due to apoptosis and no structure was left (FIG. 113B).

According to the results of the present test, it was confirmed that particulate matter induces the apoptosis of a lung organoid. According to the method of treating the lung organoid formed without a culture scaffold with particulate matter, it becomes easier to model lung diseases caused by particulate matter and an accurate prediction of the effect of particulate matter is possible.

Test Example 12-11. Promotion of Lung Alveolar Differentiation in Mouse Lung Organoid of LuEM In order to newly implement an organoid that is specifically differentiated into alveolar cells, which are one of the most important functional structures in the lung, an organoid was fabricated by regulating the Notch signaling. In order to induce differentiation, DAPT, a reagent that inhibits the Notch signaling, was added to a conventional culture medium and then cultured. Also, hydrogels were prepared at respective concentrations of the LuEM to attempt to induce culture and differentiation of a lung organoid. MATRIGEL® was used as a control group.

When the lung organoids cultured at the respective LuEM hydrogel concentrations were observed on day 14 of culture, the organoids were well formed into similar shapes in all the groups (FIG. 114A).

When the gene expression of Sftpc and Hopx, alveolar-specific markers, were compared on day 14 of culture, an expression level of Sftpc, an alveolar type 2 cell marker, increased as the concentration of the LuEM increased, and an expression level of Hopx, an alveolar type 1 cell marker, increased as the concentration of the LuEM decreased. ( $p<0.01$ versus MAT) (FIG. 114**B).

When the expression of SPC, an alveolar type 2 cell marker, and Hopx, an alveolar type 1 cell marker, was checked on day 14 of culture, a type 1 alveolar type 1 cell marker, the markers were well expressed in all the groups with a slight difference. Also, CC10 and P63, which are bronchiolar markers, was hardly observed (FIG. 114C).

According to the results of the present test, it was confirmed that an organoid whose differentiation into alveolar cells is induced can be fabricated using an LuEM scaffold and the cell composition of the organoid can be adjusted by regulating the concentration of the LuEM.

Test Example 12-12. Monolayer Formation and Analysis of Human Lung Organoid Cultured in LuEM A test was conducted to fabricate a monolayer from a human lung organoid so that it can be easily used for various applications such as infection test and drug screening.

Specifically, a lung organoid cultured in an LuEM hydrogel was disassembled into single cells through enzymatic treatment and then cultured in a well plate to induce formation of a monolayer.

It was confirmed by immunostaining that ciliated cells (acetylated α-tubulin), goblet cells (MUC5AC) and basal cells (P63) were well maintained in the fabricated monolayer (FIG. 115A). Also, it was confirmed that cells constituting the monolayer well expressed cell-surface proteins such as ACE2 and TMPRSS2, which are important for COVID-19 infection (FIG. 115B).

Based on the present test, a method of forming a monolayer suitable for various experimental uses from a lung organoid cultured using an LuEM scaffold was established.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure.

We claim:

1. A scaffold composition containing an organ extracellular matrix, wherein the organ is selected from the group consisting of intestine, stomach, liver, and lung, and wherein the organ extracellular matrix is contained at a concentration of:

(a) 2 mg/mL to 3 mg/mL when the organ is intestine, (b) 1 mg/mL to 7 mg/ml when the organ is stomach, (c) 2 mg/ml to 6 mg/ml when the organ is liver, and (d) 3 mg/ml to 7 mg/ml when the organ is lung.

* * * * *